United States Patent
Kshirsagar et al.

(10) Patent No.: US 8,846,710 B2
(45) Date of Patent: Sep. 30, 2014

(54) METHOD OF PREFERENTIALLY INDUCING THE BIOSYNTHESIS OF INTERFERON

(75) Inventors: Tushar A. Kshirsagar, Woodbury, MN (US); Bryon A. Merrill, River Falls, WI (US); Scott E. Langer, Woodbury, MN (US); Kyle J. Lindstrom, Houlton, WI (US); Sarah C. Slania, Minneapolis, MN (US); Gregory J. Marszalek, Woodbury, MN (US); Joshua R. Wurst, Saint Paul, MN (US); Karl J. Manske, Minneapolis, MN (US); Shri Niwas, Maple Grove, MN (US); Gregory D. Lundquist, Jr., Eagan, MN (US); Philip D. Heppner, Forrest Lake, MN (US); George W. Griesgraber, Eagan, MN (US); Michael E. Danielson, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1835 days.

(21) Appl. No.: 11/884,982

(22) PCT Filed: Feb. 22, 2006

(86) PCT No.: PCT/US2006/006222
§ 371 (c)(1),
(2), (4) Date: Sep. 5, 2008

(87) PCT Pub. No.: WO2006/091647
PCT Pub. Date: Aug. 31, 2006

(65) Prior Publication Data
US 2009/0030031 A1    Jan. 29, 2009

Related U.S. Application Data

(60) Provisional application No. 60/655,452, filed on Feb. 23, 2005, provisional application No. 60/655,508, filed on Feb. 23, 2005, provisional application No. 60/655,380, filed on Feb. 23, 2005, provisional application No. 60/655,495, filed on Feb. 23, 2005.

(51) Int. Cl.
*A61K 31/4745* (2006.01)
*C07D 471/04* (2006.01)
*C07D 471/14* (2006.01)

(52) U.S. Cl.
CPC .......... *A61K 31/4745* (2013.01); *C07D 471/04* (2013.01); *C07D 471/14* (2013.01)
USPC ............... 514/293; 514/303; 546/82; 546/83; 546/84

(58) Field of Classification Search
CPC . A61K 31/4745; C07D 471/04; C07D 471/14
USPC .......................... 514/293, 303; 546/82, 83, 84
See application file for complete search history.

(56) References Cited

U.S. PATENT DOCUMENTS 3,314,941 A    4/1967    Littell et al.
(Continued)

FOREIGN PATENT DOCUMENTS

EP    0 394 026    10/1990
(Continued)

OTHER PUBLICATIONS

Yutilov et al., Synthesis and some reactions of 4-nitroimidazo[4-5-c]pyridin-2-ones. Viniti. 1978:1193-78. Russian. CAPLUS English Abstract DN 91:175261.
(Continued)

*Primary Examiner* — Savitha Rao

(57) ABSTRACT

A method of preferentially inducing IFN-α biosynthesis in an animal comprising administering certain imidazo[4,5-c] ring compounds with a hydroxymethyl or hydroxyethyl substituent at the 2-position or pharmaceutical compositions containing the compounds, intermediates, methods of making, and methods of using these compounds a immunomodulators for treatment of diseases including viral and neoplastic diseases comprising preferentially inducing IFN-α biosynthesis in an animal are disclosed.

16 Claims, 4 Drawing Sheets

(56) References Cited

U.S. PATENT DOCUMENTS

| | | |
|---|---|---|
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,605,899 A | 2/1997 | Gerster et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,465,654 B2 | 10/2002 | Gerster et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 * | 1/2004 | Griesgraber .......... 514/293 |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Rice et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 * | 5/2008 | Gorden et al. .......... 530/300 |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |

(56) References Cited

U.S. PATENT DOCUMENTS

| | | |
|---|---|---|
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,968,562 B2 | 6/2011 | Skwierczynski et al. |
| 7,968,563 B2 | 6/2011 | Kshirsagar et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Miller et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0155767 A1 | 7/2007 | Radmer et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Moller et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |
| 2008/0085895 A1 | 4/2008 | Griesgraber et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269192 A1 | 10/2008 | Griesgraber et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 92/15581 A1 | 9/1992 |
| WO | WO 92/15582 A1 | 9/1992 |
| WO | WO 02/36592 | 5/2002 |
| WO | WO 03/009852 A1 | 2/2003 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Wozniak et al., "The Amination of 3-nitro-1, 5-napththyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

(56) References Cited

OTHER PUBLICATIONS

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

* cited by examiner

METHOD OF PREFERENTIALLY INDUCING THE BIOSYNTHESIS OF INTERFERON

CROSS-REFERENCE TO RELATED APPLICATIONS

This application is a national stage filing under 35 U.S.C. §371 of PCT International application PCT/US2006/006222 designating the United States of America, and filed Feb. 22, 2006. This application claims the benefit under 35 U.S.C. §119 of U.S. provisional application Ser. Nos. 60/655,452, filed Feb. 23, 2005, 60/655,508 filed Feb. 23, 2005, 60/655,380, filed Feb. 23, 2005, and 60/655,495 filed Feb. 23, 2005.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

The present invention provides a method of preferentially inducing the biosynthesis of interferon ($\alpha$) (IFN-$\alpha$) in an animal comprising administering an effective amount of a compound of Formulas I, II, and/or III:

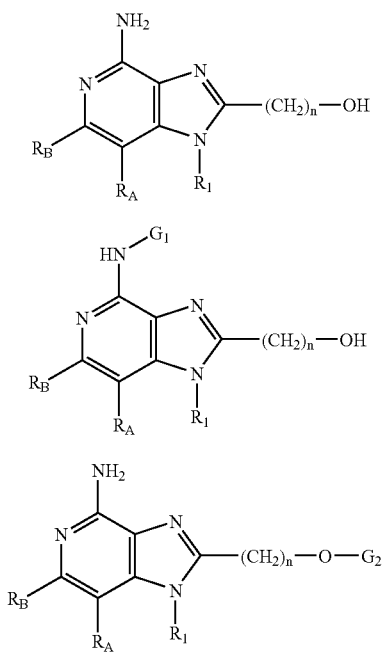

wherein $R_A$, $R_B$, $R_1$, $G_1$, $G_2$, and n are as defined below.

It has now surprisingly been discovered that the amount of TNF-$\alpha$ induced by the 2-(hydroxyalkyl) substituted compounds of Formula I is substantially less than the amount of TNF-$\alpha$ induced by closely related analogs having an alkyl or alkyl ether substituent at the 2-position and that the compounds of Formula I, which can be administered as Formula I, Formula II, and/or Formula III, and/or a pharmaceutically acceptable salt thereof, can still retain the ability to induce the biosynthesis of IFN-$\alpha$. See, for example, FIGS. 1-8 below. The reduction in the amount of TNF-$\alpha$ induced is seen over a broad range of test concentrations. In some embodiments the amount of TNF-$\alpha$ induced by the compounds of Formulas I, II, and/or III is at least two-fold less than the amount of TNF-$\alpha$ induced by analogs having an alkyl or alkyl ether substituent at the 2-position. In other embodiments the amount of TNF-$\alpha$ induced by the compounds of Formulas I, II, and/or III is at least three-fold less than the amount of TNF-$\alpha$ induced by analogs having an alkyl or alkyl ether substituent at the 2-position. In still other embodiments the amount of TNF-$\alpha$ induced by the compounds of Formulas I, II, and/or III is at least four-fold less than the amount of TNF-$\alpha$ induced by analogs having an alkyl or alkyl ether substituent at the 2-position.

The compounds or salts of Formulas I, II, and III are especially useful as immune response modifiers due to their ability to preferentially induce interferon-$\alpha$, thus providing a benefit over compounds that also induce pro-inflammatory cytokines (e.g. TNF-$\alpha$) or that induce pro-inflammatory cytokines at higher levels.

A compound is said to preferentially induce IFN-$\alpha$ if, when tested according to the test methods described herein, the effective minimum concentration for IFN-$\alpha$ induction is less than the effective minimum concentration for TNF-$\alpha$ induction. In some embodiments, the effective minimum concentration for IFN-$\alpha$ induction is at least 3-fold less than the effective minimum concentration for TNF-$\alpha$ induction. In some embodiments, the effective minimum concentration for IFN-$\alpha$ induction is at least 6-fold less than the effective minimum concentration for TNF-$\alpha$ induction. In other embodiments, the effective minimum concentration for IFN-$\alpha$ induction is at least 9-fold less than the effective minimum concentration for TNF-$\alpha$ induction. In some embodiments, when tested according to the test methods described herein, the amount TNF-$\alpha$ induced by compounds of Formulas I, II, and/or III is at or below the background level of TNF-$\alpha$ in the test method.

The invention further provides a method of preferentially inducing the biosynthesis of IFN-$\alpha$ in an animal wherein an effective amount of the compound or salt of Formulas I, II, and/or III (or any one of the embodiments described herein) is administered as a pharmaceutical composition comprising a therapeutically effective amount of a compound or salt of Formulas I, II, and/or III (or any one of the embodiments described herein) and a pharmaceutically acceptable carrier.

The invention further provides a method of treating a viral infection or disease and/or treating a neoplastic disease in an animal comprising preferentially inducing the biosynthesis of IFN-$\alpha$ in the animal by administering an effective amount of a compound or salt of Formulas I, II, and/or III (or any one of the embodiments described herein) or a pharmaceutical composition containing an effective amount of a compound or salt of Formulas I, II, and/or III (or any one of the embodiments described herein) to the animal.

In addition, methods of synthesizing compounds of Formulas I, II, and III and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

Figure 1:
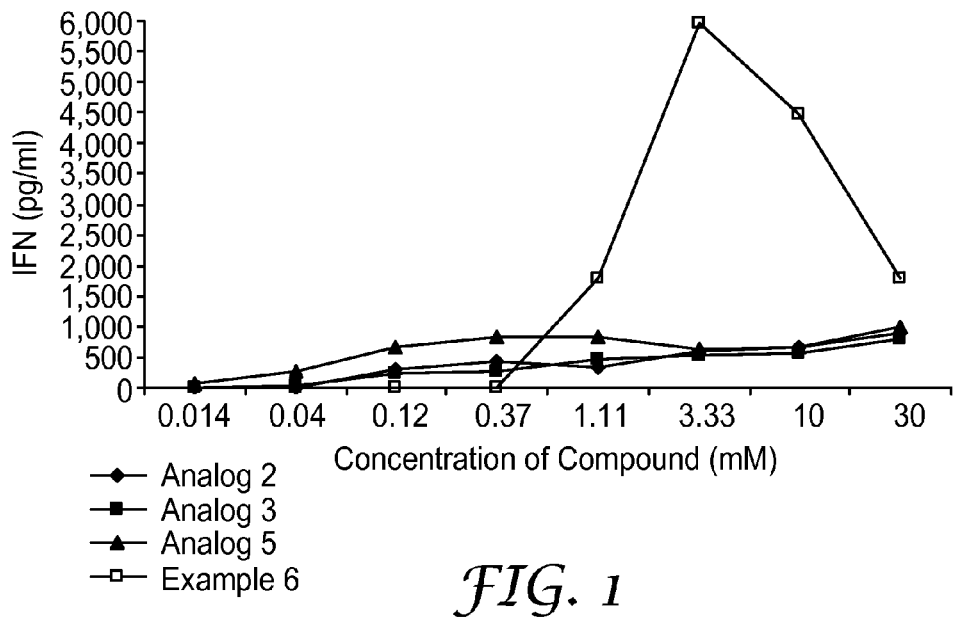
FIG. 1 shows the IFN-α dose response curves (corresponding to values shown in Table 7 below) for Example 6, Analog 2, Analog 3, and Analog 5.

The present invention provides a method of preferentially inducing the biosynthesis of IFN-α in an animal comprising administering an effective amount of a compound of Formulas I, II, and/or III:

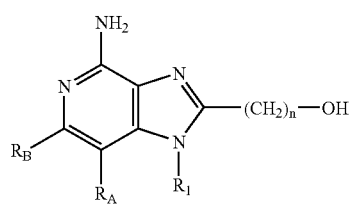

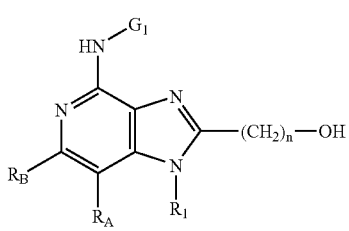

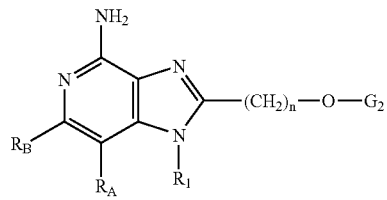

wherein $R_A$, $R_B$, $R_1$, $G_1$, $G_2$, and n are as defined below; and pharmaceutically acceptable salts thereof.

In one embodiment, the present invention provides a method of preferentially inducing the biosynthesis of IFN-α in an animal comprising administering an effective amount of a compound of the following Formula I:

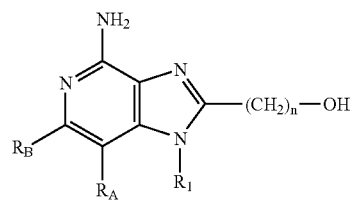

wherein:
n is 1 or 2;
$R_A$ and $R_B$ are each independently selected from the group consisting of:
  hydrogen,
  halogen,
  alkyl,
  alkenyl,
  alkoxy,
  alkylthio and
  —$N(R_9)_2$;
  or when taken together, $R_A$ and $R_B$ form a fused aryl ring or heteroaryl ring containing one heteroatom selected from the group consisting of N and S wherein the aryl or heteroaryl ring is unsubstituted or substituted by one or more R groups, or substituted by one $R_3$ group, or substituted by one $R_3$ group and one R group;
  or when taken together, $R_A$ and $R_B$ form a fused 5 to 7 membered saturated ring, optionally containing one heteroatom selected from the group consisting of N and S, and unsubstituted or substituted by one or more R groups;
R is selected from the group consisting of:
  halogen,
  hydroxy,
  alkyl,
  alkenyl,
  haloalkyl,
  alkoxy,
  alkylthio, and
  —$N(R_9)_2$;
$R_1$ is selected from the group consisting of:
  —$R_4$,
  —X—$R_4$,
  —X—Y—$R_4$,
  —X—Y—X—Y—$R_4$, and
  —X—$R_5$;
$R_3$ is selected from the group consisting of:
  —Z—$R_4$,
  —Z—X—$R_4$,
  —Z—X—Y—$R_4$, —Z—X—Y—X—Y—R$_4$, and

—Z—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

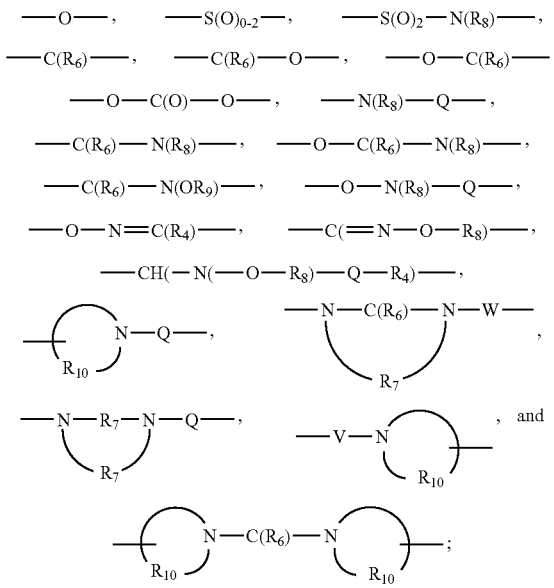

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

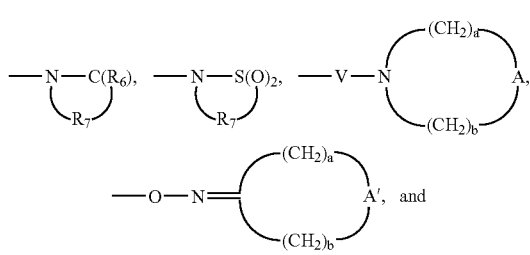

-continued

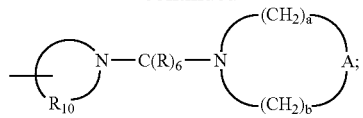

R$_6$ is selected from the group consisting of =O and =S;

R$_7$ is C$_{2-7}$ alkylene;

R$_8$ is selected from the group consisting of hydrogen, alkyl, alkoxyalkylenyl, hydroxyalkylenyl, arylalkylenyl, and heteroarylalkylenyl;

R$_9$ is selected from the group consisting of hydrogen and alkyl;

R$_{10}$ is C$_{3-8}$ alkylene;

A is selected from the group consisting of —O—, —C(O)—, —CH$_2$—, —S(O)$_{0-2}$—, and —N(Q-R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof to the animal.

In another embodiment, the present invention provides a method of preferentially inducing the biosynthesis of IFN-α in an animal comprising administering an effective amount of a compound of the following Formula II, which is a prodrug:

II

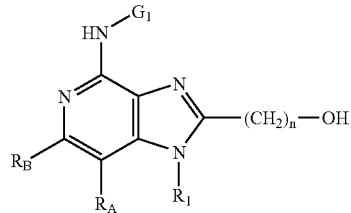

wherein:

G$_1$ is selected from the group consisting of:
—C(O)—R',
α-aminoacyl,
α-aminoacyl-α-aminoacyl,
—C(O)—O—R',
—C(O)—N(R")R',
—C(=NY')—R',
—CH(OH)—C(O)—OY',
—CH(OC$_{1-4}$alkyl)Y$_0$,
—CH$_2$Y$_1$, and
—CH(CH$_3$)Y$_1$;

R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an α-aminoacyl group derived from an α-amino acid selected from the group consisting of racemic, D-, and L-amino acids;

Y' is selected from the group consisting of hydrogen, C$_{1-6}$ alkyl, and benzyl;

Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl;

Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;

n is 1 or 2;

R$_A$ and R$_B$ are each independently selected from the group consisting of:
hydrogen,
halogen,
alkyl,
alkenyl,
alkoxy,
alkylthio and
—N(R$_9$)$_2$;

or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups, or substituted by one R$_3$ group, or substituted by one R$_3$ group and one R group;

or when taken together, R$_A$ and R$_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N(R$_9$)$_2$;

R$_1$ is selected from the group consisting of:
—R$_4$,
—X—R$_4$,
—X—Y—R$_4$,
—X—Y—X—Y—R$_4$, and
—X—R$_5$;

R$_3$ is selected from the group consisting of:
—Z—R$_4$,
—Z—X—R$_4$,
—Z—X—Y—R$_4$,
—Z—X—Y—X—Y—R$_4$, and
—Z—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

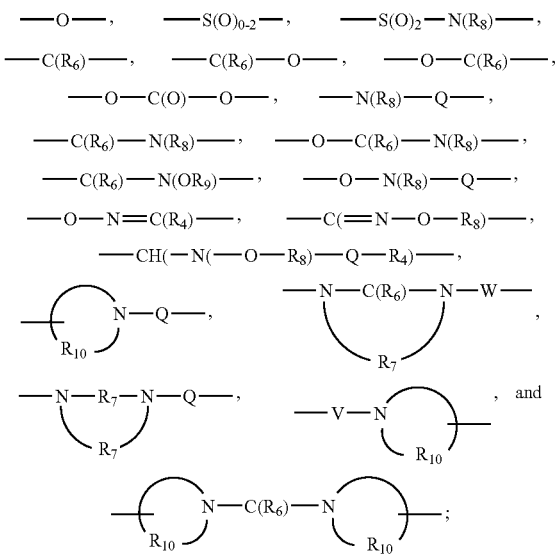

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

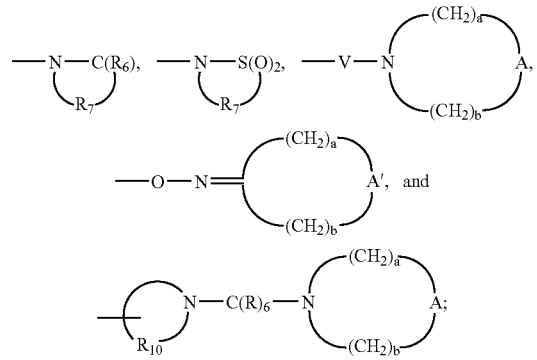

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;

$R_{10}$ is $C_{3-8}$ alkylene;

A is selected from the group consisting of —O—, —C(O)—, —CH$_2$—, —S(O)$_{0-2}$—, and —N(Q-R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof to the animal.

In another embodiment, the present invention provides a method of preferentially inducing the biosynthesis of IFN-α in an animal comprising administering an effective amount of a compound of the following Formula III, which is a prodrug:

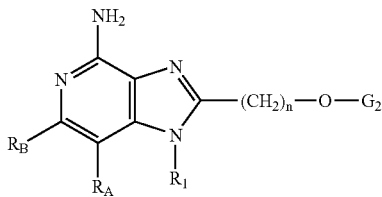

III wherein:

G$_2$ is selected from the group consisting of:
—X$_2$—C(O)—R',
α-aminoacyl,
α-aminoacyl-α-aminoacyl,
—X$_2$—C(O)—O—R', and
—C(O)—N(R")R';

X$_2$ is selected from the group consisting of a bond; —CH$_2$—O—; —CH(CH$_3$)—O—, —C(CH$_3$)$_2$—O—; and, in the case of —X$_2$—C(O)—O—R', —CH$_2$—NH—;

R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an α-aminoacyl group derived from an α-amino acid selected from the group consisting of racemic, D-, and L-amino acids;

n is 1 or 2;

R$_A$ and R$_B$ are each independently selected from the group consisting of:
hydrogen,
halogen,
alkyl,
alkenyl,
alkoxy,
alkylthio and
—N(R$_9$)$_2$;

or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups, or substituted by one R$_3$ group, or substituted by one R$_3$ group and one R group;

or when taken together, R$_A$ and R$_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N(R$_9$)$_2$;

R$_1$ is selected from the group consisting of:
—R$_4$
—X—R$_4$,
—X—Y—R$_4$,
—X—Y—X—Y—R$_4$, and
—X—R$_5$;

R$_3$ is selected from the group consisting of:
—Z—R$_4$,
—Z—X—R$_4$,
—Z—X—Y—X—Y—R$_4$, and
—Z—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—, —S(O)$_{0-2}$—, —S(O)$_2$—N(R$_8$)—,
—C(R$_6$)—, —C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,
—C(R$_6$)—N(OR$_9$)—, —O—N(R$_8$)—Q—,
—O—N=C(R$_4$)—, —C(=N—O—R$_8$)—,
—CH(—N(—O—R$_8$)—Q—R$_4$)—,

[ring structures with N—Q, R$_{10}$, N—C(R$_6$)—N—W, R$_7$, etc.]

—N—R$_7$—N—Q—, —V—N (ring with R$_{10}$), and (ring with R$_{10}$, N—C(R$_6$)—N, R$_{10}$);

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

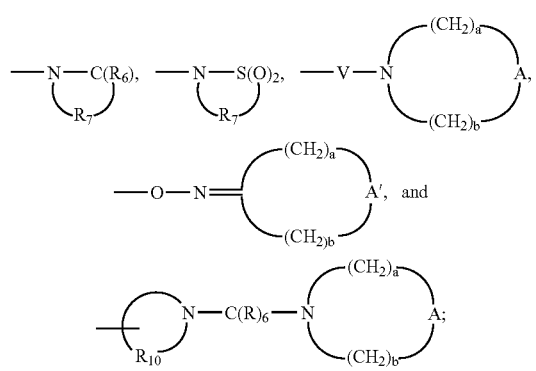

$R_6$ is selected from the group consisting of =O and —S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —CH$_2$—, —S(O)$_{0-2}$—, and —N(Q-R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_5$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
or a pharmaceutically acceptable salt thereof to the animal.

As used herein "substantially less than the amount of TNF-α" means that there is at least a two-fold reduction in the maximal TNF-α response as determined using the test methods described herein.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, 2,2,2-trifluoroethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl(azepanyl), 1,4-oxazepanyl, homopiperazinyl(diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_8$)—C(O)—N($R_8$)— each $R_8$ group is independently selected. In another example, when $R_1$ and $R_3$ each contain an $R_4$ group then each $R_4$ group is independently selected. In a further example, when two Y groups are present and each Y group contains one or more $R_8$ groups, then each Y group and each $R_8$ group is independently selected.

The compounds described herein can be administered according to the methods of the present invention in any of the compounds' pharmaceutically acceptable forms, including isomers (e.g., diastereomers and enantiomers), salts, solvates, polymorphs, and the like. In particular, if a compound is optically active, the methods of the invention specifically include the use each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., X, Y, Z, $R_A$, $R_B$, $R_1$, $R_3$, $R_4$, $R_5$, Q, $G_1$, $G_2$, and so on) in any of its embodiments can be combined with any one or more of the other variables in any of their embodiments and associated with any one of the formulas described herein, as would be understood by one of skill in the art. Each of the resulting combinations of variables describes a compound or compounds which can be administered according to any one of the methods of the present invention, and the resulting method is an embodiment of the present invention.

For certain embodiments of any one of the above methods, n is 1.

For certain embodiments of any one of the above methods, n is 2.

For certain embodiments of any one of the above methods, including any one of the above embodiments, $R_A$ and $R_B$ form a fused benzene ring which is unsubstituted or substituted by one or more R groups, or substituted by one $R_3$ group, or substituted by one $R_3$ group and one R group. For certain of these embodiments, the fused benzene ring is substituted by an $R_3$ group at the 7-position.

For certain embodiments of any one of the above methods, including any one of the above embodiments except where $R_A$ and $R_B$ form the fused benzene ring, $R_A$ and $R_B$ form a fused pyridine ring which is unsubstituted or substituted by one or more R groups, or substituted by one $R_3$ group, or substituted by one $R_3$ group and one R group.

For certain embodiments of any one of the above methods, including any one of the above embodiments except where $R_A$ and $R_B$ form the fused benzene or pyridine ring, $R_A$ and $R_B$ form a fused 5 to 7 membered saturated ring, optionally containing one heteroatom selected from the group consisting of N and S, wherein the ring is unsubstituted or substituted by one or more R groups.

For certain embodiments of any one of the above methods, including any one of the above embodiments except where $R_A$ and $R_B$ form the fused benzene, pyridine, or 5 to 7 membered saturated ring, $R_A$ and $R_B$ are each independently selected from the group consisting of hydrogen, halogen, alkyl, alkenyl, alkoxy, alkylthio, and —N($R_9$)$_2$. For certain of these embodiments, $R_A$ and $R_B$ are each methyl.

For certain embodiments of any one of the above methods, including any one of the above embodiments, $R_1$ is selected from the group consisting of —$R_4$, —X—$R_4$, —X—Y—$R_4$, —X—Y—$X^1$—$Y^1$—$R_4$, and —X—$R_5$; wherein X is alkylene that is optionally interrupted or terminated by heterocyclylene and optionally interrupted by one —O— group; Y is selected from the group consisting of —O—, —S(O)$_2$—, —S(O)$_2$—N($R_8$)—, —C(O)—, —C(O)—O—, —O—C(O)—, —N($R_8$)-Q-, —C(O)—N($R_8$)—,

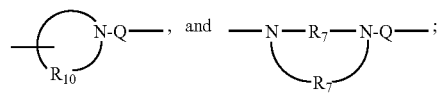

$X^1$ is selected from the group consisting of alkylene and arylene; $Y^1$ is selected from the group consisting of —S—, —C(O)—, —C(O)—O—, —C(O)—N($R_8$)—, —S(O)$_2$—N($R_8$)—, and —N($R_8$)—C(O)—; $R_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo; $R_5$ is selected from the group consisting of:

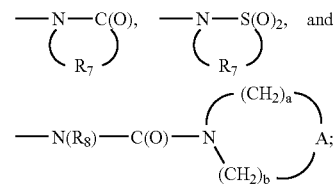

$R_6$ is selected from the group consisting of =O and =S; $R_7$ is $C_{2-7}$ alkylene; $R_8$ is selected from the group consisting of hydrogen, alkyl, alkoxyalkylenyl, hydroxyalkylenyl, arylalkylenyl, and heteroarylalkylenyl; $R_{10}$ is $C_{3-8}$ alkylene; A is selected from the group consisting of —O—, —C(O)—, and —N($R_4$)—; Q is selected from the group consisting of a bond, —C($R_6$)—, —S(O)$_2$—, —C($R_6$)—N($R_8$)—W—, —S(O)$_2$—N($R_8$)—, —C(O)—O—, and —C(O)—S—; W is selected from the group consisting of a bond and —C(O)—; and a and b are independently integers from 1 to 6 with the proviso that a+b is ≤7.

For certain embodiments of any one of the above methods, including any one of the above embodiments, $R_1$ is selected from the group consisting of $C_{1-5}$ alkyl, $C_{2-5}$ alkynyl, aryl$C_{1-4}$ alkylenyl, cycloalkyl$C_{1-4}$ alkylenyl, $C_{1-4}$ alkyl-$S(O)_2$—$C_{1-4}$ alkylenyl, aryl-$S(O)_2$—$C_{1-4}$ alkylenyl, $C_{1-4}$ alkyl-$S(O)_2$—$C_{1-4}$ alkylenyl-O—$C_{1-4}$ alkylenyl, $C_{1-4}$ alkyl-$S(O)_2$—NH—$C_{1-4}$ alkylenyl, hydroxy$C_{1-4}$ alkylenyl, dihydroxy$C_{1-4}$alkylenyl, halo$C_{1-4}$ alkylenyl, amino$C_{1-4}$ alkylenyl, $C_{1-4}$ alkyl-$C(O)$—O—$C_{1-4}$ alkylenyl, $C_{1-6}$ alkyl-$C(O)$—NH—$C_{1-4}$ alkylenyl, aryl-$C(O)$—NH—$C_{1-4}$ alkylenyl wherein aryl is unsubstituted or substituted with one or two halogen groups, heteroaryl-$C(O)$—NH—$C_{1-4}$ alkylenyl, di($C_{1-4}$ alkyl)amino-$S(O)_2$—NH—$C_{1-4}$ alkylenyl, aryl-$S(O)_2$—NH—$C_{1-4}$ alkylenyl, aryl-NH—$C(O)$—NH—$C_{1-4}$ alkylenyl, heteroaryl-NH—$C(S)$—NH—$C_{1-4}$ alkylenyl, di($C_{1-4}$ alkyl)amino-$C(O)$—NH—$C_{1-4}$ alkylenyl, $C_{1-4}$ alkylamino-$C(O)$—NH—$C_{1-4}$ alkylenyl, di($C_{1-4}$ alkyl)amino-$S(O)_2$—$C_{1-4}$ alkylenyl, $C_{1-4}$ alkylamino-$S(O)_2$—$C_{1-4}$ alkylenyl, amino-$S(O)_2$—$C_{1-4}$ alkylenyl, heteroaryl$C_{1-4}$ alkylenyl wherein heteroaryl is unsubstituted or substituted by a substituent selected from the group consisting of aryl, heteroaryl, and alkyl, and heterocyclyl$C_{1-4}$ alkylenyl wherein heterocyclyl is unsubstituted or substituted by one, two, or three substituents selected from the group consisting of alkyl, aryl, heteroaryl, and oxo.

For certain embodiments of any one of the above methods, including any one of the above embodiments, $R_1$ is selected from the group consisting of methyl, ethyl, propyl, 2-methylpropyl, 2,2-dimethylpropyl, butyl, pent-4-ynyl, 2-phenylethyl, 2-hydroxy-2-methylpropyl, 2-fluoro-2-methylpropyl, 2,3-dihydroxypropyl, 4-hydroxybutyl, 2-amino-2-methylpropyl, 2-aminoethyl, 4-aminobutyl, 2-(methylsulfonyl)ethyl, 2-(propylsulfonyl)ethyl, 4-(methylsulfonyl)butyl, 2,2-dimethyl-3-(methylsulfonyl)propyl, 3-(phenylsulfonyl)propyl, 2-methyl-2-[2-(methylsulfonyl)ethoxy]propyl, 4-acetoxybutyl, 2-[(methylsulfonyl)amino]ethyl, 4-[(methylsulfonyl)amino]butyl, 2-methyl-2-[(methylsulfonyl)amino]propyl, 2-{[(1-methylethyl)sulfonyl]amino}ethyl, 2-(benzenesulfonylamino)ethyl, 2-(dimethylaminosulfonylamino)ethyl, 4-(aminosulfonyl)butyl, 4-[(methylamino)sulfonyl]butyl, 4-[(dimethylamino)sulfonyl]butyl, 2-[(cyclohexylcarbonyl)amino]-2-methylpropyl, 2-[(cyclopropylcarbonyl)amino]ethyl, 4-[(cyclopropylcarbonyl)amino]butyl, 2-[(cyclopropylcarbonyl)amino]-2-methylpropyl, 2-methyl-2-{[(1-methylethyl)carbonyl]amino}propyl, 2-methyl-2-[(ethylcarbonyl)amino]propyl, 2-methyl-2-[(pyridin-3-ylcarbonyl)amino]propyl, 2-methyl-2-[(pyridin-4-ylcarbonyl)amino]propyl, 2-(acetylamino)-2-methylpropyl, 2-(benzoylamino)ethyl, 2-(benzoylamino)-2-methylpropyl, 2-[(4-fluorobenzoyl)amino]-2-methylpropyl, 2-[(3,4-difluorobenzoyl)amino]-2-methylpropyl, 2-[(pyridin-3-ylcarbonyl)amino]ethyl, 2-{[(1-methylethyl)carbonyl]amino}ethyl, 4-{[(1-methylethyl)carbonyl]amino}butyl, 2-methyl-2-({[(1-methylethyl)amino]carbonyl}amino)propyl, 2-({[(1-methylethyl)amino]carbonyl}amino)ethyl, 4-(4-pyridin-2-ylpiperazin-1-yl)butyl, tetrahydro-2H-pyran-4-ylmethyl, 4-(1,1-dioxidoisothiazolidin-2-yl)butyl, (2,2-dimethyl-1,3-dioxolan-4-yl)methyl, 3-(3-methylisoxazol-5-yl)propyl, 3-(3-isopropylisoxazol-5-yl)propyl, 3-(3-phenylisoxazol-5-yl)propyl, 3-(3-pyridin-3-ylisoxazol-5-yl)propyl, 4-(3,5,5-trimethyl-1,2,4-oxadiazol-4(5H)-yl)butyl, 4-(3-methyl-1-oxa-2,4-diazaspiro[4.4]non-2-en-4-yl)butyl, 2-{[(pyridin-3-ylamino)carbonothioyl]amino}ethyl, 2-{[(dimethylamino)carbonyl]amino}ethyl, and 2-{[(phenylamino)carbonyl]amino}ethyl.

For certain embodiments of any one of the above methods, including any one of the above embodiments, $R_1$ is selected from the group consisting of alkyl, aminoalkyl, dihydroxyalkyl, haloalkyl, and hydroxyalkyl, except where $R_1$ as defined does not include this definition. For certain of these embodiments, $R_1$ is selected from the group consisting of methyl, ethyl, n-propyl, n-butyl, 2-methylpropyl, 2-amino-2-methylpropyl, 3-amino-2,2-dimethylpropyl, 2,3-dihydroxypropyl, 2-fluoro-2-methylpropyl, and 2-hydroxy-2-methylpropyl. Alternatively, for certain of these embodiments, $R_1$ is selected from the group consisting of (1-hydroxycyclobutyl)methyl, (1-hydroxycyclopentyl)methyl, and (1-hydroxycyclohexyl)methyl.

For certain embodiments of any one of the above methods, including any one of the above embodiments, $R_1$ is heterocyclylalkylenyl wherein heterocyclyl is unsubstituted or substituted by one or more substituents independently selected from the group consisting of alkyl, aryl, heteroaryl, hydroxy, and oxo, except where $R_1$ as defined does not include this definition. For certain of these embodiments as well as any one of the above embodiments wherein $R_1$ as defined includes heterocyclyl, heterocyclyl is selected from the group consisting of 1,3-dioxolanyl, tetrahydropyranyl, tetrahydrofuranyl, pyrrolidinyl, piperidinyl, and morpholinyl, each of which is unsubstituted or substituted by one, two, or three substituents selected from the group consisting of alkyl, aryl, heteroaryl, and oxo. For certain of these embodiments wherein $R_1$ is heterocyclylalkylenyl, heterocyclyl is selected from the group consisting of 1,3-dioxolanyl, tetrahydropyranyl, tetrahydrofuranyl, pyrrolidinyl, piperidinyl, and morpholinyl, and alkylenyl is $C_{1-4}$ alkylenyl. For certain of these embodiments, $R_1$ is selected from the group consisting of tetrahydro-2H-pyran-4-ylmethyl and (2,2-dimethyl-1,3-dioxolan-4-yl)methyl. Alternatively, for certain of these embodiments, $R_1$ is (4-hydroxytetrahydro-2H-pyran-4-yl)methyl.

For certain embodiments of any one of the above methods, including any one of the above embodiments, $R_1$ is —X—Y—$R_4$, except where $R_1$ as defined does not include this definition, wherein X is $C_{1-6}$ alkylene which may be interrupted by one —O— group; Y is selected from the group consisting of —$N(R_8)$—$C(O)$—, —$N(R_8)$—$S(O)_2$—, —$N(R_8)$—$C(O)$—$N(R_8)$—, and —$S(O)_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl. For certain of these embodiments, $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino]carbonyl}amino)propyl, 2-methyl-2-[2-(methylsulfonyl)ethoxy]propyl, and 2,2-dimethyl-3-(methylsulfonyl)propy.

For certain embodiments of any one of the above methods, including any one of the above embodiments, $R_1$ is —X—Y—$R_4$, except where $R_1$ as defined does not include this definition, wherein X is $C_{1-6}$ alkylene which may be interrupted by an —O— group; Y is selected from the group consisting of —$N(R_8)$—$C(O)$—, —$N(R_8)$—$S(O)_2$—, —N(R$_8$)—C(O)—N(R$_8$)—, —N(R$_8$)—S(O)$_2$—N(R$_8$)—, —S(O)$_2$—, and

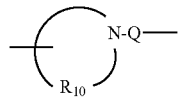

wherein Q is —C(O)—, —C(O)—NH—, or S(O)$_2$—, R$_{10}$ is pentylene, R$_8$ is hydrogen or methyl; and R$_4$ is selected from the group consisting of C$_{1-6}$ alkyl, hydroxyC$_{1-6}$ alkyl, isoquinolinyl, N-methylimidazolyl, pyridinyl, quinolinyl, benzyl, 1-phenylethyl, phenyl, and phenyl substituted by a substituent selected from the group consisting of chloro, cyano, fluoro, hydroxy, and methyl. For certain of these embodiments, X is C$_{1-6}$ alkylene, Y is selected from the group consisting of —N(R$_8$)—C(O)—, —N(R$_8$)—S(O)$_2$—, and —N(R$_8$)—C(O)—N(R$_8$)—, and R$_4$ is selected from the group consisting of C$_{1-4}$ alkyl, hydroxyC$_{1-4}$ alkyl, pyridinyl, benzyl, 1-phenylethyl, phenyl, and phenyl substituted by a substituent selected from the group consisting of chloro, cyano, fluoro, hydroxy, and methyl. Alternatively, for certain of these embodiments, X is C$_{1-6}$ alkylene, Y is

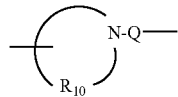

wherein Q is —C(O)—, —C(O)—NH—, or S(O)$_2$—, and R$_{10}$ is pentylene, and R$_4$ is C$_{1-4}$ alkyl. For certain of these embodiments where Y is

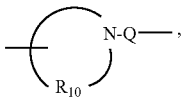

X is methylene. Alternatively, for certain of these embodiments, Y is —NH—S(O)$_2$—N(R$_8$)—, R$_8$ is methyl, and R$_4$ is C$_{1-4}$ alkyl. For certain of these embodiments where Y is —NH—S(O)$_2$—N(R$_8$)—, X is C$_{2-6}$ alkylene.

For certain embodiments of any one of the above methods, including any one of the above embodiments, R$_1$ is —X—R$_5$, except where R$_1$ as defined does not include this definition, wherein X is C$_{1-6}$ alkylene, and R$_5$ is

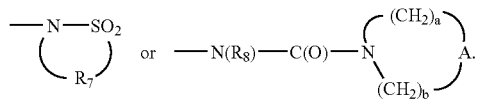

For certain of these embodiments, R$_5$ is

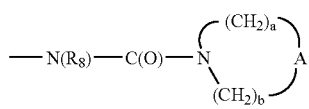

wherein R$_8$ is hydrogen, A is —O—, —CH$_2$—, or —N(Q-R$_4$)—, and a and b are each 2. For certain of these embodiments, Q-R$_4$ is methyl. Alternatively, for certain of these embodiments, R$_5$ is

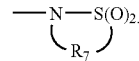

For certain of these embodiments, R$_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl.

For certain embodiments of any one of the above methods, including any one of the above embodiments, R$_1$ is —X—R$_5$, except where R$_1$ as defined does not include this definition, wherein X is C$_{1-4}$ alkylene, and R$_5$ is

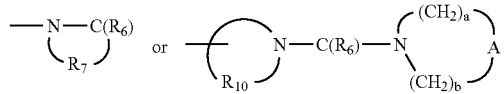

wherein R$_6$ is =O, R$_7$ is propylene, R$_{10}$ is pentylene, A is —O—, and a and b are each 2. For certain of these embodiments, X is ethylene or butylene.

For certain embodiments of any one of the above methods, including any one of the above embodiments having an R$_3$ group, R$_3$ is selected from the group consisting of aryl, arylalkyleneoxy, heteroaryl, and heteroarylalkyleneoxy, wherein aryl, arylalkyleneoxy, heteroaryl, and heteroarylalkylenoxy are unsubstituted or substituted with one or more substituents selected from the group consisting of alkyl, alkoxy, halogen, hydroxy, and hydroxyalkyl. For certain of these embodiments, R$_3$ is phenyl, pyridin-2-yl, pyridin-3-yl, pyridin-4-yl, quinolin-3-yl, or thiazol-4-ylmethoxy, any of which may be unsubstituted or substituted by one or more substituents selected from the group consisting of alkyl, alkoxy, halogen, hydroxy, and hydroxyalkyl. For certain of these embodiments, R$_3$ is selected from the group consisting of pyridin-3-yl, pyridin-4-yl, 6-fluoropyridin-3-yl, 5-(hydroxymethyl)pyridin-3-yl, 2-ethoxyphenyl, quinolin-3-yl, and thiazol-4-ylmethoxy.

For certain embodiments of any one of the above methods, including any one of the above embodiments having an R$_3$ group, R$_3$ is thien-3-yl, phenyl, pyridin-2-yl, pyridin-3-yl, pyridin-4-yl, or quinolin-3-yl any of which may be unsubstituted or substituted by one or more substituents selected from the group consisting of alkyl, alkoxy, halogen, cyano, hydroxy, and hydroxyalkyl, except where R$_3$ as defined does not include this definition.

For certain embodiments of any one of the above methods, including any one of the above embodiments having an R$_3$ group, R$_3$ is —Z—X—Y—R$_4$, except where R$_3$ as defined does not include this definition, wherein Z is a bond, X is phenylene, Y is selected from the group consisting of —C(O)—, —C(O)—N(R$_8$)—, —N(R$_9$)—C(O)—, —N(R$_8$)—S(O)$_2$—, and —N(R$_8$)—C(O)—N(R$_8$)— wherein R$_8$ is selected from hydrogen and methyl; and R$_4$ is selected from the group consisting of C$_{1-6}$ alkyl, morpholin-4-yl, phenyl, and phenyl substituted by a substituent selected from the group consisting of allyl, alkoxy, halogen, hydroxy, and hydroxyalkyl. For certain of these embodiments, R$_3$ is 2-(4-morpholinecarbonyl)phenyl.

For certain embodiments of any one of the above methods, including any one of the above embodiments having an R$_3$ group, except where R$_3$ as defined does not include this definition, $R_3$ is —X—Y—$R_4$, wherein X is phenylene, Y is selected from the group consisting of —C(O)—, —C(O)—N($R_8$)—, —N($R_8$)—C(O)—, —N($R_8$)—S(O)$_2$—, and —N($R_8$)—C(O)—N($R_8$)— wherein $R_8$ is selected from hydrogen and methyl; and $R_4$ is selected from the group consisting of $C_{1-6}$ alkyl, phenyl, and phenyl substituted by a substituent selected from the group consisting of alkyl, alkoxy, halogen, hydroxy, and hydroxyalkyl; with the proviso that when Y is —C(O)—N($R_8$)— or —N($R_8$)—C(O)—N($R_8$)— then $R_4$ can also be hydrogen; and with the further proviso that when Y is —C(O)— or —N($R_8$)—C(O)— then $R_4$ can also be morpholin-4-yl, piperidin-1-yl, or pyrrolidin-1-yl. For certain of these embodiments, Y is —C(O)—NH—, and $R_4$ is hydrogen or $C_{1-4}$ alkyl. For certain of these embodiments, $R_4$ is hydrogen. Alternatively, for certain of these embodiments, Y is —NH—C(O)—, and $R_4$ is $C_{1-4}$ alkyl. Alternatively, for certain of these embodiments, Y is —C(O)—, and $R_4$ is morpholin-4-yl, piperidin-1-yl, or pyrrolidin-1-yl. For certain of these embodiments, $R_3$ is 3-(methylsulfonylamino)phenyl, 3-(pyrrolidin-1-ylcarbonyl)phenyl, or 3-(morpholin-4-ylcarbonyl)phenyl.

For certain embodiments of any one of the above methods, including any one of the above embodiments which includes an R group, R is not present.

For certain embodiments of any one of the above methods, including any one of the above embodiments which includes an R group and an $R_3$ group, neither $R_3$ nor R is present.

For certain embodiments of any one of the above methods, including any one of the above embodiments which includes an R group, R is selected from the group consisting of hydroxy and methoxy.

For certain embodiments of any one of the above methods, including any one of the above embodiments which includes an $R_3$ group, $R_3$ is not present.

For certain embodiments of any one of the above methods, including any one of the above embodiments, an effective amount of the compound or salt is administered as a pharmaceutical composition comprising a therapeutically effective amount of the compound or salt and a pharmaceutically acceptable carrier.

For certain embodiments, the present invention provides a method of treating a viral disease in an animal in need thereof comprising preferentially inducing the biosynthesis of IFN-α in the animal according to any one of the above methods.

For certain embodiments, the present invention provides a method of treating a neoplastic disease in an animal in need thereof comprising preferentially inducing the biosynthesis of IFN-α in the animal according to any one of the above methods.

For certain embodiments of any one of the above methods, including any one of the above embodiments, the compound or salt is administered systemically.

For certain embodiments, $R_A$ and $R_B$ form a fused aryl ring or heteroaryl ring containing one heteroatom selected from the group consisting of N and S wherein the aryl or heteroaryl ring is unsubstituted or substituted by one or more R groups, or substituted by one $R_3$ group, or substituted by one $R_3$ group and one R group.

For certain embodiments, $R_A$ and $R_B$ form a fused aryl ring which is unsubstituted or substituted by one or more R groups, or substituted by one $R_3$ group, or substituted by one $R_3$ group and one R group.

For certain embodiments, $R_A$ and $R_B$ form a fused benzene ring which is unsubstituted or substituted by one or more R groups, or substituted by one $R_3$ group, or substituted by one $R_3$ group and one R group.

For certain embodiments $R_A$ and $R_B$ form a fused benzene ring which is unsubstituted.

For certain embodiments $R_A$ and $R_B$ form a fused benzene ring which is substituted by one or more R groups, or substituted by one $R_3$ group, or substituted by one $R_3$ group and one R group.

For certain embodiments $R_A$ and $R_B$ form a fused benzene ring which is substituted by one $R_3$ group. For certain of these embodiments, the $R_3$ group is at the 7-position.

For certain embodiments $R_A$ and $R_B$ form a fused benzene ring which is substituted by one or more R groups.

For certain embodiments, $R_A$ and $R_B$ form a fused heteroaryl ring containing one heteroatom selected from the group consisting of N and S wherein the heteroaryl ring is unsubstituted or substituted by one or more R groups, or substituted by one $R_3$ group, or substituted by one $R_3$ group and one R group.

For certain embodiments, $R_A$ and $R_B$ form a fused pyridine ring which is unsubstituted or substituted by one or more R groups, or substituted by one $R_3$ group, or substituted by one $R_3$ group and one R group.

For certain embodiments, $R_A$ and $R_B$ form a fused pyridine ring which is unsubstituted.

For certain embodiments, $R_A$ and $R_B$ form a fused pyridine ring which is substituted by one or more R groups, or substituted by one $R_3$ group, or substituted by one $R_3$ group and one R group. For certain of these embodiments, the fused pyridine ring is

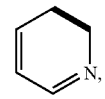

wherein the highlighted bond is the position where the ring is fused. For certain or these embodiments, $R_A$ and $R_B$ form a fused pyridine ring which is substituted by one $R_3$ group. For certain of these embodiments, the fused pyridine ring is

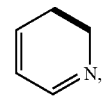

wherein the highlighted bond is the position where the ring is fused. For certain of these embodiments, the $R_3$ group is at the 7-position.

For certain embodiments, $R_A$ and $R_B$ form a fused pyridine ring which is substituted by one or more R groups.

For certain embodiments, $R_A$ and $R_B$ form a fused 5 to 7 membered saturated ring, optionally containing one heteroatom selected from the group consisting of N and S, and unsubstituted or substituted at a carbon atom by one or more R groups.

For certain embodiments, $R_A$ and $R_B$ form a fused 5 to 7 membered saturated ring, wherein the ring is unsubstituted or substituted by one or more R groups. For certain of these embodiments, the fused ring is a cyclohexene ring wherein the double bond is the position where the ring is fused. For certain of these embodiments, the fused cyclohexene ring is unsubstituted.

For certain embodiments, $R_A$ and $R_B$ form a fused 5 to 7 membered saturated ring, containing one nitrogen atom, and unsubstituted or substituted at a carbon atom by one or more R groups. For certain of these embodiments, the fused ring is a tetrahydropyridine ring. For certain of these embodiments, the fused tetrahydropyridine ring is

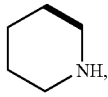

wherein the highlighted bond indicates the position where the ring is fused. For certain of these embodiments, the fused tetrahydropyridine ring is unsubstituted.

For certain embodiments, $R_A$ and $R_B$ are each independently selected from the group consisting of hydrogen, halogen, alkyl, alkenyl, alkoxy, alkylthio, and —N(R$_9$)$_2$. For certain of these embodiments, $R_A$ and $R_B$ are each independently alkyl. For certain of these embodiments, $R_A$ and $R_B$ are each methyl.

For certain embodiments, R is selected from the group consisting of halogen, hydroxy, alkyl, alkenyl, haloalkyl, alkoxy, alkylthio, and —N(R$_9$)$_2$.

For certain embodiments, R is selected from the group consisting of hydroxy and methoxy.

For certain embodiments, R is not present.

For certain embodiments, $R_1$ is selected from the group consisting of —R$_4$, —X—R$_4$, —X—Y—R$_4$, —X—Y—X—Y—R$_4$, and —X—R$_5$.

For certain embodiments, $R_1$ is selected from the group consisting of —R$_4$, —X—R$_4$, —X—Y—R$_4$, —X—Y—X$^1$—Y$^1$—R$_4$, and —X—R$_5$; wherein X is alkylene that is optionally interrupted or terminated by heterocyclylene and optionally interrupted by one —O— group; Y is selected from the group consisting of —O—, —S(O)$_2$—, —S(O)$_2$—N(R$_8$)—, —C(O)—, —C(O)—O—, —O—C(O)—, —N(R$_8$)-Q-, —C(O)—N(R$_8$)—,

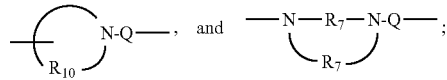

$X^1$ is selected from the group consisting of alkylene and arylene; $Y^1$ is selected from the group consisting of —S—, —C(O)—, —C(O)—O—, —C(O)—N(R$_8$)—, —S(O)$_2$—N(R$_8$)—, and —N(R$_8$)—C(O)—; $R_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo; $R_5$ is selected from the group consisting of:

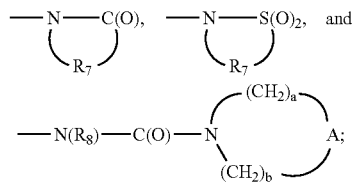

$R_6$ is selected from the group consisting of =O and =S; $R_7$ is C$_{2-7}$ alkylene; $R_8$ is selected from the group consisting of hydrogen, alkyl, alkoxyalkylenyl, hydroxyalkylenyl, arylalkylenyl, and heteroarylalkylenyl; $R_{10}$ is C$_{3-8}$ alkylene; A is selected from the group consisting of —O—, —C(O)—, and —N(R$_4$)—; Q is selected from the group consisting of a bond, —C(R$_6$)—, —S(O)$_2$—, —C(R$_6$)—N(R$_8$)—W—, —S(O)$_2$—N(R$_8$)—, —C(O)—O—, and —C(O)—S—; W is selected from the group consisting of a bond and —C(O)—; and a and b are independently integers from 1 to 6 with the proviso that a+b is ≤7.

For certain embodiments, $R_1$ is selected from the group consisting of C$_{1-5}$ alkyl, C$_{2-5}$ alkynyl, arylC$_{1-4}$ alkylenyl, cycloalkylC$_{1-4}$ alkylenyl, C$_{1-4}$ alkyl-S(O)$_2$—C$_{1-4}$ alkylenyl, aryl-S(O)$_2$—C$_{1-4}$ alkylenyl, C$_{1-4}$ alkyl-S(O)$_2$—C$_{1-4}$ alkylenyl-O—C$_{1-4}$ alkylenyl, C$_{1-4}$ alkyl-S(O)$_2$—NH—C$_{1-4}$ alkylenyl, hydroxyC$_{1-4}$ alkylenyl, dihydroxyC$_{1-4}$alkylenyl, haloC$_{1-4}$ alkylenyl, aminoC$_{1-4}$ alkylenyl, C$_{1-4}$ alkyl-C(O)—O—C$_{1-4}$ alkylenyl, C$_{1-6}$ alkyl-C(O)—NH—C$_{1-4}$ alkylenyl, aryl-C(O)—NH—C$_{1-4}$ alkylenyl wherein aryl is unsubstituted or substituted with one or two halogen groups, heteroaryl-C(O)—NH—C$_{1-4}$ alkylenyl, di(C$_{1-4}$ alkyl)amino-S(O)$_2$—NH—C$_{1-4}$ alkylenyl, aryl-S(O)$_2$—NH—C$_{1-4}$ alkylenyl, aryl-NH—C(O)—NH—C$_{1-4}$ alkylenyl, heteroaryl-NH—C(S)—NH—C$_{1-4}$ alkylenyl, di(C$_{1-4}$alkyl)amino-C(O)—NH—C$_{1-4}$ alkylenyl, C$_{1-4}$ alkylamino-C(O)—NH—C$_{1-4}$ alkylenyl, di(C$_{1-4}$ alkyl)amino-S(O)$_2$—C$_{1-4}$ alkylenyl, C$_{1-4}$ alkylamino-S(O)$_2$—C$_{1-4}$ alkylenyl, amino-S(O)$_2$—C$_{1-4}$ alkylenyl, heteroarylC$_{1-4}$ alkylenyl wherein heteroaryl is unsubstituted or substituted by a substituent selected from the group consisting of aryl, heteroaryl, and alkyl, and heterocyclylC$_{1-4}$ alkylenyl wherein heterocyclyl is unsubstituted or substituted by one, two, or three substituents selected from the group consisting of alkyl, aryl, heteroaryl, and oxo.

For certain embodiments, $R_1$ is selected from the group consisting of methyl, ethyl, propyl, 2-methylpropyl, 2,2-dimethylpropyl, butyl, pent-4-ynyl, 2-phenylethyl, 2-hydroxy-2-methylpropyl, 2-fluoro-2-methylpropyl, 2,3-dihydroxypropyl, 4-hydroxybutyl, 2-amino-2-methylpropyl, 2-aminoethyl, 4-aminobutyl, 2-(methylsulfonyl)ethyl, 2-(propylsulfonyl)ethyl, 4-(methylsulfonyl)butyl, 2,2-dimethyl-3-(methylsulfonyl)propyl, 3-(phenylsulfonyl)propyl, 2-methyl-2-[2-(methylsulfonyl)ethoxy]propyl, 4-acetoxybutyl, 2-[(methylsulfonyl)amino]ethyl, 4-[(methylsulfonyl)amino]butyl, 2-methyl-2-[(methylsulfonyl)amino]propyl, 2-{[(1-methylethyl)sulfonyl]amino}ethyl, 2-(benzenesulfonylamino)ethyl, 2-(dimethylaminosulfonylamino)ethyl, 4-(aminosulfonyl)butyl, 4-[(methylamino)sulfonyl]butyl, 4-[(dimethylamino)sulfonyl]butyl, 2-[(cyclohexylcarbonyl)amino]-2-methylpropyl, 2-[(cyclopropylcarbonyl)amino]ethyl, 4-[(cyclopropylcarbonyl)amino]butyl, 2-[(cyclopropylcarbonyl)amino]-2-methylpropyl, 2-methyl-2-{[(1-methylethyl)carbonyl]amino}propyl, 2-methyl-2-[(ethylcarbonyl)amino]propyl, 2-methyl-2-[(pyridin-3-ylcarbonyl)amino]propyl, 2-methyl-2-[(pyridin-4-ylcarbonyl)amino]propyl, 2-(acetylamino)-2-methylpropyl, 2-(benzoylamino)ethyl, 2-(benzoylamino)-2-methylpropyl, 2-[(4-fluorobenzoyl)amino]-2-methylpropyl, 2-[(3,4-difluorobenzoyl)amino]-2-methylpropyl, 2-[(pyridin-3-ylcarbonyl)amino]ethyl, 2-{[(1-methylethyl)carbonyl]amino}ethyl, 4-{[(1-methylethyl)carbonyl]amino}butyl, 2-methyl-2-({[(1-methylethyl)amino]carbonyl}amino)propyl, 2-({[(1-methylethyl)amino]carbonyl}amino)ethyl, 4-(4-pyridin-2-ylpiperazin-1-yl)butyl, tetrahydro-2H-pyran-4-ylmethyl, 4-(1,1-dioxidoisothiazolidin-2-yl)butyl, (2,2-dimethyl-1,3-dioxolan-4-yl)methyl, 3-(3-methylisoxazol-5-yl)propyl, 3-(3-isopropylisoxazol-5-yl)propyl, 3-(3-phenylisoxazol-5-yl)propyl, 3-(3-pyridin-3-ylisoxazol-5-yl)propyl, 4-(3,5,5-trimethyl-1,2,4-oxadiazol-4(5H)-yl)butyl, 4-(3-methyl-1- oxa-2,4-diazaspiro[4.4]non-2-en-4-yl)butyl, 2-{[(pyridin-3-ylamino)carbonothioyl]amino}ethyl, 2-{[(dimethylamino)carbonyl]amino}ethyl, and 2-{[(phenylamino)carbonyl]amino}ethyl.

For certain embodiments, $R_1$ is —$R_4$.

For certain embodiments, $R_1$ is selected from the group consisting of alkyl, aminoalkyl, dihydroxyalkyl, haloalkyl, and hydroxyalkyl.

For certain embodiments, $R_1$ is selected from the group consisting of methyl, ethyl, n-propyl, n-butyl, 2-methylpropyl, 2-amino-2-methylpropyl, 3-amino-2,2-dimethylpropyl, 2,3-dihydroxypropyl, 2-fluoro-2-methylpropyl, and 2-hydroxy-2-methylpropyl.

For certain embodiments, $R_1$ is selected from the group consisting of (1-hydroxycyclobutyl)methyl, (1-hydroxycyclopentyl)methyl, and (1-hydroxycyclohexyl)methyl.

For certain embodiments, $R_1$ is heterocyclylalkylenyl wherein heterocyclyl is unsubstituted or substituted by one or more substituents independently selected from the group consisting of alkyl, aryl, heteroaryl, hydroxy, and oxo.

For certain embodiments, $R_1$ is heterocyclylalkylenyl wherein heterocyclyl is selected from the group consisting of 1,3-dioxolanyl, tetrahydropyranyl, tetrahydrofuranyl, pyrrolidinyl, piperidinyl, and morpholinyl, and alkylenyl is $C_{1-4}$ alkylenyl.

For certain embodiments, $R_1$ is selected from the group consisting of tetrahydro-2H-pyran-4-ylmethyl and (2,2-dimethyl-1,3-dioxolan-4-yl)methyl.

For certain embodiments, $R_1$ is (4-hydroxytetrahydro-2H-pyran-4-yl)methyl.

For certain embodiments, $R_1$ is —X—Y—$R_4$.

For certain embodiments, $R_1$ is —X—Y—$R_4$ wherein X is $C_{1-6}$ alkylene which may be interrupted by one —O— group; Y is selected from the group consisting of —N($R_9$)—C(O)—, —N($R_9$)—S(O)$_2$—, —N($R_8$)—C(O)—N($R_8$)—, and —S(O)$_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

For certain embodiments, $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino]carbonyl}amino)propyl, 2-methyl-2-[2-(methylsulfonyl)ethoxy]propyl, and 2,2-dimethyl-3-(methylsulfonyl)propyl.

For certain embodiments, $R_1$ is —X—Y—$R_4$ wherein X is $C_{1-6}$ alkylene which may be interrupted by an —O— group; Y is selected from the group consisting of —N($R_8$)—C(O)—, —N($R_8$)—S(O)$_2$—, —N($R_8$)—C(O)—N($R_8$)—, —N($R_8$)—S(O)$_2$—N($R_8$)—, —S(O)$_2$—, and

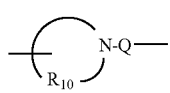

wherein Q is —C(O)—, —C(O)—NH—, or S(O)$_2$—, $R_{10}$ is pentylene, $R_8$ is hydrogen or methyl; and $R_4$ is selected from the group consisting of $C_{1-6}$ alkyl, hydroxy$C_{1-6}$ alkyl, iso-quinolinyl, N-methylimidazolyl, pyridinyl, quinolinyl, benzyl, 1-phenylethyl, phenyl, and phenyl substituted by a substituent selected from the group consisting of chloro, cyano, fluoro, hydroxy, and methyl.

For certain embodiments, $R_1$ is —X—Y—$R_4$ wherein X is $C_{1-4}$ alkylene; Y is

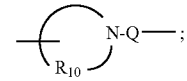

and $R_4$ is $C_{1-4}$ alkyl. For certain of these embodiments, $R_{10}$ is pentylene, and Q is selected from the group consisting of —S(O)$_2$—, —C(O)—, and —C(O)—NH—.

For certain embodiments, $R_1$ is —X—Y—$R_4$ wherein Y is —NH—S(O)$_2$—N($R_8$)—, $R_8$ is methyl, and $R_4$ is $C_{1-4}$ alkyl.

For certain embodiments, $R_1$ is —X—$R_5$.

For certain embodiments, $R_1$ is —X—$R_5$ wherein X is $C_{1-6}$ alkylene, and $R_5$ is

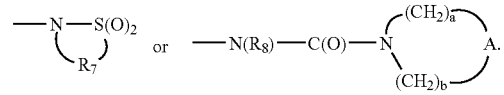

For certain embodiments, $R_1$ is —X—$R_5$ wherein X is $C_{1-6}$ alkylene, and $R_5$ is

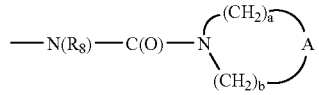

wherein $R_8$ is hydrogen, A is —O—, —CH$_2$—, or —N(Q-$R_4$)—, and a and b are each 2.

For certain embodiments, $R_1$ is —X—$R_5$ wherein X is $C_{1-6}$ alkylene, $R_5$ is

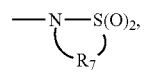

and $R_7$ is propylene.

For certain embodiments, $R_1$ is —X—$R_5$, wherein X is $C_{1-4}$ alkylene, and $R_5$ is

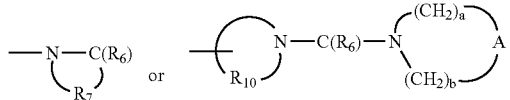

wherein $R_6$ is =O, $R_7$ is propylene, $R_{10}$ is pentylene, A is —O—, and a and b are each 2.

For certain embodiments, $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl.

For certain embodiments, $R_3$ is selected from the group consisting of —Z—$R_4$, —Z—X—$R_4$, —Z—X—Y—$R_4$, —Z—X—Y—X—Y—$R_4$, and —Z—X—$R_5$.

For certain embodiments, $R_3$ is —Z—$R_4$.

For certain embodiments, $R_3$ is selected from the group consisting of aryl, arylalkyleneoxy, heteroaryl, and heteroarylalkyleneoxy, wherein aryl, arylalkyleneoxy, heteroaryl, and heteroarylalkyleneoxy are unsubstituted or substituted with one or more substituents selected from the group consisting of alkyl, alkoxy, halogen, hydroxy, and hydroxyalkyl.

For certain embodiments, $R_3$ is selected from the group consisting of aryl, arylalkyleneoxy, and heteroaryl, wherein aryl, arylalkyleneoxy, and heteroaryl are unsubstituted or substituted with one or more substituents selected from the group consisting of alkyl, alkoxy, halogen, hydroxy, and hydroxyalkyl.

For certain embodiments, $R_3$ is thien-3-yl, phenyl, pyridin-2-yl, pyridin-3-yl, pyridin-4-yl, or quinolin-3-yl any of which may be unsubstituted or substituted by one or more substituents selected from the group consisting of alkyl, alkoxy, halogen, cyano, hydroxy, and hydroxyalkyl.

For certain embodiments, $R_3$ is phenyl, pyridin-2-yl, pyridin-3-yl, pyridin-4-yl, quinolin-3-yl, or thiazol-4-ylmethoxy, any of which may be unsubstituted or substituted by one or more substituents selected from the group consisting of alkyl, alkoxy, halogen, hydroxy, and hydroxyalkyl.

For certain embodiments, $R_3$ is selected from the group consisting of pyridin-3-yl, pyridin-4-yl, 6-fluoropyridin-3-yl, 5-(hydroxymethyl)pyridin-3-yl, 2-ethoxyphenyl, quinolin-3-yl, or thiazol-4-ylmethoxy.

For certain embodiments, $R_3$ is —Z—X—Y—$R_4$.

For certain embodiments, $R_3$ is —Z—X—Y—$R_4$ wherein X is phenylene, Y is selected from the group consisting of —C(O)—, —C(O)—N($R_8$)—, —N($R_8$)—C(O)—, —N($R_8$)—S(O)$_2$—, and —N($R_8$)—C(O)—N($R_8$)— wherein $R_8$ is selected from hydrogen and methyl; Z is a bond; and $R_4$ is selected from the group consisting of $C_{1-6}$ alkyl, phenyl, morpholin-4-yl, and phenyl substituted by a substituent selected from the group consisting of alkyl, alkoxy, halogen, hydroxy, and hydroxyalkyl.

For certain embodiments, $R_3$ is —Z—X—Y—$R_4$ wherein X is phenylene, Y is selected from the group consisting of —N($R_8$)—C(O)—, —N($R_8$)—S(O)$_2$—, and —N($R_8$)—C(O)—N($R_8$)— wherein $R_8$ is selected from hydrogen and methyl; Z is a bond; and $R_4$ is selected from the group consisting of $C_{1-6}$ alkyl, phenyl, and phenyl substituted by a substituent selected from the group consisting of alkyl, alkoxy, halogen, hydroxy, and hydroxyalkyl.

For certain embodiments, $R_3$ is —Z—X—Y—$R_4$, wherein Z is a bond, X is phenylene, Y is selected from the group consisting of —C(O)—, —C(O)—N($R_8$)—, —N($R_8$)—C(O)—, —N($R_8$)—S(O)$_2$—, and —N($R_8$)—C(O)—N($R_8$)— wherein $R_8$ is selected from hydrogen and methyl; and $R_4$ is selected from the group consisting of $C_{1-6}$ alkyl, phenyl, and phenyl substituted by a substituent selected from the group consisting of alkyl, alkoxy, halogen, hydroxy, and hydroxyalkyl; with the proviso that when Y is —C(O)—N($R_8$)— or —N($R_8$)—C(O)—N($R_8$)— then $R_4$ can also be hydrogen; and with the further proviso that when Y is —C(O)— or —N($R_8$)—C(O)— then $R_4$ can also be morpholin-4-yl, piperidin-1-yl, or pyrrolidin-1-yl.

For certain embodiments, $R_3$ is —Z—X—Y—$R_4$, wherein Z is a bond, X is phenylene, Y is —C(O)—NH—, and $R_4$ is hydrogen or $C_{1-4}$ alkyl.

For certain embodiments, $R_3$ is —Z—X—Y—$R_4$, wherein Z is a bond, X is phenylene, Y is —NH—C(O)—, and $R_4$ is $C_{1-4}$ alkyl.

For certain embodiments, $R_3$ is —Z—X—Y—$R_4$, wherein Z is a bond, X is phenylene, Y is —C(O)—, and $R_4$ is morpholin-4-yl, piperidin-1-yl, or pyrrolidin-1-yl.

For certain embodiments, $R_3$ is 3-(methylsulfonylamino) phenyl, 3-(pyrrolidin-1-ylcarbonyl)phenyl, or 3-(morpholin-4-ylcarbonyl)phenyl.

For certain embodiments, $R_3$ is 2-(4-morpholinecarbonyl) phenyl.

For certain embodiments, $R_3$ is not present.

For certain embodiments, neither $R_3$ nor R is present.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_4$ is selected from the group consisting of hydrogen, alkyl, alkenyl, aryl, arylalkylenyl, heteroaryl, heteroarylalkylenyl, and heterocyclyl, wherein the alkyl, alkenyl, aryl, arylalkylenyl, heteroaryl, heteroarylalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and, in the case of alkyl, alkenyl, and heterocyclyl, oxo.

For certain embodiments, $R_4$ is selected from the group consisting of hydrogen, alkyl, alkenyl, aryl, arylalkylenyl, heteroaryl, and heteroarylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and, in the case of alkyl and alkenyl, oxo.

For certain embodiments, $R_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo.

For certain embodiments, $R_4$ is selected from the group consisting of $C_{1-6}$ alkyl, hydroxy$C_{1-6}$ alkyl, isoquinolinyl, N-methylimidazolyl, pyridinyl, quinolinyl, benzyl, 1-phenylethyl, phenyl, and phenyl substituted by a substituent selected from the group consisting of chloro, cyano, fluoro, hydroxy, and methyl.

For certain embodiments, $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

For certain embodiments, $R_4$ is selected from the group consisting of $C_{1-6}$ alkyl, morpholin-4-yl, phenyl, and phenyl substituted by a substituent selected from the group consisting of alkyl, alkoxy, halogen, hydroxy, and hydroxyalkyl.

For certain embodiments, $R_4$ is selected from the group consisting of $C_{1-6}$ alkyl, phenyl, and phenyl substituted by a substituent selected from the group consisting of alkyl, alkoxy, halogen, hydroxy, and hydroxyalkyl.

For certain embodiments, $R_4$ is morpholin-4-yl, piperidin-1-yl, or pyrrolidin-1-yl.

For certain embodiments, $R_4$ is $C_{1-6}$ alkyl.

For certain embodiments, $R_4$ is hydrogen or $C_{1-4}$ allyl.

For certain embodiments, $R_4$ is $C_{1-4}$ alkyl.

For certain embodiments, $R_4$ is hydrogen.

For certain embodiments, $R_5$ is selected from the group consisting of:

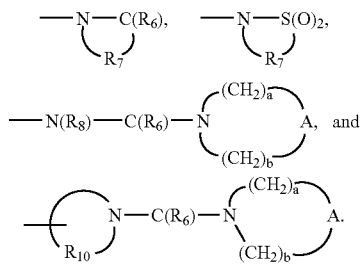

For certain embodiments, $R_5$ is selected from the group consisting of:

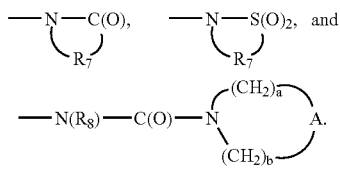

For certain embodiments, $R_5$ is

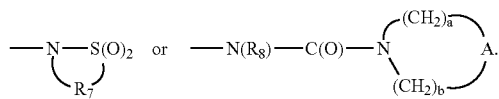

For certain embodiments, $R_5$ is

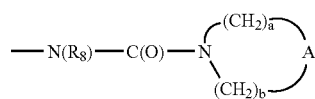

wherein $R_8$ is hydrogen, A is —O—, —CH$_2$—, or —N(Q-R$_4$)—, and a and b are each 2.

For certain embodiments, $R_5$ is

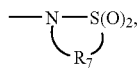

and $R_7$ is propylene.

For certain embodiments, $R_5$ is

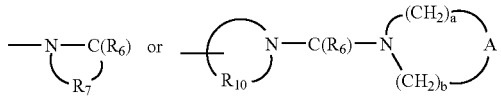

wherein $R_6$ is =O, $R_7$ is propylene, $R_{10}$ is pentylene, A is —O—, and a and b are each 2.

For certain embodiments, $R_6$ is selected from the group consisting of =O and =S.

For certain embodiments, $R_6$ is =O—.

For certain embodiments, $R_6$ is =S.

For certain embodiments, $R_7$ is $C_{2-7}$ alkylene.

For certain embodiments, $R_7$ is $C_{2-4}$ alkylene.

For certain embodiments, $R_8$ is selected from the group consisting of hydrogen, alkyl, alkoxyalkylenyl, hydroxyalkylenyl, arylalkylenyl, and heteroarylalkylenyl.

For certain embodiments, $R_8$ is selected from the group consisting of hydrogen, $C_{1-4}$ alkyl, and $C_{1-4}$ alkoxy$C_{1-4}$ alkylenyl.

For certain embodiments, $R_8$ is hydrogen or $C_{1-4}$ alkyl.

For certain embodiments, $R_8$ is selected from hydrogen and methyl

For certain embodiments, $R_8$ is methyl.

For certain embodiments, $R_8$ is hydrogen.

For certain embodiments, $R_9$ is selected from the group consisting of hydrogen and alkyl.

For certain embodiments, $R_{10}$ is $C_{3-8}$ alkylene.

For certain embodiments, $R_{10}$ is $C_{4-6}$ alkylene.

For certain embodiments, $R_{10}$ is pentylene.

For certain embodiments, A is selected from the group consisting of —O—, —C(O)—, —CH$_2$—, —S(O)$_{0-2}$—, and —N(Q-R$_4$)—.

For certain embodiments, A is —O—, —CH$_2$—, —S—, or —S(O)$_2$—.

For certain embodiments, A is —O—, —CH$_2$—, or —N(Q-R$_4$)—.

For certain embodiments, A is —O— or —S(O)$_2$—.

For certain embodiments, A is —O—.

For certain embodiments, A is —CH$_2$—.

For certain embodiments, A is —N(Q-R$_4$)—.

For certain embodiments, A is —N(CH$_3$)—.

For certain embodiments, A' is selected from the group consisting of —O—, —S(O)$_{0-2}$—, —N(-Q-R$_4$)—, and —CH$_2$—.

For certain embodiments, including any one of the above embodiments of Formula II, $G_1$ is selected from the group consisting of —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R' can also be hydrogen; α-aminoacyl is an α-aminoacyl group derived from an α-amino acid selected from the group consisting of racemic, D-, and L-amino acids; Y' is selected from the group consisting of hydrogen, $C_{1-6}$ alkyl, and benzyl; $Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, including any one of the above embodiments of Formula II, $G_1$ is selected from the group consisting of —C(O)—R', α-aminoacyl, and —C(O)—O—R'. For certain of these embodiments, R' contains one to ten carbon atoms. For certain of these embodiments, α-aminoacyl is an α-$C_{2-11}$ aminoacyl group derived from an α-amino acid selected from the group consisting of racemic, D-, and L-amino acids containing a total of at least 2 carbon atoms and a total of up to 11 carbon atoms, and may also include one or more heteroatoms selected from the group consisting of O, S, and N.

For certain embodiments, including any one of the above embodiments of Formula III, $G_2$ is selected from the group consisting of —$X_2$—C(O)—R', α-aminoacyl, α-aminoacyl-α-aminoacyl, —$X_2$—C(O)—O—R', and —C(O)—N(R")R'. For certain of these embodiments, $X_2$ is selected from the group consisting of a bond; —$CH_2$—O—; —CH($CH_3$)—O—; —C($CH_3$)$_2$—O—; and, in the case of —$X_2$—C(O)—O—R', —$CH_2$—NH—; R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, O—$CH_2$—C(O)—$NH_2$, —$NH_2$, and —$S(O)_2$—$NH_2$, with the proviso that R" can also be hydrogen; and α-aminoacyl is an α-aminoacyl group derived from an α-amino acid selected from the group consisting of racemic, D-, and L-amino acids.

For certain embodiments, including any one of the above embodiments of Formula III, $G_2$ is selected from the group consisting of —C(O)—R' and α-aminoacyl, wherein R' is $C_{1-6}$ alkyl or phenyl which is unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$.

For certain embodiments, including any one of the above embodiments of Formula III, $G_2$ is selected from the group consisting of α-amino-$C_{2-5}$ alkanoyl, $C_{2-6}$ alkanoyl, $C_{1-6}$ alkoxycarbonyl, and $C_{1-6}$ alkylcarbamoyl.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the amino acid is selected from the group consisting of racemic, D-, and L-amino acids.

For certain embodiments, the hydrogen atom of the hydroxy group of Formula II (including any one of its embodiments) is replaced by $G_2$, wherein $G_2$ is defined as in any one of the above embodiments of $G_2$.

For certain embodiments, Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, —C($R_6$)—S—, and —C($R_6$)—N($OR_9$)—.

For certain embodiments, Q is selected from the group consisting of a bond, —C($R_6$)—, —$S(O)_2$, —C($R_6$)—N($R_8$)—, —$S(O)_2$—N($R_8$)—, —C($R_6$)—O—, and —C($R_6$)—S—.

For certain embodiments, Q is selected from the group consisting of a bond, —C($R_6$)—, —$S(O)_2$—, and —C($R_6$)—N($R_8$)—.

For certain embodiments, Q is selected from the group consisting of —C(O)—, —$S(O)_2$—, and —C(O)—N($R_8$)—. In certain of these embodiments, $R_8$ is hydrogen or methyl.

For certain embodiments, Q is selected from the group consisting of —$S(O)_2$—, —C(O)—, and —C(O)—NH—.

For certain embodiments, Q is —C(O)—.

For certain embodiments, Q is —$S(O)_2$—.

For certain embodiments, Q is —C($R_6$)—N($R_8$)—.

For certain embodiments, Q is —C(O)—N($R_8$)— wherein $R_8$ is hydrogen or methyl.

For certain embodiments, V is selected from the group consisting of —C($R_6$)—, —O—C($R_6$)—, —N($R_9$)—C($R_6$)—, and —$S(O)_2$—.

For certain embodiments, V is —C($R_6$)—.

For certain embodiments, W is selected from the group consisting of a bond, —C(O)—, and —$S(O)_2$—.

For certain embodiments, W is a bond.

For certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups.

For certain embodiments, X is alkylene that is optionally interrupted or terminated by heterocyclylene and optionally interrupted by one —O— group.

For certain embodiments, X is $C_{1-6}$ alkylene which may be interrupted by one —O— group.

For certain embodiments, X is $C_{1-6}$ alkylene.

For certain embodiments, X is $C_{2-6}$ alkylene.

For certain embodiments, X is $C_{1-4}$ alkylene.

For certain embodiments, X is phenylene.

For certain embodiments, X is methylene.

For certain embodiments, X is ethylene,

For certain embodiments, X is butylene.

For certain embodiments, Y is selected from the group consisting of —O—, —$S(O)_{0-2}$—, —$S(O)_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N($OR_8$)—, —O—N($R_8$)-Q-, —O—N=C($R_4$)—, —C(=N—O—$R_8$)—,

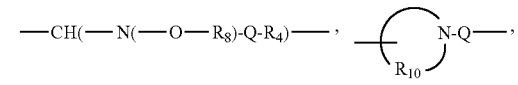

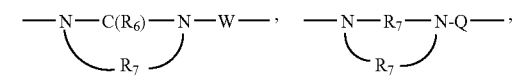

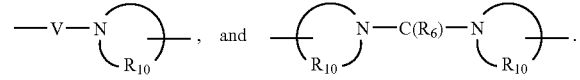

For certain embodiments, Y is selected from the group consisting of —O—, —S(O)$_2$—,

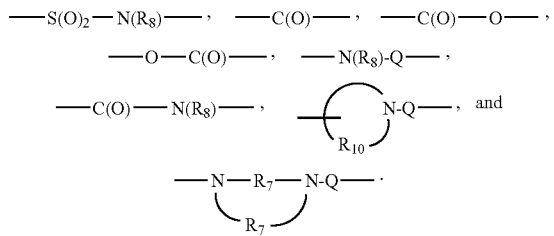

For certain embodiments, Y is selected from the group consisting of —O—, —C(R$_6$)—,

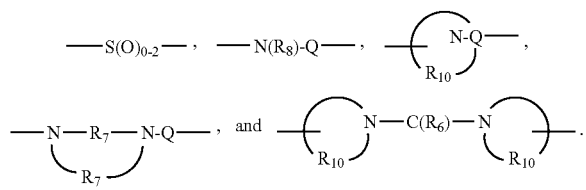

For certain embodiments, Y is selected from the group consisting of —N(R$_8$)—C(O)—, —N(R$_8$)—S(O)$_2$—, —N(R$_8$)—C(O)—N(R$_8$)—, —N(R$_8$)—S(O)$_2$—N(R$_8$)—, —S(O)$_2$—, and

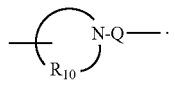

In certain of these embodiments, Q is —C(O)—, —C(O)—NH—, or S(O)$_2$—, R$_{10}$ is pentylene, and R$_8$ is hydrogen or methyl.

For certain embodiments, Y is selected from the group consisting of —N(R$_8$)—C(O)—, —N(R$_8$)—S(O)$_2$—, —N(R$_8$)—C(O)—N(R$_8$)—, and —S(O)$_2$—. In certain of these embodiments, R$_8$ is selected from hydrogen and methyl.

For certain embodiments, Y is selected from the group consisting of —N(R$_8$)—C(O)—, —N(R$_8$)—S(O)$_2$—, and —N(R$_8$)—C(O)—N(R$_8$)— wherein R$_8$ is selected from hydrogen and methyl.

For certain embodiments, Y is selected from the group consisting of —C(O)—, —C(O)—N(R$_8$)—, —N(R$_8$)—C(O)—, —N(R$_8$)—S(O)$_2$—, and —N(R$_8$)—C(O)—N(R$_8$)—. In certain of these embodiments, R$_8$ is selected from hydrogen and methyl.

For certain embodiments, Y is

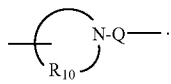

For certain of these embodiments, R$_{10}$ is pentylene, and Q is selected from the group consisting of —S(O)$_2$—, —C(O)—, and —C(O)—NH—.

For certain embodiments, Y is —NH—S(O)$_2$—N(R$_8$)—. In certain of these embodiments, R$_8$ is methyl.

For certain embodiments, Y$^1$ is selected from the group consisting of —S—, —C(O)—, —C(O)—O—, —C(O)—N(R$_8$)—, —S(O)$_2$—N(R$_8$)—, and —N(R$_8$)—C(O)—.

For certain embodiments, Z is a bond or —O—.

For certain embodiments, Z is a bond.

For certain embodiments, Z is —O—.

For certain embodiments, a and b are independently integers from 1 to 6 with the proviso that a+b is ≤7.

For certain embodiments, a and b are each independently 1 to 3.

For certain embodiments, a and b are each 2.

For certain embodiments, a is 1, 2, or 3, and b is 2.

For certain embodiments, n is 1 or 2.

For certain embodiments, n is 1.

For certain embodiments, n is 2.

For certain embodiments, the compound, 1-[4-amino-2-hydroxymethyl-7-(thiazol-4-ylmethoxy)-1H-imidazo[4,5-c]quinolin-1-yl]-2-methylpropan-2-ol, pharmaceutically acceptable salts thereof, pharmaceutical compositions containing this compound or salt thereof in combination with a pharmaceutically acceptable carrier, and the use of this compound in the methods described herein are provided.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W.

Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

In some embodiments, compounds of the invention can be prepared according to Reaction Scheme I, wherein $R_1$, R, m, and n are as defined above and allyl is methyl or ethyl.

In Reaction Scheme I an ether substituted 1H-imidazo[4,5-c]quinolin-4-amine of Formula X is cleaved to provide a hydroxyalkyl substituted 1H-imidazo[4,5-c]quinolin-4-amine of Formula I. The reaction is conveniently carried out by adding a solution of boron tribromide in a suitable solvent such as dichloromethane to a solution or suspension of a compound of Formula X in a suitable solvent such as dichloromethane at ambient or at a sub-ambient temperature, for example, at 0° C. The product or pharmaceutically acceptable salt thereof can be isolated using conventional methods.

Numerous compounds of Formula X are known; others can be prepared using known synthetic methods. See, for example, U.S. Pat. Nos. 6,069,149; 6,331,539; 6,451,810; 6,541,485; 6,756,382; 6,677,349; 6,573,273; 6,664,264; 6,664,265; 6,677,347; 6,660,735; 6,683,088; and 6,667,312 and the references cited therein.

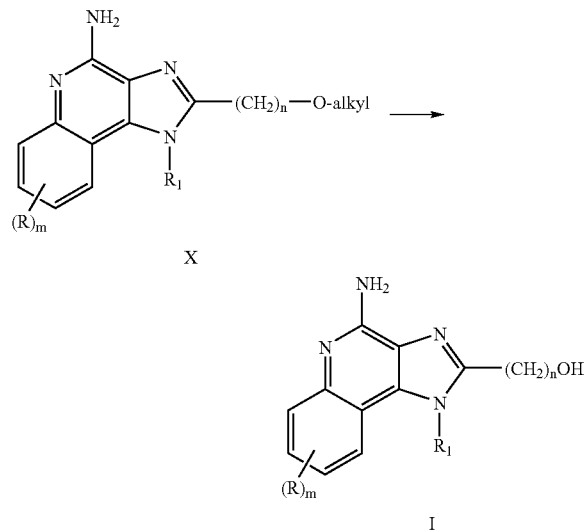

Reaction Scheme I

In some embodiments, compounds of the invention can be prepared according to Reaction Scheme II, wherein $R_1$, $G_1$, and n are as defined above. Compounds of Formula I can be prepared according to the method described above. The amino group of a compound of Formula I can be converted by conventional methods to a functional group such as an amide, carbamate, urea, amidine, or another hydrolyzable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; wherein R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; each α-aminoacyl is an α-aminoacyl group derived from an α-amino acid selected from the group consisting of racemic, D-, and L-amino acids; Y' is selected from the group consisting of hydrogen, C$_{1-6}$ alkyl, and benzyl; Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl; and Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl. Particularly useful compounds of Formula II are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at ambient temperature.

Alternatively, the hydroxy group on a compound of Formula I can be protected using a suitable silyl group such as tert-butyl dimethylsilyl using conventional methods. The $G_1$ group may then be installed using conventional methods followed by the removal of the hydroxy protecting group under acidic conditions to provide a compound of Formula II.

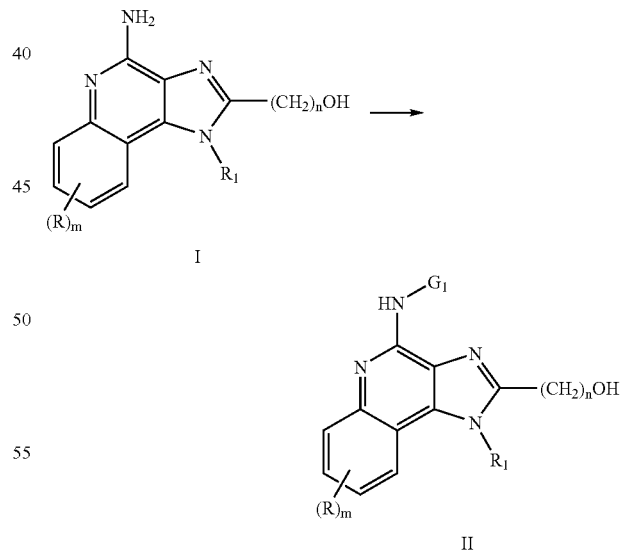

Reaction Scheme II

In some embodiments, compounds of the invention can be prepared according to Reaction Scheme III, wherein $R_1$, $G_2$, and n are as defined above. Compounds of Formula I can be prepared according to the method described above. The hydrogen atom of the alcohol group of a compound of Formula I can be replaced using conventional methods with a group such as X$_2$—C(O)—R', α-aminoacyl, α-aminoacyl-α- aminoacyl, —$X_2$—C(O)—O—R', and —C(O)—N(R")R'; wherein $X_2$ is selected from the group consisting of a bond; —$CH_2$—O—; —CH($CH_3$)—O—; —C($CH_3$)$_2$—O—; and, in the case of —$X_2$—C(O)—O—R', —$CH_2$—NH—; R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R" can also be hydrogen; and each α-aminoacyl is an α-aminoacyl group derived from an α-amino acid selected from the group consisting of racemic, D-, and L-amino acids. Particularly useful compounds of Formula III are esters made from carboxylic acids containing one to six carbon atoms, unsubstituted or substituted benzoic acid esters, or esters made from naturally occurring amino acids. For example, the reaction can be carried out by treating a compound of Formula I with a carboxylic acid or amino acid under Mitsunobu reaction conditions by adding triphenylphosphine and a carboxylic acid to a solution or suspension of a compound of Formula I in a suitable solvent such as tetrahydrofuran and then slowly adding diisopropyl azodicarboxylate. The reaction can be run at a sub-ambient temperature such as 0° C.

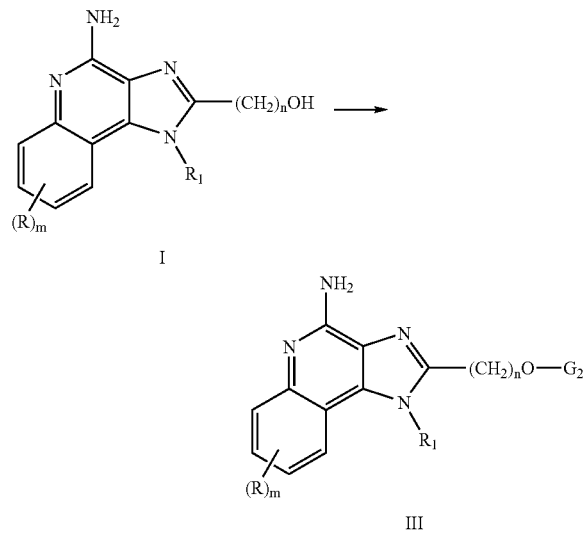

Reaction Scheme III

In some embodiments, compounds of the invention can also be prepared using the synthetic methods described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Cytokine induction can include preferentially inducing the biosynthesis of IFN-α. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m² to about 5.0 mg/m², computed according to the Dubois method, in which the body surface area of a subject (m²) is computed using the subject's body weight: m²=(wt $kg^{0.425}$×height $cm^{0.725}$)×0.007184, although in some embodiments the methods may be performed by administering a compound or salt or composition in a dose outside this range. In some of these embodiments, the method includes administering sufficient compound to provide a dose of from about 0.1 mg/m² to about 2.0 mg/m² to the subject, for example, a dose of from about 0.4 mg/m² to about 1.2 mg/m².

A variety of dosage forms may be used, such as tablets, lozenges, capsules, parenteral formulations (e.g., intravenous formulations), syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders. The compounds or salts of the invention are especially useful as immune response modifiers due to their ability to preferentially induce interferon-α, thus providing a benefit over compounds that also induce pro-inflammatory cytokines (e.g. TNF-α) or that induce pro-inflammatory cytokines at higher levels. While interferon-α and pro-inflammatory cytokines are beneficial in treating certain conditions, interferon-α preferentially induced is believed to be better tolerated by patients, because the significantly lower levels of pro-inflammatory cytokines can result in fewer or less severe adverse side effects experienced by patients. For example, if a subject is treated for a disease (e.g., hepatitis C, metastatic cancer) with a compound that induces significant levels of pro-inflammatory cytokines, while treating the disease, the compound may also cause side effects, such as severe and/or widespread inflammation, tissue destruction, or emesis, that render the subject unable or unwilling to receive the treatment. Alternatively, if a subject is treated with a compound that preferentially induces interferon-α then the compound may treat the disease with less risk of adverse side effects from pro-inflammatory cytokines such as TNF-α. Therefore, by maintaining the ability to treat a condition and reducing adverse side effects, compounds that preferentially induce IFN-α provide an advantage over compounds that would also induce pro-inflammatory cytokines, such as TNF-α, at higher levels.

The ability of the compounds or salts of the invention to preferentially induce the biosynthesis of IFN-α may be particularly advantageous when administered systemically, since adverse side effects, including for example widespread inflammation, may be reduced or even eliminated. Compounds of the invention may be administered systemically in a number of ways, including but not limited to oral and intravenous administration.

Cytokines whose biosynthesis may be induced by compounds or salts of the invention include IFN-α, IP-10, MCP-1, and a variety of other cytokines. In some instances, cytokines such as TNF-α, IL-12 may be induced, albeit at significantly reduced levels. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, the compounds or salts may cause maturation of dendritic cells or proliferation and differentiation of B-lymphocytes.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, or Bordetella;

(c) other infectious diseases, such as chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as dendritic cells and B-cells to produce an amount of one or more cytokines such as, for example, IFN-α, IP-10, and MCP-1 that is increased (induced) over a background level of such cytokines. The precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention provides a method of treating a disease which is responsive to the induction of cytokine biosynthesis, particularly the preferential induction of IFN-α, including a method of treating a viral infection in an animal and a method of treating a neoplastic disease in an animal, comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In the examples below normal high performance flash chromatography (prep HPLC) was carried out using a COMBIFLASH system (an automated high-performance flash purification product available from Teledyne Isco, Inc., Lincoln, Nebr., USA) or a HORIZON HPFC system (an automated high-performance flash purification product available from Biotage, Inc, Charlottesville, Va., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

N-{3-[4-Amino-2-(2-hydroxyethyl)-1H-imidazo[4,5-c]quinolin-1-yl]propyl}-4-methylbenzenesulfonamide

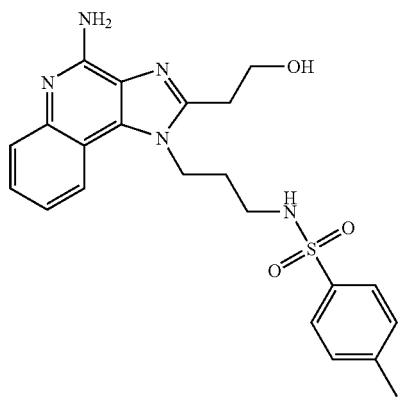 [SMILES: Cc1ccc(S(=O)(=O)NCCCn2c(CCO)nc3c(N)nc4ccccc4c32)cc1]

Boron tribromide (5.50 mL of 1 M in dichloromethane) was added dropwise to a chilled (0° C.) suspension of N-{3-[4-amino-2-(2-methoxyethyl)-1H-imidazo[4,5-c]quinolin-1-yl]propyl}-4-methylbenzenesulfonamide (1.0 g, 2.2 mmol; U.S. Pat. No. 6,677,349, Example 253) in dichloromethane (20 mL). The reaction mixture was stirred at 0° C. for 3 hours. The reaction mixture was quenched with methanol. Hydrochloric acid (about 10 mL of 6 N) was added and the mixture was stirred at 50° C. overnight. The mixture was diluted with water (50 mL) and ethyl acetate (100 mL) and then brought to neutral pH with solid sodium hydroxide. The layers were separated and the aqueous was extracted with ethyl acetate (×2). The combined organics were dried over magnesium sulfate, filtered, and then concentrated under reduced pressure to provide a yellow solid. This material was purified by prep HPLC (COMBIFLASH system eluting first with a gradient of 0 to 5% methanol in dichloromethane containing 1% ammonium hydroxide and then with a gradient of 5 to 10% methanol in dichloromethane containing 1% ammonium hydroxide) to provide a white solid. This material was suspended in hot acetonitrile, allowed to cool, and then the solvent was decanted. The resulting material was dried under vacuum to provide about 200 mg of N-{3-[4-amino-2-(2-hydroxyethyl)-1H-imidazo[4,5-c]quinolin-1-yl]propyl}-4-methylbenzenesulfonamide as a white solid, m.p. 231-232° C. Anal, calcd for $C_{22}H_{25}N_5O_3S \cdot 0.20 \, CH_4O$: % C, 59.79; % H, 5.85; % N, 15.70. Found: % C, 59.44; % H, 5.89; % N, 15.52.

Example 2

N-{3-[4-Amino-2-(2-hydroxyethyl)-1H-imidazo[4,5-c]quinolin-1-yl]propyl}isoquinoline-3-carboxamide

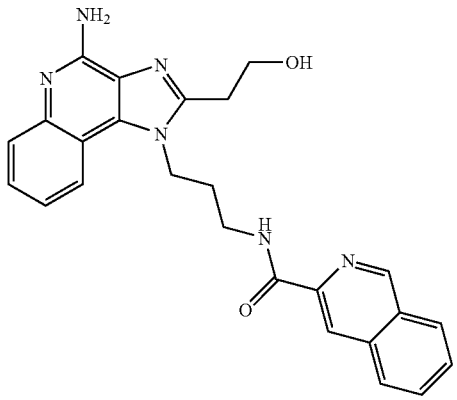 [SMILES: Nc1nc2ccccc2c2c1nc(CCO)n2CCCNC(=O)c1cc2ccccc2cn1]

Boron tribromide (5.50 mL of 1 M in dichloromethane) was added dropwise to a chilled (0° C.) suspension of N-{3-[4-amino-2-(2-methoxyethyl)-1H-imidazo[4,5-c]quinolin-1-yl]propyl}isoquinoline-3-carboxamide (1.0 g, 2.2 mmol; U.S. Pat. No. 6,756,382, Example 192) in dichloromethane (20 mL). The reaction mixture was stirred at 0° C. for 45 minutes and then allowed to warm to ambient temperature. After 5 hours the reaction mixture was concentrated under reduced pressure and the residue was allowed to stand over the weekend. The residue was diluted with methanol (20 mL) and then heated to 50° C. Hydrochloric acid (about 10 mL of 6 N) was added and the mixture was stirred for about 2.5 hours. The mixture was made basic with aqueous sodium hydroxide and then extracted with ethyl acetate (×2). The combined extracts were dried over magnesium sulfate, filtered, and then concentrated under reduced pressure to provide a yellow solid. This material was purified by prep HPLC (COMBIFLASH system eluting first with a gradient of 0 to 5% methanol in dichloromethane containing 1% ammonium hydroxide and then with a gradient of 5 to 10% methanol in dichloromethane containing 1% ammonium hydroxide) to provide a white solid. This material was suspended in hot acetonitrile, allowed to cool, and then the solvent was decanted. The resulting material was dried under vacuum to provide about 400 mg of N-{3-[4-amino-2-(2-hydroxyethyl)-1H-imidazo[4,5-c]quinolin-1-yl]propyl}isoquinoline-3-carboxamide as a white solid, mp 245-246° C. Anal calcd for $C_{25}H_{24}N_6O_2$: % C, 67.73; % H, 5.59; % N, 18.80. Found: % C, 67.38; % H, 5.54; % N, 18.84.

Example 3

N-{4-[4-Amino-2-(2-hydroxyethyl)-1H-imidazo[4,5-c]quinolin 1-yl]butyl}methanesulfonamide

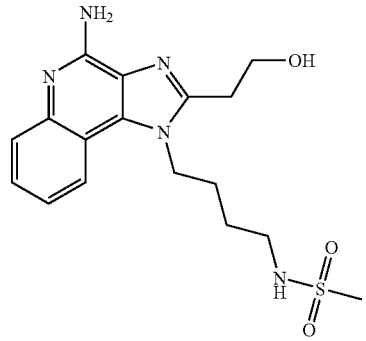 [SMILES: CS(=O)(=O)NCCCCn1c(CCO)nc2c(N)nc3ccccc3c21]

Part A

3-Methoxypropionyl chloride (15.4 g, 126 mmol) was added dropwise over a period of 20 minutes to a chilled (ice bath) solution of tert-butyl N-{4-[(3-aminoquinolin-4-yl)amino]butyl}carbamate (38 g, 115 mmol, U.S. Pat. No. 6,541,485, Example 2, Part B) in pyridine. The reaction mixture was stirred for 4 hours and then allowed to stand at ambient temperature over the weekend. Pyridine hydrochloride (3.9 g, 34 mmol) was added and the reaction mixture was heated at reflux overnight. The reaction mixture was concentrated under reduced pressure and the residue was diluted with dichloromethane (250 mL) and aqueous sodium bicarbonate (250 mL). The layers were separated. The separatory funnel was rinsed with a small amount of methanol to remove a residue coating the walls. The combined organics were concentrated under reduced pressure. The residue was purified by prep HPLC (COMBIFLASH system eluting first with a gradient of 0 to 5% methanol in dichloromethane containing 1% ammonium hydroxide and then with a gradient of 5 to 10% methanol in dichloromethane containing 1% ammonium hydroxide) to provide 18 g of tert-butyl N-{4-[2-(2-methoxyethyl)-1H-imidazo[4,5-c]quinolin-1-yl]butyl}carbamate.

Part B

3-Chloroperoxybenzoic acid (20 g of 77%) was added in a single portion to a solution of the material from Part A (18 g, 45.2 mmol) in dichloroethane (170 mL). After 2 hours concentrated ammonium hydroxide (150 mL) was added and the reaction mixture was stirred until the phases were mixed well. Para-Toluenesulfonyl chloride (10.6 g, 54 mmol) was added in a single portion along with a small amount of dichloroethane. The reaction mixture was stirred overnight at ambient temperature and then diluted with water and dichloromethane. The layers were separated and the aqueous layer was extracted with dichloromethane (×2). The combined organics were dried over magnesium sulfate, filtered, and then concentrated under reduced pressure to provide 23 g of crude tert-butyl N-{4-[4-amino-2-(2-methoxyethyl)-1H-imidazo[4,5-c]quinolin-1-yl]butyl}carbamate as a red tar.

Part C

The material from Part B was combined with a solution of hydrochloric acid in dioxane (325 mL of 4 M) and stirred at ambient temperature for 3 hours. The reaction mixture was concentrated under reduced pressure. The residue was dissolved in methanol (30 mL) and 6 M sodium hydroxide was added with stirring to about pH 9. Attempts to extract with dichloromethane and ethyl acetate were not successful. The organic and aqueous layers were concentrated under reduced pressure and combined to provide a dark orange solid. This material was purified by prep HPLC (COMBIFLASH system eluting first with a gradient of 0 to 8% methanol in dichloromethane containing 1% ammonium hydroxide and then with a gradient of 9 to 35% methanol in dichloromethane containing 1% ammonium hydroxide) to provide 10.65 g of 1-(4-aminobutyl)-2-(2-methoxyethyl)-1H-imidazo[4,5-c]quinolin-4-amine as an orange solid.

Part D

Triethylamine (10.5 mL, 75.0 mmol) was added to a mixture of a portion (4.7 g, 15 mmol) of the material from Part C in pyridine (50 mL). The reaction mixture was stirred for several minutes and then methanesulfonyl chloride (1.27 mL, 16.5 mmol) was added dropwise. The reaction mixture was stirred at ambient temperature for 2 hours and then at 50° C. for 2 hours. More methanesulfonyl chloride (0.5 eq) was added and the reaction mixture was stirred at 50° C. for 2 hours. Another portion of methanesulfonyl chloride (0.25 eq) was added and the reaction mixture was stirred at ambient temperature overnight. The reaction mixture was diluted with dichloromethane and water. The layers were separated and the aqueous layer was extracted with dichloromethane (×3). The combined organics were dried over magnesium sulfate, filtered, and then concentrated under reduced pressure to provide 5 g of crude N-{4-[4-amino-2-(2-methoxyethyl)-1H-imidazo[4,5-c]quinolin-1-yl]butyl}methanesulfonamide as a red oil.

Part E

Boron tribromide (22.4 mL of 1 M in dichloromethane) was added slowly to a chilled (ice bath) mixture of a portion of the material from Part D (3.5 g, about 8.9 mmol) and dichloromethane (50 mL). After the addition was complete the ice bath was removed and the reaction mixture was allowed to stir at ambient temperature for 3 hours. The reaction mixture was concentrated under reduced pressure. The residue was dissolved in methanol and then combined with hydrochloric acid (50 mL of 6 M). The mixture was stirred at 50° C. for 2 hours and then concentrated under reduced pressure. The residue was combined with ammonia in methanol (about 50 mL of 7 M) to neutralize the acid and then concentrated. This procedure was repeated 3 times. The crude product was purified by prep HPLC (COMBIFLASH system eluting with a gradient of 0 to 10% methanol in dichloromethane containing 1% ammonium hydroxide). The product was stirred with hot acetonitrile, allowed to stand overnight, and then isolated by filtration, washed with acetonitrile, and dried in a vacuum oven to provide 1.1 g of N-{4-[4-amino-2-(2-hydroxyethyl)-1H-imidazo[4,5-c]quinolin-1-yl]butyl}methanesulfonamide, mp 206-208° C. Anal calcd for $C_{17}H_{23}N_5O_3S$: % C, 54.09; % H, 6.14; % N, 18.55. Found: % C, 53.83; % H, 6.29; % N, 18.29.

Example 4

1-(2-Amino-2-methylpropyl)-2-hydroxymethyl-1H-imidazo[4,5-c]quinolin-4-amine

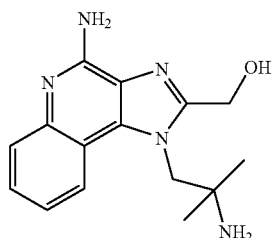

Part A

Under a nitrogen atmosphere, triethylamine (6.6 mL, 47 mmol) was added slowly to a solution of 2,4-dichloro-3-nitroquinoline (10.0 g, 41.1 mmol) in anhydrous 1-methyl-2-pyrrolidinone (40 mL). The reaction mixture was cooled to 0° C. with an ice bath. A solution of 1,2-diamino-2-methylpropane (4.1 g, 47.3 mmol) in anhydrous 1-methyl-2-pyrrolidinone (5 mL) was added dropwise over a period of 15 minutes while maintaining the temperature of the reaction mixture below 4° C. After the addition was completed the ice bath was removed and the reaction mixture was allowed to stir at ambient temperature for 4 hours. The reaction mixture was slowly poured into vigorously stirred warm water (300 mL). The resulting suspension was stirred for 1 hour and then cooled to 13° C. by adding ice. The solid was isolated by filtration and then washed with cold water until the filtrate was clear to provide 12.1 g of $N^1$-(2-chloro-3-nitroquinolin-4-yl)-2-methylpropane-1,2-diamine as a damp yellow solid.

Part B

A solution of sodium hydroxide (1.8 g of solid sodium hydroxide dissolved in 45 mL of water) was added slowly to a solution of the material from Part A (41.1 mmol) in tetrahydrofuran (96 mL). A solution of di-tert-butyl dicarbonate (10.8 g, 49.4 mmol) in tetrahydrofuran (30 mL) was added dropwise over a period of 15 minutes. The reaction solution was stirred at ambient temperature. After 6 hours 10% sodium hydroxide (2 mL) and additional di-tert-butyl dicarbonate (1.5 g) were added and the reaction solution was stirred at ambient temperature overnight. The layers were separated and the tetrahydrofuran was removed under reduced pressure to provide a mixture. The mixture was diluted with water (200 mL) and then extracted with dichloromethane (2×100 mL). The organics were combined, washed sequentially with aqueous sodium carbonate (2×150 mL) and brine (100 mL), dried over sodium sulfate and magnesium sulfate, filtered, and then concentrated under reduced pressure. The residue was triturated with heptane (75 mL) for 15 minutes at 65° C. and then filtered while hot. The isolated solids were washed with heptane (20 mL) to provide 13.2 g of tert-butyl N-{2-[(2-chloro-3-nitroquinolin-4-yl)amino]-1,1-dimethylethyl}carbamate as a yellow powdery solid.

Part C

A Parr vessel was charged with 5% Pt/C (0.5 g) and acetonitrile (10 mL). A solution of the material from Part B in acetonitrile (450 mL) was added. The vessel was placed on a Parr shaker under hydrogen pressure (40 psi, $2.8×10^5$ Pa) for 5 hours. The reaction mixture was filtered through a layer of CELITE filter aid to remove the catalyst. The filtrate was carried on to the next step.

Part D

The solution of tert-butyl N-{2-[(3-amino-2-chloroquinolin-4-yl)amino]-1,1-dimethylethyl}carbamate in acetonitrile from Part C was cooled to 5° C. using an ice bath. A solution of acetoxyacetyl chloride (4.8 g, 35.1 mmol) in acetonitrile (20 mL) was added dropwise at a rate such that the temperature of the reaction mixture was maintained at 5° C. After the addition was complete the ice bath was removed and the reaction mixture was allowed to stir at ambient temperature for 5 hours. The reaction mixture was concentrated under reduced pressure to provide 16.7 g of N-{2-[(3-acetoxyacetylamino-2-chloroquinolin-4-yl)amino]-1,1-dimethylethyl}carbamate hydrochloride as a yellow powder.

Part E

A mixture of the material from Part D (15.7 g) and ammonia in methanol (235 mL of 7 N) was divided into equal portions and placed in pressure vessels. The vessels were sealed, heated at 160° C. for 20 hrs, and then allowed to cool to ambient temperature overnight. The reaction mixtures were filtered. The isolated solids were washed with water and dried in a vacuum oven at 60° C. overnight to provide 6.0 g of a tan powder. A portion (1 g) was treated with activated charcoal and recrystallized from ethanol (75 mL) to provide 0.5 g of 1-(2-amino-2-methylpropyl)-2-hydroxymethyl-1H-imidazo[4,5-c]quinolin-4-amine as a white granular solid, mp 248-250° C. Anal calcd for $C_{15}H_{19}N_5O$: % C, 63.14; % H, 6.71; % N, 24.54. Found: % C, 63.13; % H, 6.81; % N, 24.64.

Example 5

N-[2-(4-Amino-2-hydroxymethyl-1H-imidazo[4,5-c]quinolin-1-yl)-1,1-dimethylethyl]cyclohexanecarboxamide

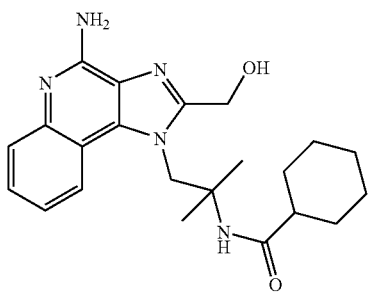 [SMILES: CC(C)(Cn1c(CO)nc2c(N)nc3ccccc3c21)NC(=O)C1CCCCC1]

A solution of 1-(2-amino-2-methylpropyl)-2-hydroxymethyl-1H-imidazo[4,5-c]quinolin-4-amine (2.0 g, 7.0 mmol) in 1-methyl-2-pyrrolidinone (30 mL) was cooled to −20° C. Triethylamine (1.1 mL, 7.7 mmol) was added in a single portion. A chilled (−5° C.) solution of cyclohexanecarbonyl chloride (1.03 g, 7.0 mmol) in 1-methyl-2-pyrrolidinone (2 mL) was added dropwise over a period of 20 minutes while maintaining the reaction mixture at −20° C. The reaction mixture was stirred at ambient temperature overnight. Additional cyclohexanecarbonyl chloride (0.1 g) was added and the reaction mixture stirred for 2 hours. The reaction mixture was poured into water with vigorous stirring. The resulting precipitate was isolated by filtration to provide 1.7 g of an ivory powder. Analysis by high performance liquid chromatography and NMR indicated that the powder was a mixture of the desired product and an ester formed from the reaction of the hydroxy group of the desired product with cyclohexanecarbonyl chloride.

The powder was dissolved in ethanol (25 mL), combined with a solution of sodium hydroxide (0.21 g) in water (25 mL), and then heated at 50° C. for 3 hours. The ethanol was removed under reduced pressure and the solids were isolated by filtration to provide 1.2 g of a light tan powder. The powder was dissolved in a mixture of acetonitrile (100 mL), water (2 mL) and ethanol (25 mL). The solution was allowed to stand overnight and was then concentrated to a volume of 5 mL to provide a white paste. The paste was triturated with warm (70° C.) acetonitrile (50 mL) for 30 minutes, heated to reflux, and then allowed to cool to ambient temperature. The resulting solid was isolated by filtration to provide 1.05 g of N-[2-(4-amino-2-hydroxymethyl-1H-imidazo[4,5-c]quinolin-1-yl)-1,1-dimethylethyl]cyclohexanecarboxamide as a light yellow powder, mp 248-250° C. Anal calcd for $C_{22}H_{29}N_5O_2$: % C, 66.81; % H, 7.39; % N, 17.71. Found: % C, 66.56; % H, 7.60; % N, 17.82.

Example 6

N-{2-[4-Amino-2-(2-hydroxyethyl)-1H-imidazo[4,5-c]quinolin-1-yl]-1,1-dimethylethyl}methanesulfonamide

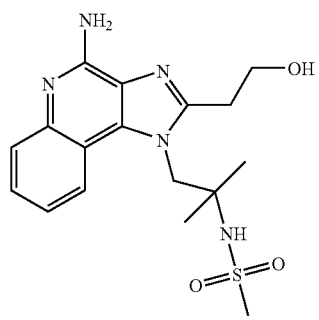 [SMILES: CC(C)(Cn1c(CCO)nc2c(N)nc3ccccc3c21)NS(C)(=O)=O]

Part A

Triethylamine (39.3 mL, 0.282 mol) was added to a chilled (ice bath) solution of $N^1$-(2-chloro-3-nitroquinolin-4-yl)-2-methylpropane-1,2-diamine (41.42 g, 0.141 mol) in dichloromethane (about 500 mL). Under a nitrogen atmosphere a solution of methanesulfonic anhydride in (29.47 g, 0.169 mol) in dichloromethane (100 mL) was added via a cannula to the reaction mixture over a period of 45 minutes. After the addition was complete the ice bath was removed and the reaction mixture was allowed to stir at ambient temperature overnight. The reaction mixture was washed sequentially with saturated aqueous sodium bicarbonate (×2) and brine, dried over a mixture of sodium sulfate and magnesium sulfate, filtered, and then concentrated under reduced pressure to provide 46.22 g of an orange solid. This material was recrystallized from toluene (about 1 L), isolated by filtration, rinsed with cold toluene, and dried under high vacuum at 60° C. to provide 33.09 g of N-{2-[(2-chloro-3-nitroquinolin-4-yl)amino]-1,1-dimethylethyl}methanesulfonamide.

Part B

A hydrogenation vessel was charged with 5% Pt/C (4.14 g) and a solution of N-{2-[(2-chloro-3-nitroquinolin-4-yl)amino]-1,1-dimethylethyl}methanesulfonamide (54.59 g, 0.147 mol) in acetonitrile (1800 mL). The vessel was placed under hydrogen pressure (48 psi, $3.3 \times 10^5$ Pa) overnight. An additional portion (4.25 g) of catalyst was added and the vessel was placed under hydrogen pressure (48 psi, $3.3 \times 10^5$ Pa) for 4 hours. The reaction mixture was filtered through a layer of CELITE filter aid and the filter cake was rinsed with fresh acetonitrile until the washes were clear.

Part C

Under a nitrogen atmosphere, 3-methoxypropionyl chloride (17.6 mL, 0.162 mol) was added dropwise to the solution of N-{2-[(3-amino-2-chloroquinolin-4-yl)amino]-1,1-dimethylethyl}methanesulfonamide (0.147 mol) in acetonitrile (2.2 L) from Part B. The reaction mixture was allowed to stir at ambient temperature over the weekend. The resulting precipitate was isolated by filtration, rinsed with a small amount of acetonitrile, and then dried under high vacuum at 60° C. to provide 55.84 g of N-{2-chloro-4-[2-(methanesulfonylamino)-2-methylpropyl]quinolin-3-yl}-3-methoxypropionamide.

Part D

A Parr bomb was charged with 25.0 g of N-{2-chloro-4-[2-(methanesulfonylamino)-2-methylpropyl]aminoquinolin-3-yl}-3-methoxypropionamide and ammonia in methanol (300 mL of 7 N). A second vessel was charged with 30.21 g of N-{2-chloro-4-[2-(methanesulfonylamino)-2-methylpropyl]

quinolin-3-yl}-3-methoxypropionamide and ammonia in methanol (400 mL of 7 N). Both vessels were sealed and then heated at 170° C. for 14 hours. The reaction mixtures were combined and the solvent was removed under reduced pressure. The residue was partitioned between dichloromethane and saturated aqueous sodium bicarbonate. The organic layer was washed sequentially with saturated aqueous sodium bicarbonate and brine, dried over sodium sulfate, filtered, and then concentrated under reduced pressure to provide 38.16 g of N-{2-[4-amino-2-(2-methoxyethyl)-1H-imidazo[4,5-c] quinolin-1-yl]-1,1-dimethylethyl}methanesulfonamide as an off white foam.

Part E

Under a nitrogen atmosphere, boron tribromide (3.5 mL of 1 M in dichloromethane) was added dropwise to a chilled (0° C.) solution of N-{2-[4-amino-2-(2-methoxyethyl)-1H-imidazo[4,5-c]quinolin-1-yl]-1,1-dimethylethyl}methanesulfonamide (0.55 g, 1.40 mmol) in dichloromethane (20 mL). The reaction was allowed to warm to ambient temperature overnight. The reaction was quenched with methanol (10 mL) and the solvent was removed under reduced pressure. The residue was dissolved in hydrochloric acid (6 N), stirred at 50° C. for about 2.5 hours, and then allowed to cool to ambient temperature. The reaction mixture was adjusted to pH 11 with ammonium hydroxide and then extracted with dichloromethane (×10). The combined organics were washed with brine, dried over sodium sulfate, filtered, and then concentrated under reduced pressure to provide 0.47 g of a white solid. This material was purified by prep HPLC (HORIZON HPFC system, eluting with a gradient of 30-50% CMA in chloroform for 15 column volumes followed by 50% CMA in chloroform for 5 column volumes) and then dried under high vacuum to provide 250 mg of N-{2-[4-amino-2-(2-hydroxyethyl)-1H-imidazo[4,5-c]quinolin-1-yl]-1,1-dimethylethyl}methanesulfonamide as white solid, m.p. 209-212° C. $^1$H NMR (500 MHz, DMSO-$d_6$) δ 8.30 (d, J=8.2 Hz, 1H), 7.60 (d, J=8.2 Hz, 1H), 7.39 (m, 1H), 7.27 (s, 1H), 7.21 (m, 1H), 6.49 (s, 2H), 4.84 (t, J=5.4 Hz, 2H), 4.82 (br s, 1H), 3.88 (m, 2H), 3.18 (br s, 2H), 3.00 (s, 3H), 1.27 (br s, 6H); $^{13}$C NMR (125 MHz, DMSO-$d_6$) δ 153.6, 152.0, 145.4, 133.5, 126.9, 126.8, 126.5, 121.3, 120.8, 115.6, 60.5, 57.9, 54.1, 44.8, 31.4, 25.8; MS (ESI) m/z 378 (M+H)$^+$; Anal. calcd for $C_{17}H_{23}N_5O_3S$: % C, 54.09; % H, 6.14; % N, 18.55. Found: % C, 53.76; % H, 6.02; % N, 18.32.

Example 7

N-[2-(4-Amino-2-hydroxymethyl-1H-imidazo[4,5-c] quinolin-1-yl)-1,1-dimethylethyl]methanesulfonamide

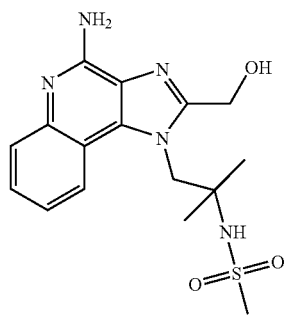 [SMILES: CC(C)(Cn1c(CO)nc2c(N)nc3ccccc3c21)NS(C)(=O)=O]

Part A

A pressure vessel was charged with a solution of N-{2-[(2-chloro-3-nitroquinolin-4-yl)amino]-1,1-dimethylethyl}methanesulfonamide (5 g, 13 mmol) in acetonitrile (150 mL). Catalyst was added (0.5 g of 5% Pt/C) and the vessel was placed under hydrogen pressure (50 psi, 3.4× 10$^5$ Pa) for 2 hours. The reaction mixture was filtered through a layer of CELITE filter aid.

Part B

The solution of N-{2-[(3-amino-2-chloroquinolin-4-yl) amino]-1,1-dimethylethyl}methanesulfonamide in acetonitrile from Part A was chilled in an ice bath. Acetoxyacetyl chloride (1.5 mL, 14 mmol) was added over a period of 5 minutes. The reaction mixture was allowed to stir for 3 hours. A precipitate was isolated by filtration and rinsed with acetonitrile to provide crude N-{2-chloro-4-[2-(methanesulfonylamino)-2-methylpropyl]quinolin-3-yl}acetoxyacetamide hydrochloride.

Part C

A solution of sodium hydroxide (0.8 g) in water (15 mL) was added to a suspension of the material from Part B in ethanol (60 mL) until all of the solid dissolved. The reaction mixture was heated at 60° C. overnight and then concentrated under reduced pressure. The residue was dissolved in water (50 mL), sodium chloride (10 g) was added, and the mixture was extracted with chloroform (3×300 mL). The extracts were concentrated under reduced pressure to provide about 4 g of crude N-[2-(4-chloro-2-hydroxymethyl-1H-imidazo[4, 5-c]quinolin-1-yl)-1,1-dimethylethyl]methanesulfonamide.

Part D

The material from Part C was combined with a solution of ammonia in methanol (50 mL of 7 N) and heated at 150° C. for 10 hours. The reaction mixture was allowed to cool to ambient temperature. A precipitate was isolated by filtration, rinsed with methanol (20 mL), slurried with water (50 mL), isolated by filtration, washed with water (20 mL), and dried to provide 2.7 g of a brown crystalline solid. This material was combined with methanol (50 mL), heated at 50° C. overnight, and then isolated by filtration to provide 2.3 g of N-[2-(4-amino-2-hydroxymethyl-1H-imidazo[4,5-c]quinolin-1-yl)-1,1-dimethylethyl]methanesulfonamide, mp 262-265° C. Anal. calcd for $C_{16}H_{21}N_5O_3S$: % C, 52.88; % H, 5.82; % N, 19.27. Found: % C, 52.64; % H, 5.95; % N, 19.50.

Examples 8-72

Part A

A reagent (1.1 eq) from Table 1 below was added to a test tube containing a solution of 1-(4-aminobutyl)-2-(2-methoxyethyl)-1H-imidazo[4,5-c]quinolin-4-amine (73 mg) in N,N-dimethylacetamide (1 mL) containing N,N-diisopropylethylamine (2 eq). The test tube was placed on a shaker overnight. The solvent was removed by vacuum centrifugation. The reaction mixtures were separated by solid-supported liquid-liquid extraction according to the following procedure. Each sample was dissolved in chloroform (1 mL) then loaded onto diatomaceous earth that had been equilibrated with de-ionized water (600 μL) for about 20 minutes. After 10 minutes chloroform (500 μL) was added to elute the product from the diatomaceous earth into a well of a collection plate. After an additional 10 minutes the process was repeated with additional chloroform (500 μL). The solvent was then removed by vacuum centrifugation.

Part B

The residue (in a test tube) was combined with dichloromethane (1 mL) and the mixture was sonicated to dissolve the solids. The solution was cooled (0° C.) and then combined with boron tribromide (400 μL of 1 M in heptane). The mixture was shaken for 5 minutes, placed in an ice bath for 30 minutes, and then shaken overnight. The solvents were removed by vacuum centrifugation. The residue was diluted with methanol (1 mL) and hydrochloric acid (500 μL of 6 N). The mixture was shaken for 30 minutes and then the solvents were removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. Table 1 below shows the reagent used for each example, the structure of the resulting compound, and the observed accurate mass for the isolated trifluoroacetate salt.

TABLE 1

| Example | Reagent | R | Measured Mass (M + H) |
|---|---|---|---|
| 8 | None | –H | 300.1840 |
| 9 | Cyclopropanecarbonyl chloride | –C(O)-cyclopropyl | 368.2063 |
| 10 | Isobutyryl chloride | –C(O)CH(CH$_3$)$_2$ | 370.2224 |
| 11 | Pivaloyl chloride | –C(O)C(CH$_3$)$_3$ | 384.2390 |
| 12 | Benzoyl chloride | –C(O)Ph | 404.2103 |
| 13 | Phenyl chloroformate | –C(O)OPh | 420.2056 |

TABLE 1-continued

| Example | Reagent | R | Measured Mass (M + H) |
|---|---|---|---|
| 14 | 3-Cyanobenzoyl chloride | 3-cyanobenzoyl | 429.2031 |
| 15 | Hydrocinnamoyl chloride | hydrocinnamoyl | 432.2377 |
| 16 | Isonicotinoyl chloride hydrochloride | isonicotinoyl | 405.2071 |
| 17 | Nicotinoyl chloride hydrochloride | nicotinoyl | 405.2058 |
| 18 | Methanesulfonyl chloride | methanesulfonyl | 378.1592 |
| 19 | Ethanesulfonyl chloride | ethanesulfonyl | 392.1729 |
| 20 | 1-Propanesulfonyl chloride | 1-propanesulfonyl | 406.1899 |

TABLE 1-continued

[Structure: 4-amino-1H-imidazo[4,5-c]quinoline with 2-(2-hydroxyethyl) substituent and 1-(4-(NHR)butyl) substituent]

| Example | Reagent | R | Measured Mass (M + H) |
|---------|---------|---|----------------------|
| 21 | Isopropylsulfonyl chloride | –S(O)₂–CH(CH₃)₂ | 406.1888 |
| 22 | Dimethylsulfamoyl chloride | –S(O)₂–N(CH₃)₂ | 407.1853 |
| 23 | 1-Butanesulfonyl chloride | –S(O)₂–CH₂CH₂CH₂CH₃ | 420.2050 |
| 24 | Benzenesulfonyl chloride | –S(O)₂–phenyl | 440.1741 |
| 25 | 1-Methylimidazole-4-sulfonyl chloride | –S(O)₂–(1-methylimidazol-4-yl) | 444.1806 |
| 26 | 3-Methylbenzenesulfonyl chloride | –S(O)₂–(3-methylphenyl) | 454.1895 |

TABLE 1-continued

| Example | Reagent | R | Measured Mass (M + H) |
|---|---|---|---|
| 27 | alpha-Toluenesulfonyl chloride | benzylsulfonyl | 454.1923 |
| 28 | o-Toluenesulfonyl chloride | 2-methylphenylsulfonyl | 454.1944 |
| 29 | p-Toluenesulfonyl chloride | 4-methylphenylsulfonyl | 454.1907 |
| 30 | 2-Fluorobenzenesulfonyl chloride | 2-fluorophenylsulfonyl | 458.1664 |
| 31 | 3-Fluorobenzenesulfonyl chloride | 3-fluorophenylsulfonyl | 458.1652 |
| 32 | 4-Fluorobenzenesulfonyl chloride | 4-fluorophenylsulfonyl | 458.1639 |

TABLE 1-continued

[Structure: 4-amino-1H-imidazo[4,5-c]quinoline with 2-(2-hydroxyethyl) substituent and 1-(4-(R-amino)butyl) substituent]

| Example | Reagent | R | Measured Mass (M + H) |
|---------|---------|---|----------------------|
| 33 | 3-Cyanobenzenesulfonyl chloride | 3-cyanophenylsulfonyl | 465.1678 |
| 34 | 4-Cyanobenzenesulfonyl chloride | 4-cyanophenylsulfonyl | 465.1668 |
| 35 | beta-Styrene sulfonyl chloride | (E)-styrylsulfonyl | 466.1895 |
| 36 | 2,5-Dimethylbenzenesulfonyl chloride | 2,5-dimethylphenylsulfonyl | 468.2063 |
| 37 | 3,5-Dimethylbenzenesulfonyl chloride | 3,5-dimethylphenylsulfonyl | 468.2046 |

TABLE 1-continued

| Example | Reagent | R | Measured Mass (M + H) |
|---|---|---|---|
| 38 | 2-Chlorobenzenesulfonyl chloride | 2-chlorophenylsulfonyl | 474.1351 |
| 39 | 3-Chlorobenzenesulfonyl chloride | 3-chlorophenylsulfonyl | 474.1385 |
| 40 | 4-Chlorobenzenesulfonyl chloride | 4-chlorophenylsulfonyl | 474.1390 |
| 41 | 1-Naphthalenesulfonyl chloride | 1-naphthylsulfonyl | 490.1891 |
| 42 | 2-Naphthalenesulfonyl chloride | 2-naphthylsulfonyl | 490.1885 |

TABLE 1-continued

| Example | Reagent | R | Measured Mass (M + H) |
|---|---|---|---|
| 43 | 2-(Trifluoromethyl)benzenesulfonyl chloride | 2-(trifluoromethyl)phenylsulfonyl | 508.1592 |
| 44 | 3-(Trifluoromethyl)benzenesulfonyl chloride | 3-(trifluoromethyl)phenylsulfonyl | 508.1612 |
| 45 | 4-(Trifluoromethyl)benzenesulfonyl chloride | 4-(trifluoromethyl)phenylsulfonyl | 508.1640 |
| 46 | 2,3-Dichlorobenzenesulfonyl chloride | 2,3-dichlorophenylsulfonyl | 508.0967 |
| 47 | 2,4-Dichlorobenzenesulfonyl chloride | 2,4-dichlorophenylsulfonyl | 508.0979 |

TABLE 1-continued

| Example | Reagent | R | Measured Mass (M + H) |
|---|---|---|---|
| 48 | 2,5-Dichlorobenzenesulfonyl chloride | 2,5-dichlorophenylsulfonyl | 508.0987 |
| 49 | 2,6-Dichlorobenzenesulfonyl chloride | 2,6-dichlorophenylsulfonyl | 508.0968 |
| 50 | 3,4-Dichlorobenzenesulfonyl chloride | 3,4-dichlorophenylsulfonyl | 508.0961 |
| 51 | 3,5-Dichlorobenzenesulfonyl chloride | 3,5-dichlorophenylsulfonyl | 508.0985 |
| 52 | Methyl isocyanate | C(=O)NHCH₃ | 357.2073 |
| 53 | Ethyl isocyanate | C(=O)NHCH₂CH₃ | 371.2203 |

TABLE 1-continued

[Structure: 4-amino-1H-imidazo[4,5-c]quinoline with 2-(2-hydroxyethyl) substituent and 1-(4-(NHR)butyl) substituent]

| Example | Reagent | R | Measured Mass (M + H) |
|---|---|---|---|
| 54 | Isopropyl isocyanate | –C(O)NH–CH(CH₃)₂ | 385.2347 |
| 55 | n-Propyl isocyanate | –C(O)NH–CH₂CH₂CH₃ | 385.2349 |
| 56 | n-Butyl isocyanate | –C(O)NH–(CH₂)₃CH₃ | 399.2494 |
| 57 | sec-Butyl isocyanate | –C(O)NH–CH(CH₃)CH₂CH₃ | 399.2517 |
| 58 | Cyclopentyl isocyanate | –C(O)NH–cyclopentyl | 411.2516 |
| 59 | Cyclopropylmethyl isothiocyanate | –C(S)NH–CH₂–cyclopropyl | 413.2133 |
| 60 | Phenyl isocyanate | –C(O)NH–phenyl | 419.2226 |

TABLE 1-continued
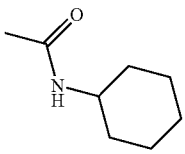
| Example | Reagent | R | Measured Mass (M + H) |
|---|---|---|---|
| 61 | Cyclohexyl isocyanate | 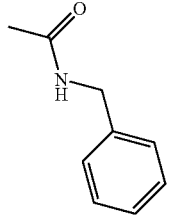 | 425.2701 |
| 62 | Benzyl isocyanate | 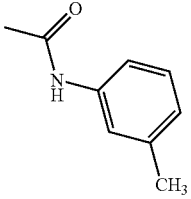 | 433.2374 |
| 63 | m-Tolyl isocyanate | 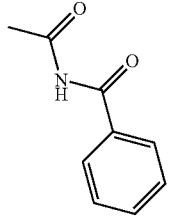 | 433.2344 |
| 64 | Benzoyl isocyanate | 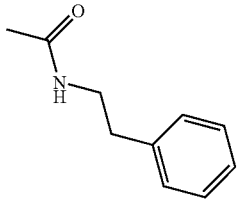 | 447.2126 |
| 65 | 2-Phenyl ethylisocyanate | 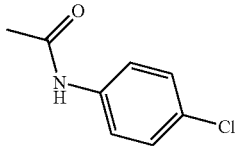 | 447.2512 |
| 66 | 4-Chlorophenyl isocyanate |  | 453.1797 |

TABLE 1-continued

| Example | Reagent | R | Measured Mass (M + H) |
|---|---|---|---|
| 67 | trans-2-Phenylcyclopropyl isocyanate | (acetyl-NH-trans-2-phenylcyclopropyl) | 459.2518 |
| 68 | N,N-Dimethylcarbamoyl chloride | (acetyl-N(CH₃)₂) | 371.2185 |
| 69 | 1-Pyrrolidinecarbonyl chloride | (acetyl-pyrrolidinyl) | 397.2382 |
| 70 | 1-Piperidinecarbonyl chloride | (acetyl-piperidinyl) | 411.2526 |
| 71 | 4-Morpholinylcarbonyl chloride | (acetyl-morpholinyl) | 413.2330 |
| 72 | N-Methyl-N-phenylcarbamoyl chloride | (acetyl-N(CH₃)-phenyl) | 433.2364 |

Examples 73-110

Part A

Tert-Butyl 3-[4-amino-2-(2-methoxyethyl)-1H-imidazo[4,5-c]quinolin-1-yl]propylcarbamate (5 g, U.S. Pat. No. 6,573,273, example 148) and hydrochloric acid in dioxane (100 mL of 4 M) were combined and stirred for 4 hours at ambient temperature. The reaction mixture was concentrated under reduced pressure. The residue was dissolved in methanol (30 mL). The pH was adjusted to pH 8 with 6 M sodium hydroxide. The solution was diluted with dichloromethane, ethyl acetate, triethylamine, and brine. The organic layer was concentrated under reduced pressure to provide an orange solid. This material was purified by prep HPLC (COMBI-FLASH system eluting first with a gradient of 0 to 10% methanol in dichloromethane containing 1% ammonium hydroxide and then with a gradient of 9 to 30% methanol in dichloromethane containing 1% ammonium hydroxide) to provide 1.58 g of 1-(3-aminopropyl)-2-(2-methoxyethyl)-1H-imidazo[4,5-c]quinolin-4-amine as a yellow solid.

Part B

A reagent (1.1 eq) from Table 2 below was added to a test tube containing a solution of 1-(3-aminopropyl)-2-(2-methoxyethyl)-1H-imidazo[4,5-c]quinolin-4-amine (30 mg) in chloroform (1 mL) containing N,N-diisopropylethylamine (1.5 eq). The test tube was placed on a shaker overnight. The reaction mixtures were separated by solid-supported liquid-liquid extraction according to the following procedure. Each reaction mixture was loaded onto diatomaceous earth that had been equilibrated with de-ionized water (600 μL) for about 20 minutes. After 10 minutes chloroform (500 μL) was added to elute the product from the diatomaceous earth into a well of a collection plate. After an additional 10 minutes the process was repeated with additional chloroform (500 μL). The solvent was then removed by vacuum centrifugation.

Part C

The ether was cleaved and the resulting product was purified using the method of Part B in Examples 8-72. Table 2 below shows the reagent used for each example, the structure of the resulting compound, and the observed accurate mass for the isolated trifluoroacetate salt.

TABLE 2

| Example | Reagent | R | Measured Mass (M + H) |
|---|---|---|---|
| 73 | None | H | 286.1689 |
| 74 | Propionyl chloride | C(O)CH$_2$CH$_3$ | 342.1956 |
| 75 | Cyclopropanecarbonyl chloride | C(O)-cyclopropyl | 354.1946 |
| 76 | Butyryl chloride | C(O)CH$_2$CH$_2$CH$_3$ | 356.2122 |
| 77 | Isobutyryl chloride | C(O)CH(CH$_3$)$_2$ | 356.2119 |
| 78 | Cyclobutanecarbonyl chloride | C(O)-cyclobutyl | 368.2120 |
| 79 | 3-Chlorobenzoyl chloride | C(O)-(3-chlorophenyl) | 424.1570 |

TABLE 2-continued

| Example | Reagent | R | Measured Mass (M + H) |
|---|---|---|---|
| 80 | 4-Chlorobenzoyl chloride | 4-chlorobenzoyl | 424.1583 |
| 81 | Nicotinoyl chloride hydrochloride | nicotinoyl | 391.1913 |
| 82 | trans-2-Phenyl-1-cyclopropanecarbonyl chloride | trans-2-phenylcyclopropanecarbonyl | 430.2257 |
| 83 | Methanesulfonyl chloride | methanesulfonyl | 364.1479 |
| 84 | Ethanesulfonyl chloride | ethanesulfonyl | 378.1639 |
| 85 | 1-Propanesulfonyl chloride | 1-propanesulfonyl | 392.1783 |
| 86 | Isopropylsulfonyl chloride | isopropylsulfonyl | 392.1788 |
| 87 | Dimethylsulfamoyl chloride | dimethylsulfamoyl | 393.1715 |
| 88 | 1-Butanesulfonyl chloride | 1-butanesulfonyl | 406.1946 |

TABLE 2-continued
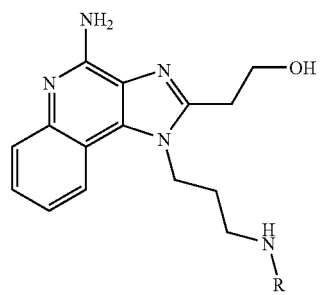
| Example | Reagent | R | Measured Mass (M + H) |
|---|---|---|---|
| 89 | Benzenesulfonyl chloride | | 426.1633 |
| 90 | 2,2,2-Trifluoroethanesulfonyl chloride | | 432.1355 |
| 91 | 3-Methylbenzenesulfonyl chloride | | 440.1774 |
| 92 | alpha-Toluenesulfonyl chloride | | 440.1762 |
| 93 | p-Toluenesulfonyl chloride | | 440.1790 |
| 94 | 3-Fluorobenzenesulfonyl chloride | | 444.1523 |
| 95 | 4-Fluorobenzenesulfonyl chloride | | 444.1545 |
| 96 | 3-Cyanobenzenesulfonyl chloride | | 451.1554 |

TABLE 2-continued
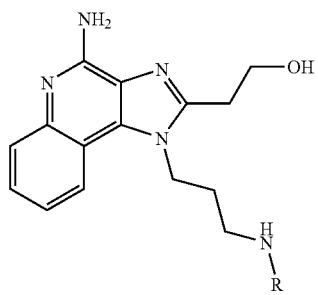
| Example | Reagent | R | Measured Mass (M + H) |
|---|---|---|---|
| 97 | 4-Cyanobenzenesulfonyl chloride | [sulfonyl-phenyl-CN] | 451.1582 |
| 98 | Ethyl isocyanate | [C(O)NH-ethyl] | 357.2050 |
| 99 | Isopropyl isocyanate | [C(O)NH-isopropyl] | 371.2234 |
| 100 | n-Butyl isocyanate | [C(O)NH-n-butyl] | 385.2364 |
| 101 | Cyclopentyl isocyanate | [C(O)NH-cyclopentyl] | 397.2359 |
| 102 | Cyclopropylmethyl isothiocyanate | [C(S)NH-CH2-cyclopropyl] | 399.1979 |
| 103 | Phenyl isocyanate | [C(O)NH-phenyl] | 405.2040 |

TABLE 2-continued
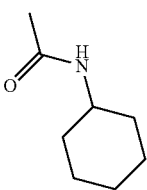
| Example | Reagent | R | Measured Mass (M + H) |
|---|---|---|---|
| 104 | Cyclohexyl isocyanate | 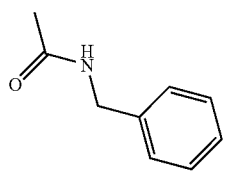 | 411.2526 |
| 105 | Benzyl isocyanate | 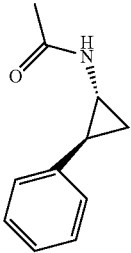 | 419.2239 |
| 106 | trans-2-Phenylcyclopropyl isocyanate | 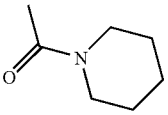 | 445.2388 |
| 107 | 1-Piperidinecarbonyl chloride | 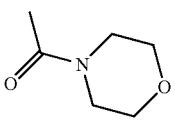 | 397.2384 |
| 108 | 4-Morpholinylcarbonyl chloride | 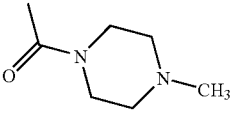 | 399.2173 |
| 109 | 4-Methyl-1-piperazinecarbonyl chloride | 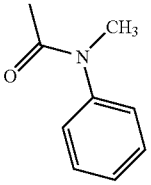 | 412.2485 |
| 110 | N-Methyl-N-phenylcarbamoyl chloride | | 419.2229 |

Examples 111-140

Boron tribromide (400 μL of 1 M in heptane) was added to a tube containing a chilled (0° C.) solution of a compound of Formula Xa (about 25 mg) in dichloromethane (1 mL). The tube was vortexed, maintained at 0° C. for 0.5 hour, and then shaken overnight at ambient temperature. The reaction mixture was diluted with methanol (1 mL) and hydrochloric acid (250 μL of 6 N), vortexed, and then the solvents were removed by vacuum centrifugation. The compounds were purified by prep HPLC as described in Examples 8-72. Table 3 shows the structure of the starting material, a reference for the starting material, the structure of the resulting compound, and the observed accurate mass for the isolated trifluoroacetate salt.

TABLE 3

| Example | Reference Formula Xa | $R_1$ | Measured Mass (M + H) |
|---|---|---|---|
| 111 | U.S. Pat. No. 6,756,382 Example 57 | | 455.2222 |
| 112 | U.S. Pat. No. 6,331,539 Example 121 | | 458.1657 |
| 113 | U.S. Pat. No. 6,331,539 Example 111 | | 378.1599 |
| 114 | Example 3 Part C | | 300.1853 |

TABLE 3-continued
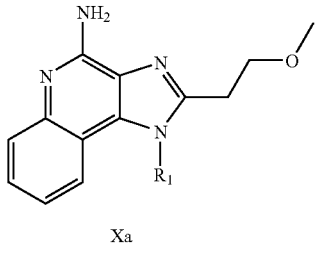
| Example | Reference Formula Xa | $R_1$ | Measured Mass (M + H) |
|---|---|---|---|
| 115 | U.S. Pat. No. 6,541,485 Example 121 | 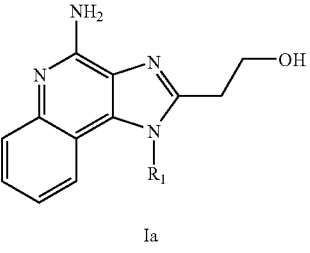 | 413.2301 |
| 116 | U.S. Pat. No. 6,756,382 Example 182 | 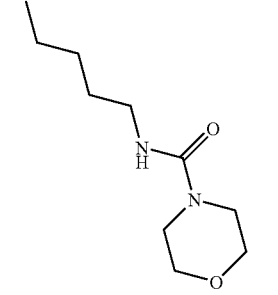 | 455.2198 |
| 117 | U.S. Pat. No. 6,756,382 Example 183 | 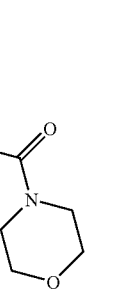 | 456.2161 |

TABLE 3-continued

| Example | Reference Formula Xa | R₁ | Measured Mass (M + H) |
|---|---|---|---|
| 118 | U.S. Pat. No. 6,573,273 Example 145 | (nonyl chain)-NH-C(=O)-NH-phenyl | 475.2829 |
| 119 | U.S. Pat. No. 6,677,349 Example 243 | (nonyl chain)-NH-S(=O)₂-CH₃ | 434.2253 |
| 120 | Example 73 Part A | (butyl chain)-NH₂ | 286.1683 |
| 121 | U.S. Pat. No. 6,756,382 Example 187 | (nonyl chain)-NH-C(=O)-phenyl | 460.2737 |

TABLE 3-continued

| Example | Reference Formula Xa | R₁ | Measured Mass (M + H) |
|---|---|---|---|
| 122 | U.S. Pat. No. 6,677,349 Example 247 | -(CH₂)₄-NH-S(O)₂-CH₃ | 364.1446 |
| 123 | U.S. Pat. No. 6,573,273 Example 158 | -(CH₂)₄-NH-C(O)-NH-cyclohexyl | 411.2505 |
| 124 | U.S. Pat. No. 6,756,382 Example 190 | -CH₂-C(CH₃)(C₂H₅)-CH₂-NH-C(O)-phenyl | 418.2275 |
| 125 | U.S. Pat. No. 6,664,264 Example 16 | -(CH₂)₆-S(O)₂-CH₃ | 377.1655 |
| 126 | U.S. Pat. No. 6,573,273 Example 162 | -(CH₂)₄-NH-C(O)-NH-(CH₂)₃-CH₃ | 385.2358 |

TABLE 3-continued

| Example | Reference Formula Xa | R₁ | Measured Mass (M + H) |
|---|---|---|---|
| 127 | U.S. Pat. No. 6,677,349 Example 253 | butyl-NH-SO₂-(4-methylphenyl) | 440.1720 |
| 128 | U.S. Pat. No. 6,573,273 Example 163 | butyl-NH-C(O)-morpholine | 399.2145 |
| 129 | U.S. Pat. No. 6,677,349# | 2,2-dimethylbutyl-NH₂ | 314.1980 |
| 130 | U.S. Pat. No. 6,573,273 Example 169 | 2,2-dimethylbutyl-NH-C(O)-NH-phenyl | 433.2321 |
| 131 | U.S. Pat. No. 6,677,349 Example 256 | 2,2-dimethylbutyl-NH-SO₂-CH₃ | 392.1757 |

TABLE 3-continued
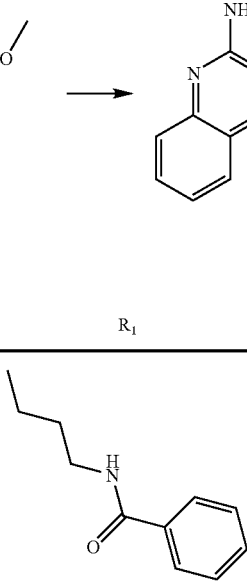
| Example | Reference Formula Xa | R₁ | Measured Mass (M + H) |
|---|---|---|---|
| 132 | U.S. Pat. No. 6,756,382 Example 196 | 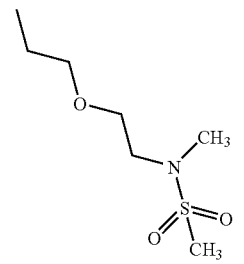 | 390.1929 |
| 133 | U.S. Pat. No. 6,683,088 Example 3 | 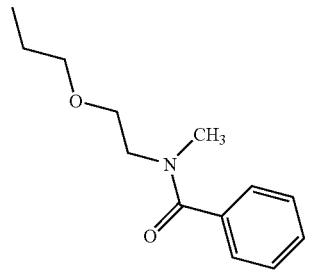 | 408.1714 |
| 134 | U.S. Pat. No. 6,664,265 Example 8 | 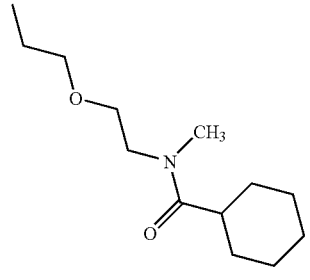 | 434.2197 |
| 135 | U.S. Pat. No. 6,664,265 Example 73 | 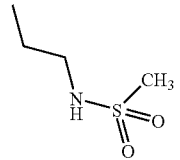 | 440.2672 |
| 136 | U.S. Pat. No. 6,677,349[#] | | 350.1316 |

TABLE 3-continued

Xa → Ia

| Example | Reference Formula Xa | $R_1$ | Measured Mass (M + H) |
|---|---|---|---|
| 137 | U.S. Pat. No. 6,573,273[#] | propyl-NH-C(O)-NH-ethyl (ethylaminocarbonylamino-propyl) | 343.1884 |
| 138 | U.S. Pat. No. 6,451,810[#] | propyl-NH-C(O)-CH$_2$-CH(CH$_3$)$_2$ | 356.2078 |
| 139 | U.S. Pat. No. 6,677,349[#] | C(CH$_3$)$_2$(CH$_2$CH$_3$)-NH-S(O)$_2$-CH$_3$ | 378.1595 |
| 140 | U.S. Patent Publication 2004/0091491 IRM3 | propyl-O-CH$_2$CH$_2$-NH-C(O)-(CH$_2$)$_{n}$-CH$_3$ (long alkyl chain) | 554.4064 |

[#]Although not specifically exemplified the compound can be readily prepared using the disclosed synthetic routes.

Example 141

N-{3-[4-Amino-2-(2-hydroxyethyl)-1H-imidazo[4,5-c]quinolin-1-yl]propyl}-2-methylpropionamide

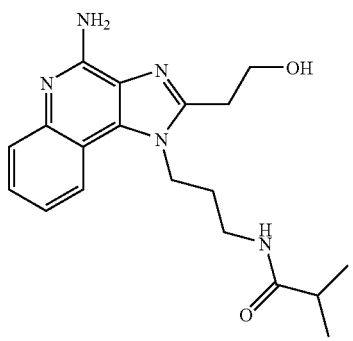 [SMILES: CC(C)C(=O)NCCCn1c(CCO)nc2c(N)nc3ccccc3c21]

Part A 1-(3-Aminopropyl)-2-(2-methoxyethyl)-1H-imidazo[4,5-c]quinolin-4-amine dihydrochloride (6 g, 16 mmol) was combined with triethylamine (11.2 mL, 80 mmol) and pyridine (100 mL). Isobutyryl chloride (1.9 g, 18 mmol) was added dropwise and the reaction mixture was stirred at ambient temperature for 1 hour. The reaction mixture was combined with saturated aqueous sodium bicarbonate and extracted with dichloromethane (3×200 mL). The combined organics were dried over magnesium sulfate, filtered through a layer of CELITE filter aid, and then concentrated under reduced pressure to provide 6.2 g of crude N-{3-[4-amino-2-(2-methoxyethyl)-1H-imidazo[4,5-c]quinolin-1-yl]propyl}-2-methylpropionamide as a brown solid.

Part B

The material from Part A was combined with dichloromethane (40 mL), stirred until homogeneous, and then chilled in an ice bath. Boron tribromide (40 mL of 1 M in dichloromethane) was slowly added. The ice bath was removed and the reaction mixture was stirred overnight at ambient temperature. The reaction mixture was concentrated under reduced pressure. The residue was combined with methanol (50 mL) and hydrochloric acid (50 mL of 6 N) and heated at 50° C. for 2 hours. The solution was adjusted to pH 9 with sodium hydroxide (6 M) and then extracted first with ethyl acetate (3×100 mL) and then with dichloromethane. The organics were dried over magnesium sulfate, filtered through a layer of CELITE filter aid, and then concentrated under reduced pressure. The residue was purified by prep HPLC (HORIZON HPFC system, eluting with a gradient of 0-10% methanol in dichloromethane), recrystallized from acetonitrile, and then dried in a vacuum oven to provide 208 mg of N-{3-[4-amino-2-(2-hydroxyethyl)-1H-imidazo[4,5-c]quinolin-1-yl]propyl}-2-methylpropionamide as an off-white solid, mp 196-198° C. Anal. calcd for $C_{19}H_{25}N_5O_2$: % C, 64.20; % H, 7.09; % N, 19.70. Found: % C, 63.99; % H, 7.28; % N, 19.63.

Example 142

1-[2-(4-Amino-2-hydroxymethyl-1H-imidazo[4,5-c]quinolin-1-yl)-1,1-dimethylethyl]-3-(1-methylethyl)urea

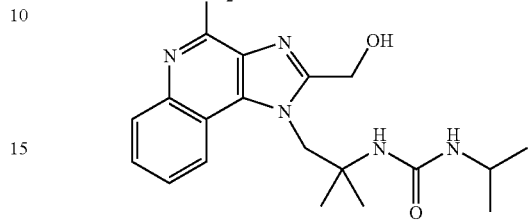

Part A

Under a nitrogen atmosphere, a solution of 1,2-diamino-2-methylpropane (52.20 mL, 503.3 mmol), triethylamine (131.8 mL, 958.8 mmol), and dichloromethane (1.0 L) was chilled in an ice water bath. 4-Chloro-3-nitroquinoline (100.0 g, 479.4 mmol) was added in portions over a period of 5 minutes. The reaction mixture was stirred at 0° C. for 2 hours and then allowed to slowly warm to ambient temperature. After 16 hours the reaction mixture was concentrated under reduced pressure. The residue was triturated with water (500 mL) for 1 hour. The resulting solid was isolated by filtration and dried overnight in a vacuum desiccator to provide 124.6 g of $N^1$-(3-nitroquinolin-1-yl)-2-methylpropane-1,2-diamine as a yellow crystalline solid.

Part B

Under a nitrogen atmosphere, a suspension of $N^1$-(3-nitroquinolin-1-yl)-2-methylpropane-1,2-diamine (60.0 g, 231 mmol) in dichloromethane (1.0 L) was chilled in an ice bath. Isopropyl isocyanate (23.8 mL, 242 mmol) was added dropwise over a period of 10 minutes. The reaction was allowed to slowly warm to room temperature. After 17 hours additional isopropyl isocyanate (about 2 mL) was added. After an additional 3 hours more isopropyl isocyanate (1 mL) was added. After 2 more hours the reaction mixture was concentrated under reduced pressure to provide 79.8 g of 1-{1,1-dimethyl-2-[(3-nitroquinolin-1-yl)amino]ethyl}-3-(1-methylethyl)urea as a bright yellow solid.

Part C

A pressure vessel was charged with the material from Part B, 5% Pt/C (4.24 g), and acetonitrile (1.5 L). The mixture was placed under hydrogen pressure for 20 hours and then filtered through a layer of CELITE filter aid. The filter cake was rinsed with additional acetonitrile. The filtrate was concentrated under reduced pressure. The residue was dissolved in toluene (750 mL) and then concentrated under reduced pressure to remove residual water. The toluene concentration was repeated. The residue was dissolved in dichloromethane (about 1 L), concentrated under reduced pressure, and then dried under high vacuum to provide 66.4 g of 1-{1,1-dimethyl-2-[(3-aminoquinolin-1-yl)amino]ethyl}-3-(1-methylethyl)urea as an orange foam.

Part D

Under a nitrogen atmosphere, a solution of 1-{1,1-dimethyl-2-[(3-aminoquinolin-1-yl)amino]ethyl}-3-(1-methylethyl)urea (66.0 g, 209 mmol) and triethylamine (32.1 mL, 230 mmol) in dichloromethane (1.0 L) was chilled in an ice bath. Ethoxyacetyl chloride (23.6 mL, 291 mmol) was added dropwise over a period of 10 minutes. The reaction mixture was allowed to slowly warm to ambient temperature overnight. The reaction mixture was concentrated under reduced pressure. The residue was combined with 1-butanol (800 mL) and triethylamine (87 mL, 627 mmol) and heated at 140° C. for 3 hours. The reaction mixture was cooled to ambient temperature and then concentrated under reduced pressure to provide a light brown foam. This material was purified by column chromatography (silica gel, eluting with 98/2/0.5 chloroform/methanol/ammonium hydroxide) to provide 29.36 g of 1-[2-(2-ethoxymethyl-1H-imidazo[4,5-c]quinolin-1-yl)-1,1-dimethylethyl]-3-(1-methylethyl)urea as a light yellow foam.

Part E

3-Chloroperoxybenzoic acid (26.33 g of 60%, 91.56 mmol) was added in portions over a period of 5 minutes to a chilled solution of the material from Part D in chloroform (350 mL). The reaction mixture was allowed to slowly warm to ambient temperature. After 2 hours the reaction mixture was chilled in an ice bath and ammonium hydroxide (100 mL) was added with vigorous stirring to homogenize. Para-toluenesulfonyl chloride (15.27 g, 80.12 mmol) was added in portions over a period of 10 minutes. The ice bath was removed and the reaction mixture was stirred for 30 minutes. The reaction mixture was diluted with water (100 mL) and chloroform (250 mL). The layers were separated. The organic layer was washed with 10% sodium carbonate (200 mL) and water (200 mL). The combined aqueous was back extracted with chloroform (100 mL). The combined organics were washed with brine (200 mL), dried over magnesium sulfate, filtered, and then concentrated under reduced pressure to provide a light brown foam. The foam was purified by column chromatography (silica gel, eluting with 95/5 chloroform/methanol) and then recrystallized from acetonitrile to provide 3.75 g of 1-[2-(4-amino-2-ethoxymethyl-1H-imidazo[4,5-c]quinolin-1-yl)-1,1-dimethylethyl]-3-(1-methylethyl)urea as an off white solid.

Part F

Under a nitrogen atmosphere, a suspension of 1-[2-(4-amino-2-ethoxymethyl-1H-imidazo[4,5-c]quinolin-1-yl)-1,1-dimethylethyl]-3-(1-methylethyl)urea (1.19 g, 2.99 mmol) in dichloromethane (30 mL) was chilled in an ice bath. Boron tribromide (7.47 mL of 1 M in dichloromethane) was added. The reaction mixture was allowed to warm slowly to ambient temperature and then stirred for 18 hours. Additional boron tribromide (2 eq) was added. After 2 hours the reaction mixture was diluted with acetonitrile (10 mL) and the reaction mixture was stirred overnight. The reaction mixture was diluted with dichloromethane (10 mL) and acetonitrile (10 mL), stirred for an additional 16 hours, quenched with methanol (25 mL), and then concentrated under reduced pressure to provide an orange foam. The foam was dissolved in hydrochloric acid (25 mL of 6 N) and heated at 50° C. for 2 hours. The solution was neutralized with 50% sodium hydroxide. The resulting gummy precipitate was extracted with chloroform (3×15 mL). The combined organics were washed with brine (15 mL), dried over magnesium sulfate, filtered, and then concentrated under reduced pressure to provide an off white solid. This material was purified by prep HPLC (HORIZON HPFC system, eluting with a gradient of 15-50% CMA in chloroform) and then recrystallized from acetonitrile to provide 335 g of 1-[2-(4-amino-2-hydroxymethyl-1H-imidazo[4,5-c]quinolin-1-yl)-1,1-dimethylethyl]-3-(1-methylethyl)urea as a white crystalline solid, mp 196-199° C.; $^1$H NMR (300 MHz, DMSO-$d_6$) δ 8.38 (d, J=8.0 Hz, 1H), 7.59 (d, J=7.5 Hz, 1H), 7.43-7.38 (m, 1H), 7.24-7.19 (m, 1H), 6.54 (s, 2H), 5.72 (s, 1H), 5.63 (d, J=7.6 Hz, 1H), 5.46 (t, J=5.7 Hz, 1H), 5.01 (s, 2H), 4.78 (s, 2H), 3.78-3.67 (m, 1H), 1.17 (bs, 6H), 1.05 (d, J=6.9 Hz, 6H); $^{13}$C NMR (75 MHz, DMSO-$d_6$) δ 157.2, 154.2, 152.3, 145.6, 134.3, 126.8, 126.7, 121.5, 120.9, 115.8, 56.5, 54.2, 52.1, 26.4, 23.6; MS (APCI) m/z 371 (M+H)$^+$; Anal. Calcd for $C_{19}H_{26}N_6O_2 \cdot 0.3H_2O$: % C, 60.72; % H, 7.13; % N, 22.36. Found: % C, 60.44; % H, 7.42; % N, 22.52.

Example 143

N-[2-(4-Amino-2-hydroxymethyl-1H-imidazo[4,5-c][1,5]naphthyridin-1-yl)-1,1-dimethylethyl]cyclohexanecarboxamide

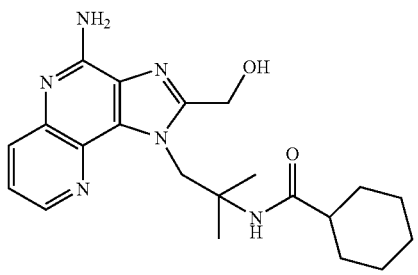 [SMILES: CC(C)(Cn1c(CO)nc2c(N)nc3cccnc3c21)NC(=O)C1CCCCC1]

Part A 1,2-Diamino-2-methylpropane (8.4 mL, 80.0 mmol) was added to a chilled (0° C.) solution of 4-chloro-3-nitro[1,5]naphthyridine (15.2 g, 72.7 mmol) and triethylamine (20.2 mL, 145 mmol) in dichloromethane (350 mL). The reaction mixture was stirred overnight and then concentrated under reduced pressure. The residue was combined with water (300 mL) and heated at reflux with stirring for 1 hour. The reaction mixture was cooled and filtered. The isolated solid was washed with water and then dried under high vacuum to provide 18.5 g of $N^1$-(3-nitro[1,5]naphthyridin-4-yl)-2-methylpropane-1,2-diamine as a bright yellow powder.

Part B

Under a nitrogen atmosphere, a solution of sodium hydroxide (3.12 g, 78.0 mmol) in water (50 mL) was added to a solution of the material from Part A (18.5 g, 70.9 mmol) in tetrahydrofuran (200 mL). A solution of di-tert-butyl dicarbonate (17.0 g, 78.0 mmol) in tetrahydrofuran (100 mL) was added dropwise over a period of 30 minutes. Two (2) days later additional di-tert-butyl dicarbonate (2.0 g) was added. The reaction mixture was stirred for another 8 hours and then concentrated under reduced pressure. The residue was dissolved in ethyl acetate (250 mL), washed sequentially with water (×2) and brine, dried over sodium sulfate, filtered, and then concentrated under reduced pressure. The residue was dissolved in warm 1/1 ethyl acetate/hexanes. The solution was allowed to slowly cool. The resulting precipitate was isolated by filtration and washed with hexanes to provide 17.7 g of tert-butyl N-{2-[(3-nitro[1,5]naphthyridin-4-yl)amino]-1,1-dimethylethyl}carbamate as a bright yellow crystalline solid.

Part C

A Parr vessel was charged with a solution of tert-butyl N-{2-[(3-nitro[1,5]naphthyridin-4-yl)amino]-1,1-dimethylethyl}carbamate (12.62 g, 34.9 mmol) in acetonitrile (100 mL) and 5% Pt/C (2.00 g). The vessel was placed under hydrogen pressure (50 psi, 3.4×10$^5$ Pa) until hydrogen uptake ceased. The reaction mixture was filtered through a layer of CELITE filter aid and the filter cake was rinsed with acetonitrile. The filtrate was concentrated under reduced pressure to provide 11.07 g of tert-butyl N-{2-[(3-amino[1,5]naphthyridin-4-yl)amino]-1,1-dimethylethyl]carbamate as a bright yellow foam.

Part D

Under a nitrogen atmosphere, a solution of the material from Part C (11.07 g, 33.4 mmol) in dichloromethane (330 mL) was cooled to 0° C. Triethylamine (5.11 mL, 36.7 mmol) and ethoxyacetyl chloride (3.70 mL, 36.7 mmol) were added sequentially. The reaction mixture was stirred overnight while warming to ambient temperature and then concentrated under reduced pressure. The residue was dissolved in ethanol (300 mL). Triethylamine (16 mL) was added and the solution was heated at reflux under a nitrogen atmosphere over the weekend. The reaction mixture was allowed to cool to ambient temperature and then concentrated under reduced pressure. The residue was dissolved in dichloromethane (250 mL), washed sequentially with water and brine, dried over magnesium sulfate, filtered, and then concentrated under reduced pressure. The residue was purified by flash chromatography (6×12 cm silica gel column eluting with ethyl acetate) to provide 11.5 g of a purple foam. This material was purified by flash chromatography (eluting with 2.5% methanol in chloroform) to provide 10.07 g of tert-butyl N-[2-(2-ethoxymethyl-1H-imidazo[4,5-c][1,5]naphthyridin-1-yl)-1,1-dimethylethyl]carbamate a purple foam.

Part E

3-Chloroperoxybenzoic acid (7.50 g of 57-86%) was added to a solution of the material from Part D in dichloromethane (250 mL). After 2.5 hours, additional 3-chloroperoxybenzoic acid (250 mg) was added and the reaction mixture was stirred for 1.5 hours. The reaction mixture was washed sequentially with 1% sodium carbonate (4×75 mL), water, and brine, dried over sodium sulfate, filtered, and then concentrated under reduced pressure to provide 10.32 g of tert-butyl N-[2-(2-ethoxymethyl-5N-oxide-1H-imidazo[4,5-c][1,5]naphthyridin-1-yl)-1,1-dimethylethyl]carbamate as a purple foam.

Part F

Concentrated ammonium hydroxide (20 mL) was added to a solution of the material from Part E (10.32 g, 24.9 mmol) in dichloromethane (200 mL). Toluenesulfonyl chloride (5.02 g, 26.3 mmol) was added in small portions over a period of 2 minutes. The reaction mixture was stirred for 2 hours and then diluted with water. The layers were separated. The organic layer was washed sequentially with 1% sodium carbonate (×3), water, and brine, dried over sodium sulfate, filtered, and then concentrated under reduced pressure. The residue was purified by flash chromatography (6×15 cm column of silica gel, eluting with 10% CMA in chloroform) to provide about 8 g of a purple foam. The foam was dissolved in ethanol, combined with activated charcoal (2 g), heated at reflux for 15 minutes, filtered, and then concentrated under reduced pressure to provide 7.59 g of tert-butyl N-[2-(4-amino-2-ethoxymethyl-1H-imidazo[4,5-c][1,5]naphthyridin-1-yl)-1,1-dimethylethyl]carbamate as a violet foam.

Part G

A solution of hydrochloric acid in ethanol (17 mL of 4.3 M) was added to a solution of the material from Part F in ethanol (100 mL). The reaction mixture was heated at 90° C. for 2 hours, allowed to cool, and then concentrated under reduced pressure. The residue was dissolved in water (100 mL) and extracted with chloroform (2×25 mL). The extracts were discarded. The aqueous was made basic with concentrated ammonium hydroxide and then extracted with chloroform (4×50 mL). The combined extracts were dried over sodium sulfate, filtered, and then concentrated under reduced pressure. The residue was crystallized from ethyl acetate/hexanes (about 100 mL). The solid was isolated by filtration, rinsed with cold 20% ethyl acetate in hexanes, and dried under vacuum. A second crop was obtained and combined with the first crop to provide 3.82 g of 1-(2-amino-2-methylpropyl)-2-ethoxymethyl-1H-imidazo[4,5-c][1,5]naphthyridin-4-amine as a gray crystalline solid.

Part H

Under a nitrogen atmosphere, a solution of 1-(2-amino-2-methylpropyl)-2-ethoxymethyl-1H-imidazo[4,5-c][1,5]naphthyridin-4-amine (1.552 g, 4.94 mmol) in dichloromethane (50 mL) was cooled to 0° C. Triethylamine (1.38 mL, 9.92 mmol) and cyclohexylcarbonyl chloride (661 µL, 4.94 mmol) were added sequentially. Two (2) days later the reaction mixture was cooled and additional cyclohexylcarbonyl chloride (40 µL) was added. The reaction mixture was stirred overnight and then diluted with saturated sodium bicarbonate and dichloromethane (50 mL). The layers were separated. The organic layer was washed sequentially with water (×2) and brine, dried over sodium sulfate, filtered, and then concentrated under reduced pressure. The residue was purified by flash chromatography (4×13 cm silica gel column, eluting with 3% methanol in chloroform). The purified material was dissolved in refluxing propyl acetate (80 mL) with the aid of methanol, the methanol was boiled off, and the solution was allowed to slowly cool. The resulting precipitate was isolated by filtration, rinsed with cold propyl acetate, and dried under high vacuum at 70° C. to provide 1.37 g of N-[2-(4-amino-2-ethoxymethyl-1H-imidazo[4,5-c][1,5]naphthyridin-1-yl)-1,1-dimethylethyl]cyclohexanecarboxamide as a colorless crystalline solid, mp 210-211° C. Anal. calcd for $C_{23}H_{32}N_6O_2$: % C, 65.07; % H, 7.60; % N, 19.80. Found: % C, 64.93; % H, 7.76; % N, 19.97.

Part I

Boron tribromide (1.24 mL of 1 M in dichloromethane) was added dropwise to a chilled (ice bath) suspension of N-[2-(4-amino-2-ethoxymethyl-1H-imidazo[4,5-c][1,5]naphthyridin-1-yl)-1,1-dimethylethyl]cyclohexanecarboxamide (500 mg, 1.18 mmol) in dichloromethane (15 mL). The reaction mixture was allowed to slowly warm to ambient temperature and then stirred over the weekend. Additional boron tribromide (1 mL) was added and the reaction mixture was stirred for 24 hours. The reaction was quenched with methanol (10 mL) and then concentrated under reduced pressure. The residue was combined with hydrochloric acid (15 mL of 6 M), heated to 50° C., and stirred for 2 hours. The resulting solution was cooled to ambient temperature and then neutralized (pH 7) with 10% sodium hydroxide. The resulting gummy precipitate was extracted with chloroform (3×15 mL). The combined extracts were washed with brine (15 mL), dried over sodium sulfate, filtered, and then concentrated under reduced pressure to provide an off white solid. This material was purified by prep HPLC (HORIZON HPFC system, eluting with a gradient of 10-50% CMA in chloroform) to provide a white solid. The solid was triturated with hot acetonitrile, allowed to cool, isolated by filtration, and dried under vacuum to provide 233 mg of N-[2-(4-amino-2-hydroxymethyl-1H-imidazo[4,5-c][1,5]naphthyridin-1-yl)-1,1-dimethylethyl]cyclohexanecarboxamide as a fine white solid, mp 230-232° C.; $^1$H NMR (300 MHz, DMSO-d$_6$, 350 K) δ 8.53 (dd, J=4.3, 1.6 Hz, 1H), 7.95 (dd, J=8.4, 1.5 Hz, 1H), 7.87 (s, 1H), 7.47 (dd, J=8.4, 4.4 Hz, 1H), 6.55 (s, 2H), 5.31 (s, 1H), 5.15 (s, 2H), 4.79 (d, J=5.4 Hz, 2H), 1.90-1.80 (m, 1H), 1.67-1.43 (m, 5H), 1.31 (s, 6H), 1.24-1.02 (m, 5H); $^{13}$C NMR (75 MHz, DMSO-d$_6$) δ 175.9, 154.6, 152.8, 142.8, 140.8, 134.2, 133.5, 133.3, 129.3, 122.5, 56.4, 55.0, 52.3, 44.9, 29.4, 25.7, 25.6, 24.9; MS (ESI) m/z 397 (M+H)$^+$; Anal. Calcd for $C_{21}H_{28}N_6O_2$: C, 63.62; H, 7.12; N, 21.20. Found: C, 63.77; H, 7.34; N, 21.50.

Example 144

N-[2-(4-Amino-2-hydroxymethyl-1H-imidazo[4,5-c] [1,5]naphthyridin-1-yl)-1,1-dimethylethyl]methanesulfonamide

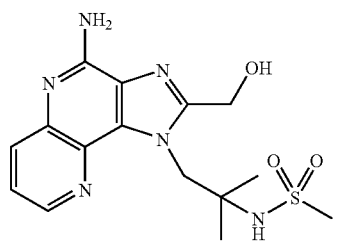 [SMILES: CC(C)(Cn1c(CO)nc2c(N)nc3cccnc3c21)NS(C)(=O)=O]

Part A

Under a nitrogen atmosphere, a solution of 1-(2-amino-2-methylpropyl)-2-ethoxymethyl-1H-imidazo[4,5-c][1,5] naphthyridin-4-amine (1.588 g, 5.06 mmol) in dichloromethane (50 mL) was cooled to 0° C. Triethylamine (1.41 mL, 10.12 mmol) and methanesulfonyl chloride (392 µL, 5.06 mmol) were added sequentially. The reaction mixture was allowed to slowly warm to ambient temperature overnight. Additional methanesulfonyl chloride (40 µL) was added and the reaction mixture was stirred at ambient temperature for an additional 5 hours. The reaction mixture was diluted with aqueous saturated sodium bicarbonate and the layers were separated. The organic layer was washed sequentially with water and brine, dried over sodium sulfate, filtered, and then concentrated under reduced pressure. The residue was purified by flash chromatography (4×15 cm silica gel column, eluting with a gradient of 5-7.5% methanol in chloroform). The purified material was dissolved in refluxing propyl acetate (80 mL) with the aid of methanol, the methanol was boiled off, and the solution was allowed to slowly cool. The resulting precipitate was isolated by filtration, rinsed with cold propyl acetate, and dried under high vacuum at 70° C. to provide 1.35 g of N-[2-(4-amino-2-ethoxoxymethyl-1H-imidazo[4,5-c][1,5]naphthyridin-1-yl)-1,1-dimethylethyl]methanesulfonamide as colorless needles, mp 209-210° C. Anal. calcd for $C_{17}H_{24}N_6O_3S$: % C, 52.02; % H, 6.16; % N, 21.41. Found: % C, 52.09; % H, 6.35; % N, 21.60.

Part B

Boron tribromide (1.34 mL of 1 M in dichloromethane) was added dropwise to a chilled (ice bath) suspension of N-[2-(4-amino-2-ethoxoxymethyl-1H-imidazo[4,5-c][1,5] naphthyridin-1-yl)-1,1-dimethylethyl]methanesulfonamide (500 mg, 1.27 mmol) in dichloromethane (15 mL). The reaction mixture was allowed to slowly warm to ambient temperature and then stirred over the weekend. Additional boron tribromide (1.5 mL) was added and the reaction mixture was stirred for 4 hours. Additional boron tribromide (1.5 mL) was added and the reaction mixture was stirred overnight. The reaction was quenched with methanol (15 mL) and then concentrated under reduced pressure. The residue was combined with hydrochloric acid (15 mL of 6 M), heated to 50° C., and stirred for 2 hours. The resulting solution was cooled to ambient temperature and then neutralized (pH 7) with 10% sodium hydroxide. The resulting precipitate was isolated by filtration and rinsed with water to provide a white solid. This material was purified by prep HPLC (HORIZON HPFC system, eluting with a gradient of 10-50% CMA in chloroform) to provide a white solid. This material was recrystallized from acetonitrile and dried in a vacuum oven to provide 103 mg of N-[2-(4-amino-2-hydroxymethyl-1H-imidazo[4,5-c][1,5]naphthyridin-1-yl)-1,1-dimethylethyl]methanesulfonamide as a white crystalline solid, mp 268-271° C.; $^1$H NMR (300 MHz, DMSO-$d_6$) δ 8.50 (dd, J=4.4, 1.6 Hz, 1H), 7.95 (dd, J=8.4, 1.5 Hz, 1H), 7.90 (s, 1H), 7.48 (dd, J=8.4, 4.4 Hz, 1H), 6.91 (s, 2H), 5.62 (t, J=5.9 Hz, 1H), 5.10 (bs, 2H), 4.92 (s, 2H), 2.87 (s, 3H), 1.35 (s, 6H); $^{13}$C NMR (75 MHz, DMSO-$d_6$) δ 154.2, 152.3, 142.3, 140.3, 133.4, 133.1, 132.9, 128.8, 122.1, 57.2, 56.4, 54.3, 44.1, 25.1; MS (APCI) m/z 365 (M+H)$^+$; Anal. Calcd for $C_{15}H_{20}N_6O_3S$: C, 49.44; H, 5.53; N, 23.06. Found: C, 49.48; H, 5.40; N, 23.31.

Example 145

N-{4-{4-Amino-2-(2-hydroxyethyl)-1H-imidazo[4, 5-c][1,5]naphthyridin-1-yl] butyl}methanesulfonamide

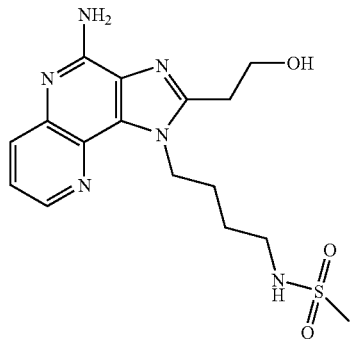 [SMILES: CS(=O)(=O)NCCCCn1c(CCO)nc2c(N)nc3cccnc3c21]

Part A

3-Methoxypropionyl chloride (2.7 g, 22 mmol) was added dropwise to a chilled (ice bath) solution of tert-butyl N-{4-[(3-amino[1,5]naphthyridin-4-yl)amino]butyl}carbamate 6.7 g, 20 mmol, U.S. Pat. No. 6,194,425, Example 42) in anhydrous pyridine (75 mL). The reaction mixture was heated at 120° C. overnight. The reaction was repeated on the same scale. The reaction mixtures were combined and concentrated under reduced pressure to provide 28 g of crude tert-butyl N-((4-{([3-(3-methoxypropionyl)amino[1,5]naphthyridin-4-yl]amino}butyl))carbamate as a red oil.

Part B

The crude material from Part A was dissolved in pyridine (150 mL). Pyridine hydrochloride (2.1 g) was added and the reaction mixture was heated at reflux overnight. The reaction mixture was concentrated under reduced pressure. The residue was diluted with dichloromethane and washed with brine. The aqueous layer was extracted with dichloromethane (×4). The combined organics were concentrated under reduced pressure. The residue was purified by prep HPLC (COMBI-FLASH system eluting with a gradient of 0-7% methanol in dichloromethane containing 1% ammonium hydroxide) to provide 9.72 g of tert-butyl N-{4-[2-(2-methoxyethyl)-1H-imidazo[4,5-c][1,5]naphthyridin-1-yl]butyl}carbamate as a brown glassy solid.

Part C

3-Chloroperoxybenzoic acid (7.8 g of 77%) was added in a single portion to a solution of tert-butyl N-{4-[2-(2-methoxyethyl)-1H-imidazo[4,5-c][1,5]naphthyridin-1-yl]butyl}carbamate (7 g) in dichloroethane (100 mL). The reaction mixture was stirred at ambient temperature for 3 hours. Concentrated ammonium hydroxide (100 mL) was added and the reaction mixture was stirred until a suspension formed. Para-toluenesulfonyl chloride (3.6 g) was added in a single portion. The reaction mixture was stirred at ambient temperature for 2 hours and then diluted with dichloromethane and brine. The organic layer was separated, washed with brine (×2), dried over magnesium sulfate, filtered through a layer of CELITE filter aid, and then concentrated under reduced pressure to provide 8.83 g of crude tert-butyl N-{4-[4-amino-2-(2-methoxyethyl)-1H-imidazo[4,5-c][1,5]naphthyridin-1-yl]butyl}carbamate as a brown solid.

Part D

The material from Part C was diluted with a small amount of dichloromethane and then hydrochloric acid in dioxane (126 mL of 4 M) was slowly added. The reaction mixture was stirred at ambient temperature overnight and then concentrated under reduced pressure. The residue was purified by prep HPLC (COMBIFLASH system eluting with a gradient of 0-7% methanol in dichloromethane containing 1% ammonium hydroxide) to provide 8 g of crude 1-(4-aminobutyl)-2-(2-methoxyethyl)-1H-imidazo[4,5-c][1,5]naphthyridin-4-amine.

Part E

Triethylamine (3.9 mL) was added to a solution of a portion (1.8 g) of the material from Part D in pyridine (20 mL). Methanesulfonyl chloride (485 µL) was added dropwise. The reaction mixture was stirred at ambient temperature for 2 hours, quenched with water (25 mL), and the stirred overnight. The reaction mixture was concentrated under reduced pressure and then diluted with dichloromethane. The organic layer was washed with brine (×2) and then concentrated under reduced pressure. The residue was purified by prep HPLC (COMBIFLASH system eluting with a gradient of 0-5% methanol in dichloromethane containing 1% ammonium hydroxide for 5 minutes and then holding at 5%) to provide 400 mg of N-{4-{4-amino-2-(2-methoxyethyl)-11H-imidazo[4,5-c][1,5]naphthyridin-1-yl]butyl}methanesulfonamide.

Part F

Boron tribromide (2.55 mL of 1 M in dichloromethane) was slowly added to a chilled mixture of the material from Part E in dichloromethane (10 mL). The reaction mixture was stirred at ambient temperature overnight and then concentrated under reduced pressure. The residue was dissolved in methanol, combined with hydrochloric acid (50 mL of 6 M), heated at 50° C. for 2 hours, and concentrated under reduced pressure. The residue was combined with a solution of ammonia in methanol (about 50 mL of 7 M) and then concentrated again. This procedure was repeated 3 times. The residue from the final concentration was purified by prep HPLC (COMBIFLASH system eluting with a gradient of 0-10% methanol in dichloromethane containing 1% ammonium hydroxide for 10 minutes). The combined fractions were concentrated and then distributed onto solid phase extraction cartridges. The cartridges were eluted with ammonia in methanol (7 M). The resulting material was triturated with hot acetonitrile, cooled, isolated, and then dried in a vacuum oven to provide 111 mg of N-{4-{4-amino-2-(2-hydroxyethyl)-1H-imidazo[4,5-c][1,5]naphthyridin-1-yl]butyl}methanesulfonamide, mp 194-195° C. Anal. calcd for $C_{16}H_{22}N_6O_3S$: % C, 50.78; % H, 5.86; % N, 22.21. Found: % C, 50.83; % H, 6.12; % N, 21.70.

Example 146

N-[2-(4-Amino-2-hydroxymethyl-1H-imidazo[4,5-c][1,5]naphthyridin-1-yl)ethyl]methanesulfonamide

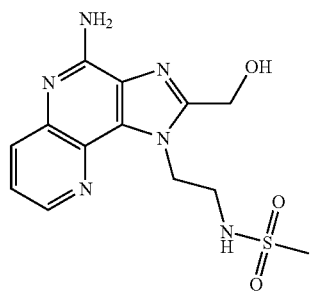 [SMILES: CS(=O)(=O)NCCn1c(CO)nc2c(N)nc3cccnc3c21]

Part A

Methoxyacetyl chloride (5.9 g, 54 mmol) was added dropwise to a chilled (ice bath) solution of tert-butyl N-{2-[(3-amino[1,5]naphthyridin-4-yl)amino]ethyl}carbamate (15.0 g, 49.5 mmol, U.S. Pat. No. 6,194,425, Example 87) in anhydrous pyridine (100 mL). The reaction mixture was heated at reflux until analysis by liquid chromatography/mass spectroscopy (LCMS) indicated that the reaction was complete. The reaction mixture was concentrated under reduced pressure. The residue was diluted with ethanol (100 mL), combined with potassium carbonate solution (200 mL of 2 M), and heated at reflux for 4 hours. The reaction mixture was cooled and then concentrated under reduced pressure. The residue was partitioned between water and dichloromethane. The aqueous layer was extracted with dichloromethane. The combined organics were dried over magnesium sulfate, filtered, and then concentrated under reduced pressure to provide 14 g of tert-butyl N-[2-(2-methoxymethyl-1H-imidazo[4,5-c][1,5]naphthyridin-1-yl)ethyl]carbamate.

Part B

Using the method of Example 145 Part C, the material from Part A was oxidized and then aminated to provide 17 g of crude tert-butyl N-[2-(4-amino-2-methoxymethyl-1H-imidazo[4,5-c][1,5]naphthyridin-1-yl)ethyl]carbamate as a sticky amber solid.

Part C

The material from Part B was dissolved in a mixture of dichloromethane (20 mL) and methanol (5 mL). Hydrochloric acid in dioxane (28 mL of 4 M) was added. More dichloromethane was added to facilitate stirring. The reaction mixture was stirred at ambient temperature overnight and then concentrated under reduced pressure to provide crude 1-(2-aminoethyl)-2-methoxymethyl-1H-imidazo[4,5-c][1,5]naphthyridin-4-amine as an orange solid.

Part D

Triethylamine (35.6 mL) was added to a mixture of the material from Part C and pyridine (100 mL). The reaction mixture was cooled in an ice bath and then methanesulfonyl chloride (4.3 mL) was added dropwise. The reaction mixture was stirred at ambient temperature for 1 hour. Twice, more methanesulfonyl chloride (0.43 mL) was added and the reaction mixture was stirred at ambient temperature for 2 hours. The reaction mixture was partitioned between water and dichloromethane. The aqueous layer was extracted with dichloromethane (×2). The combined organics were dried over magnesium sulfate, filtered through a layer of CELITE filter aid, and then concentrated under reduced pressure to provide 14 g of N-[2-(4-amino-2-methoxymethyl-1H-imidazo[4,5-c][1,5]naphthyridin-1-yl)ethyl]methanesulfonamide.

Part E

Boron tribromide (71.4 mL of 1 M in dichloromethane) was slowly added to a chilled (ice bath) mixture of the material from Part D in dichloromethane (50 mL). The reaction mixture was stirred at ambient temperature for 2 hours. Additional boron tribromide (0.5 eq) was added and the reaction mixture was stirred at ambient temperature overnight. The reaction mixture was concentrated under reduced pressure. The residue was dissolved in methanol, combined with hydrochloric acid (50 mL of 6 M), heated at 50° C. for 2 hours, and concentrated under reduced pressure. The residue was combined with a solution of ammonia in methanol (about 40 mL of 7 M) and then concentrated again. This procedure was repeated 3 times. The residue from the final concentration was purified by prep HPLC (COMBIFLASH system eluting with a gradient of 0-5% methanol in dichloromethane containing 1% ammonium hydroxide with a 10 minute ramp and a 20 minute hold, then with gradient of 6-10% methanol in dichloromethane containing 1% ammonium hydroxide with a 10 minute ramp and a 20 minute hold, and finally with gradient of 11-20% methanol in dichloromethane containing 1% ammonium hydroxide with a 10 minute ramp and a 20 minute hold) to provide 2.4 g of a brown solid. A small portion of this material was combined with hot acetonitrile containing a small amount of methanol, cooled, and then isolated by filtration. This procedure was carried out 3 times. After the final isolation the material was rinsed with ether and dried in a vacuum oven to provide 75 mg of N-[2-(4-amino-2-hydroxymethyl-1H-imidazo[4,5-c][1,5]naphthyridin-1-yl)ethyl]methanesulfonamide as a beige solid, mp 239-242° C. Anal. calcd for $C_{13}H_{16}N_6O_3S$: % C, 46.42; % H, 4.79; % N, 24.98. Found: % C, 46.35; % H, 4.70; % N, 24.70.

Example 147

N-{2-[4-Amino-2-(2-hydroxyethyl)-1H-imidazo[4,5-c][1,5]naphthyridin-1-yl]ethyl}methanesulfonamide

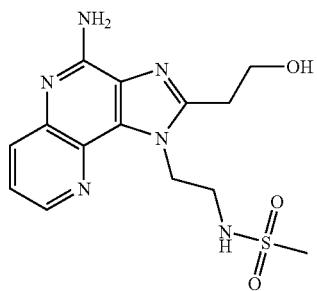 [SMILES: CS(=O)(=O)NCCn1c(CCO)nc2c(N)nc3cccnc3c21]

Part A

Using the general method of Example 146 Part A, tert-butyl N-{2-[(3-amino[1,5]naphthyridin-4-yl)amino]ethyl}carbamate (17.0 g, 56.1 mmol) was reacted with 3-methoxypropionyl chloride (7.5 g, 61.7 mmol) to provide 9.0 g of crude product. Analysis by LCMS indicated that the crude product was about a 1:1 mixture of tert-butyl N-{2-[2-(2-methoxyethyl)-1H-imidazo[4,5-c][1,5]naphthyridin-1-yl]ethyl}carbamate and 1-(2-aminoethyl)-2-(2-methoxyethyl)-1H-imidazo[4,5-c][1,5]naphthyridine.

Part B

Triethylamine (13.8 mL) was added to a mixture of the material from Part A and dichloromethane (70 mL). The resulting solution was chilled in an ice bath. Di-tert-butyl dicarbonate (8.6 g) was added. The reaction mixture was stirred at ambient temperature for 2 hours and then quenched with water. The layers were separated. The organic layer was washed with sodium carbonate, dried over magnesium sulfate, filtered through a layer of CELITE filter aid, and then concentrated under reduced pressure to provide 11 g of tert-butyl N-{2-[2-(2-methoxyethyl)-1H-imidazo[4,5-c][1,5]naphthyridin-1-yl]ethyl}carbamate as a tan solid.

Part C

3-Chloroperoxybenzoic acid (13.2 g of 77%) was added in a single portion to a solution of the material from Part B (11 g, 29.6 mmol) in dichloroethane (50 mL). The reaction mixture was stirred at ambient temperature for 1.5 hours, then diluted with dichloromethane and washed with aqueous ammonium hydroxide (25 mL of concentrated ammonium hydroxide in 250 mL of water). The aqueous layer was extracted with dichloromethane. The combined organics were concentrated under reduced pressure. The residue was dissolved in dichloroethane (100 mL). Concentrated ammonium hydroxide (70 mL) was added and the reaction mixture was stirred until a suspension formed. Para-Toluenesulfonyl chloride (6.2 g, 32.5 mmol) was added in a single portion. The reaction mixture was stirred at ambient temperature for 1.5 hours, then diluted with aqueous sodium bicarbonate and extracted with dichloromethane (×3). The combined organics were dried over magnesium sulfate, filtered through a layer of CELITE filter aid, and then concentrated under reduced pressure. The residue was purified by prep HPLC (COMBIFLASH system eluting with a gradient of 0-5% methanol in dichloromethane containing 1% ammonium hydroxide over 6 minutes and then holding at 5%) to provide 3.5 g of tert-butyl N-{2-[4-amino-2-(2-methoxyethyl)-1H-imidazo[4,5-c][1,5]naphthyridin-1-yl]ethyl}carbamate as an orange solid.

Part D

A solution of hydrochloric acid in dioxane (58 mL of 4 M) was added to a solution of tert-butyl N-{2-[4-amino-2-(2-methoxyethyl)-1H-imidazo[4,5-c][1,5]naphthyridin-1-yl]ethyl}carbamate (3 g) in a small amount of dichloromethane/methanol. The reaction mixture was stirred overnight at ambient temperature and then concentrated under reduced pressure to provide 3.7 g of crude 1-(2-aminoethyl)-2-(2-methoxyethyl)-1H-imidazo[4,5-c][1,5]naphthyridine-4-amine hydrochloride.

Part E

Using the general method of Example 146 Part D, a portion (1.1 g) of the material from Part D was reacted with methanesulfonyl chloride (322 μL) to provide 1.0 g of N-{2-[4-amino-2-(2-methoxyethyl)-1H-imidazo[4,5-c][1,5]naphthyridin-1-yl]ethyl}methanesulfonamide as a red solid.

Part F

Boron tribromide (7 mL of 1 M in dichloromethane) was slowly added to a chilled (ice bath) mixture of the material from Part E in dichloromethane (25 mL). The reaction mixture was stirred at ambient temperature overnight and then concentrated under reduced pressure. The residue was dissolved in methanol, combined with hydrochloric acid (50 mL of 6 M), heated at 50° C. for 2 hours, and concentrated under reduced pressure. The residue was combined with a solution of ammonia in methanol (about 30 mL of 7 M) and then concentrated again. This procedure was repeated 3 times. The residue from the final concentration was purified by prep HPLC (COMBIFLASH system eluting with a gradient of 0-10% methanol in dichloromethane containing 1% ammonium hydroxide). The residue was combined with hot acetonitrile, cooled, and the acetonitrile was decanted off. This procedure was carried out 3 times. The material was isolated by filtration, rinsed with ether and dried in a vacuum oven to provide 950 mg of N-{2-[4-amino-2-(2-hydroxyethyl)-1H-imidazo[4,5-c][1,5]naphthyridin-1-yl]ethyl}methanesulfonamide, mp 136-138° C. Anal. calcd for $C_{14}H_{18}N_6O_3S$: % C, 47.99; % H, 5.18; % N, 23.98. Found: % C, 47.69; % H, 5.36; % N, 23.77.

Example 148

1-(4-Amino-2-hydroxymethyl-1H-imidazo[4,5-c][1,5]naphthyridin-1-yl)-2-methylpropan-2-ol

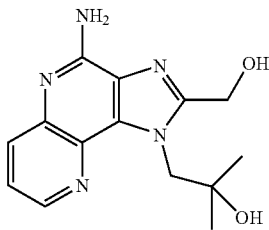 [SMILES: CC(C)(O)Cn1c(CO)nc2c(N)nc3cccnc3c21]

Part A

Under a nitrogen atmosphere, 1-amino-2-methylpropan-2-ol (25.5 g, 0.28 mol) was added over a period of 30 minutes to a solution of 4-chloro-3-nitro[1,5]naphthyridine (54.5 g, 0.26 mol) in dichloromethane (1 L). A water bath was used to control the exotherm and maintain the temperature of the reaction at or below 27° C. The reaction mixture was stirred at ambient temperature overnight. The resulting precipitate (crop 1) was isolated by filtration. The filtrate was concentrated under reduced pressure to provide crop 2. The two crops were slurried separately with de-ionized water for 2 hours and then isolated by filtration. Crop 1: 40.53 g of 2-methyl-2-[(3-nitro[1,5]naphthyridin-4-yl)amino]propan-2-ol as a yellow solid. Crop 2: tan solid. Crop 2 was dissolved in dichloromethane and loaded onto an alumina column. The column was eluted first with 1% methanol in dichloromethane and then with acetone. The combined eluents were concentrated under reduced pressure. The residue was recrystallized from ethanol (10 mL/g) to provide 6.95 g of 2-methyl-1-[(3-nitro[1,5]naphthyridin-4-yl)amino]propan-2-ol.

Part B

A Parr vessel was charged with 2-methyl-1-[(3-nitro[1,5]naphthyridin-4-yl)amino]propan-2-ol (44.12 g, 0.17 mol), 5% Pt/C (4.4 g) and isopropyl alcohol (890 mL). The vessel was placed under hydrogen pressure (35 psi, $2.4 \times 10^5$ Pa) until hydrogen uptake ceased. The reaction mixture was filtered through a layer of filter aid. The filter cake was rinsed with additional isopropyl alcohol. The filtrate was concentrated under reduced pressure to provide 1-[(3-amino[1,5]naphthyridin-4-yl)amino]-2-methylpropan-2-ol as a thick oil.

Part C

Under a nitrogen atmosphere, ethoxyacetyl chloride (19.1 g, 0.156 mol) was added over a period of 12 minutes to a mixture of 1-[(3-amino[1,5]naphthyridin-4-yl)amino]-2-methylpropan-2-ol (28.95 g, 0.125 mol) in pyridine (300 mL). The reaction mixture was stirred at ambient temperature for 4 hours and then at reflux for 4 hours. The reaction mixture was allowed to cool to ambient temperature overnight and then concentrated under high vacuum. The residue was dissolved in 5% potassium carbonate (200 mL) and then extracted with dichloromethane (200 mL). The extract was filtered to remove some insoluble material, dried over magnesium sulfate, filtered, and then concentrated under high vacuum. The residue was dissolved in dichloromethane (150 mL) and eluted through a short column of alumina. The eluent was concentrated under reduced pressure and air dried to provide 31.9 g of 1-(2-ethoxymethyl-1H-imidazo[4,5-c][1,5]naphthyridin-1-yl)-2-methylpropan-2-ol.

Part D

A flask containing a solution of 1-(2-ethoxymethyl-1H-imidazo[4,5-c][1,5]naphthyridin-1-yl)-2-methylpropan-2-ol (29.94 g, 83 mmol) in dichloromethane (300 mL) was covered with aluminum foil. 3-Chloroperoxybenzoic acid (28.65 g of 50%) was added in portions over a period of 50 minutes. The reaction mixture was stirred for an additional 40 minutes, then diluted with 5% aqueous potassium carbonate and stirred. The organic layer was separated, washed with brine (100 mL), dried over magnesium sulfate, filtered, and then concentrated under reduced pressure to provide a yellow paste. This material was combined with ether (100 mL) and stirred overnight. The resulting solid was isolated by filtration to provide 11.84 g of 1-(2-ethoxymethyl-5-oxo-1H-imidazo[4,5-c][1,5]naphthyridin-1-yl)-2-methylpropan-2-ol. The aqueous potassium carbonate layer was partially concentrated, saturated with additional potassium carbonate, and then extracted with dichloromethane. The extract was dried over magnesium sulfate, filtered, and then concentrated under reduced pressure to provide 15.23 g of a dark oil. The oil was combined with ether (100 mL) and stirred overnight. The resulting solid was isolated by filtration to provide 11.51 g of 1-(2-ethoxymethyl-5-oxo-1H-imidazo[4,5-c][1,5]naphthyridin-1-yl)-2-methylpropan-2-ol.

Part E

Concentrated ammonium hydroxide (241 mL) was added to a solution of 1-(2-ethoxymethyl-5-oxo-1H-imidazo[4,5-c][1,5]naphthyridin-1-yl)-2-methylpropan-2-ol (23.35 g, 74 mmol) in dichloromethane (300 mL). A solution of para-toluenesulfonyl chloride (15.52 g, 81 mmol) in dichloromethane (50 mL) was added with rapid stirring over a period of 25 minutes. The reaction mixture was stirred overnight. Concentrated ammonium hydroxide (25 mL) and a solution of para-toluenesulfonyl chloride (2 g) in dichloromethane (10 mL) was added and the reaction mixture was stirred for 5 hours. The organic phase was separated, washed with a solution of potassium carbonate (16 g) in water (300 mL), dried over magnesium sulfate, filtered, and concentrated under reduced pressure to provide 30.17 g of crude product. This material was combined with acetonitrile (300 mL), stirred, heated to reflux, and then allowed to cool with stirring to ambient temperature. The resulting solid was isolated by filtration and then dried at 75° C. under vacuum to provide 14.4 g of a solid. This material was recrystallized from ethyl acetate (17.5 mL/g), isolated by filtration, and then dried under vacuum at 75° C. for 22 hours to provide 12.29 g of 1-(4-amino-2-ethoxymethyl-1H-imidazo[4,5-c][1,5]naphthyridin-1-yl)-2-methylpropan-2-ol as an off white solid, mp 157-159° C. Anal. calcd for $C_{16}H_{21}N_5O_2$: % C, 60.94; % H, 6.71; % N, 22.21. Found: % C, 61.06; % H, 6.67; % N, 22.37.

Part F

A solution of boron tribromide in dichloromethane (11.8 mL of 1 M) was added to a chilled (0° C.) suspension of 1-(4-amino-2-ethoxymethyl-1H-imidazo[4,5-c][1,5]naphthyridin-1-yl)-2-methylpropan-2-ol hydrobromide (1.24 g, 3.93 mmol) in dichloromethane (30 mL). The reaction mixture was allowed to come to ambient temperature with stirring for 16 hours. Methanol (15 mL) and hydrochloric acid (10 mL of 6 N) were added and the reaction mixture was heated at reflux for 2.5 hours. The reaction mixture was made basic with sodium hydroxide and the layers were separated. The aqueous layer was extracted with ethyl acetate (3×100 mL). The combined extracts were washed sequentially with water and brine, dried over magnesium sulfate, and then concentrated under reduced pressure to provide a white solid. This material was crystallized from ethyl acetate and then dried under vacuum at 95° C. for 16 hours to provide 0.55 g of 1-(4-amino-2-hydroxymethyl-1H-imidazo[4,5-c][1,5]naphthyridin-1-yl)-2-methylpropan-2-ol as a white powder, mp 235-237° C. Anal. calcd for $C_{14}H_{17}N_5O_2$: % C, 58.52; % H, 5.96; % N, 24.37. Found: % C, 58.40; % H, 5.82; % N, 24.45.

Example 149

1-[4-Amino-2-(2-hydroxyethyl)-1H-imidazo[4,5-c][1,5]naphthyridin-1-yl]-2-methylpropan-2-ol

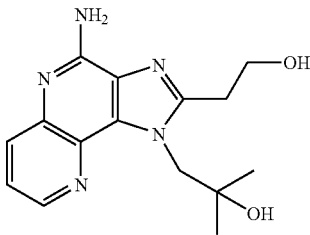 [SMILES: CC(C)(O)Cn1c(CCO)nc2c(N)nc3cccnc3c21]

Part A

A mixture of triethyl orthoformate (10 mL, 60.1 mmol) and 2,2-dimethyl-[1,3]-dioxane-4,6-dione (40.9 g, 0.23 mol) (Meldrum's acid) was heated at 92° C. for 90 minutes and then cooled to 70° C. over one hour. 3-Amino-5-bromopyridine (40.9 g, 0.20 mol) was slowly added over 10 minutes with an ethanol rinse while maintaining the reaction temperature between 60 and 70° C. The reaction was then heated for an additional 20 minutes and allowed to cool to room temperature. The reaction mixture was filtered and washed with ethanol (150 mL) yielding a tan solid. The solid was dried under vacuum for 2 hours to yield 59.14 g of 5-{[(5-bromopyridin-3-yl)imino]methyl}-2,2-dimethyl-1,3-dioxane-4,6-dione as a light yellow crystalline solid, mp 200-202° C.

Part B

5-{[(5-Bromopyridin-3-yl)imino]methyl}-2,2-dimethyl-1,3-dioxane-4,6-dione (59 g, 0.18 mol) was slowly added to DOWTHERM A heat transfer fluid (2000 mL) over a period of 5 minutes at 235-238° C. Following addition, the reaction was maintained for an additional 5 minutes and then allowed to cool to 40° C. A brown precipitate formed, which was filtered and washed with hexanes (150 mL). The brown solid was suspended in an ethanol/water mixture (90:10, 1500 mL), heated to a boil for 30 minutes, isolated by filtration, and washed with ethanol (200 mL) to yield 30.8 g of 7-bromo[1,5]naphthyridin-4-ol as a dark brown powder.

Part C

A mixture of 7-bromo[1,5]naphthyridin-4-ol (33 g, 0.147 mol) and fuming nitric acid (350 mL) was heated at reflux (90° C. internal reaction vessel temperature) for 3 hours. The reaction mixture was cooled to 50° C., poured over 1 L of ice and neutralized to pH 2-3 with a solution of 50% aqueous sodium hydroxide. The resulting precipitate was filtered, washed with water, and dried over vacuum for 3 days to yield 25.1 g of 7-bromo-3-nitro[1,5]naphthyridin-4-ol as a yellow crystalline solid.

Part D

Phosphorous oxychloride (16.76 g, 10.19 mL, 109.3 mmol) was added slowly dropwise to a suspension of 7-bromo-3-nitro[1,5]naphthyridin-4-ol (21.09 g, 78.1 mmol) in N,N-dimethylformamide (250 mL) (DMF) at ambient temperature and maintained overnight. The reaction mixture was then added to ice water (400 mL) with stirring. A solid precipitate formed, which was isolated by vacuum filtration and washed with water. The material was dried under high vacuum at ambient temperature overnight to yield 20.79 g of 7-bromo-4-chloro-3-nitro[1,5]naphthyridine as a tan solid.

Part E

Triethylamine (35.95 mL, 257.9 mmol) was added to a suspension of 7-bromo-4-chloro-3-nitro[1,5]naphthyridine (49.6 g, 172 mmol) in dichloromethane (500 mL). 1-Amino-2-methylpropan-2-ol (16.86 g, 189 mmol) was added dropwise. The reaction mixture was stirred at ambient temperature for 16 hours and then concentrated under reduced pressure. The residue was triturated with water and stirred for 1 hour. The precipitated solid was isolated by filtration, washed with water, and dried. This material was suspended in diethyl ether (400 mL), sonicated, isolated by filtration, and then dried in a vacuum oven at 40° C. for 16 hours to provide 58.1 g of 1-[(7-bromo-3-nitro[1,5]naphthyridin-4-yl)amino]-2-methylpropan-2-ol as a yellow solid, mp 189-190° C.

Part F

A Parr vessel was charged with 5% Pt/C (5.8 g) and a suspension of 1-[(7-bromo-3-nitro[1,5]naphthyridin-4-yl)amino]-2-methylpropan-2-ol (58.00 g) in acetonitrile (800 mL) and methanol (400 mL). The vessel was placed under hydrogen pressure (30 psi, $2.1 \times 10^5$ Pa) for 8 hours. The reaction mixture was filtered through a layer of CELITE filter aid. The filtrate was concentrated under reduced pressure to provide 52.70 g of 1-[(3-amino-7-bromo[1,5]naphthyridin-4-yl)amino]-2-methylpropan-2-ol as a yellow foam.

Part G

3-Methoxypropionyl chloride (24.90 g, 203 mmol) was added over a period of 5 minutes to a mixture of 1-[(3-amino-7-bromo[1,5]naphthyridin-4-yl)amino]-2-methylpropan-2-ol (52.70 g, 169 mmol), chloroform (100 mL), and acetonitrile (530 mL). The reaction mixture was stirred at ambient temperature overnight. The precipitated solid was isolated by filtration, washed well with acetonitrile, and then dried to provide 60.10 g of N-{7-bromo-4-[(2-hydroxy-2-methylpropyl)amino][1,5]naphthyridin-3-yl}-3-methoxypropionamide hydrochloride as a brown solid, mp 206-208° C.

Part H

A mixture of N-{7-bromo-4-[(2-hydroxy-2-methylpropyl)amino][1,5]naphthyridin-3-yl}-3-methoxypropionamide hydrochloride (60.00 g, 138 mmol), potassium carbonate (60 g), water (300 mL), and ethanol (900 mL) was heated at reflux for 16 hours and then concentrated under reduced pressure. The precipitated solid was isolated by filtration, washed sequentially with water and methanol, and dried to provide a brown solid. This material was dissolved in a 3/1 mixture of chloroform/methanol and decolorized with activated charcoal to provide 38.5 g of 1-[7-bromo-2-(2-methoxyethyl)-1H-imidazo[4,5-c][1,5]naphthyridin-1-yl]-2-methylpropan-2-ol as a white solid, mp 125° C. Anal. calcd for $C_{16}H_{19}BrN_4O_2$: % C, 50.67; % H, 5.05; % N, 14.77. Found: % C, 50.86; % H, 4.94; % N, 15.01.

Part I

3-Chloroperoxybenzoic acid (34.77 g of 75%, 151 mmol) was added to a solution of 1-[7-bromo-2-(2-methoxyethyl)-1H-imidazo[4,5-c][1,5]naphthyridin-1-yl]-2-methylpropan-2-ol (38.2 g, 101 mmol) in dichloromethane (450 mL) and the reaction mixture was stirred for 3 hours. The reaction mixture was diluted with dichloromethane (200 mL), washed sequentially with 4% aqueous sodium carbonate (2×150 mL) and brine (1×150 mL), and concentrated under reduced pressure to provide the N-oxide derivative. The N-oxide derivative was combined with dichloromethane (450 mL) and concentrated ammonium hydroxide (200 mL) and the mixture was cooled in an ice bath. Para-Toluenesulfonyl chloride (24 g) was added in portions. After the addition was complete the ice bath was removed and the reaction mixture was stirred at ambient temperature for 16 hours. The reaction mixture was diluted with dichloromethane (200 mL). Suspended solids were isolated by filtration, washed with water, and dried to provide 7.60 g of 1-[4-amino-7-bromo-2-(2-methoxyethyl)-1H-imidazo[4,5-c][1,5]naphthyridin-1-yl]-2-methylpropan-2-ol as an off white solid, mp 210-211° C. Anal. calcd for $C_{16}H_{20}BrN_5O_2$: % C, 48.74; % H, 5.11; % N, 17.76. Found: % C, 48.63; % H, 5.10; % N, 17.80.

Part J

A Parr vessel was charged with 10% Pd/C (0.6 g) and a suspension of 1-[4-amino-7-bromo-2-(2-methoxyethyl)-1H-imidazo[4,5-c][1,5]naphthyridin-1-yl]-2-methylpropan-2-ol (4.0 g) in acetonitrile (150 mL) and methanol (50 mL). The vessel was placed under hydrogen pressure (50 psi, $3.4×10^5$ Pa) for 3 hours. The reaction mixture was diluted with 1/1 chloroform/methanol (100 mL), filtered through a layer of CELITE filter aid, and concentrated under reduced pressure. The residue was triturated with acetonitrile to provide 3.55 g of 1-[4-amino-2-(2-methoxyethyl)-1H-imidazo[4,5-c][1,5]naphthyridin-1-yl]-2-methylpropan-2-ol hydrobromide as a white powder, mp 234-235° C. Anal. calcd for $C_{16}H_{22}BrN_5O_2$: % C, 48.49; % H, 5.60; % N, 17.67. Found: % C, 48.64; % H, 5.69; % N, 17.62.

Part K

A solution of boron tribromide in dichloromethane (22.71 mL of 1 M) was added to a chilled (0° C.) suspension of 1-[4-amino-2-(2-methoxyethyl)-1H-imidazo[4,5-c][1,5]naphthyridin-1-yl]-2-methylpropan-2-ol hydrobromide (3.00 g, 7.57 mmol) in dichloromethane (100 mL). The reaction mixture was allowed to come to ambient temperature with stirring for 16 hours. Methanol (30 mL) and hydrochloric acid (30 mL of 6 N) were added and the reaction mixture was heated at reflux for 2.5 hours. The reaction mixture was made basic with sodium hydroxide and the layers were separated. The aqueous layer was extracted with dichloromethane (100 mL). The extract was washed sequentially with water and brine, dried over magnesium sulfate, and then concentrated under reduced pressure to provide a pink solid. This material was crystallized from acetonitrile to provide 0.68 g of 1-[4-amino-2-(2-hydroxyethyl)-1H-imidazo[4,5-c][1,5]naphthyridin-1-yl]-2-methylpropan-2-ol. The aqueous layer was combined with the water and brine washings and allowed to stand overnight. A precipitate was isolated by filtration, washed with water, and dried under vacuum at 95° C. for 3 hours to provide 1.16 g of 1-[4-amino-2-(2-hydroxyethyl)-1H-imidazo[4,5-c][1,5]naphthyridin-1-yl]-2-methylpropan-2-ol as a pink crystalline solid, mp 194-195° C. Anal. calcd for $C_{15}H_{19}N_5O_2$: % C, 59.79; % H, 6.36; % N, 23.24. Found: % C, 59.51; % H, 6.59; % N, 23.34.

Examples 150-155

Preparation of N-[2-(4-amino-2-ethoxymethyl-1H-imidazo[4,5-c][1,5]naphthyridin-1-yl)-1,1-dimethylethyl]-2-methylpropionamide

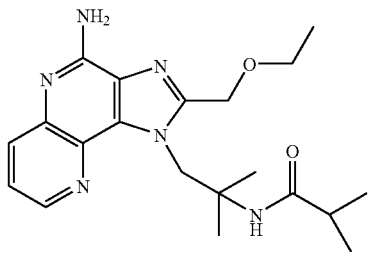 [SMILES: CCOCc1nc2c(N)nc3cccnc3c2n1CC(C)(C)NC(=O)C(C)C]

Triethylamine (556 µL, 4.00 mmol) and isobutyryl chloride (230 µL, 2.20 mmol) were added sequentially to a chilled (0° C.) solution of 1-(2-amino-2-methylpropyl)-2-ethoxymethyl-1H-imidazo[4,5-c][1,5]naphthyridin-4-amine (628 mg, 2.00 mmol) in dichloromethane (20 mL). The reaction mixture was allowed to warm slowly to ambient temperature overnight. The reaction mixture was quenched with aqueous saturated sodium bicarbonate and diluted with dichloromethane (50 mL). The organic layer was separated, washed sequentially with water and brine, dried over sodium sulfate, filtered, and then concentrated under reduced pressure to an amber foam. This material was dissolved in hot propyl acetate (10 mL) and then allowed to cool overnight. Hexanes were added and the now cloudy solution was heated until clear and then allowed stand until crystals formed. The solvent was removed by pipette. The crystals were rinsed with cold propyl acetate/hexanes and then dried under high vacuum at 70° C. to provide 464 mg of N-[2-(4-amino-2-ethoxymethyl-1H-imidazo[4,5-c][1,5]naphthyridin-1-yl)-1,1-dimethylethyl]-2-methylpropionamide as an off white crystalline solid, mp 154.5-155.5° C. Anal. calcd for $C_{20}H_{28}N_6O_2$: % C, 62.48; % H, 7.34; % N, 21.86. Found: % C, 62.14; % H, 7.62; % N, 21.71.

Preparation of 1-[2-(4-amino-2-ethoxymethyl-1H-imidazo[4,5-c][1,5]naphthyridin-1-yl)-1,1-dimethylethyl]-3-(1-methylethyl)urea

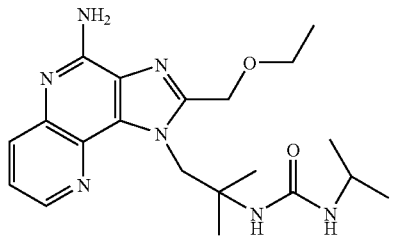 [SMILES: CCOCc1nc2c(N)nc3cccnc3c2n1CC(C)(C)NC(=O)NC(C)C]

Under a nitrogen atmosphere, isopropyl isocyanate (206 µL, 2.10 mmol) was added to a chilled (0° C.) solution of 1-(2-amino-2-methylpropyl)-2-ethoxymethyl-1H-imidazo[4,5-c][1,5]naphthyridin-4-amine (628 mg, 2.00 mmol) in dichloromethane (20 mL). The reaction mixture was allowed to warm slowly to ambient temperature overnight. The resulting precipitate was isolated by filtration and then dried under vacuum at 70° C. to provide 669 mg of 1-[2-(4-amino-2-ethoxymethyl-1H-imidazo[4,5-c][1,5]naphthyridin-1-yl)-1,1-dimethylethyl]-3-(1-methylethyl)urea as white powder, mp 172.5-173.5° C. Anal. calcd for $C_{20}H_{29}N_7O_2$: % C, 60.13; % H, 7.32; % N, 24.54. Found: % C, 59.88; % H, 7.55; % N, 24.51.

A solution of boron tribromide in dichloromethane (about 4 eq of 1 M) was added to a tube containing a chilled (0° C.) solution of a compound of Formula Xb (25 mg, 1 eq) in dichloromethane (1 mL). The tube was vortexed, maintained at 0° C. for 0.5 hour, and then shaken overnight at ambient temperature. The reaction mixture was diluted with methanol (1 mL) and hydrochloric acid (500 µL of 6 N), vortexed, and then the solvents were removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. Table 4 shows the structure of the starting material, the structure of the resulting compound, and the observed accurate mass for the isolated trifluoroacetate salt.

TABLE 4

| Example | $R_1$ | Measured Mass (M + H) |
|---|---|---|
| 150 | (CH₃)₂C(OH)CH₂CH₃ group | 288.1440 |
| 151 | ethyl-dimethyl-C-NH-S(=O)₂-CH₃ group | 365.1378 |
| 152 | ethyl-dimethyl-C-NH-C(=O)-cyclohexyl group | 397.2348 |

TABLE 4-continued

| Example | $R_1$ | Measured Mass (M + H) |
|---|---|---|
| 153 | ethyl-dimethyl-C-NH₂ group | 287.1607 |
| 154 | ethyl-dimethyl-C-NH-C(=O)-CH(CH₃)₂ group | 357.2055 |
| 155 | ethyl-dimethyl-C-NH-C(=O)-NH-CH(CH₃)₂ group | 372.2157 |

Examples 156-161

A solution of boron tribromide in heptane (400 µL of 1 M) was added to a tube containing a chilled (0° C.) solution of a compound of Formula Xc (about 25 mg) in dichloromethane (1 mL). The tube was vortexed, maintained at 0° C. for 0.5 hour, and then shaken overnight at ambient temperature. The reaction mixture was diluted with methanol (1 mL) and hydrochloric acid (250 µL of 6 N), vortexed, and then the solvents were removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. Table 5 shows the structure of the starting material, a reference for the starting material, the structure of the resulting compound, and the observed accurate mass for the isolated trifluoroacetate salt.

TABLE 5

| Example | Reference Formula Xc | R₁ | R₃ | Measured Mass (M + H) |
|---|---|---|---|---|
| 156 | U.S. Patent Publication 2004/0147543 Example 206 | -(CH₂)₄-(2-oxopyrrolidin-1-yl) | phenyl | 430.2227 |
| 157 | U.S. Patent Publication 2004/0147543 Example 136 | -CH₂-C(CH₃)₂-OH | phenyl | 377.1985 |
| 158 | U.S. Patent Publication 2004/0147543 Example 145 | -CH₂-CH(CH₃)₂ | pyridin-3-yl | 362.2008 |
| 159 | U.S. Patent Publication 2004/0147543 Example 146 | -CH₂-CH(CH₃)₂ | 5-(hydroxymethyl)pyridin-3-yl | 392.2104 |
| 160 | U.S. Patent Publication 2004/0147543 Example 183 | -(CH₂)₄-(2-oxopyrrolidin-1-yl) | pyridin-3-yl | 431.2209 |
| 161 | U.S. Patent Publication 2004/0147543 Example 184 | -(CH₂)₄-(2-oxopyrrolidin-1-yl) | pyridin-4-yl | 431.2220 |

Examples 162-186

Part A 1-(4-Amino-7-bromo-2-ethoxymethyl-1H-imidazo[4,5-c]quinolin-1-yl)-2-methylpropan-2-ol (2 g, U.S. Patent Publication 2004/0147543 Example 125) was dissolved in 7:3 volume:volume chloroform:methanol (100 mL). Aliquots (2 mL, 1.0 eq.) were added to test tubes and the solvent was removed by vacuum centrifugation. A tube was charged with a boronic acid (1.1 eq) from the table below. n-Propanol (1.6 mL) was added to each tube, the tube was purged with nitrogen, and then sonicated until the contents were well mixed. Each tube was then charged sequentially with 150 μL of a solution of palladium (II) acetate in toluene (60 mg of palladium (II) acetate dissolved in 15 mL of toluene), 600 μL of 2 M aqueous sodium carbonate solution, 113 μL of water, and 53 μL of a 15 mole % solution of triphenylphosphine in n-propanol. The tubes were purged with nitrogen and then heated at 80° C. overnight.

The reaction mixtures were purified by solid phase extraction. Sufficient hydrochloric acid (1 N) was added to each reaction mixture to adjust the pH to <5. Each reaction mixture was loaded onto a cartridge (Waters Oasis Samples Extraction Cartridges MCX 6 cc). Methanol (5 mL) was added to each cartridge. The cartridge was placed in a clean test tube. The cartridge was eluted with two successive 5 mL portions of 1 N ammonia in methanol. The solvent was removed by vacuum centrifugation.

Part B

Dichloromethane (1 mL) was added to each tube, the tube was sonicated to dissolve the solids, and then the tube was chilled to 0° C. in an ice bath. A solution of boron tribromide in heptane (600 μL of 1 M) was added to each tube. The tube was vortexed, maintained at 0° C. for 0.5 hour, and then shaken overnight at ambient temperature. The solvents were removed by vacuum centrifugation. Methanol (1 mL) and hydrochloric acid (1 mL of 6 N) were added to each tube, the tubes were vortexed, and then the solvents were removed by vacuum centrifugation. The compounds were purified as described above for Examples 156-161. Table 6 shows the boronic acid, the structure of the resulting compound, and the observed accurate mass for the isolated trifluoroacetate salt.

TABLE 6

| Example | Reagent | $R_3$ | Measured Mass (M + H) |
|---|---|---|---|
| 162 | Phenylboronic acid | phenyl | 363.1847 |
| 163 | Pyridine-3-boronic acid | pyridin-3-yl | 364.1779 |
| 164 | 3-Methylphenylboronic acid | 3-methylphenyl | 377.2001 |
| 165 | 4-Methylphenylboronic acid | 4-methylphenyl | 377.1979 |
| 166 | o-Tolylboronic acid | 2-methylphenyl | 377.1990 |
| 167 | (2-Hydroxyphenyl)boronic acid | 2-hydroxyphenyl | 379.1776 |
| 168 | 3-Hydroxyphenylboronic acid | 3-hydroxyphenyl | 379.1755 |

TABLE 6-continued
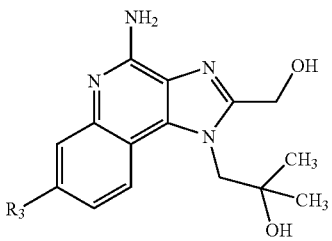
| Example | Reagent | R₃ | Measured Mass (M + H) |
|---|---|---|---|
| 169 | 3,5-Dimethylphenylboronic acid | 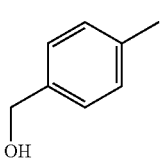 | 391.2130 |
| 170 | 4-(Hydroxymethyl)phenylboronic acid | 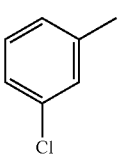 | 393.1935 |
| 171 | 3-Chlorophenylboronic acid | 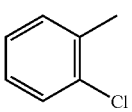 | 397.1432 |
| 172 | 2-Chlorophenylboronic acid | 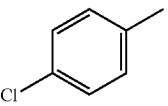 | 397.1447 |
| 173 | 4-Chlorophenylboronic acid | 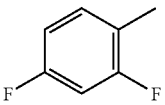 | 397.1431 |
| 174 | 2,4-Difluorophenylboronic acid | 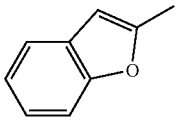 | 399.1642 |
| 175 | Benzo[b]furan-2-boronic acid | 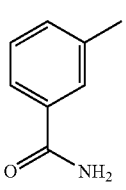 | 403.1812 |
| 176 | (3-Aminocarbonylphenyl)boronic acid | | 406.1889 |
| 177 | 4-(N,N-Dimethylamino)phenylboronic acid | 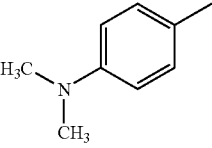 | 406.2255 |

TABLE 6-continued
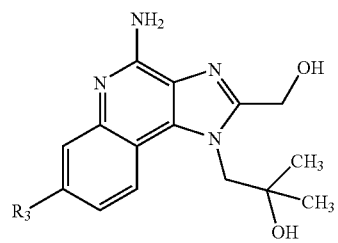
| Example | Reagent | R₃ | Measured Mass (M + H) |
|---|---|---|---|
| 178 | (3-Aminomethylphenyl)boronic acid hydrochloride | 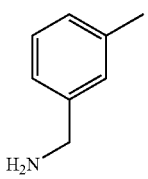 | 392.2108 |
| 179 | 3,4-Dichlorophenylboronic acid | 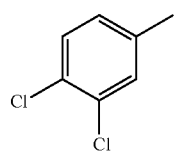 | 431.1061 |
| 180 | 4-(Ethylsulfonyl)phenylboronic acid | 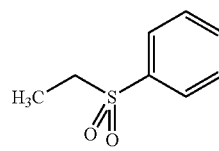 | 455.1771 |
| 181 | 3-(Methylsulfonylamino)phenylboronic acid | 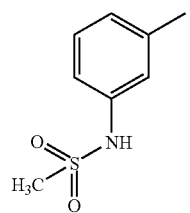 | 456.1727 |
| 182 | 3-(Pyrrolidine-1-carbonyl)phenylboronic acid | 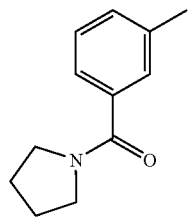 | 460.2364 |
| 183 | 4-(Pyrrolidine-1-carbonyl)phenylboronic acid | 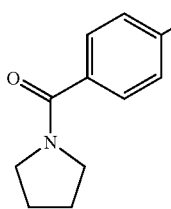 | 460.2395 |

TABLE 6-continued

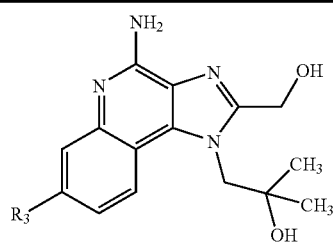

| Example | Reagent | R₃ | Measured Mass (M + H) |
|---|---|---|---|
| 184 | 3-(Butylaminocarbonyl)phenylboronic acid | | 462.2488 |
| 185 | 3-(Isobutylaminocarbonyl)phenylboronic acid | | 462.2527 |
| 186 | 4'-(4,4,5,5-Tetramethyl-1,3,2-dioxaborolan-2-yl)acetanilinde | | 420.2022 |

Example 187

1-[4-Amino-2-hydroxymethyl-7-(thiazol-4-yl-methoxy)-1H-imidazo[4,5-c]quinolin-1-yl]-2-methylpropan-2-ol

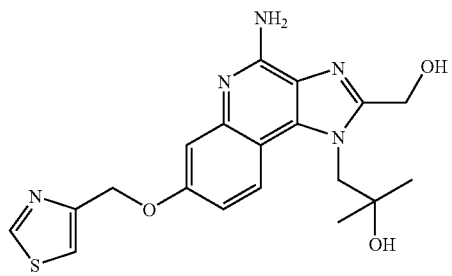 [SMILES: CC(C)(O)Cn1c(CO)nc2c(N)nc3cc(OCc4cscn4)ccc3c21]

Under a nitrogen atmosphere, a solution of 1-[4-amino-2-ethoxymethyl-7-(thiazol-4-ylmethoxy)-1H-imidazo[4,5-c]quinolin-1-yl]-2-methylpropan-2-ol (400 mg, 0.94 mmol, which can be prepared as described in International Application No. PCT/US04/28021 Example 137) in dichloromethane (50 mL) was cooled to 0° C. in an ice bath. A solution to of boron tribromide in dichloromethane (3.76 mL of 1.0 M) was added slowly. The reaction mixture was allowed to slowly warm to ambient temperature overnight. The reaction mixture was diluted with hydrochloric acid (20 mL of 6 N) and stirred for 30 minutes. The layers were separated. The organic layer was washed with 6 N hydrochloric acid (3×20 mL) and then discarded. The aqueous layer was made basic by the addition of solid potassium carbonate. A precipitate was isolated by filtration, dissolved in hot chloroform, and then purified by prep HPLC (HORIZON HPFC system eluting with 0-10% CMA in chloroform over 192 mL and then with 10-40% CMA in chloroform over 1400 mL) to provide a solid. This material was crystallized from acetonitrile to provide 181 mg of 1-[4-amino-2-hydroxymethyl-7-(thiazol-4-ylmethoxy)-1H-imidazo[4,5-c]quinolin-1-yl]-2-methylpropan-2-ol as a white solid, mp 260-262° C. Anal. calcd for $C_{19}H_{21}N_5O_3S$: % C, 56.81; % H, 5.41; % N, 17.26. Found: % C, 56.82; % H, 5.54; % N, 17.23.

Example 188

[4-Amino-7-pyridin-3-yl-1-(tetrahydro-2H-pyran-4-ylmethyl)-1H-imidazo[4,5-c]quinolin-2-yl]methanol

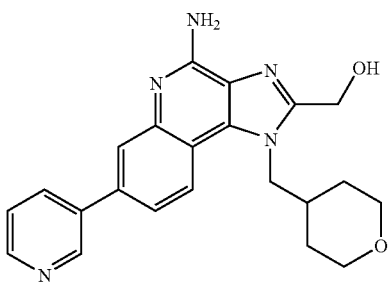 [SMILES: Nc1nc2cc(-c3cccnc3)ccc2c2c1nc(CO)n2CC1CCOCC1]

Part A

To a mixture of 1-tetrahydro-2H-pyran-4-ylmethanamine HCl (19 g, 120 mmol), dichloromethane (626 mL), and triethyl amine (43.7 mL, 313 mmol) was added 4-chloro-3-nitroquinoline at 0° C. The resulting bright yellow solution was stirred at ambient temperature for 18 hours. The reaction was then concentrated under reduced pressure. The resulting solid was stirred in water (100 mL) and filtered to give 43 g of 7-bromo-3-nitro-N-(tetrahydro-2H-pyran-4-ylmethyl)quinolin-4-amine as a yellow powder.

Part B

7-Bromo-3-nitro-N-(tetrahydro-2H-pyran-4-ylmethyl)quinolin-4-amine (20 g, 55 mmol) was dissolved in a mixture of acetonitrile (500 mL) and isopropyl alcohol (50 mL) and the solution was placed in a pressure bottle. Platinum on carbon (5%, 2 g) was then added and the reaction mixture was shaken under $H_2$ at 48 PSI ($3.3 \times 10^5$ Pa). After 2 hours, the reaction mixture was filtered through a pad of CELITE filter agent. The pad was rinsed with acetonitrile and the combined filtrates were concentrated under reduced pressure to give 7-bromo-N-(tetrahydro-2H-pyran-4-ylmethyl)quinoline-3,4-diamine which was carried forward without further purification assuming quantitative yield.

Part C

Chloroacetyl chloride (5.2 mL, 65 mmol) was added to 7-bromo-$N^4$-(tetrahydro-2H-pyran-4-ylmethyl)quinoline-3,4-diamine (55 mmol) dissolved in 273 mL of dichloromethane at 0° C. A solid formed after adding half of the chloroacetyl chloride at which point additional dichloromethane (100 mL) was added. The reaction was stirred for 1 hour at ambient temperature. The yellow suspension was quenched first with aqueous saturated sodium bicarbonate followed by 50% aqueous sodium hydroxide until a pH of 14 was reached. Filtration provided 10 g of N-{7-bromo-4-[(tetrahydro-2H-pyran-4-ylmethyl)amino]quinolin-3-yl}-2-chloroacetamide as a tan solid. The filtrate was placed in a separatory funnel and the layers were separated. The aqueous layer was extracted with additional dichloromethane. The combined organic extracts were combined, dried over sodium sulfate, filtered, and concentrated under reduced pressure to afford additional N-{7-bromo-4-[(tetrahydro-2H-pyran-4-ylmethyl)amino]quinolin-3-yl}-2-chloroacetamide as a yellow oil. The yellow oil was carried forward without further purification assuming a 50% yield (27.3 mmol). The oil was combined with ethanol (100 mL) and triethylamine (7.5 mL, 54 mmol). The resulting yellow solution was refluxed for 2 hours. The reaction was cooled to ambient temperature and the solvent was removed under reduced pressure to provide 7-bromo-2-(chloromethyl)-1-(tetrahydro-2H-pyran-4-ylmethyl)-1H-imidazo[4,5-c]quinoline as a brown oil that was used without further purification assuming quantitative yield.

Part D

Potassium acetate (5.3 g, 55 mmol) was added to 7-bromo-2-(chloromethyl)-1-(tetrahydro-2H-pyran-4-ylmethyl)-1H-imidazo[4,5-c]quinoline (27.3 mmol) dissolved in dimethylformamide (100 mL). The resulting suspension was stirred at 90° C. for 1 hour. The reaction was cooled to ambient temperature and water (200 mL) was added. The aqueous layer was extracted with chloroform. The combined organic extracts were combined, dried over sodium sulfate, filtered, and concentrated under reduced pressure to afford an orange oily solid. Chromatography ($SiO_2$, 0-30% 80/18/2 v/v/v $CHCl_3/CH_3OH$/concentrated $NH_4OH$ (CMA)/$CHCl_3$) gave material that was stirred in acetonitrile and filtered to provide 2.3 g of [7-bromo-1-(tetrahydro-2H-pyran-4-ylmethyl)-1H-imidazo[4,5-c]quinolin-2-yl]methyl acetate as a tan solid.

Part E

3-Chloroperoxybenozic acid (2.4 g, 50% pure, 7.0 mmol) was added to a mixture of [7-bromo-1-(tetrahydro-2H-pyran-4-ylmethyl)-1H-imidazo[4,5-c]quinolin-2-yl]methyl acetate (2.3 g, 5.4 mmol) and chloroform (27 mL) at ambient temperature. The reaction was stirred at this temperature for 18 hours. Saturated aqueous sodium bicarbonate (50 mL) and water (50 mL) were then added to the reaction and the layers were separated. The aqueous layer was extracted with additional dichloromethane. The organic layers were combined, dried over sodium sulfate, and concentrated under reduced pressure to a dark oil. This oil was dissolved in methanol (27 mL) and to this solution was added 15 M ammonium hydroxide (3.6 mL, 54 mmol) and benzene sulfonyl chloride (2.9 mL, 23 mmol). The resulting reaction mixture was stirred at ambient temperature for 2 hours before adding additional 15 M ammonium hydroxide (3.6 mL, 54 mmol) and benzene sulfonyl chloride (2.9 mL, 23 mmol). The reaction was stirred 18 hours. The reaction was then concentrated under reduced pressure and diluted with saturated aqueous sodium bicarbonate and chloroform. A suspension resulted that was filtered to afford a solid that was stirred with saturated aqueous sodium bicarbonate and filtered to give 1.1 g of [4-amino-7-bromo-1-(tetrahydro-2H-pyran-4-ylmethyl)-1H-imidazo[4,5-c]quinolin-2-yl]methanol as a white solid.

Part F

To a mixture of [4-amino-7-bromo-1-(tetrahydro-2H-pyran-4-ylmethyl)-1H-imidazo[4,5-c]quinolin-2-yl]methanol (500 mg, 1.28 mmol), 3-pyridyl boronic acid (233 mg, 1.90 mmol), potassium carbonate (579 mg, 4.20 mmol), dimethoxyethane (5 mL), and water (2.5 mL) under a nitrogen atmosphere was added $Pd(PPh_3)_2Cl_2$ (18 mg, 0.026 mmol). The resulting suspension was refluxed for 2 hours. The reaction was cooled to ambient temperature. The reaction mixture was diluted with chloroform and placed directly onto a silica gel column. Chromatography ($SiO_2$, 0-40% CMA/$CHCl_3$) gave material that was stirred in methanol and filtered to provide 263 mg of [4-amino-7-pyridin-3-yl-1-(tetrahydro-2H-pyran-4-ylmethyl)-1H-imidazo[4,5-c]quinolin-2-yl]methanol as tan crystals, m.p. 260-262° C. MS (APCI) m/z 500.3 (M+H)$^+$; Anal. calcd for $C_{22}H_{23}N_5O_2$: C, 67.85; H, 5.95; N, 17.98. Found: C, 67.49; H, 5.87; N, 17.83.

Examples 189-207

The compounds in the table below were prepared according to the following general procedure. The ether analog was dissolved or suspended in a solvent such as dichloromethane and the reaction mixture was stirred at 0° C. or at ambient temperature. Boron tribromide (2.5-10 equivalents, 1 M solution in dichloromethane) was added dropwise to the reaction mixture. The reaction was stirred at ambient temperature for 4 h-6 days after which it was quenched by the careful addition of methanol or water and the solvent was removed under reduced pressure. The product was isolated by a procedure similar to that described below. The residue was combined with 2-6 M hydrochloric acid, heated to 50° C., and stirred for 1-2 hours. The resulting solution was cooled (ice bath) and then free-based (pH 9) with the addition of 2-6 M aqueous sodium hydroxide. The desired material was extracted from the aqueous using an organic solvent such as dichloromethane, ethyl acetate, or chloroform. The organic layer was separated, dried (MgSO$_4$), filtered, and the solvent was evaporated under reduced pressure to afford the crude product. The final compound was isolated by prep HPLC (ISCO Combiflash Separation System or Analogix Purification System).

| Example | Structure | Analytical Data |
|---|---|---|
| 189 | 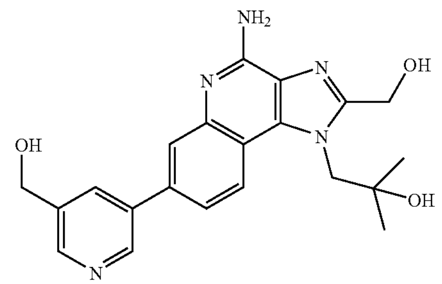 [SMILES: CC(C)(O)Cn1c(CO)nc2c(N)nc3cc(-c4cncc(CO)c4)ccc3c21] | Off-white needles, mp 180-182° C.<br>Anal. calcd for $C_{21}H_{23}N_5O_3 \cdot 2.60H_2O$: C, 57.29; H, 6.46; N, 15.91. Found: C, 57.32; H, 6.15; N, 15.73; MS (APCI) m/z 394 (M + H)$^+$. |
| 190 | 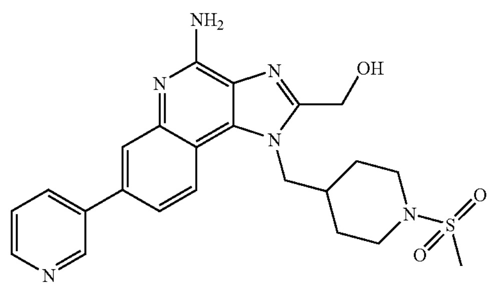 [SMILES: CS(=O)(=O)N1CCC(Cn2c(CO)nc3c(N)nc4cc(-c5cccnc5)ccc4c32)CC1] | Off-white needles, mp 196-198° C.<br>Anal. calcd for $C_{23}H_{26}N_6O_3S$: C, 59.21; H, 5.62; N, 18.01. Found: C, 59.16; H, 5.84; N, 17.98; MS (APCI) m/z 467 (M + H)$^+$. |
| 191 | 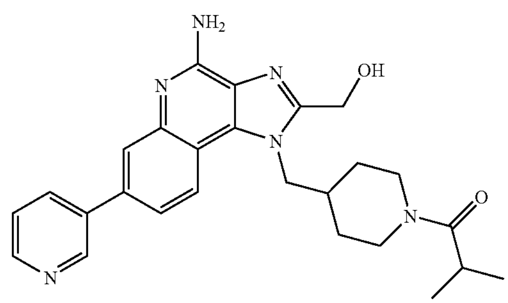 [SMILES: CC(C)C(=O)N1CCC(Cn2c(CO)nc3c(N)nc4cc(-c5cccnc5)ccc4c32)CC1] | Off-white needles, mp 154-157° C.<br>Anal. calcd for $C_{26}H_{30}N_6O_2 \cdot 0.25H_2O$: C, 67.44; H, 6.64; N, 18.15. Found: C, 67.48; H, 6.55; N, 18.00; MS (APCI) m/z 459 (M + H)$^+$. |
| 192 | 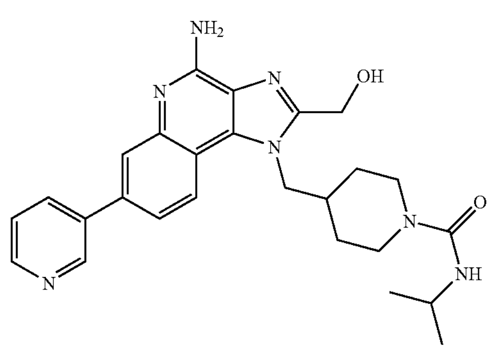 [SMILES: CC(C)NC(=O)N1CCC(Cn2c(CO)nc3c(N)nc4cc(-c5cccnc5)ccc4c32)CC1] | Off-white needles, mp 182-184° C.<br>Anal. calcd for $C_{26}H_{31}N_7O_2$: C, 65.94; H, 6.60; N, 20.70. Found: C, 65.70; H, 6.49; N, 20.39); MS (APCI) m/z 474 (M + H)$^+$. |

-continued

| Example | Structure | Analytical Data |
|---|---|---|
| 193 | 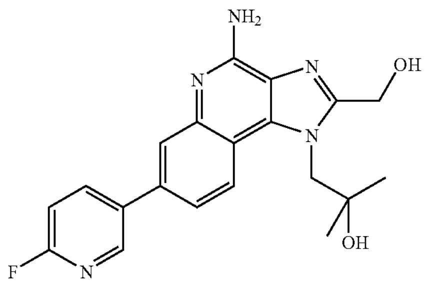 [SMILES: CC(C)(O)Cn1c(CO)nc2c(N)nc3cc(-c4ccc(F)nc4)ccc3c21] | Beige needles, mp 111-114° C.<br>Anal. calcd for $C_{20}H_{20}FN_5O_2 \cdot 2.0\ H_2O$: C, 57.55; H, 5.79; N, 16.78. Found: C, 57.33; H, 5.57; N, 16.76<br>MS (APCI) m/z 382 (M + H)$^+$ |
| 194 | 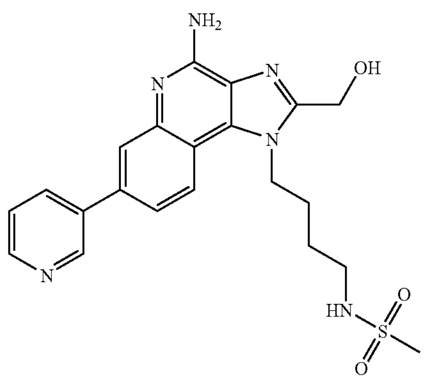 | Off-white solid, mp 188-190° C.<br>Anal. calcd for $C_{21}H_{24}N_6O_3S \cdot 1.70H_2O$<br>C: 53.53, H: 5.86, N: 17.84. Found:<br>C: 53.23, % H: 5.62, N: 17.81.<br>MS (APCI) m/z 459 (M + H)$^+$ |
| 195 | 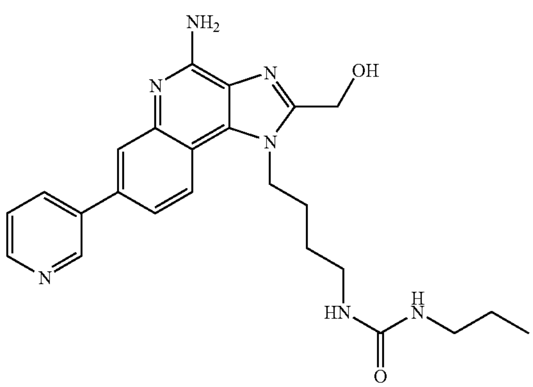 [SMILES: CCCNC(=O)NCCCCn1c(CO)nc2c(N)nc3cc(-c4cccnc4)ccc3c21] | Green solid, mp 206-209° C.<br>Anal. calcd for $C_{24}H_{29}N_7O_2 \cdot 0.27H_2O$<br>C: 63.72, H: 6.58, N: 21.67.<br>Found: C: 63.97, H: 6.26, N: 21.64.<br>MS (APCI) m/z 448 (M + H)$^+$ |
| 196 | 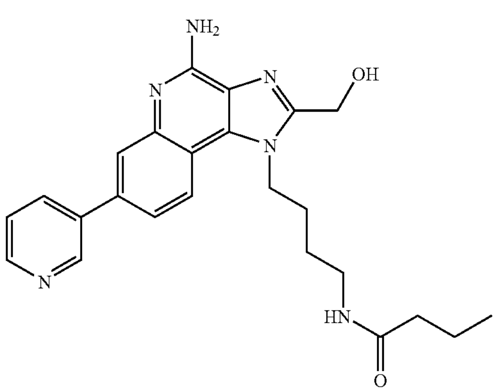 [SMILES: CCCC(=O)NCCCCn1c(CO)nc2c(N)nc3cc(-c4cccnc4)ccc3c21] | Off-white solid, mp 211-212° C.<br>Anal. calcd for $C_{24}H_{28}N_6O_2 \cdot 0.25H_2O$<br>C: 65.96, H: 6.57, N: 19.23. Found: C: 65.52 H: 6.38, N: 19.38<br>MS (APCI) m/z 433 (M + H)$^+$ |

| Example | Structure | Analytical Data |
| --- | --- | --- |
| 197 | 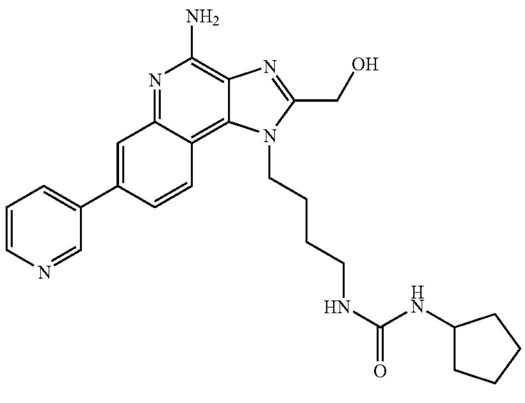 [SMILES: Nc1nc2cc(-c3cccnc3)ccc2c2c1nc(CO)n2CCCCNC(=O)NC1CCCC1] | Yellow solid, mp 225-227° C.<br>Anal. calcd for $C_{26}H_{31}N_7O_2 \cdot 0.38H_2O$<br>C: 65.00, H: 6.66, N: 20.41.<br>Found: C: 65.26, H: 6.53, N: 20.42.<br>MS (APCI) m/z 474 $(M + H)^+$ |
| 198 | 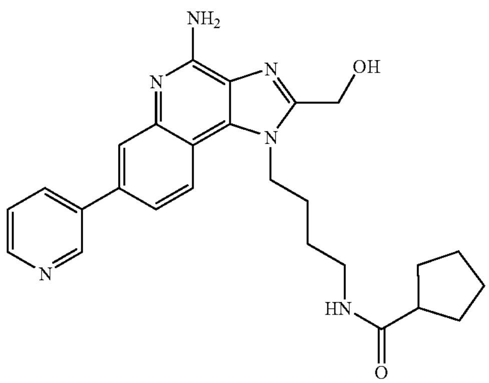 [SMILES: Nc1nc2cc(-c3cccnc3)ccc2c2c1nc(CO)n2CCCCNC(=O)C1CCCC1] | White solid, mp 241-242° C.<br>Anal. calcd for $C_{26}H_{30}N_6O_2$<br>C: 68.10, H: 6.59, N: 18.33.<br>Found: C: 67.85, H: 6.48, N: 18.32.<br>MS (APCI) m/z 459 $(M + H)^+$ |
| 199 | 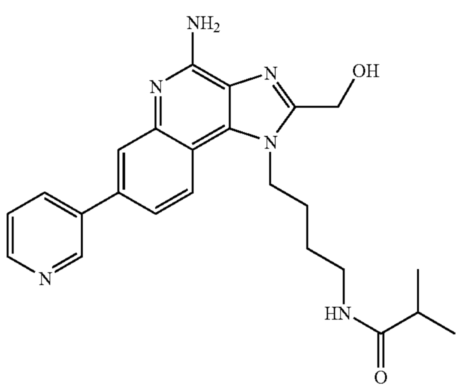 [SMILES: CC(C)C(=O)NCCCCn1c(CO)nc2c(N)nc3cc(-c4cccnc4)ccc3c21] | White solid, mp 225-227° C.<br>Anal. calcd for $C_{24}H_{28}N_6O_2 \cdot 0.38H_2O$<br>C: 65.61, H: 6.60, N: 19.13.<br>Found: C: 65.19, H: 6.74, N: 18.96.<br>MS (APCI) m/z 433 $(M + H)^+$ |
| 200 | 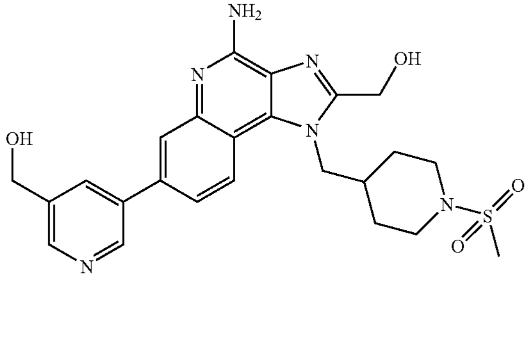 [SMILES: CS(=O)(=O)N1CCC(Cn2c(CO)nc3c(N)nc4cc(-c5cncc(CO)c5)ccc4c32)CC1] | White solid, mp >300° C.<br>Anal. calcd for $C_{24}H_{28}N_6O_4S \cdot HBr \cdot 0.2H_2O$:<br>C: 49.61; H, 5.10; N, 14.46, Found: C,<br>49.26; H, 4.84; N, 14.29<br>MS (APCI) m/z 497 $(M + H)^+$ |

-continued

| Example | Structure | Analytical Data |
|---|---|---|
| 201 | 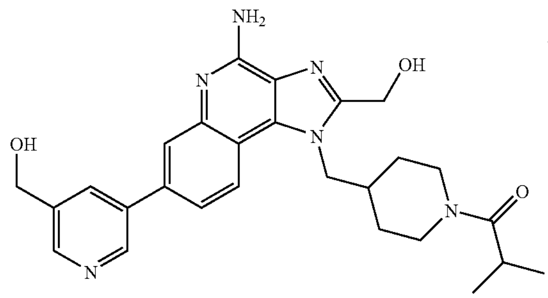 [SMILES: CC(C)C(=O)N1CCC(Cn2c(CO)nc3c(N)nc4cc(-c5cncc(CO)c5)ccc4c32)CC1] | Tan solid, mp >300° C.<br>Anal. calcd for $C_{27}H_{32}N_6O_3 \cdot HBr$: C, 56.94; H, 5.84; N, 14.76. Found: C, 56.66; H, 5.69; N, 14.63.<br>MS (APCI) m/z 489 (M + H)$^+$ |
| 202 | 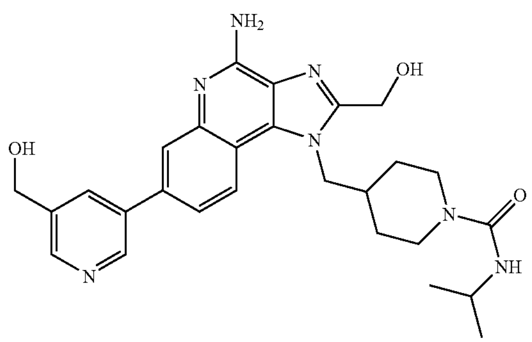 [SMILES: CC(C)NC(=O)N1CCC(Cn2c(CO)nc3c(N)nc4cc(-c5cncc(CO)c5)ccc4c32)CC1] | Off-white solid, mp >300° C.<br>Anal. calcd for $C_{27}H_{33}N_7O_3 \cdot HBr$: C, 55.14; H, 5.90; N, 16.67. Found: C, 54.86; H, 5.60; N, 16.64.<br>MS (APCI) m/z 504 (M + H)$^+$ |
| 203 | 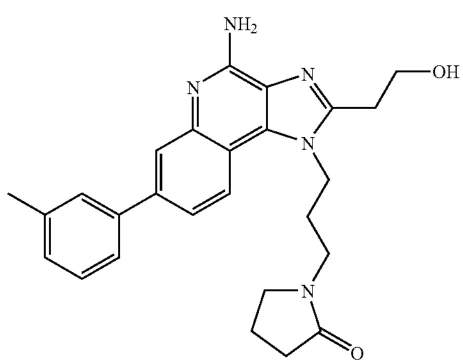 [SMILES: Cc1cccc(-c2ccc3c(c2)nc(N)c2nc(CCO)n(CCCN4CCCC4=O)c23)c1] | Off white needles, mp 218-221° C.<br>Anal. calcd for $C_{26}H_{29}N_5O_2 \cdot 1.25\ H_2O$: C, 67.00; H, 6.81; N, 15.03. Found: C, 67.04; H, 6.78, N, 14.90.<br>MS (APCI) m/z 444 (M + H)$^+$ |
| 204 | 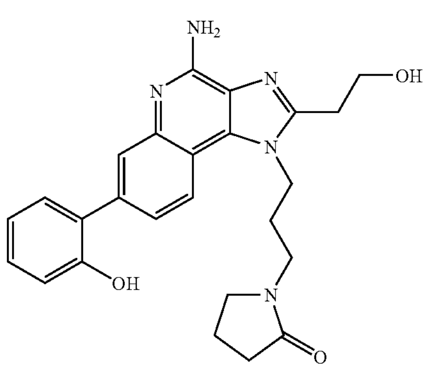 [SMILES: Nc1nc2cc(-c3ccccc3O)ccc2c2c1nc(CCO)n2CCCN1CCCC1=O] | Off white solid, mp >250° C.<br>Anal. calcd for $C_{25}H_{27}N_5O_3 \cdot 0.75\ H_2O$: C, 65.41; H, 6.26; N, 15.26. Found: C, 65.48; H, 6.40; N, 15.07.<br>MS (APCI) m/z 446 (M + H)$^+$ |

-continued

| Example | Structure | Analytical Data |
|---------|-----------|-----------------|
| 205 | 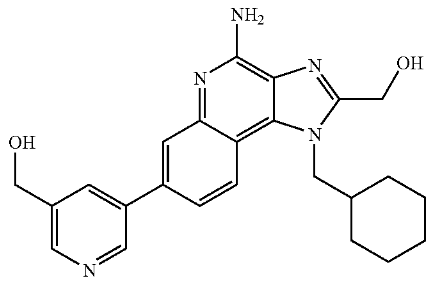 [SMILES: Nc1nc2cc(-c3cncc(CO)c3)ccc2c2c1nc(CO)n2CC1CCCCC1] | Off-white solid, mp 166-170° C.<br>Anal. calcd for $C_{24}H_{27}N_5O_2 \cdot 0.9$ $H_2O$: C, 66.46; H, 6.69; N, 16.15. Found: C, 66.09; H, 6.73; N, 15.97.<br>MS (APCI) m/z 418 (M + H)$^+$ |
| 206 | 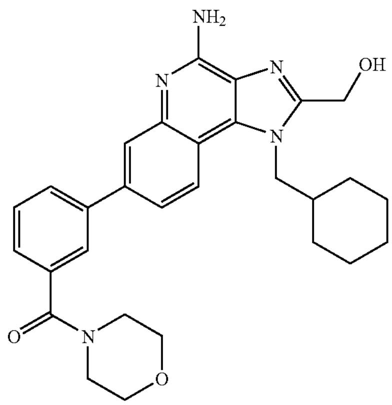 [SMILES: Nc1nc2cc(-c3cccc(C(=O)N4CCOCC4)c3)ccc2c2c1nc(CO)n2CC1CCCCC1] | Off-white solid, mp 260-264° C.<br>Anal. calcd for $C_{29}H_{33}N_5O_3 \cdot 0.6$ $H_2O \cdot 1.0$ HCl: C, 63.69; H, 6.49; N, 12.81. Found: C, 63.37; H, 6.23; N, 12.62.<br>MS (APCI) m/z 500 (M + H)$^+$ |
| 207 | 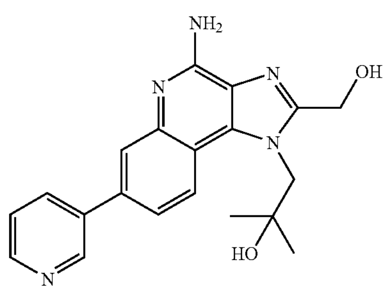 [SMILES: CC(C)(O)Cn1c(CO)nc2c(N)nc3cc(-c4cccnc4)ccc3c21] | Off-white needles, mp 141-143° C.<br>Anal. calcd for $C_{20}H_{21}N_5O_2 \cdot 1.00CH_4O \cdot 1.0$ $H_2O$: C, 61.15 H, 6.35 N, 16.98. Found: C, 61.15 H, 6.06 N, 17.34.<br>MS (APCI) m/z 364 (M + H)$^+$ |

Examples 208-318

Part A

A solution of 1-(4-aminobutyl)-2-ethoxymethyl-7-(pyridin-3-yl)-1H-imidazo[4,5-c]quinoline-4-amine (43 mg, 0.10 mmol, 1 eq, U.S. Patent Application Publication 2004/0147543, Example 372) and triethylamine (5 eq) in chloroform (1 mL) was added to a tube containing a reagent (1.1 eq) from the table below. The reaction mixture was vortexed overnight and then purified by solid-supported liquid-liquid extraction according to the following procedure. The reaction mixture was loaded onto diatomaceous earth that had been equilibrated with 1 N sodium hydroxide (600 µL) for about 20 minutes. After 10 minutes chloroform (300 µL) was added to elute the product from the diatomaceous earth into a well of a collection plate. After an additional 10 minutes the process was repeated with additional chloroform (500 µL). The solvent was then removed by vacuum centrifugation.

Part B

The material from Part A was dissolved in dichloromethane (600 µL) and the solution was cooled to 0° C. Boron tribromide (400 µL of 1 M in dichloromethane) was added, the reaction mixture was vortexed, chilled for 15 minutes, and then vortexed at ambient temperature overnight. The solvent was removed by vacuum centrifugation. Methanol (300 µL) and 6 N hydrochloric acid (300 µL) were added and the reaction mixture was vortexed for 10 minutes. The solvent was removed by vacuum centrifugation. The compounds were purified as described above for Examples 156-161. The table below shows the reagent used for each example, the structure of the resulting compound, and the observed accurate mass for the isolated trifluoroacetate salt.

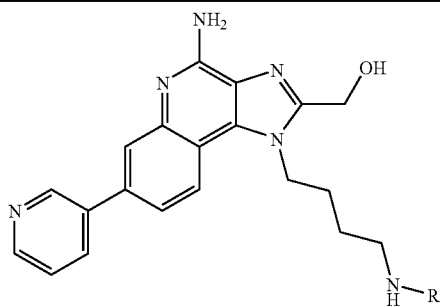
| Example | Reagent | R | Measured Mass (M + H) |
|---|---|---|---|
| 208 | None | H | 363.1964 |
| 209 | Propionyl chloride | C(=O)CH₂CH₃ | 419.2168 |
| 210 | Cyclopropanecarbonyl chloride | C(=O)-cyclopropyl | 431.2213 |
| 211 | Butyryl chloride | C(=O)CH₂CH₂CH₃ | 433.2345 |
| 212 | Isobutyryl chloride | C(=O)CH(CH₃)₂ | 433.2346 |
| 213 | Methoxyacetyl chloride | C(=O)CH₂OH | 421.1982 |
| 214 | Cyclobutanecarbonyl chloride | C(=O)-cyclobutyl | 445.2338 |
| 215 | Isovaleryl chloride | C(=O)CH₂CH(CH₃)₂ | 447.2536 |
| 216 | Cyclohexanecarbonyl chloride | C(=O)-cyclohexyl | 473.2679 |

-continued
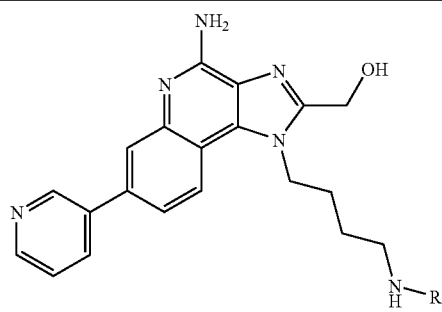
| Example | Reagent | R | Measured Mass (M + H) |
|---|---|---|---|
| 217 | Phenylacetyl chloride | -C(O)CH₂-phenyl | 481.2368 |
| 218 | 4-Cyanobenzoyl chloride | -C(O)-(4-cyanophenyl) | 492.2143 |
| 219 | 3-Methoxybenzoyl chloride | -C(O)-(3-hydroxyphenyl) | 483.2121 |
| 220 | p-Anisoyl chloride | -C(O)-(4-hydroxyphenyl) | 483.2115 |
| 221 | 2-Chlorobenzoyl chloride | -C(O)-(2-chlorophenyl) | 501.1813 |
| 222 | 3-Chlorobenzoyl chloride | -C(O)-(3-chlorophenyl) | 501.1812 |

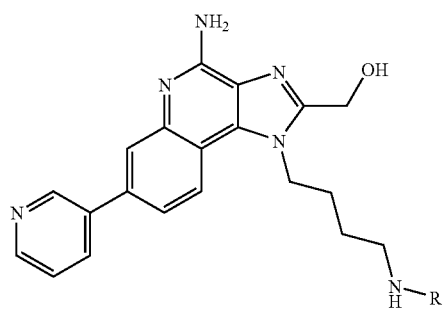
| Example | Reagent | R | Measured Mass (M + H) |
|---|---|---|---|
| 223 | Nicotinoyl chloride hydrochloride | 3-pyridyl-C(=O)– | 468.2122 |
| 224 | Picolinoyl chloride hydrochloride | 2-pyridyl-C(=O)– | 468.2124 |
| 225 | 1-Propanesulfonyl chloride | CH₃CH₂CH₂-S(=O)₂– | 469.2039 |
| 226 | Dimethylsulfamoyl chloride | (CH₃)₂N-S(=O)₂– | 470.1961 |
| 227 | 1-Butanesulfonyl chloride | CH₃CH₂CH₂CH₂-S(=O)₂– | 483.2160 |
| 228 | 3-Methylbenzenesulfonyl chloride | 3-methylphenyl-S(=O)₂– | 517.2044 |

-continued
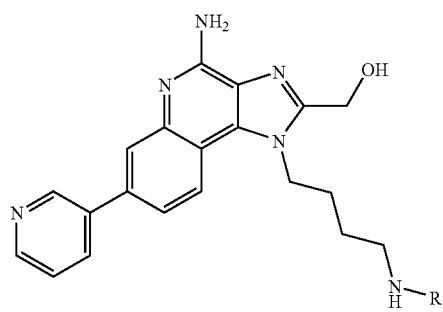
| Example | Reagent | R | Measured Mass (M + H) |
|---|---|---|---|
| 229 | o-Toluenesulfonyl chloride | 2-methylphenylsulfonyl | 517.2071 |
| 300 | p-Toluenesulfonyl chloride | 4-methylphenylsulfonyl | 517.2020 |
| 301 | 2-Fluorobenzenesulfonyl chloride | 2-fluorophenylsulfonyl | 521.1786 |
| 302 | 3-Cyanobenzenesulfonyl chloride | 3-cyanophenylsulfonyl | 528.1805 |
| 303 | 3-Methoxybenzenesulfonyl chloride | 3-hydroxyphenylsulfonyl | 519.1829 |

-continued
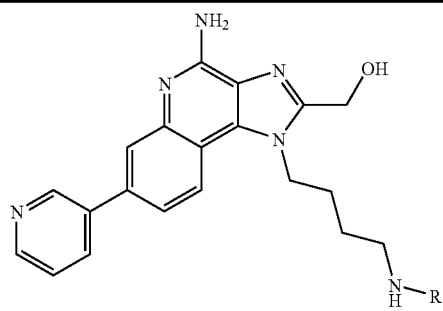
| Example | Reagent | R | Measured Mass (M + H) |
|---|---|---|---|
| 304 | 4-Methoxybenzenesulfonyl chloride | *sulfonyl-phenyl-OH* | 519.1799 |
| 305 | 3-Pyridinesulfonyl chloride hydrochloride | *sulfonyl-pyridin-3-yl* | 504.1852 |
| 306 | Ethyl isocyanate | *C(=O)NH-CH₂CH₃* | 434.2307 |
| 307 | Isopropyl isocyanate | *C(=O)NH-CH(CH₃)₂* | 448.2498 |
| 308 | n-Propyl isocyanate | *C(=O)NH-CH₂CH₂CH₃* | 448.2448 |
| 309 | Cyclopentyl isocyanate | *C(=O)NH-cyclopentyl* | 474.2629 |
| 310 | Phenyl isocyanate | *C(=O)NH-phenyl* | 482.2338 |

-continued

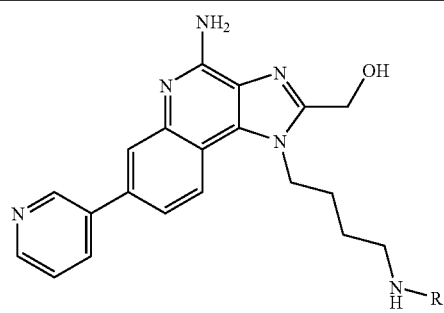

| Example | Reagent | R | Measured Mass (M + H) |
|---|---|---|---|
| 311 | Cyclohexyl isocyanate | *N-cyclohexyl carbamoyl* | 488.2759 |
| 312 | 2-Fluorophenyl isocyanate | *N-(2-fluorophenyl) carbamoyl* | 500.2209 |
| 313 | 3-Fluorophenyl isocyanate | *N-(3-fluorophenyl) carbamoyl* | 500.2206 |
| 314 | 4-Fluorophenyl isocyanate | *N-(4-fluorophenyl) carbamoyl* | 500.2209 |
| 315 | (R)-(+)-alpha-Methylbenzyl isocyanate | *N-[(R)-1-phenylethyl] carbamoyl* | 510.2580 |
| 316 | (S)-(−)-alpha-Methylbenzyl isocyanate | *N-[(S)-1-phenylethyl] carbamoyl* | 510.2588 |

-continued

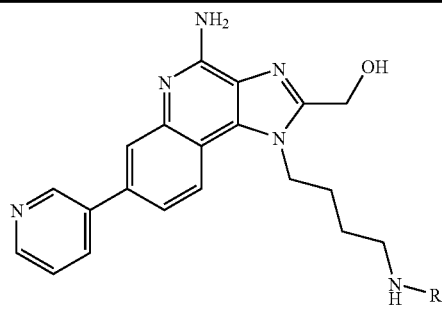

| Example | Reagent | R | Measured Mass (M + H) |
|---|---|---|---|
| 317 | 1-Piperidinecarbonyl chloride | | 474.2606 |
| 318 | 4-Methyl-1-piperazinecarbonyl chloride | | 489.2725 |

Examples 319-345

The compounds in the table below were prepared and purified according to the general method of Examples 162-186 using N-{4-[4-amino-7-bromo-2-ethoxymethyl-1H-imidazo[4,5-c]quinolin-1-yl]butyl}methanesulfonamide (U.S. Patent Application Publication 2004/0147543, Example 612) in lieu of 1-(4-amino-7-bromo-2-ethoxymethyl-1H-imidazo[4,5-c]quinolin-1-yl)-2-methylpropan-2-ol. Prior to purification by solid phase extraction, the reaction mixture for Example 345 was combined with water (500 μL), glacial acetic acid (500 μL), and tetrahydrofuran (500 μL) and then heated at 60° C. for 2 hours. The table below shows the boronic acid, the structure of the resulting compound, and the observed accurate mass for the isolated trifluoroacetate salt.

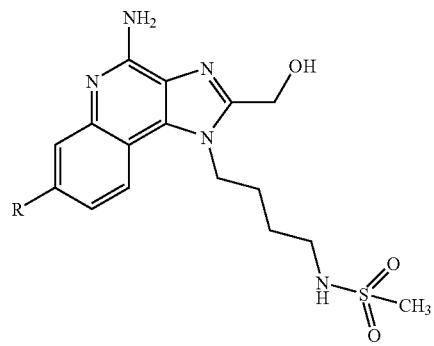

| Example | Reagent | R | Measured Mass (M + H) |
|---|---|---|---|
| 319 | Phenylboronic acid | | 440.1745 |

-continued

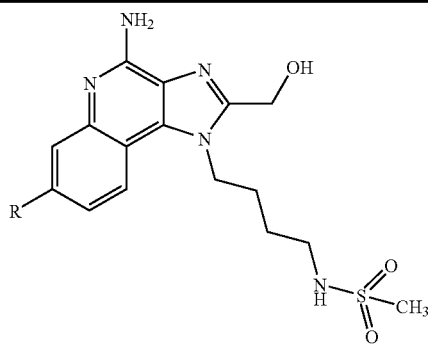

| Example | Reagent | R | Measured Mass (M + H) |
|---|---|---|---|
| 320 | Pyridine-3-boronic acid | 3-pyridyl | 441.1745 |
| 321 | Pyridine-4-boronic acid | 4-pyridyl | 441.1679 |
| 322 | Thiophene-3-boronic acid | 3-thienyl | 446.1307 |
| 323 | 2-Fluorophenylboronic acid | 2-fluorophenyl | 458.1668 |
| 324 | 3-Fluorophenylboronic acid | 3-fluorophenyl | 458.1671 |
| 325 | 4-Fluorophenylboronie acid | 4-fluorophenyl | 458,1674 |
| 326 | 4-Cyanophenylboronic acid | 4-cyanophenyl | 465.1684 |
| 327 | 3-(Hydroxymethyl)phenylboronic acid | 3-(hydroxymethyl)phenyl | 470.1882 |
| 328 | 4-(Hydroxymethyl)phenylboronic acid | 4-(hydroxymethyl)phenyl | 470.1909 |

-continued

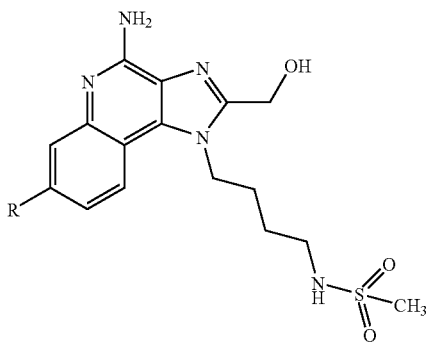

| Example | Reagent | R | Measured Mass (M + H) |
|---|---|---|---|
| 329 | 3-Chlorophenylboronic acid | 3-chlorophenyl | 474.1408 |
| 330 | 2-Chlorophenylboronic acid | 2-chlorophenyl | 474.1366 |
| 331 | 4-Chlorophenylboronic acid | 4-chlorophenyl | 474.1384 |
| 332 | (2-Aminocarbonylphenyl)boronic acid | 2-(aminocarbonyl)phenyl | 483.1796 |
| 333 | (3-Aminocarbonylphenyl)boronic acid | 3-(aminocarbonyl)phenyl | 483.1812 |
| 334 | (2-Acetylaminophenyl)boronic acid | 2-(acetylamino)phenyl | 497.1938 |
| 335 | [3-(3-Hydroxypropyl)phenyl]boronic acid | 3-(3-hydroxypropyl)phenyl | 498.2136 |

-continued

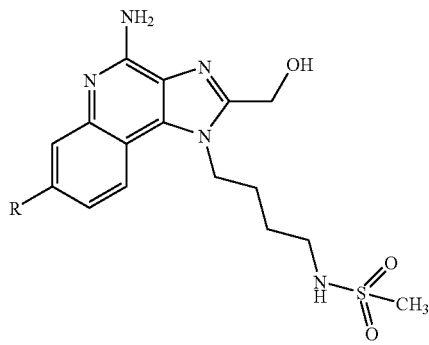

| Example | Reagent | R | Measured Mass (M + H) |
|---|---|---|---|
| 336 | 3,4-Dichlorophenylboronic acid | 3,4-dichlorophenyl | 508.0989 |
| 337 | 3-(N-Isopropylaminocarbonyl)phenylboronic acid | 3-(N-isopropylaminocarbonyl)phenyl | 525.2331 |
| 338 | 3-(N-Propylaminocarbonyl)phenylboronic acid | 3-(N-propylaminocarbonyl)phenyl | 525.2284 |
| 339 | 3-(Methylsulfonylamino)phenylboronic acid | 3-(methylsulfonylamino)phenyl | 533.1659 |
| 340 | 3-(Pyrrolidine-1-carbonyl)phenylboronic acid | 3-(pyrrolidine-1-carbonyl)phenyl | 537.2320 |

-continued

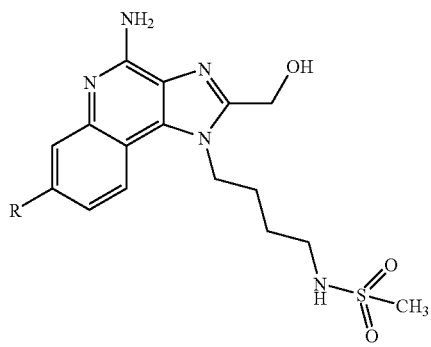

| Example | Reagent | R | Measured Mass (M + H) |
|---|---|---|---|
| 341 | 4-(Pyrrolidine-1-carbonyl)phenylboronic acid | 4-(pyrrolidin-1-ylcarbonyl)phenyl | 537.2271 |
| 342 | 3-(Isobutylaminocarbonyl)phenylboronic acid | 3-(isobutylaminocarbonyl)phenyl | 539.2418 |
| 343 | 4-(Isobutylaminocarbonyl)phenylboronic acid | 4-(isobutylaminocarbonyl)phenyl | 539.2429 |
| 344 | 3-(Piperidine-1-carbonyl)phenylboronic acid | 3-(piperidin-1-ylcarbonyl)phenyl | 551.2483 |
| 345 | 5-tert-butyldimethylsilanyloxymethyl)pyridine-3-boronic acid | 5-(hydroxymethyl)pyridin-3-yl | 471.1819 |

Examples 346-362

The compounds in the table below were prepared according to the following method. A test tube containing a solution of the corresponding ether analog (ethoxymethyl or methoxyethyl) in dichloromethane (1 mL) was cooled to 0° C. in an ice bath. Boron tribromide (4 eq of 1 M in dichloromethane) was added. The tube was vortexed, maintained at 0° C. for 0.5 hr, and then stirred at ambient temperature for 9 hours. Methanol (1 mL) and 6 N hydrochloric acid (500 µL) were added and the tube was vortexed for 5 minutes. The solvent was removed by vacuum centrifugation. The compounds were purified as described above for Examples 156-161. The table below shows a reference for the starting ether, the structure of the resulting compound, and the observed accurate mass for the isolated trifluoroacetate salt.

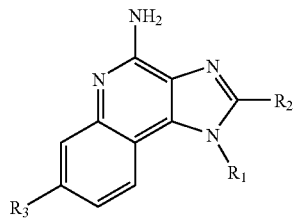

| Example | Reference for ether starting material | $R_1$ | $R_2$ | $R_3$ | Measured Mass (M + H) |
|---|---|---|---|---|---|
| 346 | Example 102 | isobutyl (CH(CH3)CH2CH3) | CH2CH2OH | phenyl | 347.1904 |
| 347 | Example 111 | isobutyl | CH2CH2OH | 3-cyanophenyl | 372.1819 |
| 348 | Example 201 | C(CH3)2CH2CH3 with NHSO2CH3 | CH2CH2OH | phenyl | 440.1755 |
| 349 | Example 113 | isobutyl | CH2CH2OH | 3-pyridyl | 348.1810 |
| 350 | Example 194 | 4-ethylpiperidinyl-N-C(O)CH(CH3)- | CH2CH2OH | phenyl | 458.2540 |
| 351 | Example 139 | C(CH3)2OH ethyl | CH2CH2CH2OH | 3-(NHSO2CH3)phenyl | 470.1832 |

-continued

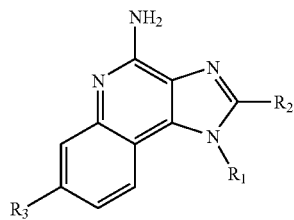

| Example | Reference for ether starting material | R₁ | R₂ | R₃ | Measured Mass (M + H) |
|---|---|---|---|---|---|
| 352 | Example 152 | pentyl-isothiazolidine 1,1-dioxide | —OH | phenyl | 466.1897 |
| 353 | Example 180 | 4-ethylpiperidine-1-carbonyl morpholine | —OH | 3-pyridyl | 502.2554 |
| 354 | Example 129 | 2-methylbutan-2-ol | —OH | 3-(pyrrolidine-1-carbonyl)phenyl | 460.2326 |
| 355 | Example 130 | 2-methylbutan-2-ol | —OH | 3-(morpholine-4-carbonyl)phenyl | 476.2285 |
| 356 | Example 376 | N-pentyl propanesulfonamide | —OH | 3-pyridyl | 469.2024 |
| 357 | Example 438 | 2-cyclohexylethyl | —OH | 3-pyridyl | 388.2130 |

-continued

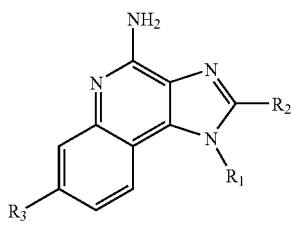

| Example | Reference for ether starting material | R₁ | R₂ | R₃ | Measured Mass (M + H) |
|---|---|---|---|---|---|
| 358 | Example 492 | (2-ethyl-1-(methylsulfonyl)piperidine) | OH | 3-pyridyl methyl | 467.1852 |
| 359 | Example 488 | (2R)-butane-1,2-diol | OH | 3-pyridyl methyl | 366.1574 |
| 360 | Example 422 | N-(2-methylbutan-2-yl) isobutyramide | OH | 3-pyridyl methyl | 433.2374 |
| 361 | Example 480 | 4-ethyltetrahydropyran | OH | 3-(methylsulfonamido)phenyl methyl | 482.1815 |
| 362 | * | N-pentyl morpholine-4-carboxamide | OH | 3-pyridyl methyl | 476.2383 |

*Although not specifically exemplified, the compound is readily prepared using the disclosed synthetic methods. All references are to U.S. Patent Application Publication 2004/0147543.

Example 363

[4-Amino-7-[3-(pyrrolidin-1-ylcarbonyl)phenyl]-1-(tetrahydro-2H-pyran-4-ylmethyl)-1H-imidazo[4,5-c]quinolin-2-yl]methanol

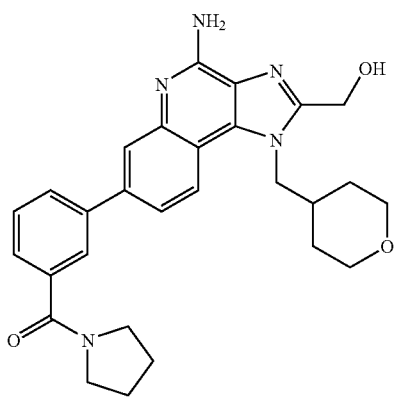 [SMILES: Nc1nc2cc(-c3cccc(C(=O)N4CCCC4)c3)ccc2c2c1nc(CO)n2CC1CCOCC1]

To a mixture of [4-amino-7-bromo-1-(tetrahydro-2H-pyran-4-ylmethyl)-1H-imidazo[4,5-c]quinolin-2-yl]methanol (400 mg, 1.00 mmol), 3-pyrrolidinylcarbonyl phenyl boronic acid (328 mg, 1.50 mmol), potassium carbonate (455 mg, 3.30 mmol), dimethoxyethane (4 mL), and water (2 mL) under a nitrogen atmosphere was added Pd(PPh$_3$)$_2$Cl$_2$ (14 mg, 0.02 mmol). The resulting suspension was refluxed for 18 hours. The reaction was cooled to ambient temperature. The reaction mixture was diluted with water and extracted with chloroform. The organic layer was dried over sodium sulfate, filtered and concentrated under reduced pressure. Chromatography (SiO$_2$, 0-40% CMA/CHCl$_3$) gave material that was stirred in acetonitrile and filtered to provide 100 mg of [4-amino-7-[3-(pyrrolidin-1-ylcarbonyl)phenyl]-1-(tetrahydro-2H-pyran-4-ylmethyl)-1H-imidazo[4,5-c]quinolin-2-yl]methanol as a white powder, m.p. 281-284° C. MS (APCI) m/z 486.3 (M+H)$^+$; Anal. calcd for C$_{28}$H$_{31}$N$_5$O$_3$: C, 69.26; H, 6.43; N, 14.42. Found: C, 68.99; H, 6.16; N, 14.46.

Example 364

{4-Amino-1-[2,2-dimethyl-3-(methylsulfonyl)propyl]-1H-imidazo[4,5-c]quinolin-2-yl}methanol

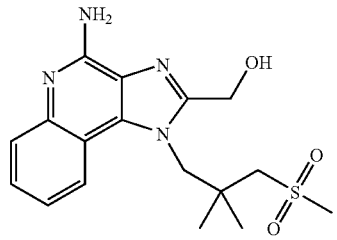 [SMILES: CC(C)(Cn1c(CO)nc2c(N)nc3ccccc3c21)CS(C)(=O)=O]

To a suspension of 1-[2,2-dimethyl-3-(methylsulfonyl)propyl]-2-(ethoxymethyl)-1H-imidazo[4,5-c]quinolin-4-amine (0.4 g, 1.02 mmol) in dichloromethane (5 mL) was added boron tribromide (5.1 mL, 1M solution in dichloromethane). An exotherm was observed upon addition and the mixture turned light purple. After stirring at ambient temperature for 20 hours, the remaining starting material was consumed by adding boron tribromide (2.5 mL, 1M solution in dichloromethane). The reaction was quenched with aqueous hydrochloric acid (1N, 20 mL) to afford a homogeneous mixture. The layers were separated and the aqueous layer washed with dichloromethane (20 mL). The pH of the aqueous layer was adjusted to 12 by addition of aqueous sodium hydroxide (50%) at which time a solid precipitated out of solution. The solid was stirred for 18 hours, collected by filtration and washed with water. The crude product was purified by chromatography over silica gel (eluting with CMA) to afford a white powder. The powder was triturated with methanol (20 mL). The resulting solid was isolated by filtration, washed with methanol and dried for 4 hours at 65° C. to provide 150 mg of {4-amino-1-[2,2-dimethyl-3-(methylsulfonyl)propyl]-1H-imidazo[4,5-c]quinolin-2-yl}methanol as a white powder, mp 230-232° C.

Anal. Calcd for C$_{17}$H$_{22}$N$_4$O$_3$S: % C, 56.33; % H, 6.12; % N, 15.46. Found: % C, 56.33; % H, 6.31; % N, 15.27.

Example 365

N-{2-[4-amino-2-(hydroxymethyl)-1H-imidazo[4,5-c]quinolin-1-yl]ethyl}-N'-isopropylurea

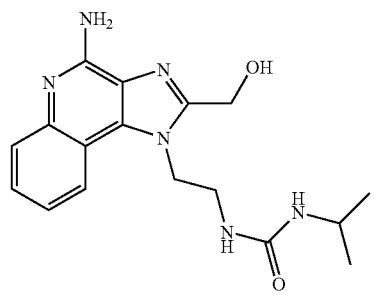 [SMILES: CC(C)NC(=O)NCCn1c(CO)nc2c(N)nc3ccccc3c21]

A stirring solution of N-{2-[4-amino-2-(ethoxymethyl)-1H-imidazo[4,5-c]quinolin-1-yl]ethyl}-N'-isopropylurea (400 mg, 1.1 mmol) in dichloromethane (50 mL) was sealed with a septum and purged with nitrogen gas. The solution was cooled in an ice/water bath and a 1.0 M solution of boron tribromide in dichloromethane (2.2 mL) was added via syringe. The resulting mixture was stirred for 2 hours while warming to ambient temperature. The mixture was cooled back to 0° C. in an ice/water bath and the second portion of boron tribromide (1.0 M, 5.5 mL) was added. The reaction was stirred for 18 hours while warming to ambient temperature. Aqueous hydrochloric acid (6N, 10 ml) was added and the mixture was stirred for 1 hour. The layers were separated and the aqueous fraction was neutralized by the slow addition of solid sodium hydroxide until the pH reached 14. A fine precipitate formed. The aqueous mixture was extracted with chloroform (2×50 mL) and filtered. The resulting solid (filter cake) was combined with the organic extracts, methanol (50 mL), and silica gel (5 g). The mixture was concentrated under reduced pressure. The crude product absorbed on silica was purified by chromatography using a HORIZON HPFC system (silica cartridge, eluting with 0-35% CMA in chloroform over 2.6 L) followed by recrystallization from acetonitrile to provide 170 mg of N-{2-[4-amino-2-(hydroxymethyl)-1H-imidazo[4,5-c]quinolin-1-yl]ethyl}-N-isopropylurea as an off-white solid, mp>240° C.

$^1$H NMR (500 MHz, DMSO-$d_6$) δ 8.30 (d, J=7.9 Hz, 1H), 7.61 (dd, J=8.3, 0.9 Hz, 1H), 7.43 (m, 1H), 7.24 (m, 1H), 6.53 (br s, 2H), 5.99 (t, J=5.8 Hz, 1H), 5.82 (d, J=7.8 Hz, 1H), 5.67 (d, J=5.8 Hz, 1H), 4.75 (d, J=5.8 Hz, 2H), 4.66 (t, J=6.7 Hz, 2H), 3.69 (m, 1H), 3.48 (q, J=6.4 Hz, 2H), 1.01 (d, J=6.5 Hz, 6H);

MS (APCI) m/z 343 (M+H)$^+$;

Anal. Calcd. for $C_{17}H_{22}N_6O_2$: % C, 59.63; % H, 6.48; % N, 24.54. Found: % C, 59.64; % H, 6.59; % N, 24.58.

Example 366

N-{4-[4-amino-2-(hydroxymethyl)-1H-imidazo[4,5-c]quinolin-1-yl]butyl}cyclopentanecarboxamide

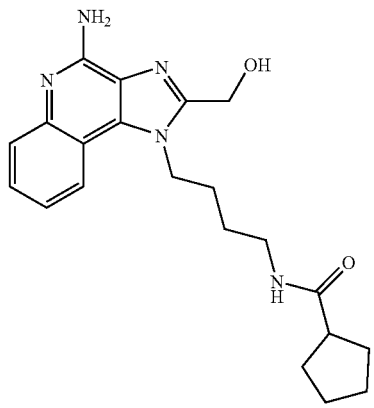 [SMILES: Nc1nc2ccccc2c2c1nc(CO)n2CCCCNC(=O)C1CCCC1]

Boron tribromide (2.5 equivalents, 14.6 mL of 1 M solution in dichloromethane) was added dropwise to a cooled (ice bath) suspension of N-{4-[4-amino-2-(ethoxymethyl)-1H-imidazo[4,5-c]quinolin-1-yl]butyl}cyclopentanecarboxamide (2.4 g, 5.8 mmol) in dichloromethane (25 mL). The reaction mixture was allowed to slowly warm to ambient temperature and then stirred for 6 days. Additional boron tribromide (5 equivalents, 29 mmol, 29 mL) was added and the reaction was stirred at ambient until starting material was consumed. The reaction was quenched slowly with methanol (100 mL) and then concentrated under reduced pressure. The residue was combined with 6 M hydrochloric acid (100 mL), heated to 50° C., and stirred for 2 hours. The resulting solution was cooled (ice bath) and then free-based (pH 9) with the addition of 6 M aqueous sodium hydroxide. A brown gummy solid formed in the basic aqueous solution. The aqueous liquid was decanted from the solid and acetonitrile was added (30 mL). A white precipitate formed and was isolated by filtration. The white precipitate was then triturated with hot acetonitrile, allowed to cool, isolated by filtration, washed with ether, and dried under vacuum to provide N-{4-[4-amino-2-(hydroxymethyl)-1H-imidazo[4,5-c]quinolin-1-yl]butyl}cyclopentanecarboxamide (0.48 g) as a fine white solid, mp 183-186° C.; MS (ESI) m/z 382 (M+H)$^+$; Anal. Calcd for $C_{21}H_{27}N_5O_2$: C, 65.35; H, 7.18; N, 18.14. Found C, 65.06; H, 6.90; N, 18.13.

Example 367

N-[4-(4-amino-2-hydroxymethyl-1H-imidazo[4,5-c]quinolin-1-yl)butyl]isobutyramide

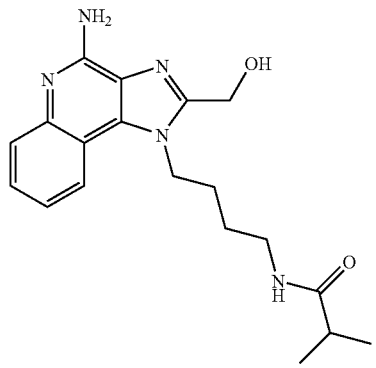 [SMILES: CC(C)C(=O)NCCCCn1c(CO)nc2c(N)nc3ccccc3c21]

Boron tribromide (2.5 equivalents, 15.6 mL of 1 M solution in dichloromethane) was added dropwise to a cooled (ice bath) suspension of N-[4-(4-amino-2-ethoxymethyl-1H-imidazo[4,5-c]quinolin-1-yl)butyl]isobutyramide (2.4 g, 6.2 mmol) in dichloromethane (25 mL). The reaction mixture was allowed to slowly warm to ambient temperature and then stirred for 1 day. Additional boron tribromide (5 equivalents, 31 mmol, 31 mL) was added to the mixture. The reaction was quenched slowly with methanol (100 mL) and then concentrated under reduced pressure. The residue was combined with 6 M hydrochloric acid (100 mL), heated to 5° C., and stirred for 2 hours. The resulting solution was cooled (ice bath) and then free-based (pH 9) with the addition of 6 M sodium hydroxide. A brown gummy solid formed in the basic aqueous solution. The resulting solid was extracted with dichloromethane (6×50 mL). The combined extracts were washed with brine (100 mL), dried with magnesium sulfate, filtered, and then concentrated under reduced pressure. This material was purified by prep HPLC (Analogix Separation System, Biotage Si 40+M column, eluted with a gradient of 0-20% methanol in dichloromethane with 1% ammonium hydroxide) to provide a light brown solid. The solid was triturated with hot acetonitrile, allowed to cool, isolated by filtration, washed with ether, and dried under vacuum to provide N-[4-(4-amino-2-hydroxymethyl-1H-imidazo[4,5-c]quinolin-1-yl)butyl]isobutyramide (0.049 g) as a white solid, mp 222-224° C.; MS (ESI) m/z 356 (M+H)$^+$; Anal. Calcd for $C_{19}H_{25}N_5O_2 \cdot 0.25HBr \cdot 0.10H_2O$: C, 60.46; H, 6.80; N, 18.55. Found C, 60.26; H, 6.64; N, 18.43.

Example 368

N-[4-(4-amino-2-hydroxymethyl-1H-imidazo[4,5-c]quinolin-1-yl)butyl]methanesulfonamide

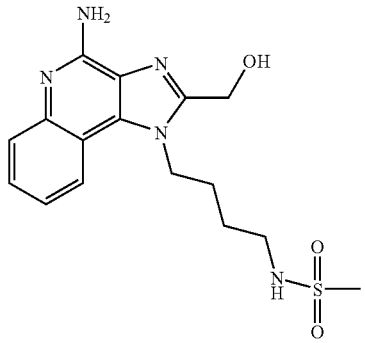 [SMILES: CS(=O)(=O)NCCCCn1c(CO)nc2c(N)nc3ccccc3c21]

Boron tribromide (2.5 equivalents, 20 mL of 1 M solution in dichloromethane) was added dropwise to a cooled (ice bath) suspension of N-[4-(4-amino-2-ethoxymethyl-1H-imidazo[4,5-c]quinolin-1-yl)butyl]methanesulfonamide (3 g, 7.92 mmol) in dichloromethane (20 mL). The reaction mixture was allowed to slowly warm to ambient temperature and then stirred for 4 hours. Additional boron tribromide (2 mL) was added and the mixture was stirred for 3 hours. The reaction was quenched slowly with methanol (20 mL) and then concentrated under reduced pressure. The residue was combined with 6 M hydrochloric acid (50 mL), heated to 50° C., and stirred for 2 hours. The resulting solution was concentrated under reduced pressure to a slurry that cooled (ice bath) and then free-based with the addition of 7 M ammonia in methanol (40 mL). The mixture was concentrated under reduced pressure and the addition of 7 M ammonia in methanol (40 mL) was repeated 2 more times. The concentrated brown sludge like material was purified by prep HPLC (ISCO Combiflash Separation System, Biotage Si 40+M column, eluted with a gradient of methanol in dichloromethane with 1% ammonium hydroxide) to provide a light brown solid. The solid was triturated with hot acetonitrile, allowed to cool, isolated by filtration, washed with ether, and dried under vacuum to provide N-[4-(4-amino-2-hydroxymethyl-1H-imidazo[4,5-c]quinolin-1-yl)butyl]methanesulfonamide (0.1 g) as a fine beige solid, mp 216-219° C.; MS (ESI) m/z 364 (M+H)$^+$; Anal. Calcd for $C_{16}H_{21}N_5O_3S$: C, 52.88; H, 5.82; N, 19.27. Found C, 52.62; H, 5.71; N, 19.02.

Example 369

(4-Amino-1-{4-[(methylsulfonyl)amino]butyl}-1H-imidazo[4,5-c]quinolin-2-yl)methyl N-[(benzyloxy)carbonyl]-L-valinate

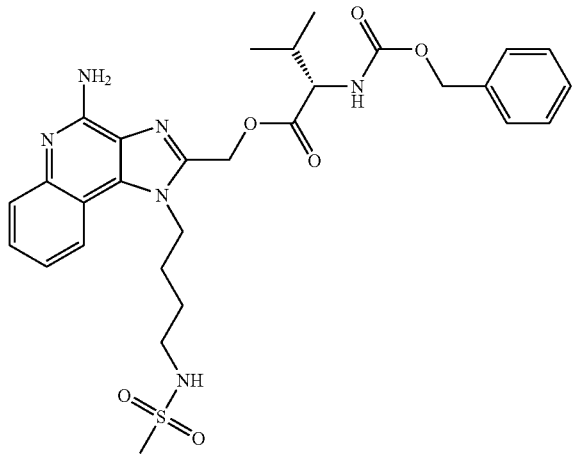 [SMILES: CC(C)[C@H](NC(=O)OCc1ccccc1)C(=O)OCc1nc2c(N)nc3ccccc3c2n1CCCCNS(C)(=O)=O]

To a stirred suspension of N-[4-(4-amino-2-hydroxymethyl-1H-imidazo[4,5-c]quinolin-1-yl)butyl]methanesulfonamide (2.1 g, 5.8 mmol) in THF was added triphenylphosphine (1.5 equivalents, 8.7 mmol, 2.2 g) followed by CBZ-L-valine (1.5 equivalents, 8.7 mmol, 2.3 g). The suspension was stirred for 5 min after which it was cooled in an ice-bath. To this cooled reaction mixture diisopropyl azodicarboxylate (DIAD, 1.8 equivalents, 10.4 mmol, 2.0 mL) was added and the reaction was warmed to room temperature and stirred overnight. The solvent was evaporated under reduced pressure and the crude solid was purified by prep HPLC (ISCO Combiflash Separation System, Biotage Si 40+M column, eluted with a gradient of 0-8% methanol in dichloromethane with 1% ammonium hydroxide) to provide a solid. The solid was heated in diethyl ether and filtered to afford (4-amino-1-{4-[(methylsulfonyl)amino]butyl}-1H-imidazo[4,5-c]quinolin-2-yl)methyl N-[(benzyloxy)carbonyl]-L-valinate (2 g) as a beige solid, mp 99-100° C.; MS (ESI) m/z 597 (M+H)$^+$; Anal. Calcd for $C_{29}H_{36}N_6O_6S$: C, 58.37; H, 6.08; N, 14.08. Found C, 57.98; H, 6.31; N, 13.82.

Example 370

(4-Amino-1-{4-[(methylsulfonyl)amino]butyl}-1H-imidazo[4,5-c]quinolin-2-yl)methyl L-valinate

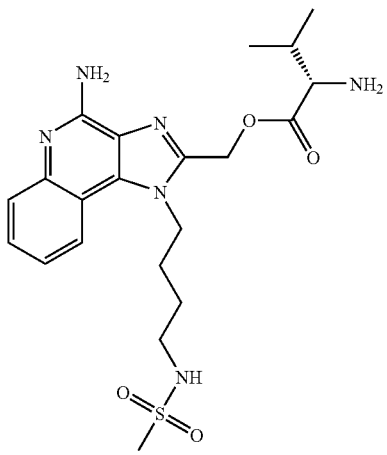 [SMILES: CC(C)[C@H](N)C(=O)OCc1nc2c(N)nc3ccccc3c2n1CCCCNS(C)(=O)=O]

To a hydrogenation bottle was added (4-amino-1-{4-[(methylsulfonyl)amino]butyl}-1H-imidazo[4,5-c]quinolin-2-yl)methyl N-[(benzyloxy)carbonyl]-L-valinate (1.5 g, 2.5 mmol) followed by a mixture of methanol (30 mL), THF (15 mL) and water (5 mL) and conc HCl (5 mL). To this was added Pd/C (90 mg) and the reaction was hydrogenated at 40 psi (2.8×10$^5$ Pa) overnight. To the reaction mixture was added conc. HCl (5 mL) and Pd/C (90 mg) and the reaction was hydrogenated at 40 psi (2.8×10$^5$ Pa) for 18 hours. The reaction was filtered through CELITE filter aid and the filtrate was evaporated to afford a clear oil. The product was isolated by prep HPLC (ISCO Combiflash Separation System, Biotage Si 40+M column, eluted with a gradient of 0-8% methanol in dichloromethane with 1% ammonium hydroxide) to provide (4-amino-1-{4-[(methylsulfonyl)amino]butyl}-1H-imidazo[4,5-c]quinolin-2-yl)methyl L-valinate (0.495 g) as an off white solid, mp 161-163° C.; MS (ESI) m/z 463 (M+H)$^+$; Anal. Calcd for $C_{21}H_{30}N_6O_4S$: C, 54.53; H, 6.54; N, 18.17. Found C, 53.96; H, 6.62; N, 17.85, delta C=0.57.

Example 371

[4-Amino-1-(tetrahydro-2H-pyran-4-ylmethyl)-1H-imidazo[4,5-c]quinolin-2-yl]methanol

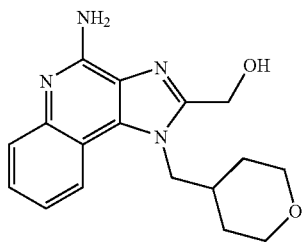 [SMILES: Nc1nc2ccccc2c2c1nc(CO)n2CC1CCOCC1]

Part A

Under a nitrogen atmosphere THF (90 mL) and triethylamine (17.5 mL, 125.6 mmol) were added sequentially to a mixture of crude 4-chloro-3-nitroquinoline (13.10 g, 62.81 mmol) and 1-tetrahydro-2H-pyran-4-ylmethylamine hydrochloride (10.0 g, 65.95 mmol). The reaction mixture was placed in an oil bath at 45° C. for 1 hour and then concentrated under reduced pressure. The residue was diluted with THF (30 mL) and water (200 mL). The THF was removed under reduced pressure. A solid was isolated by filtration and dried to provide 16.10 g of 3-nitro-N-(tetrahydro-2H-pyran-4-ylmethyl)quinolin-4-amine as a light yellow solid.

Part B

A mixture of 3-nitro-N-(tetrahydro-2H-pyran-4-ylmethyl)quinolin-4-amine (2.50 g), 10% palladium on carbon (0.25 g), and ethanol (40 mL) was placed under hydrogen pressure on a Parr apparatus. When the reaction was complete, the mixture was filtered through a layer of CELITE filter agent. The filter cake was washed with ethanol. The filtrate was concentrated under reduced pressure to provide 2.23 g of $N^4$-(tetrahydro-2H-pyran-4-ylmethyl)quinoline-3,4-diamine as a yellowish-orange oil.

Part C

Chloroacetyl chloride (12 mL, 151 mmol) was dissolved in dichloromethane (30 mL) and added via addition funnel, over 20 minutes, to a stirring solution of N4-(tetrahydro-2H-pyran-4-ylmethyl)quinoline-3,4-diamine (35.3 g, 137 mmol) in dichloromethane (300 mL). The resulting solution was stirred at ambient temperature under nitrogen for 24 hours at which point the solution was heated to 40° C. for an additional 24 hours. The mixture was cooled to ambient temperature, diluted with dichloromethane (150 mL) and transferred to a separatory funnel. The organic layer was washed with water (2×200 mL) and brine (2×200 mL), dried over magnesium sulfate, filtered and concentrated under reduced pressure to provide 38.3 g of 2-(chloromethyl)-1-(tetrahydro-2H-pyran-4-ylmethyl)-1H-imidazo[4,5-c]quinoline as a light brown solid.

Part D

3-Chloroperoxybenzoic acid (mCPBA) (3.8 g of 77% pure material, 14.2 mmol) was added to a stirring solution of 2-(chloromethyl)-1-(tetrahydro-2H-pyran-4-ylmethyl)-1H-imidazo[4,5-c]quinoline (3.0 g, 9.50 mmol) in dichloromethane (60 mL). After 15.5 hours, ammonium hydroxide (12 mL) and then p-toluenesulfonyl chloride (2.2 g, 11.4 mmol) were added to the stirring solution and the biphasic mixture was stirred at ambient temperature for 3 hours. The reaction was diluted with water (50 mL) and then transferred to a separatory funnel. The aqueous layer was extracted with dichloromethane (3×100 mL) and the combined organic fractions dried over magnesium sulfate, filtered and concentrated under reduced pressure. The residue was purified by column chromatography using a HORIZON HPFC system (silica cartridge, eluting with 3-20% methanol in dichloromethane) to provide 1.6 g of 2-(chloromethyl)-1-(tetrahydro-2H-pyran-4-ylmethyl)-1H-imidazo[4,5-c]quinolin-4-amine as a yellow solid.

Part E

Potassium acetate (0.41 g, 4.16 mmol) and potassium iodide (0.28 g, 1.66 mmol) were added to a stirring solution of 2-(chloromethyl)-1-(tetrahydro-2H-pyran-4-ylmethyl)-1H-imidazo[4,5-c]quinolin-4-amine (0.55 g, 1.66 mmol) and the resulting suspension was heated to 50° C. After 17 hours, the suspension was cooled to ambient temperature and concentrated under reduced pressure. The residue was suspended in methanol (10 mL) and water (5 mL) and lithium hydroxide monohydrate (0.35 g, 8.31 mmol) was added in one portion. The resulting solution was stirred at ambient temperature 18 hours and concentrated under reduced pressure. The residue was diluted with water (20 mL) and neutralized with hydrochloric acid (6 N in water). The aqueous layer was extracted with dichloromethane (2×50 mL) and ethyl acetate (50 mL). The combined organic fractions were concentrated to a yellow solid which was crystallized from acetonitrile. The crystals were isolated by filtration and dried in a vacuum oven at 65° C. to provide 0.20 g of [4-amino-1-(tetrahydro-2H-pyran-4-ylmethyl)-1H-imidazo[4,5-c]quinolin-2-yl]methanol as an off-white solid, mp 239-241° C.

Anal. calcd for $C_{17}H_{20}N_4O_2 \cdot 0.2H_2O$: C, 64.62; H, 6.51; N, 17.73. Found: C, 64.45; H, 6.69; N, 17.62.

Examples 372-450

Part A

A solution of 1-(4-aminobutyl)-2-methoxymethyl-1H-imidazo[4,5-c]quinoline-4-amine (30 mg, 1 eq, prepared according to the general method of Example 3 using methoxyacetyl chloride in lieu of 3-methoxypropionyl chloride) and N,N-diisopropylethylamine (2 eq) in N,N-dimethylacetamide (1 mL) was added to a tube containing a reagent (1.1 eq) from the table below. The reaction mixture was vortexed overnight and then quenched with water (100 μL). The solvents were removed by vacuum centrifugation. The residue was purified by solid-supported liquid-liquid extraction according to the following procedure. The sample was dissolved in chloroform (1 mL) then loaded onto diatomaceous earth that had been equilibrated with 1 M sodium hydroxide (600 μL) for about 20 minutes. After 10 minutes chloroform (500 μL) was added to elute the product from the diatomaceous earth into a well of a collection plate. After an additional 10 minutes the process was repeated with additional chloroform (500 μL). The solvent was then removed by vacuum centrifugation.

Part B

The residue (in a test tube) was combined with dichloromethane (500 μL) and the tube was vortexed to dissolve the solids. The solution was cooled (0° C.) and then combined with boron tribromide (400 μL of 1 M in dichloromethane). The mixture was vortexed for 5 minutes, chilled for 30 minutes, and then vortexed at ambient temperature for 64 hours. Additional dichloromethane (500 μL) and boron tribromide (400 μL of 1 M in dichloromethane) were added and the mixture was vortexed overnight. The solvent was then removed by vacuum centrifugation. The residue was diluted with methanol (500 μL) and hydrochloric acid (500 μL of 6 N). The solvents were removed by vacuum centrifugation. The compounds were purified according to the method described in Examples 8-72. The table below shows the reagent used for each example, the structure of the resulting compound, and the observed accurate mass for the isolated trifluoroacetate salt.

| Example | Reagent | R | Measured Mass (M + H) |
|---|---|---|---|
| 372 | None | H | 286.1658 |
| 373 | Cyclopropanecarbonyl chloride | C(=O)-cyclopropyl | 354.1907 |
| 374 | Methoxyacetyl chloride | C(=O)CH$_2$OH | 344.1699 |
| 375 | Cyclobutanecarbonyl chloride | C(=O)-cyclobutyl | 368.2050 |
| 376 | Isovaleryl chloride | C(=O)CH$_2$CH(CH$_3$)$_2$ | 370.2206 |
| 377 | Pentanoyl chloride | C(=O)CH$_2$CH$_2$CH$_2$CH$_3$ | 370.2208 |
| 378 | Benzoyl chloride | C(=O)-phenyl | 390.1909 |
| 379 | Cyclohexanecarbonyl chloride | C(=O)-cyclohexyl | 396.2412 |

-continued

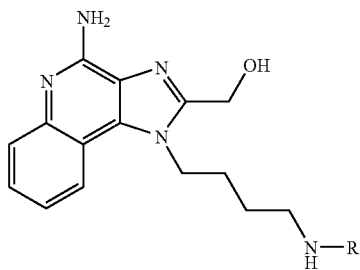

| Example | Reagent | R | Measured Mass (M + H) |
|---|---|---|---|
| 380 | Cyclopentylacetyl chloride | (cyclopentylacetyl group) | 396.2411 |
| 381 | m-Toluoyl chloride | (m-toluoyl group) | 404.2069 |
| 382 | o-Toluoyl chloride | (o-toluoyl group) | 404.2072 |
| 383 | p-Toluoyl chloride | (p-toluoyl group) | 404.2108 |
| 384 | Phenylacetyl chloride | (phenylacetyl group) | 404.2056 |
| 385 | Dimethylaminoacetyl chloride hydrochloride | (dimethylaminoacetyl group) | 371.2157 |
| 386 | 2-Fluorobenzoyl chloride | (2-fluorobenzoyl group) | 408.1819 |

-continued
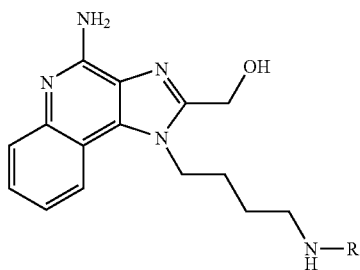
| Example | Reagent | R | Measured Mass (M + H) |
|---|---|---|---|
| 387 | 3-Fluorobenzoyl chloride | 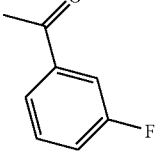 | 408.1811 |
| 388 | 4-Fluorobenzoyl chloride | 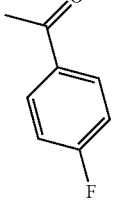 | 408.1819 |
| 389 | 3-Cyanobenzoyl chloride | 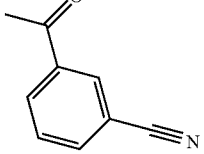 | 415.1847 |
| 390 | Hydrocinnamoyl chloride | 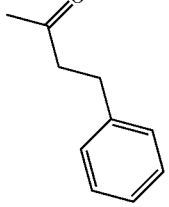 | 418.2200 |
| 391 | 2-Methoxybenzoyl chloride | 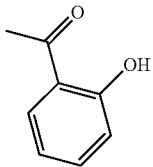 | 406.1880 |
| 392 | 3-Methoxybenzoyl chloride | 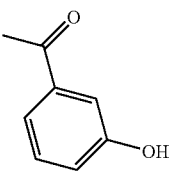 | 406.1876 |

-continued
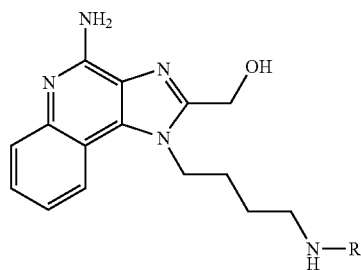
| Example | Reagent | R | Measured Mass (M + H) |
|---|---|---|---|
| 293 | p-Anisoyl chloride | 4-hydroxybenzoyl | 406.1860 |
| 394 | 3-Chlorobenzoyl chloride | 3-chlorobenzoyl | 424.1517 |
| 395 | 4-Chlorobenzoyl chloride | 4-chlorobenzoyl | 424.1525 |
| 396 | Isonicotinoyl chloride hydrochloride | isonicotinoyl | 391.1874 |
| 397 | Nicotinoyl chloride hydrochloride | nicotinoyl | 391.1895 |
| 398 | Picolinoyl chloride hydrochloride | picolinoyl | 391.1846 |

-continued

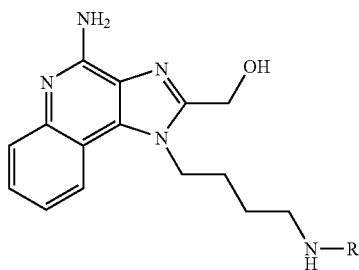

| Example | Reagent | R | Measured Mass (M + H) |
|---|---|---|---|
| 399 | trans-2-Phenyl-1-cyclopropanecarbonyl chloride | trans-2-phenylcyclopropanecarbonyl group | 430.2213 |
| 400 | Methanesulfonyl chloride | -S(O)₂CH₃ | 364.1421 |
| 401 | Ethanesulfonyl chloride | -S(O)₂CH₂CH₃ | 378.1595 |
| 402 | 1-Propanesulfonyl chloride | -S(O)₂CH₂CH₂CH₃ | 392.1753 |
| 403 | Dimethylsulfamoyl chloride | -S(O)₂N(CH₃)₂ | 393.1685 |
| 404 | 1-Butanesulfonyl chloride | -S(O)₂(CH₂)₃CH₃ | 406.1881 |
| 405 | Benzenesulfonyl chloride | -S(O)₂C₆H₅ | 426.1591 |

-continued

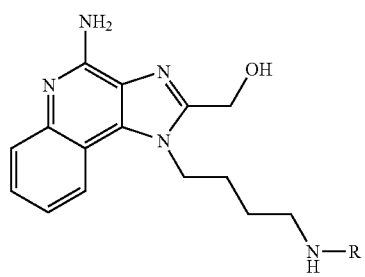

| Example | Reagent | R | Measured Mass (M + H) |
|---|---|---|---|
| 406 | 1-Methylimidazole-4-sulfonyl chloride | (1-methylimidazol-4-yl)sulfonyl | 430.1668 |
| 407 | 2-Thiophenesulfonyl chloride | (thiophen-2-yl)sulfonyl | 432.1135 |
| 408 | 3-Methylbenzenesulfonyl chloride | (3-methylphenyl)sulfonyl | 440.1728 |
| 409 | o-Toluenesulfonyl chloride | (2-methylphenyl)sulfonyl | 440.1758 |
| 410 | p-Toluenesulfonyl chloride | (4-methylphenyl)sulfonyl | 440.1766 |
| 411 | 2-Fluorobenzenesulfonyl chloride | (2-fluorophenyl)sulfonyl | 444.1479 |

-continued
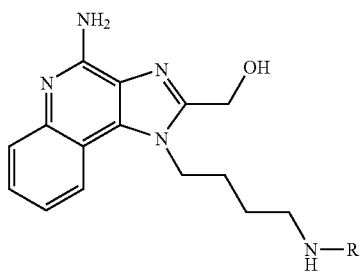
| Example | Reagent | R | Measured Mass (M + H) |
|---|---|---|---|
| 412 | 3-Fluorobenzenesulfonyl chloride | 3-F-C6H4-SO2- | 444.1517 |
| 413 | 4-Fluorobenzenesulfonyl chloride | 4-F-C6H4-SO2- | 444.1496 |
| 414 | 3-Cyanobenzenesulfonyl chloride | 3-NC-C6H4-SO2- | 451.1568 |
| 415 | 4-Cyanobenzenesulfonyl chloride | 4-NC-C6H4-SO2- | 451.1579 |
| 416 | beta-Styrenesulfonyl chloride | PhCH=CH-SO2- | 452.1725 |

-continued

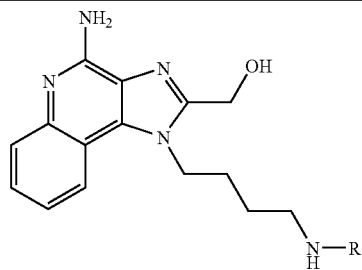

| Example | Reagent | R | Measured Mass (M + H) |
|---|---|---|---|
| 417 | 3-Methoxybenzenesulfonyl chloride | 3-hydroxyphenylsulfonyl | 442.1534 |
| 418 | 4-Methoxybenzenesulfonyl chloride | 4-hydroxyphenylsulfonyl | 442.1557 |
| 419 | 2-Chlorobenzenesulfonyl chloride | 2-chlorophenylsulfonyl | 460.1173 |
| 420 | 3-Chlorobenzenesulfonyl chloride | 3-chlorophenylsulfonyl | 460.1242 |
| 421 | 4-Chlorobenzenesulfonyl chloride | 4-chlorophenylsulfonyl | 460.1191 |
| 422 | 3-Pyridinesulfonyl chloride hydrochloride | pyridin-3-ylsulfonyl | 427.1530 |

-continued
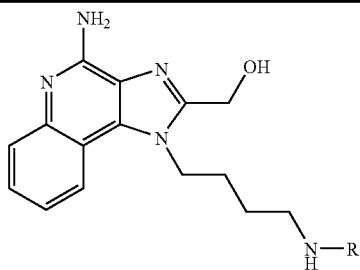
| Example | Reagent | R | Measured Mass (M + H) |
|---|---|---|---|
| 423 | 3,4-Dimethoxybenzenesulfonyl chloride | 3,4-dihydroxyphenylsulfonyl | 458.1452 |
| 424 | 3,4-Dichlorobenzenesulfonyl chloride | 3,4-dichlorophenylsulfonyl | 494.0806 |
| 425 | Methyl isocyanate | C(O)NHCH₃ | 343.1862 |
| 426 | Ethyl isocyanate | C(O)NHCH₂CH₃ | 357.2018 |
| 427 | Isopropyl isocyanate | C(O)NHCH(CH₃)₂ | 371.2181 |
| 428 | n-Propyl isocyanate | C(O)NHCH₂CH₂CH₃ | 371.2187 |
| 429 | n-Butyl isocyanate | C(O)NHCH₂CH₂CH₂CH₃ | 385.2314 |

-continued
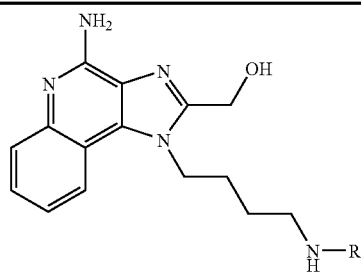
| Example | Reagent | R | Measured Mass (M + H) |
|---|---|---|---|
| 430 | Cyclopentyl isocyanate | *C(=O)NH-cyclopentyl | 397.2312 |
| 431 | Pentyl isocyanate | *C(=O)NH-(CH2)4-CH3 | 399.2512 |
| 432 | Phenyl isocyanate | *C(=O)NH-phenyl | 405.2047 |
| 433 | Cyclohexyl isocyanate | *C(=O)NH-cyclohexyl | 411.2473 |
| 434 | 2-Fluorophenyl isocyanate | *C(=O)NH-(2-F-phenyl) | 423.1959 |
| 435 | 3-Fluorophenyl isocyanate | *C(=O)NH-(3-F-phenyl) | 423.1924 |
| 436 | 4-Cyanophenyl isocyanate | *C(=O)NH-(4-CN-phenyl) | 430.1979 |

-continued

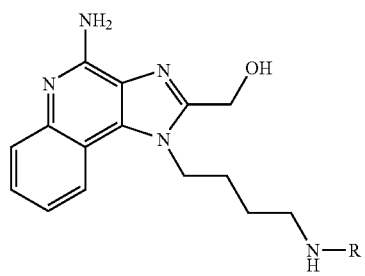

| Example | Reagent | R | Measured Mass (M + H) |
|---|---|---|---|
| 437 | (R)-(+)-alpha-Methylbenzyl isocyanate | acetamide with (R)-α-methylbenzyl group | 433.2370 |
| 438 | (S)-(−)-alpha-Methylbenzyl isocyanate | acetamide with (S)-α-methylbenzyl group | 433.2327 |
| 439 | 2-Phenylethylisocyanate | acetamide with 2-phenylethyl group | 433.2333 |
| 440 | 2-Methoxyphenyl isocyanate | acetamide with 2-hydroxyphenyl group | 421.2006 |
| 441 | 4-Methoxyphenyl isocyanate | acetamide with 4-hydroxyphenyl group | 421.1958 |
| 442 | 2-Chlorophenyl isocyanate | acetamide with 2-chlorophenyl group | 439.1650 |

-continued

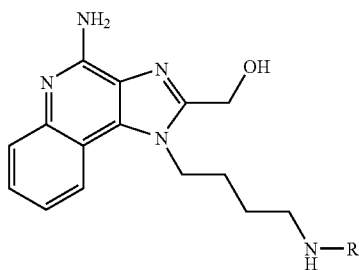

| Example | Reagent | R | Measured Mass (M + H) |
|---|---|---|---|
| 443 | 4-Chlorophenyl isocyanate | (4-chlorophenyl)aminocarbonyl | 439.1656 |
| 444 | trans-2-Phenylcyclopropyl isocyanate | (trans-2-phenylcyclopropyl)aminocarbonyl | 445.2328 |
| 445 | N,N-Dimethylcarbamoyl chloride | N,N-dimethylaminocarbonyl | 357.2005 |
| 446 | 1-Pyrrolidinecarbonyl chloride | 1-pyrrolidinylcarbonyl | 383.2168 |
| 447 | 1-Piperidinecarbonyl chloride | 1-piperidinylcarbonyl | 397.2329 |
| 448 | 4-Morpholinylcarbonyl chloride | 4-morpholinylcarbonyl | 399.2112 |
| 449 | 4-Methyl-1-Piperazinecarbonyl chloride | 4-methyl-1-piperazinylcarbonyl | 412.2439 |

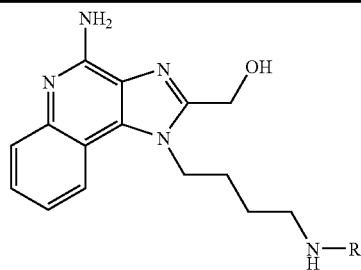

| Example | Reagent | R | Measured Mass (M + H) |
|---|---|---|---|
| 450 | N-Methyl-N-phenylcarbamoyl chloride | −C(=O)−N(CH₃)−C₆H₅ | 419.2167 |

Examples 451-466

Part A

A solution of 1-(2-amino-2-methylpropyl)-2-methoxymethyl-1H-imidazo[4,5-c]quinoline-4-amine (31 mg, 1 eq, prepared according to the general method of Example 3 using methoxyacetyl chloride in lieu of 3-methoxypropionyl chloride and tert-butyl N-{2-[(3-aminoquinolin-4-yl)amino]-1,1-dimethylethyl}carbamate in lieu of tert-butyl N-{4-[(3-aminoquinolin-4-yl)amino]butyl}carbamate) and N,N-diisopropylethylamine (2 eq) in N,N-dimethylacetamide (1 mL) was placed in a test tube. A reagent (1.1 eq) from the table below was added and the reaction mixture was vortexed overnight. The reaction was quenched with concentrated ammonium hydroxide (100 μL) and the solvents were removed by vacuum centrifugation.

Part B

The residue (in a test tube) was combined with dichloromethane (1 mL) and the tube was vortexed to dissolve the solids. The solution was cooled (0° C.) and then combined with boron tribromide (400 μL of 1 M in dichloromethane). The reaction was maintained at about 0° C. for 20 minutes. Methanol (1 mL) and hydrochloric acid (500 μL of 6 N) were added and the tube was vortexed for about 30 minutes. The solvents were removed by vacuum centrifugation. The compounds were purified according to the method described in Examples 8-72. The table below shows the reagent used for each example, the structure of the resulting compound, and the observed accurate mass for the isolated trifluoroacetate salt.

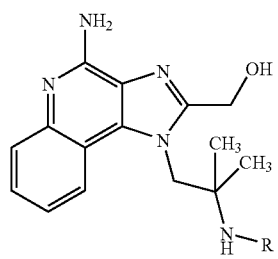

| Example | Reagent | R | Measured Mass (M + H) |
|---|---|---|---|
| 451 | None | H | 286.1687 |
| 452 | Cyclopropanecarbonyl chloride | −C(=O)−cyclopropyl | 354.1936 |

-continued

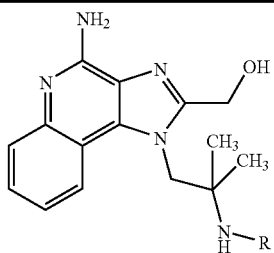

| Example | Reagent | R | Measured Mass (M + H) |
|---|---|---|---|
| 453 | Butyryl chloride | (propanoyl) | 356.2094 |
| 454 | Isobutyryl chloride | (isopropylcarbonyl) | 356.2119 |
| 455 | Cyclopentanecarbonyl chloride | (cyclopentylcarbonyl) | 382.2259 |
| 456 | Benzoyl chloride | (phenylcarbonyl) | 390.1908 |
| 457 | Nicotinoyl chloride hydrochloride | (pyridin-3-ylcarbonyl) | 391.1844 |
| 458 | Methanesulfonyl chloride | (methylsulfonyl) | 364.1414 |
| 459 | Benzenesulfonyl chloride | (phenylsulfonyl) | 426.1617 |
| 460 | 2,2,2-Trifluoroethane-sulfonyl chloride | (2,2,2-trifluoroethylsulfonyl) | 432.1339 |

-continued
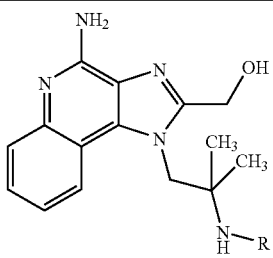
| Example | Reagent | R | Measured Mass (M + H) |
|---|---|---|---|
| 461 | 3-Fluorobenzenesulfonyl chloride | 3-fluorophenyl-SO2- | 444.1523 |
| 462 | n-Propyl isocyanate | -C(O)NH-CH2CH2CH3 | 371.2215 |
| 463 | Cyclopentyl isocyanate | -C(O)NH-cyclopentyl | 397.2327 |
| 464 | Phenyl isocyanate | -C(O)NH-phenyl | 405.2063 |
| 465 | Cyclohexyl isocyanate | -C(O)NH-cyclohexyl | 411.2515 |
| 466 | 3-Fluorophenyl isocyanate | -C(O)NH-(3-fluorophenyl) | 423.1955 |

Examples 467-478

Part A

To a round-bottomed flask containing 1-(4-aminobutyl)-2-methoxymethyl-1H-imidazo[4,5-c]quinolin-4-amine (10.0 g, 33.4 mmol) was added methanol (160 mL) followed by acetic acid (40 mL). The reaction was stirred for 5 minutes and pyridine 3-carboxaldehyde (5.4 g, 50.1 mmol) was added and the reaction was stirred overnight at ambient temperature. Sodium cyanoborohydride (1 M in THF, 33.4 mL, 33.4 mmol) was added to the resultant imine in portions over 10 minutes. After 45 minutes the solvent was evaporated to afford an oil. To the oil was added saturated aqueous sodium bicarbonate (200 mL) and the aqueous layer was washed with ethyl acetate (200 mL) and dichloromethane (200 mL). The product was extracted from the aqueous with 20% methanol (2×100 mL) in dichloromethane. The organic layers were combined and the solvent evaporated to afford crude 2-methoxymethyl-1-{4-[(pyridin-3-ylmethyl)amino]butyl}-1H-imidazo[4,5-c]quinolin-4-amine (about 2 g). The aqueous layer was again extracted with 20% dimethylformamide (2×100 mL) in dichloromethane. The organic layers were combined and the solvent evaporated to afford crude 2-methoxymethyl-1-{4-[(pyridin-3-ylmethyl)amino]butyl}-1H-imidazo[4,5-c]quinolin-4-amine (about 2 g).

Part B

A solution of 2-methoxymethyl-1-{4-[(pyridin-3-ylmethyl)amino]butyl}-1H-imidazo[4,5-c]quinolin-4-amine (40 mg, 1 eq) and N,N-diisopropylethylamine (2 eq) in N,N-dimethylacetamide (1 mL) was added to a tube containing a reagent (1.1 eq) from the table below. The reaction mixture was vortexed for 4 hours and then quenched with water (50 µL). The solvents were removed by vacuum centrifugation. The residue was purified by solid-supported liquid-liquid extraction according to the following procedure. The sample was dissolved in chloroform (1 mL) then loaded onto diatomaceous earth that had been equilibrated with 1 M sodium hydroxide (600 µL) for about 20 minutes. After 10 minutes chloroform (500 µL) was added to elute the product from the diatomaceous earth into a well of a collection plate. After an additional 10 minutes the process was repeated with additional chloroform (500 µL). The solvent was then removed by vacuum centrifugation.

Part C

The residue (in a test tube) was combined with dichloromethane (500 µL) and the tube was vortexed to dissolve the solids. The solution was cooled (0° C.) and then combined with boron tribromide (400 µL of 1 M in dichloromethane). The mixture was vortexed for 10 minutes, chilled for 30 minutes, and then vortexed at ambient temperature overnight. The solvent was then removed by vacuum centrifugation. The residue was diluted with methanol (500 µL) and hydrochloric acid (500 µL of 6 N) and the mixture was vortexed for about 30 minutes. The solvents were removed by vacuum centrifugation. The compounds were purified according to the method described in Examples 8-72. The table below shows the reagent used for each example, the structure of the resulting compound, and the observed accurate mass for the isolated trifluoroacetate salt.

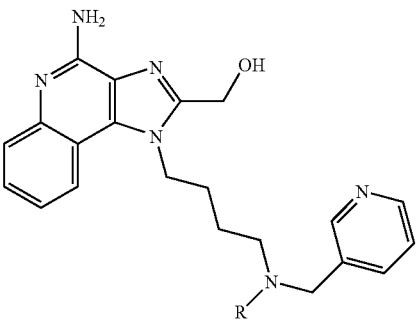

| Example | Reagent | R | Measured Mass (M + H) |
|---|---|---|---|
| 467 | None | ![H] | 377.2087 |
| 468 | Isobutyryl chloride | ![isobutyryl] | 447.2468 |
| 469 | Cyclohexanecarbonyl chloride | ![cyclohexanecarbonyl] | 487.2783 |
| 470 | Phenylacetyl chloride | ![phenylacetyl] | 495.2465 |
| 471 | 4-Fluorobenzoyl chloride | ![4-fluorobenzoyl] | 499.2272 |

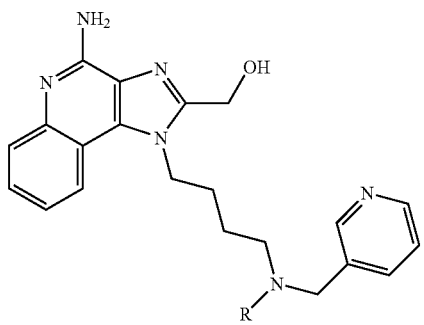

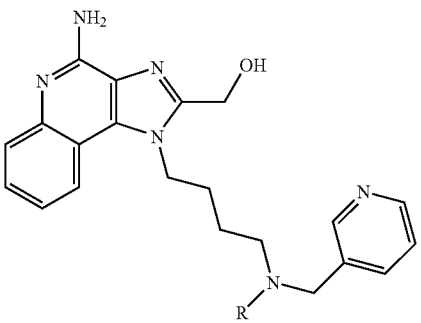

| Example | Reagent | R | Measured Mass (M + H) |
|---|---|---|---|
| 472 | 3-Methoxybenzoyl chloride | | 497.2263 |
| 473 | 1-Methylimidazole-4-sulfonyl chloride | | 521.2071 |
| 474 | 2,2,2-Trifluoroethanesulfonyl chloride | | 523.1717 |
| 475 | alpha-Toluenesulfonyl chloride | | 531.2134 |
| 476 | 3-Methoxybenzenesulfonyl chloride | | 533.1941 |

| Example | Reagent | R | Measured Mass (M + H) |
|---|---|---|---|
| 477 | Isopropyl isocyanate | | 462.2611 |
| 478 | 3-Fluorophenyl isocyanate | | 514.2357 |

Examples 479-543

The compounds in the table below were prepared and purified according to the methods of Parts B and C of Examples 467-478 using 1-(4-benzylaminobutyl)-2-ethoxymethyl-1H-imidazo[4,5-c]quinolin-4-amine in lieu of 2-methoxymethyl-1-{4-[(pyridin-3-ylmethyl)amino]butyl}-1H-imidazo[4,5-c]quinolin-4-amine. 1-(4-Benzylaminobutyl)-2-ethoxymethyl-1H-imidazo[4,5-c]quinolin-4-amine was prepared according to the general method of Part A of Examples 467-478 using benzaldehyde in lieu of pyridine 3-carboxaldehyde and 1-(4-aminobutyl)-2-ethoxymethyl-1H-imidazo[4,5-c]quinolin-4-amine in lieu of 1-(4-aminobutyl)-2-methoxymethyl-1H-imidazo[4,5-c]quinolin-4-amine. The table below shows the reagent used for each example, the structure of the resulting compound, and the observed accurate mass for the isolated trifluoroacetate salt.

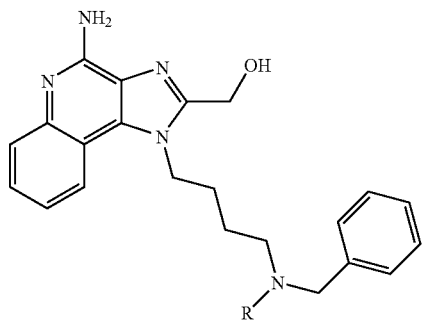
| Example | Reagent | R | Measured Mass (M + H) |
|---|---|---|---|
| 479 | Cyclobutanecarbonyl chloride | (O=C-cyclobutyl) | 458.2550 |
| 480 | DL-2-Methylbutyryl chloride | (O=C-CH(CH3)CH2CH3) | 460.2707 |
| 481 | Isovaleryl chloride | (O=C-CH2-CH(CH3)2) | 460.2714 |
| 482 | Pentanoyl chloride | (O=C-CH2CH2CH2CH3) | 460.2730 |
| 483 | Pivaloyl chloride | (O=C-C(CH3)3) | 460.2714 |
| 484 | Cyclopentanecarbonyl chloride | (O=C-cyclopentyl) | 472.2712 |
| 485 | tert-Butylacetyl chloride | (O=C-CH2-C(CH3)3) | 474.2879 |

-continued
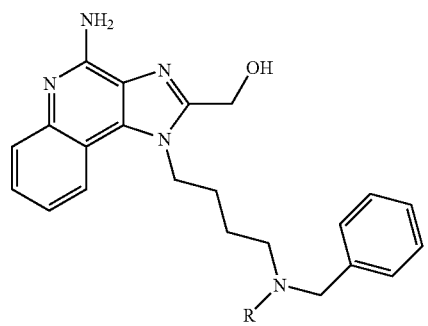
| Example | Reagent | R | Measured Mass (M + H) |
|---|---|---|---|
| 486 | Benzoyl chloride | (phenyl C=O) | 480.2398 |
| 487 | Thiophene-2-carbonyl chloride | (thiophen-2-yl C=O) | 486.1971 |
| 488 | Cyclohexanecarbonyl chloride | (cyclohexyl C=O) | 486.2893 |
| 489 | Cyclopentylacetyl chloride | (cyclopentyl-CH$_2$-C=O) | 486.2818 |
| 490 | m-Toluoyl chloride | (3-methylphenyl C=O) | 494.2577 |
| 491 | o-Toluoyl chloride | (2-methylphenyl C=O) | 494.2531 |

-continued
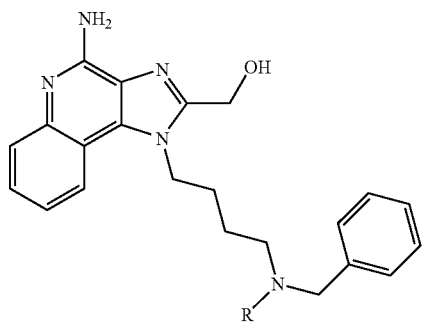
| Example | Reagent | R | Measured Mass (M + H) |
|---|---|---|---|
| 492 | p-Toluoyl chloride | 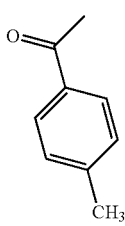 | 494.2527 |
| 493 | 3-Fluorobenzoyl chloride | 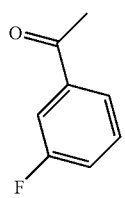 | 498.2307 |
| 494 | 4-Fluorobenzoyl chloride | 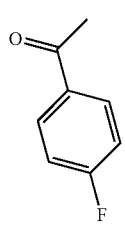 | 498.2326 |
| 495 | 3-Cyanobenzoyl chloride | 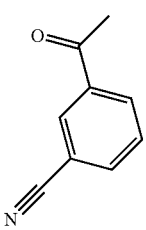 | 505.2378 |
| 496 | 4-Cyanobenzoyl chloride | 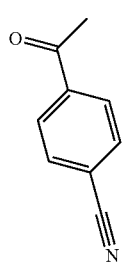 | 505.2387 |

-continued
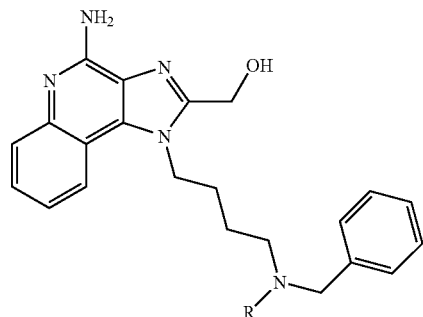
| Example | Reagent | R | Measured Mass (M + H) |
|---|---|---|---|
| 497 | Hydrocinnamoyl chloride | (3-phenylpropanoyl group) | 508.2715 |
| 498 | 2-Methoxybenzoyl chloride | 2-hydroxybenzoyl | 496.2311 |
| 499 | 3-Methoxybenzoyl chloride | 3-hydroxybenzoyl | 496.2314 |
| 500 | p-Anisoyl chloride | 4-hydroxybenzoyl | 496.2365 |
| 501 | 3-Chlorobenzoyl chloride | 3-chlorobenzoyl | 514.2026 |
| 502 | 4-Chlorobenzoyl chloride | 4-chlorobenzoyl | 514.2041 |

-continued

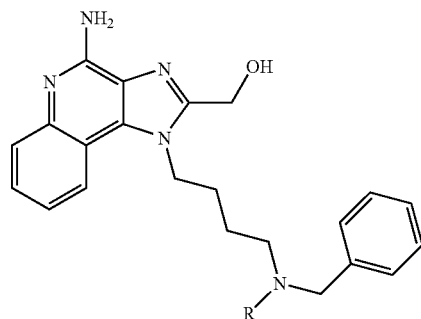

| Example | Reagent | R | Measured Mass (M + H) |
|---|---|---|---|
| 503 | Picolinoyl chloride hydrochloride | 2-pyridinylcarbonyl | 481.2361 |
| 504 | trans-2-Phenyl-1-cyclopropanecarbonyl chloride | trans-2-phenylcyclopropylcarbonyl | 520.2695 |
| 505 | 4-Dimethylaminobenzoyl chloride | 4-(dimethylamino)benzoyl | 523.2802 |
| 506 | 1-Propanesulfonyl chloride | propylsulfonyl | 482.2232 |
| 507 | Dimethylsulfamoyl chloride | dimethylsulfamoyl | 483.2196 |
| 508 | 2-Thiophenesulfonyl chloride | 2-thienylsulfonyl | 522.1613 |

-continued

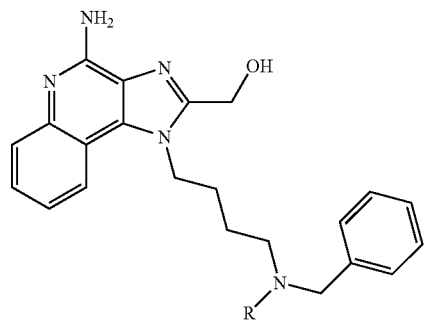

| Example | Reagent | R | Measured Mass (M + H) |
|---|---|---|---|
| 509 | alpha-Toluenesulfonyl chloride | benzyl methylsulfonyl | 530.2239 |
| 510 | o-Toluenesulfonyl chloride | 2-methylphenylsulfonyl | 530.2197 |
| 511 | 4-Fluorobenzenesulfonyl chloride | 4-fluorophenylsulfonyl | 534.2028 |
| 512 | 3,5-Dimethylisoxazole-4-sulfonyl chloride | 3,5-dimethylisoxazol-4-ylsulfonyl | 535.2106 |
| 513 | 2-Cyanobenzenesulfonyl chloride | 2-cyanophenylsulfonyl | 541.1968 |
| 514 | 3-Cyanobenzenesulfonyl chloride | 3-cyanophenylsulfonyl | 541.2035 |

-continued
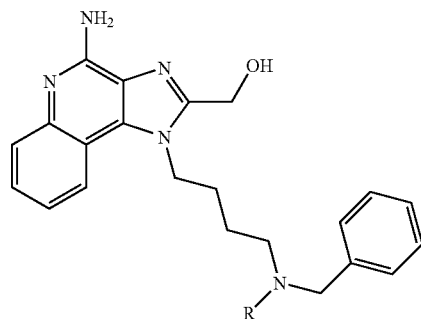
| Example | Reagent | R | Measured Mass (M + H) |
|---|---|---|---|
| 515 | beta-Styrene sulfonyl chloride | (E)-2-phenylvinyl sulfonyl | 542.2234 |
| 516 | 3-Methoxybenzenesulfonyl chloride | 3-hydroxyphenyl sulfonyl | 532.2052 |
| 517 | 4-Methoxybenzenesulfonyl chloride | 4-hydroxyphenyl sulfonyl | 532.2037 |
| 518 | 3-Pyridine sulfonyl chloride hydrochloride | pyridin-3-yl sulfonyl | 517.2015 |
| 519 | 2,5-Dimethoxybenzene-sulfonyl chloride | 2,5-dihydroxyphenyl sulfonyl | 548.1964 |

-continued
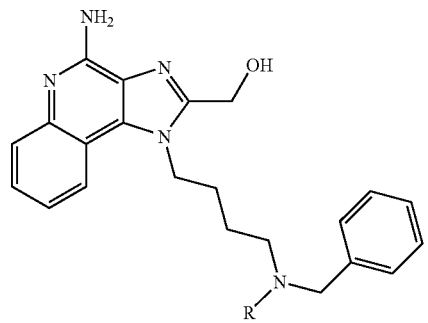
| Example | Reagent | R | Measured Mass (M + H) |
|---|---|---|---|
| 520 | 2,3-Dichloro-benzenesulfonyl chloride | 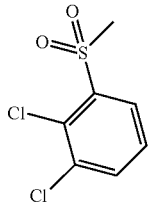 | 584.1294 |
| 521 | 3,5-Dichlorobenzene-sulfonyl chloride | 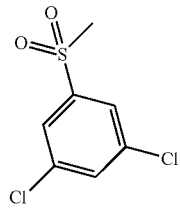 | 584.1282 |
| 522 | Methyl isocyanate | 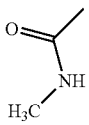 | 433.2361 |
| 523 | Ethyl isocyanate | 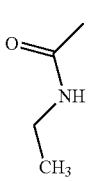 | 447.2538 |
| 524 | Isopropyl isocyanate | 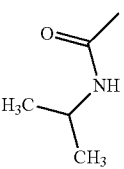 | 461.2663 |
| 525 | n-Propyl isocyanate | 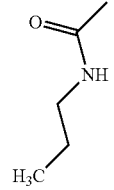 | 461.2691 |

-continued
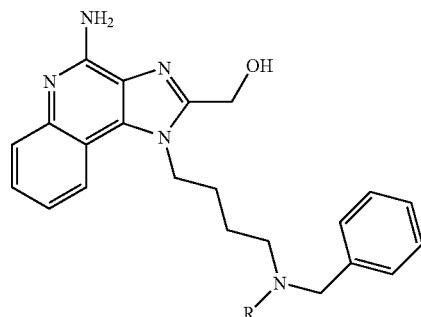
| Example | Reagent | R | Measured Mass (M + H) |
|---------|---------|---|----------------------|
| 526 | n-Butyl isocyanate | 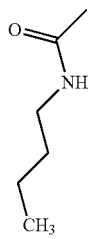 | 475.2860 |
| 527 | sec-Butyl isocyanate | 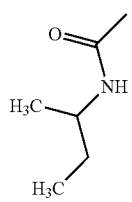 | 475.2849 |
| 528 | Pentyl isocyanate | 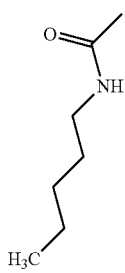 | 489.3005 |
| 529 | Phenyl isocyanate | 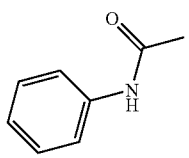 | 495.2511 |
| 530 | Cyclohexyl isocyanate | 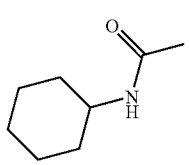 | 501.2978 |

-continued
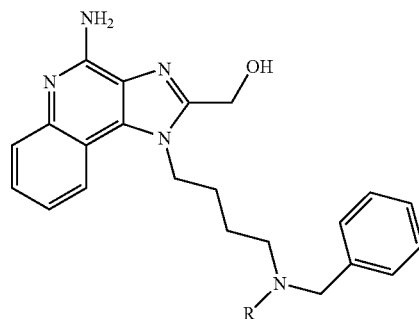
| Example | Reagent | R | Measured Mass (M + H) |
|---|---|---|---|
| 531 | Benzyl isocyanate | *N*-benzylcarbamoyl | 509.2675 |
| 532 | 3-Fluorophenyl isocyanate | (3-fluorophenyl)carbamoyl | 513.2467 |
| 533 | 4-Fluorophenyl isocyanate | (4-fluorophenyl)carbamoyl | 513.2388 |
| 534 | Cycloheptyl isocyanate | cycloheptylcarbamoyl | 515.3081 |
| 535 | Cyclohexanemethyl isocyanate | (cyclohexylmethyl)carbamoyl | 515.3163 |
| 536 | 4-Cyanophenyl isocyanate | (4-cyanophenyl)carbamoyl | 520.2483 |

-continued
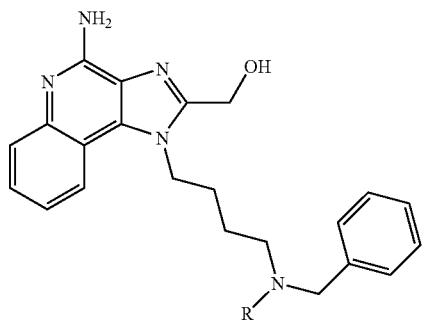
| Example | Reagent | R | Measured Mass (M + H) |
|---|---|---|---|
| 537 | 3,4-Dimethylphenyl isocyanate | 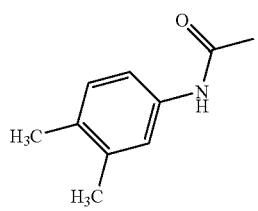 | 523.2786 |
| 538 | (S)-(−)-alpha-Methylbenzyl isocyanate | 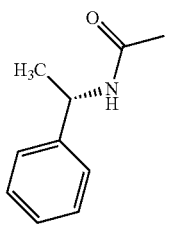 | 523.2786 |
| 539 | 2-Methylbenzyl isocyanate | 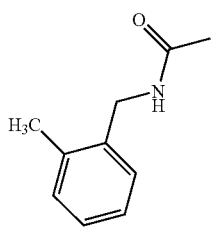 | 523.2860 |
| 540 | N,N-Dimethylcarbamoyl chloride | 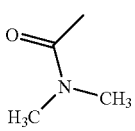 | 447.2511 |
| 541 | Diethylcarbamyl chloride | 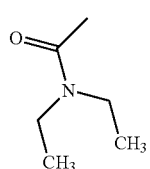 | 475.2828 |
| 542 | 1-Piperidinecarbonyl chloride | 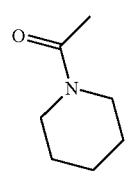 | 487.2839 |

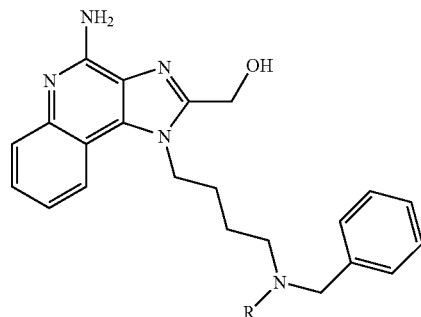

| Example | Reagent | R | Measured Mass (M + H) |
|---|---|---|---|
| 543 | N-(4-Chlorobutyl)-N-methylcarbamyl chloride | (structure: O=C(N(CH3)-(CH2)4-Cl)-) | 523.2588 |

Examples 544-550

The compounds in the table below were prepared according to the general method of Examples 111-140. The table shows a reference for the ether starting material, the structure of the resulting compound, and the observed accurate mass for the isolated trifluoroacetate salt.

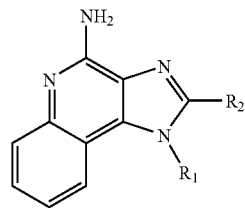

| Example | Reference (ether) | $R_1$ | $R_2$ | Measured Mass (M + H) |
|---|---|---|---|---|
| 544 | U.S. Pat. No. 6,667,312* | -CH2CH2-S(=O)(=O)-CH3 | -CH2CH2-OH | 335.1158 |
| 545 | U.S. Pat. No. 6,677,349* | -CH2CH2-NH-S(=O)(=O)-CH3 | -CH2CH2-OH | 336.1098 |

-continued
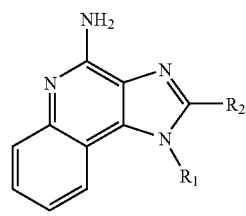
| Example | Reference (ether) | R₁ | R₂ | Measured Mass (M + H) |
|---|---|---|---|---|
| 546 | U.S. Pat. No. 6,677,349* | 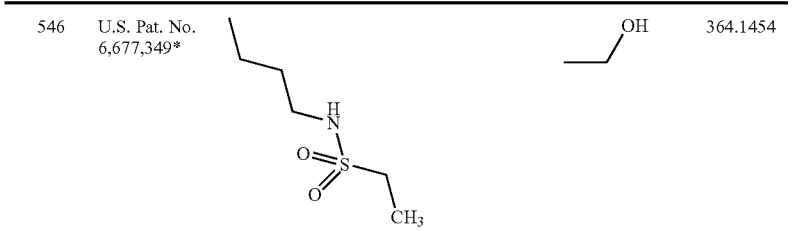 | ⟋OH | 364.1454 |
| 547 | U.S. Pat. No. 6,677,347 Example 57 | 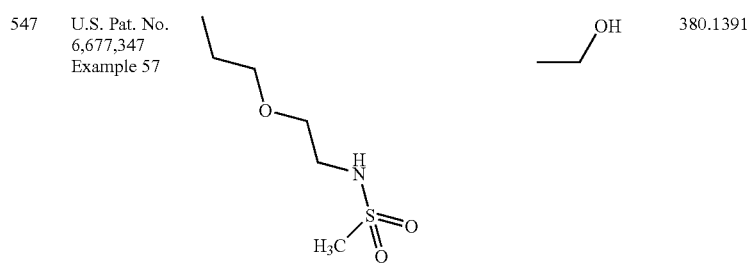 | ⟋OH | 380.1391 |
| 548 | U.S. Pat. No. 6,756,382* | 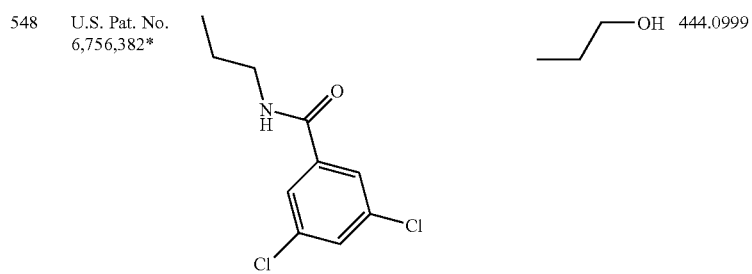 | ⟋⟋OH | 444.0999 |
| 549 | U.S. Pat. No. 6,683,088 Example 1 | 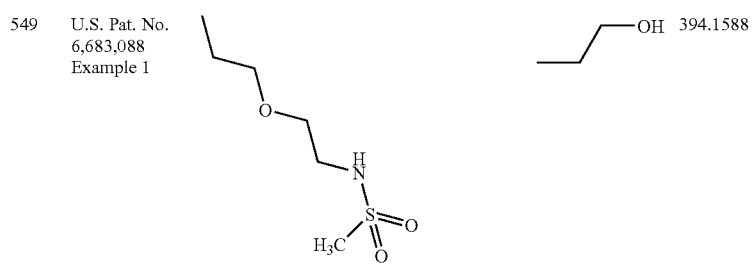 | ⟋⟋OH | 394.1588 |

-continued

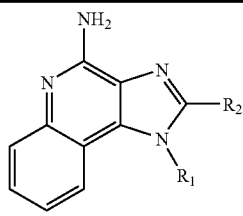

| Example | Reference (ether) | R1 | R2 | Measured Mass (M + H) |
|---|---|---|---|---|
| 550 | U.S. Pat. No. 6,677,349 Example 242 | ~~~~~NHSO2Ph | ~OH | 496.2401 |

*Although not specifically exemplified, the compound is readily prepared using the disclosed synthetic methods.

Example 551

[4-Amino-1-(2-fluoro-2-methylpropyl)-1H-imidazo[4,5-c][1,5]naphthyridin-2-yl]methanol

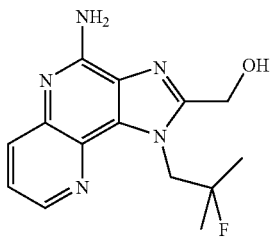 [SMILES: CC(C)(F)Cn1c(CO)nc2c(N)nc3cccnc3c21]

Part A

A solution of 1-amino-2-methylpropan-2-ol (23.4 g, 263 mmol) dissolved in 150 mL of THF was treated with 150 mL of 1.8 M aqueous NaOH solution and the mixture was placed in an ice bath. A solution of di-tert-butyl dicarbonate (57.3 g, 263 mmol) in 150 mL THF was then added drop-wise over 45 min. The mixture was allowed to warm to ambient temperature overnight. The THF was removed under reduced pressure and the remaining aqueous solution was treated with 1 M $H_2SO_4$ until the pH reached 3. The mixture was extracted with 200 mL of EtOAc. The organic portion was washed with $H_2O$ and brine, dried over $Na_2SO_4$, and concentrated under reduced pressure give tert-butyl 2-hydroxy-2-methylpropylcarbamate (50.4 g) as a colorless syrup which solidified on standing.

Part B

A stirred solution of tert-butyl 2-hydroxy-2-methylpropylcarbamate (7.81 g, 41.3 mmol) dissolved in 300 mL of anhydrous $CH_2Cl_2$ was cooled to −78° C. under an atmosphere of $N_2$. The reaction mixture was treated with diethylaminosulfur trifluoride (DAST) (6.2 mL, 47 mmol) and allowed to warm to ambient temperature overnight. The reaction mixture was treated with saturated $NaHCO_3$ solution and the layers were separated. The organic portion was washed successively with saturated $NaHCO_3$ solution, $H_2O$ and brine. The organic portion was dried over $Na_2SO_4$, filtered and concentrated under reduced pressure. Chromatography ($SiO_2$, 10% EtOAc/hexanes) gave 6.27 g of tert-butyl 2-fluoro-2-methylpropylcarbamate as an amber oil which solidified on standing.

Part C tert-Butyl 2-fluoro-2-methylpropylcarbamate (6.27 g, 32.8 mmol) was treated with 45 mL of 3.0 M HCl in ethanol and the mixture was heated to 90° C. for 2 hours. The reaction mixture was then concentrated under reduced pressure to give 4.02 g of 2-fluoro-2-methylpropan-1-amine hydrochloride as a white solid.

Part D

2-Fluoro-2-methylpropan-1-amine hydrochloride (4.02 g, 31.4 mmol) was dissolved in 80 mL of dry $CH_2Cl_2$. Triethylamine (13.1 mL, 94.2 mmol) and 4-chloro-3-nitro[1,5]naphthyridine (6.56 g, 31.4 mmol) were then added and the reaction was stirred under $N_2$ for 2 days. The reaction mixture was then concentrated under reduced pressure to give a dark-yellow solid. The solid was treated with 200 mL of $H_2O$ and the mixture was heated to reflux with rapid stirring. The mixture was cooled and the yellow solid was isolated by filtration. The material was washed with $H_2O$ and the dried under vacuum to give N-(2-fluoro-2-methylpropyl)-3-nitro[1,5]naphthyridin-4-amine (8.36 g) as a yellow powder.

Part E

A solution of N-(2-fluoro-2-methylpropyl)-3-nitro[1,5]naphthyridin-4-amine (2.64 g, 10.0 mmol) dissolved in 80 mL of acetonitrile was placed in a pressure bottle. Platinum on carbon (5%, 500 mg) was then added and the reaction mixture was shaken under $H_2$ at 50 PSI ($3.4 \times 10^5$ Pa). After 5 hours, the reaction mixture was filtered through a pad of

235

CELITE filter agent. The pad was rinsed with acetonitrile and the combined filtrates were concentrated under reduced pressure to give 2.12 g of $N^4$-(2-fluoro-2-methylpropyl)[1,5]naphthyridine-3,4-diamine as a brown foam.

Part F $N^4$-(2-Fluoro-2-methylpropyl)[1,5]naphthyridine-3,4-diamine (2.12 g, 9.06 mmol) was dissolved in 90 mL of anhydrous $CH_2Cl_2$ and the stirred solution was cooled to 0° C. under $N_2$. Triethylamine (1.39 mL, 10.0 mmol) and acetoxyacetyl chloride (1.07 mL, 10.0 mmol) were then added and the reaction mixture was stirred overnight. The reaction mixture was concentrated under reduced pressure and the resulting material was dissolved in 90 mL of ethanol and treated with 5 mL of triethylamine. The mixture was heated at reflux for 4 days. The reaction mixture was then cooled and concentrated under reduced pressure to give a purple solid. The purple solid was partitioned between $CH_2Cl_2$ (75 mL) and $H_2O$ (75 mL). The layers were separated and the aqueous portion was extracted with $CH_2Cl_2$ (2×20 mL). The combined organic portions were washed with brine, dried over $Na_2SO_4$, filtered and concentrated under reduced pressure to give a purple solid. The resulting material was dissolved in 50 mL of methanol and treated with 1 mL of saturated aqueous $K_2CO_3$ solution. After 1 hour, the mixture was treated with 3.5% $NaH_2PO_4$ solution and the methanol was removed by evaporation under reduced pressure. A brown solid precipitated out of the aqueous solution and was isolated by filtration. The brown solid was rinsed with $H_2O$ and then dried to give 1.81 g of [1-(2-fluoro-2-methylpropyl)-1H-imidazo[4,5-c][1,5]naphthyridin-2-yl]methanol.

Part G

A solution of [1-(2-fluoro-2-methylpropyl)-1H-imidazo[4,5-c][1,5]naphthyridin-2-yl]methanol (1.53 g, 5.58 mmol) dissolved in 50 mL of $CH_2Cl_2$ was treated with triethylamine (1.55 mL, 11.2 mmol), acetic anhydride (663 µL, 6.70 mmol), and 10 mg of 4-(dimethylamino)pyridine (DMAP). After stirring for 2 hours, the reaction mixture was treated with saturated $NaHCO_3$ solution and the layers were separated. The organic portion was washed successively with 3.5% $NaH_2PO_4$ solution, $H_2O$ and brine. The organic portion was dried over $Na_2SO_4$, filtered and concentrated under reduced pressure. Chromatography ($SiO_2$, 40-60% acetone/hexanes) gave 1.59 g of [1-(2-fluoro-2-methylpropyl)-1H-imidazo[4,5-c][1,5]naphthyridin-2-yl]methyl acetate as an off-white powder.

Part H

[1-(2-Fluoro-2-methylpropyl)-1H-imidazo[4,5-c][1,5]naphthyridin-2-yl]methyl acetate (1.59 g, 5.03 mmol) was dissolved in 50 mL of $CH_2Cl_2$ and treated with 3-chloroperoxybenzoic acid (1.52 g, 57-86% purity). After stirring for 2 hours, the reaction mixture was treated with 25 mL of $CH_2Cl_2$ and 20 mL of 5% $Na_2CO_3$ solution and the layers were separated. The organic layer was washed with $H_2O$ (20 mL) and brine (20 mL), dried over $Na_2SO_4$, filtered, and concentrated under reduced pressure to give 1.67 g of [1-(2-fluoro-2-methylpropyl)-5-oxido-1H-imidazo[4,5-c][1,5]naphthyridin-2-yl]methyl acetate as an off-white solid.

Part I

[1-(2-Fluoro-2-methylpropyl)-5-oxido-1H-imidazo[4,5-c][1,5]naphthyridin-2-yl]methyl acetate (1.67 g, 5.03 mmol) was dissolved in 50 mL of $CH_2Cl_2$ and treated with 5 mL of concentrated aqueous $NH_4OH$ solution. The mixture was stirred rapidly and then p-toluenesulfonyl chloride (1.05 g, 5.53 mmol) was carefully added. Rapid stirring was continued for 1 hour. The reaction mixture was then treated with 20 mL of $H_2O$. The layers were separated and the organic portion was washed successively with 5% $Na_2CO_3$ solution, $H_2O$ and brine. The organic portion was dried over $Na_2SO_4$, filtered, and concentrated under reduced pressure. Chromatography ($SiO_2$, 2.5% methanol/$CHCl_3$) gave 1.13 g of [4-amino-1-(2-fluoro-2-methylpropyl)-1H-imidazo[4,5-c][1,5]naphthyridin-2-yl]methyl acetate as a light-yellow solid.

Part J

A solution of [4-amino-1-(2-fluoro-2-methylpropyl)-1H-imidazo[4,5-c][1,5]naphthyridin-2-yl]methyl acetate (1.13 g, 3.41 mmol) dissolved in 10 mL of methanol was treated with 10 mL of a 7% solution of ammonia in methanol. The mixture was stirred for 2 hours and then concentrated under reduced pressure. The resulting solid was treated with $H_2O$ and the mixture was heated to reflux for 15 minutes. The mixture was cooled and the resulting light-yellow solid was isolated by filtration. The light-yellow solid was then treated with 20 mL of $CH_2Cl_2$ and the mixture was stirred rapidly for several minutes. The mixture was filtered and the resulting white solid was washed with several portions of cold $CH_2Cl_2$ and dried with suction. Crystallization from ethanol/$H_2O$ gave 477 mg of [4-amino-1-(2-fluoro-2-methylpropyl)-1H-imidazo[4,5-c][1,5]naphthyridin-2-yl]methanol as fluffy cream colored crystals, mp 240-241° C. $^1$H NMR (300 MHz, DMSO-$d_6$) δ 8.50 (dd, J=1.5, 4.3 Hz, 1H), 7.93 (dd, J=1.5, 8.4 Hz, 1H), 7.46 (dd, J=4.3, 8.4 Hz, 1H), 6.92 (s, 2H), 5.62 (t, J=5.8 Hz, 1H), 5.33 (br s, 2H), 4.83 (d, J=4.7 Hz, 2H), 1.33 (d, J=20.3 Hz, 6H); $^{13}$C NMR (125 MHz, DMSO-$d_6$) δ 154.3, 152.7, 143.1, 140.8, 134.2, 133.4, 133.2, 128.7, 122.5, 96.8 (d, J=170 Hz), 56.7 (d, J=9.5 Hz), 52.7 (d, J=21.4 Hz), 24.5; MS (ESI) m/z 290 (M+H)$^+$; Anal. calcd for $C_{14}H_{16}FN_5O$: C, 58.12; H, 5.57; N, 24.21. Found: C, 58.19; H, 5.54; N, 24.16.

Example 552

2-[4-Amino-1-(2-fluoro-2-methylpropyl)-1H-imidazo[4,5-c][1,5]naphthyridin-2-yl]ethanol

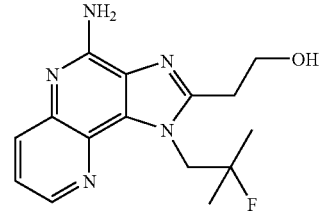 [SMILES: CC(C)(F)Cn1c(CCO)nc2c(N)nc3cccnc3c21]

Part A $N^4$-(2-Fluoro-2-methylpropyl)[1,5]naphthyridine-3,4-diamine (2.34 g, 10.0 mmol) was dissolved in 80 mL of anhydrous $CH_2Cl_2$ and the stirred solution was cooled to 0° C. under $N_2$. Triethylamine (2.78 mL, 10.0 mmol) and 3-(benzyloxy)propanoyl chloride, prepared by the method of Li, *J. Med. Chem.*, 42, pp. 706-721, (2.13 g, 10.0 mmol), were then added and the reaction mixture was stirred overnight. The reaction mixture was concentrated under reduced pressure. The resulting material was dissolved in 80 mL of ethanol and combined with 5 mL of triethylamine and the mixture was heated to reflux for 4 days. The reaction mixture was then cooled and concentrated under reduced pressure. The resulting solid was partitioned between $CH_2Cl_2$ (75 mL) and $H_2O$ (75 mL). The layers were separated and the organic portion was washed with brine, dried over $Na_2SO_4$, filtered, and concentrated under reduced pressure to give a solid. Chromatography ($SiO_2$, 1-2% CMA/$CHCl_3$) gave 0.83 g of uncyclized amide (3-(benzyloxy)-N-{4-[(2-fluoro-2-methylpropyl)amino][1,5]naphthyridin-3-yl}propanamide) and the desired 2-[2-(benzyloxy)ethyl]-1-(2-fluoro-2-methylpropyl)-1H-imidazo[4,5-c][1,5]naphthyridine. Additional chromatography (10% methanol/$CHCl_3$) of the desired material gave 1.39 g of a light-orange syrup. The isolated amide was converted to the desired imidazole by dissolving the material in 10 mL of 7% ammonia in methanol. The mixture was placed in a stainless-steel pressure vessel and the vessel was sealed and heated to 150° C. overnight. The reaction mixture was cooled and concentrated under reduced pressure. Chromatography (SiO$_2$, 2% CMA/CHCl$_3$) gave 0.50 g of the desired product which was combined with the first batch of material for the next reaction.

Part B

2-[2-(Benzyloxy)ethyl]-1-(2-fluoro-2-methylpropyl)-1H-imidazo[4,5-c][1,5]naphthyridine (1.89 g, 5.0 mmol) was dissolved in 50 mL of CH$_2$Cl$_2$ and treated with 3-chloroperoxybenzoic acid (1.50 g, 57-86% purity). After stirring for 2 hours, the reaction mixture was treated with 50 mL of 2% Na$_2$CO$_3$ solution and the layers were separated. The aqueous portion was extracted with an additional 25 mL of CH$_2$Cl$_2$. The combined organic layers were washed successively with 2% Na$_2$CO$_3$, H$_2$O and brine, dried over Na$_2$SO$_4$, filtered, and concentrated under reduced pressure to give 1.97 g of 2-[2-(benzyloxy)ethyl]-1-(2-fluoro-2-methylpropyl)-1H-imidazo[4,5-c][1,5]naphthyridine 5-oxide as an off-white solid.

Part C

2-[2-(Benzyloxy)ethyl]-1-(2-fluoro-2-methylpropyl)-1H-imidazo[4,5-c][1,5]naphthyridine 5-oxide (1.97 g, 5.00 mmol) was dissolved in 50 mL of CH$_2$Cl$_2$ and treated with 5 mL of concentrated aqueous NH$_4$OH solution. The mixture was stirred rapidly and then p-toluenesulfonyl chloride (1.00 g, 5.33 mmol) was carefully added. Rapid stirring was continued for 1 hour. The reaction mixture was then treated with 20 mL of H$_2$O. The layers were separated and the organic portion was washed successively with 5% Na$_2$CO$_3$ solution, H$_2$O and brine. The organic portion was dried over Na$_2$SO$_4$, filtered, and concentrated under reduced pressure. Chromatography (SiO$_2$, 10% CMA/CHCl$_3$) gave 0.90 g of 2-[2-(benzyloxy)ethyl]-1-(2-fluoro-2-methylpropyl)-1H-imidazo[4,5-c][1,5]naphthyridin-4-amine as a yellow solid.

Part D

A solution of 2-[2-(benzyloxy)ethyl]-1-(2-fluoro-2-methylpropyl)-1H-imidazo[4,5-c][1,5]naphthyridin-4-amine (0.78 g, 1.98 mmol) dissolved in 20 mL of methanol was treated with 10% palladium on carbon (200 mg) and 0.68 mL of 3 M HCl in ethanol. The mixture was shaken under H$_2$ at 50 PSI (3.4×10$^5$ Pa) overnight. Additional 10% palladium on carbon (200 mg) and 3 M HCl in ethanol (0.33 mL) were added and shaking was continued for 24 hours. The reaction mixture was filtered through a pad of CELITE filter agent. The pad was rinsed with methanol and the combined filtrates were concentrated under reduced pressure. The resulting material was treated with 20 mL of H$_2$O and 2 mL of concentrated NH$_4$OH solution and extracted into CHCl$_3$ (3×25 mL). The combined organic layers were concentrated under reduced pressure. Chromatography (SiO$_2$, 15-30% CMA/CHCl$_3$) gave a white powder. Crystallization from ethanol/H$_2$O gave 276 mg of 2-[4-amino-1-(2-fluoro-2-methylpropyl)-1H-imidazo[4,5-c][1,5]naphthyridin-2-yl]ethanol as white needles, mp 224-225° C.

$^1$H NMR (300 MHz, DMSO-d$_6$, 354 K) δ 8.470 (dd, J=1.3, 4.0 Hz, 1H), 7.91 (d, J=8.4 Hz, 1H), 7.40 (dd, J=4.1, 8.3 Hz, 1H), 6.46 (s, 2H), 5.25 (d, J=22.7 Hz, 2H), 4.57 (s, 1H), 3.91 (d, J=5.4 Hz, 2H), 3.14 (t, J=6.4 Hz, 2H), 1.33 (d, J=21.7 Hz, 6H); $^{13}$C NMR (125 MHz, DMSO-d$_6$) δ 154.0, 152.3, 143.0, 140.4, 134.1, 133.1, 132.6, 129.0, 122.2, 96.7 (d, J=170 Hz), 60.2, 52.5 (d, J=20.9 Hz), 30.6 (d, J=6.6 Hz), 24.4; MS (ESI) m/z 304 (M+H)$^+$; Anal. calcd for C$_{15}$H$_{18}$FN$_5$O: C, 59.39; H, 5.98; N, 23.09. Found: C, 59.57; H, 5.75; N, 23.07.

Examples 553-593

Part A

A solution of 1-(2-aminoethyl)-2-(2-methoxyethyl)-1H-imidazo[4,5-c][1,5]naphthyridin-4-amine (57 mg, 0.1 mmol, 1 eq, prepared according to the general method of Example 146 using methoxypropionyl chloride in lieu of methoxyacetyl chloride) and N,N-diisopropylethylamine (87 μL) in N,N-dimethylacetamide (1 mL) was added to a tube containing a reagent (1.1 eq) from the table below. The reaction mixture was vortexed overnight, the reaction was quenched with water (2 drops), and the solvent was removed by vacuum centrifugation. The reaction mixture was purified by solid-supported liquid-liquid extraction according to the following procedure. The sample was dissolved in chloroform (1 mL) then loaded onto diatomaceous earth that had been equilibrated with 2 M sodium carbonate solution (600 μL) for about 20 minutes. After 10 minutes chloroform (500 μL) was added to elute the product from the diatomaceous earth into a well of a collection plate. After an additional 10 minutes the process was repeated with additional chloroform (500 μL). The solvent was then removed by vacuum centrifugation.

Part B

The material from Part A was dissolved in dichloromethane (1 mL) and the solution was cooled to 0° C. Boron tribromide (400 μL of 1 M in dichloromethane) was added and the reaction mixture was vortexed overnight. Methanol (1 mL) and 6 N hydrochloric acid (500 μL) were added and the reaction mixture was vortexed for 15 minutes. The solvent was removed by vacuum. The compounds were purified as described for Examples 150-155. The table below shows the reagent used for each example, the structure of the resulting compound, and the observed accurate mass for the isolated trifluoroacetate salt.

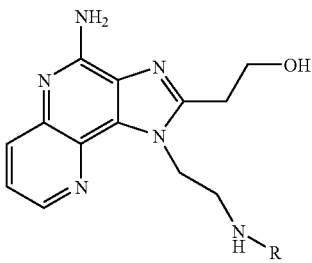

| Example | Reagent | R | Measured Mass (M + H) |
|---|---|---|---|
| 553 | None | —H | 273.1479 |

-continued
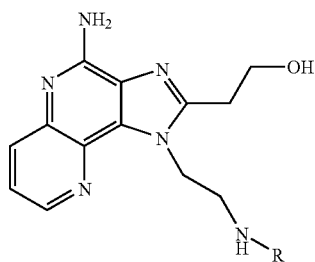
| Example | Reagent | R | Measured Mass (M + H) |
|---|---|---|---|
| 554 | Cyclopropanecarbonyl chloride | | 341.1730 |
| 555 | Isobutyryl chloride | | 343.1909 |
| 556 | Cyclobutanecarbonyl chloride | | 355.1909 |
| 557 | Cyclopentanecarbonyl chloride | | 369.2062 |
| 558 | Benzoyl chloride | | 377.1747 |
| 559 | Cyclohexanecarbonyl chloride | | 383.2206 |
| 560 | 3-Cyanobenzoyl chloride | | 402.1702 |

-continued
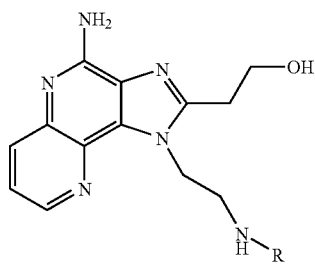
| Example | Reagent | R | Measured Mass (M + H) |
|---|---|---|---|
| 561 | 4-Cyanobenzoyl chloride | | 402.1700 |
| 562 | Cinnamoyl chloride | | 403.1890 |
| 563 | Hydrocinnamoyl chloride | | 405.2044 |
| 564 | 2-Methoxybenzoyl chloride | | 393.1672 |
| 565 | 3-Methoxybenzoyl chloride | | 393.1689 |

-continued
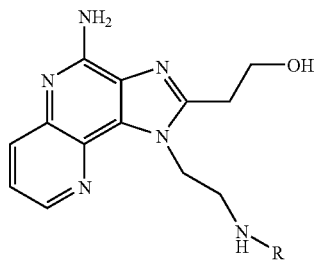
| Example | Reagent | R | Measured Mass (M + H) |
|---|---|---|---|
| 566 | p-Anisoyl chloride | 4-hydroxybenzoyl | 393.1678 |
| 567 | 2-Chlorobenzoyl chloride | 2-chlorobenzoyl | 411.1306 |
| 568 | 3-Chlorobenzoyl chloride | 3-chlorobenzoyl | 411.1369 |
| 569 | 4-Chlorobenzoyl chloride | 4-chlorobenzoyl | 411.1368 |
| 570 | Isonicotinoyl chloride hydrochloride | isonicotinoyl | 378.1698 |
| 571 | Nicotinoyl chloride hydrochloride | nicotinoyl | 378.1676 |
| 572 | Methanesulfonyl chloride | methanesulfonyl | 351.1256 |

-continued
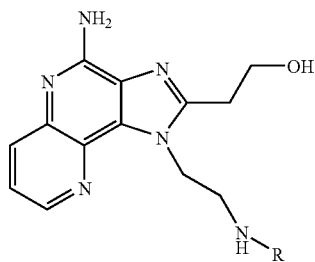
| Example | Reagent | R | Measured Mass (M + H) |
|---|---|---|---|
| 573 | Ethanesulfonyl chloride | –S(O)₂–CH₂CH₃ | 365.1386 |
| 574 | 1-Propanesulfonyl chloride | –S(O)₂–CH₂CH₂CH₃ | 379.1534 |
| 575 | Dimethylsulfamoyl chloride | –S(O)₂–N(CH₃)₂ | 380.1512 |
| 576 | Benzenesulfonyl chloride | –S(O)₂–C₆H₅ | 413.1436 |
| 577 | 1-Methylimidazole-4-sulfonyl chloride | –S(O)₂–(1-methylimidazol-4-yl) | 417.1462 |
| 578 | 2,2,2-Trifluoroethanesulfonyl chloride | –S(O)₂–CH₂CF₃ | 419.1139 |
| 579 | alpha-Toluenesulfonyl chloride | –S(O)₂–CH₂–C₆H₅ | 427.1569 |

-continued

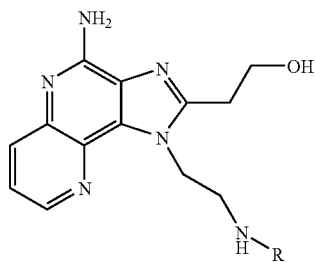

| Example | Reagent | R | Measured Mass (M + H) |
|---|---|---|---|
| 580 | 3-Cyanobenzenesulfonyl chloride | 3-cyanophenylsulfonyl | 438.1380 |
| 581 | 3-Methoxybenzenesulfonyl chloride | 3-hydroxyphenylsulfonyl | 429.1349 |
| 582 | 2-Chlorobenzenesulfonyl chloride | 2-chlorophenylsulfonyl | 447.0996 |
| 583 | 4-Chlorobenzenesulfonyl chloride | 4-chlorophenylsulfonyl | 447.1031 |
| 584 | Isopropyl isocyanate | isopropylaminocarbonyl | 358.1994 |
| 585 | Phenyl isocyanate | phenylaminocarbonyl | 392.1794 |

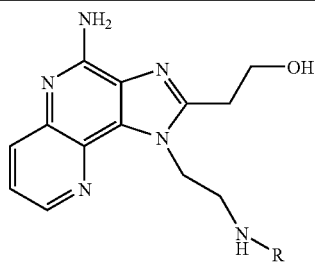
| Example | Reagent | R | Measured Mass (M + H) |
|---|---|---|---|
| 586 | Cyclohexyl isocyanate | -C(O)NH-cyclohexyl | 398.2305 |
| 587 | (R)-(+)-alpha-Methylbenzyl isocyanate | -C(O)NH-CH(CH₃)-Ph (R) | 420.2178 |
| 588 | (S)-(−)-alpha-Methylbenzyl isocyanate | -C(O)NH-CH(CH₃)-Ph (S) | 420.2149 |
| 589 | 2-Chlorophenyl isocyanate | -C(O)NH-(2-Cl-phenyl) | 426.1453 |
| 590 | 4-Chlorophenyl isocyanate | -C(O)NH-(4-Cl-phenyl) | 426.1460 |
| 591 | N,N-Dimethylcarbamoyl chloride | -C(O)N(CH₃)₂ | 344.1856 |
| 592 | 1-Piperidinecarbonyl chloride | -C(O)-piperidinyl | 384.2137 |

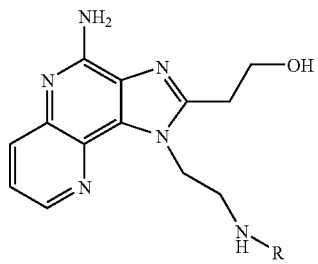

| Example | Reagent | R | Measured Mass (M + H) |
|---|---|---|---|
| 593 | 4-Morpholinylcarbonyl chloride | | 386.1976 |

Examples 594-632

The compounds in the table below were prepared and purified according to the methods described in Examples 553-593 using 1-(2-aminoethyl)-2-methoxymethyl-1H-imidazo[4,5-c][1,5]naphthyridin-4-amine in lieu of 1-(2-aminoethyl)-2-(2-methoxyethyl)-1H-imidazo[4,5-c][1,5]naphthyridin-4-amine. The table below shows the reagent used for each example, the structure of the resulting compound, and the observed accurate mass for the isolated trifluoroacetate salt.

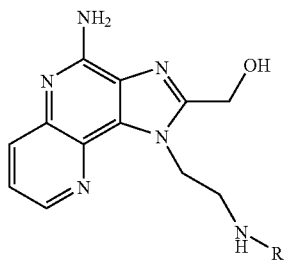

| Example | Reagent | R | Measured Mass (M + H) |
|---|---|---|---|
| 594 | Cyclopropanecarbonyl chloride | | 327.1581 |
| 595 | Isobutyryl chloride | | 329.1709 |
| 596 | Cyclopentanecarbonyl chloride | | 355.1859 |

-continued
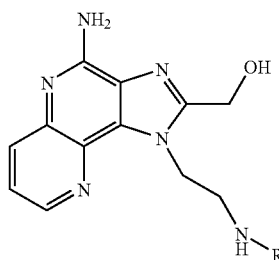
| Example | Reagent | R | Measured Mass (M + H) |
|---|---|---|---|
| 597 | Benzoyl chloride | benzoyl | 363.1563 |
| 598 | Cyclohexanecarbonyl chloride | cyclohexanecarbonyl | 369.2019 |
| 599 | 3-Cyanobenzoyl chloride | 3-cyanobenzoyl | 388.1517 |
| 600 | Hydrocinnamoyl chloride | hydrocinnamoyl | 391.1868 |
| 601 | 3-Methoxybenzoyl chloride | 3-hydroxybenzoyl | 379.1512 |
| 602 | p-Anisoyl chloride | 4-hydroxybenzoyl | 379.1526 |

-continued

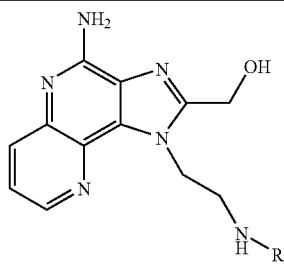

| Example | Reagent | R | Measured Mass (M + H) |
|---|---|---|---|
| 603 | 2-Chlorobenzoyl chloride | 2-chlorobenzoyl | 397.1193 |
| 604 | 3-Chlorobenzoyl chloride | 3-chlorobenzoyl | 397.1198 |
| 605 | Isonicotinoyl chloride hydrochloride | isonicotinoyl | 364.1515 |
| 606 | Nicotinoyl chloride hydrochloride | nicotinoyl | 364.1535 |
| 607 | Picolinoyl chloride hydrochloride | picolinoyl | 364.1512 |
| 608 | trans-2-Phenyl-1-cyclopropanecarbonyl chloride | trans-2-phenyl-1-cyclopropanecarbonyl | 403.1852 |
| 609 | Methanesulfonyl chloride | —S(O)₂CH₃ | 337.1070 |

-continued
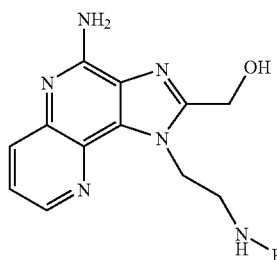
| Example | Reagent | R | Measured Mass (M + H) |
|---|---|---|---|
| 610 | Ethanesulfonyl chloride | -S(O)₂-CH₂CH₃ | 351.1212 |
| 611 | 1-Propanesulfonyl chloride | -S(O)₂-CH₂CH₂CH₃ | 365.1386 |
| 612 | Isopropylsulfonyl chloride | -S(O)₂-CH(CH₃)₂ | 365.1433 |
| 613 | Dimethylsulfamoyl chloride | -S(O)₂-N(CH₃)₂ | 366.1355 |
| 614 | Benzenesulfonyl chloride | -S(O)₂-C₆H₅ | 399.1214 |
| 615 | 1-Methylimidazole-4-sulfonyl chloride | -S(O)₂-(1-methylimidazol-4-yl) | 403.1311 |
| 616 | 2,2,2-Trifluoroethanesulfonyl chloride | -S(O)₂-CH₂CF₃ | 405.0953 |

-continued
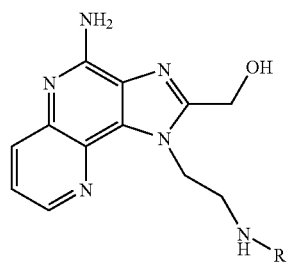
| Example | Reagent | R | Measured Mass (M + H) |
|---|---|---|---|
| 617 | 3-Cyanobenzenesulfonyl chloride | 3-cyanophenylsulfonyl | 424.1229 |
| 618 | 2-Chlorobenzenesulfonyl chloride | 2-chlorophenylsulfonyl | 433.0872 |
| 619 | 3-Chlorobenzenesulfonyl chloride | 3-chlorophenylsulfonyl | 433.0867 |
| 620 | 4-Chlorobenzenesulfonyl chloride | 4-chlorophenylsulfonyl | 433.0853 |
| 621 | Methyl isocyanate | C(=O)NHCH₃ | 316.1528 |
| 622 | Ethyl isocyanate | C(=O)NHCH₂CH₃ | 330.1660 |

-continued
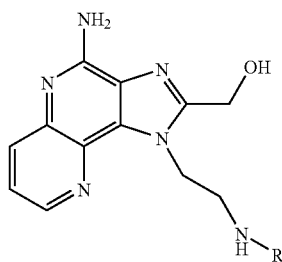
| Example | Reagent | R | Measured Mass (M + H) |
|---|---|---|---|
| 623 | Isopropyl isocyanate | -C(O)-NH-CH(CH₃)₂ | 344.1819 |
| 624 | n-Propyl isocyanate | -C(O)-NH-CH₂CH₂CH₃ | 344.1809 |
| 625 | Cyclopentyl isocyanate | -C(O)-NH-cyclopentyl | 370.1994 |
| 626 | Cyclohexyl isocyanate | -C(O)-NH-cyclohexyl | 384.2152 |
| 627 | 3-Chlorophenyl isocyanate | -C(O)-NH-(3-chlorophenyl) | 412.1300 |
| 628 | 4-Chlorophenyl isocyanate | -C(O)-NH-(4-chlorophenyl) | 412.1273 |
| 629 | N,N-Dimethylcarbamoyl chloride | -C(O)-N(CH₃)₂ | 330.1686 |

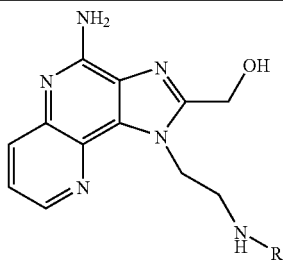

| Example | Reagent | R | Measured Mass (M + H) |
|---|---|---|---|
| 630 | 1-Piperidinecarbonyl chloride | | 370.1979 |
| 631 | 4-Morpholinylcarbonyl chloride | | 372.1811 |
| 632 | 4-Methyl-1-piperazinecarbonyl chloride | | 385.2098 |

Example 633
[4-Amino-1-(2-methylpropyl)-1H-imidazo[4,5-c][1,5]naphthyridin-2-yl]methanol

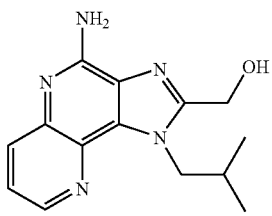 [SMILES: CC(C)Cn1c(CO)nc2c(N)nc3cccnc3c21]

To a chilled solution (ice bath) of 2-(ethoxymethyl)-1-(2-methylpropyl)-1H-imidazo[4,5-c][1,5]naphthyridin-4-amine (2.0 g, 6.69 mmol, prepared according to the general methods of Example 148 using 2-methylpropan-1-amine in lieu of 1-amino-2-methylpropan-2-ol) in dichloromethane (50 mL) was added boron tribromide (20 mL, 1M solution in dichloromethane). The mixture turned light purple and was stirred at ambient temperature for 44 hours. The reaction was quenched with methanol (20 mL) and aqueous hydrochloric acid (6N, 10 mL). After stirring for 4 hours, the pH was adjusted to 10 by the addition of aqueous sodium hydroxide (50%). Dichloromethane (50 mL) was added with stirring and the layers were separated. The aqueous fraction was extracted with chloroform (2×250 mL). The combined organic fractions were concentrated to provide 1.4 g of [4-amino-1-(2-methylpropyl)-1H-imidazo[4,5-c][1,5]naphthyridin-2-yl]methanol as a white powder, mp 226-228° C.

$^1$H NMR (300 MHz, DMSO-$d_6$) δ 8.52-8.51 (dd, J=1.6, 4.3 Hz, 1H), 7.93-7.89 (dd, J=1.6, 8.4 Hz, 1H), 7.46-7.42 (dd, J=4.3, 8.4 Hz, 1H), 6.83 (s, 2H), 5.69-5.65 (t, J=5.8 Hz, 1H), 4.79-4.77 (d, J=5.8 Hz, 2H), 4.74-4.71 (d, J=7.6 Hz, 2H), 2.44-2.39 (m, 1H), 0.91-0.88 (d, J=6.7 Hz, 6H);

Anal. calcd for $C_{14}H_{17}N_5O$: C, 61.98; H, 6.31; N, 25.81. Found: C, 61.26; H, 6.07; N, 25.75.

Example 634
2-(4-Amino-1-isobutyl-1H-imidazo[4,5-c]quinolin-2-yl)ethyl acetate

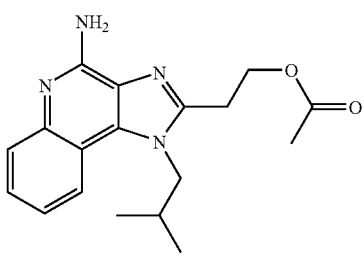 [SMILES: CC(=O)OCCc1nc2c(N)nc3ccccc3c2n1CC(C)C]

Part A

To a stirred suspension of $N^4$-isobutylquinoline-3,4-diamine (13.0 g, 60.46 mmol) in toluene was added pyridine hydrochloride (2.1 g, 8.14 mmol) followed by 3-chloropropionyl chloride (1.1 equivalents). The creamy suspension was stirred for 4 hours at ambient temperature and the solvent was then evaporated under reduced pressure. The tan solid obtained was dissolved in chloroform and the solution was transferred to a separatory funnel. The organic layer was washed with water (1×) and brine (2×). The organic layer was separated, dried (MgSO$_4$), filtered, and the solvent was evaporated under reduced pressure to afford a tan solid (21 g). A portion of the tan solid (7 g) was taken up in acetic acid (110 mL) and the reaction was stirred at ambient temperature for 4 hours. The reaction was cooled in an ice-bath and 6M NaOH (300 mL) was added in portions to afford a creamy suspension. The reaction mixture was transferred to a separatory funnel and the product was extracted with chloroform (150 mL×2). The organic layers were combined, dried (MgSO$_4$), and filtered; and the filtrate was evaporated under reduced pressure to afford 2-(1-isobutyl-1H-imidazo[4,5-c]quinolin-2-yl)ethyl acetate as a brown oil (10 g) which was taken forward to the next step.

Part B

To a stirred solution of 2-(1-isobutyl-1H-imidazo[4,5-c]quinolin-2-yl)ethyl acetate (7.41 g, 22.9 mmol) in chloroform was added 3-chloroperoxybenzoic acid (77%, 10.3 g, 49.9 mmol) and the reaction was stirred at ambient temperature for 4 hours. The reaction was then transferred to a separatory funnel and washed with brine (2×). The organic layers were combined, dried (MgSO$_4$), and filtered; and the filtrate was evaporated under reduced pressure to afford the N-oxide (15 g) as a brown solid. The brown solid was dissolved in chloroform, cooled in an ice-bath, and trichloroacetyl isocyanate (6.4 g mL, 34.3 mmol) was added in a dropwise manner. The reaction was stirred for 1 hour after which an additional 1.5 equivalents of trichloroacetyl isocyanate was added and the reaction was stirred at ambient temperature overnight. The reaction was concentrated under reduced pressure and the residue was suspended in ethanol. Potassium ethoxide was added to this suspension and the reaction was stirred for 1 hour. The reaction was concentrated under reduced pressure, taken up in dichloromethane (250 mL) and transferred to a separatory funnel. The organic layer was washed with water (250 mL), separated from the aqueous, dried (MgSO$_4$), and filtered; and the filtrate was evaporated under reduced pressure to afford a brown solid. The product was isolated by prep HPLC (ISCO Combiflash Separation System, Biotage Si 40+M column, eluted with a gradient of 0-10% methanol in dichloromethane with 1% ammonium hydroxide) to provide a solid (about 7 g). A portion of this solid was recrystallized from acetonitrile to afford 2-(4-amino-1-isobutyl-1H-imidazo[4,5-c]quinolin-2-yl)ethyl acetate as a white solid (0.109 g), mp 187-189° C.; MS (ESI) m/z 327 (M+H); Anal. Calcd for C$_{18}$H$_{22}$N$_4$O$_2$.0.40H$_2$O: C, 64.81; H, 6.89; N, 16.79. Found C, 64.54; H, 6.46; N, 16.90.

Example 635

[4-Amino-1-(2-hydroxy-2-methylpropyl)-1H-imidazo[4,5-c]quinolin-2-yl]methyl acetate

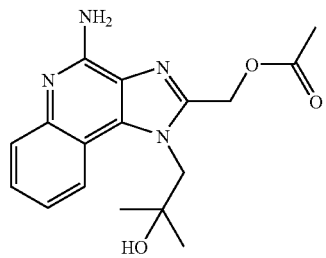 [SMILES: CC(=O)OCc1nc2c(N)nc3ccccc3c2n1CC(C)(C)O]

To a round-bottomed flask with stir bar was added 1-(4-amino-2-hydroxymethyl-1H-imidazo[4,5-c]quinolin-1-yl)-2-methylpropan-2-ol (1 g, 3.5 mmol) followed by dichloroethane (20 mL) and pyridine (3 mL). To the stirred suspension was added acetyl chloride (0.27 mL, 1.1 equivalents) and the reaction was stirred at ambient temperature for 30 min. The solvent was evaporated under reduced pressure to afford a solid. The product was isolated by two purifications by prep HPLC (ISCO Combiflash Separation System, Biotage Si 40+M column, eluted with a gradient of 0-7% methanol in dichloromethane with 1% ammonium hydroxide) to provide [4-amino-1-(2-hydroxy-2-methylpropyl)-1H-imidazo[4,5-c]quinolin-2-yl]methyl acetate as an off white solid (130 mg), mp 203-205° C.; MS (ESI) m/z 329 (M+H); Anal. Calcd for C$_{17}$H$_{20}$N$_4$O$_3$.0.25CH$_4$O: C, 61.59; H, 6.29; N, 16.66. Found C, 61.24; H, 6.22; N, 16.97.

Example 636

[4-Amino-1-(2-hydroxy-2-methylpropyl)-1H-imidazo[4,5-c]quinolin-2-yl]methyl L-valinate

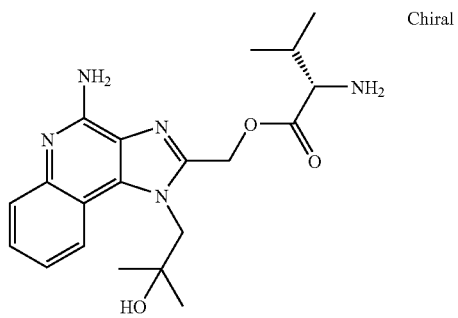 [SMILES: CC(C)[C@H](N)C(=O)OCc1nc2c(N)nc3ccccc3c2n1CC(C)(C)O]

[4-Amino-1-(2-hydroxy-2-methylpropyl)-1H-imidazo[4,5-c]quinolin-2-yl]methyl L-valinate was prepared according to the general method used to prepare (4-amino-1-{4-{(methylsulfonyl)amino]butyl}-1H-imidazo[4,5-c]quinolin-2-yl)methyl L-valinate using 1-(4-amino-2-hydroxymethyl-1H-imidazo[4,5-c]quinolin-1-yl)-2-methylpropan-2-ol in lieu of N-[4-(4-amino-2-hydroxymethyl-1H-imidazo[4,5-c]quinolin-1-yl)butyl]methanesulfonamide. The product was provided as off-white needles, mp 190-192° C.; MS (ESI) m/z 386 (M+H); Anal. Calcd for C$_{20}$H$_{27}$N$_5$O$_3$: C, 62.32; H, 7.06; N, 18.17. Found C, 62.08; H, 7.11; N, 17.96.

Exemplary Compounds Useful in Practicing Methods of the Invention

Certain exemplary compounds, including some of those described above in the Examples, have the following Formulas Ia, Ib, Ic, Id, Ie, If, Ig, Ih, Ii, Ij, Ik, Im, In, Io, or Ip and the following substituents n and R$_1$ wherein each line of the table is matched to Formula Ia, Ib, Ic, Id, Ie, If, Ig, Ih, Ii, Ij, Ik, Im, In, Io, or Ip to represent a specific compound which is useful in practicing methods of the invention.

Ia

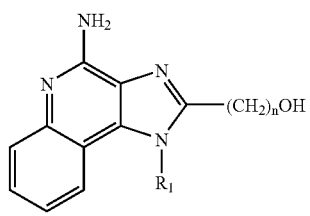

-continued
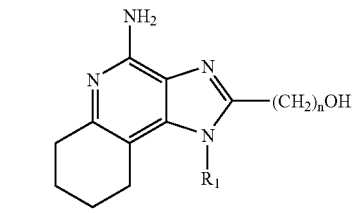
Ib
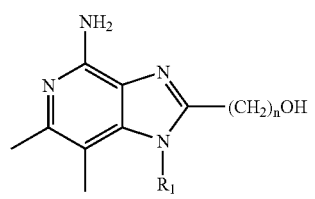
Ic
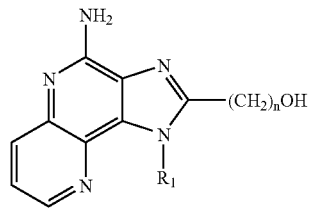
Id
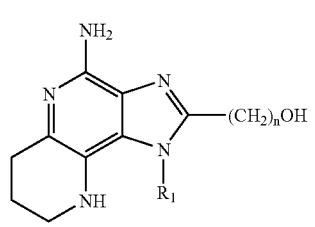
Ie
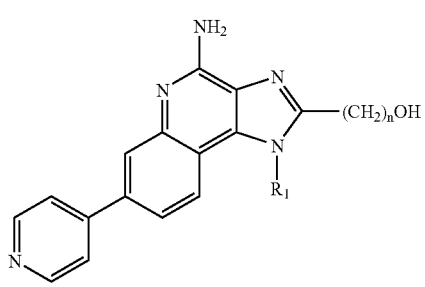
If
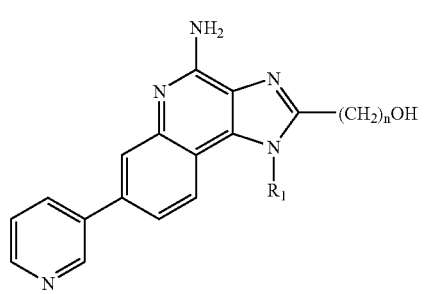
Ig
-continued
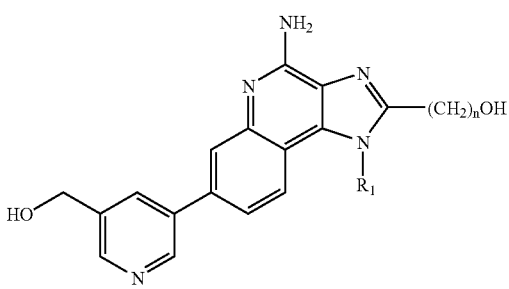
Ih
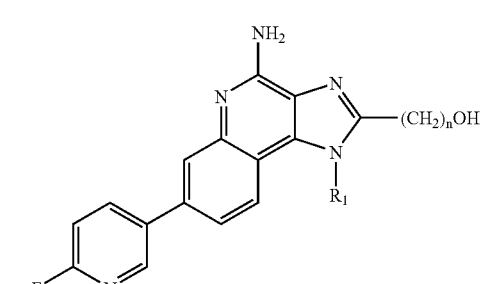
Ii
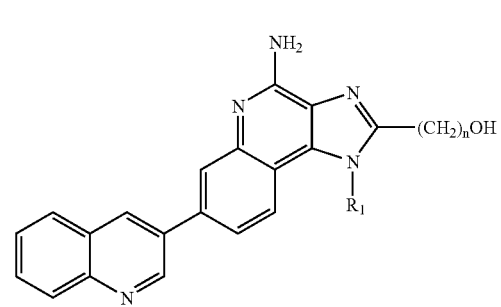
Ij
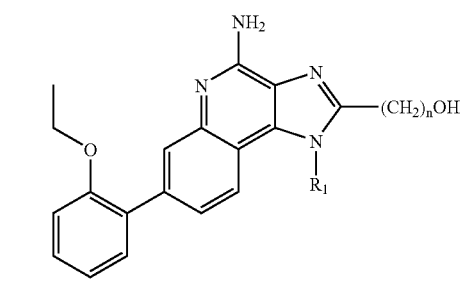
Ik
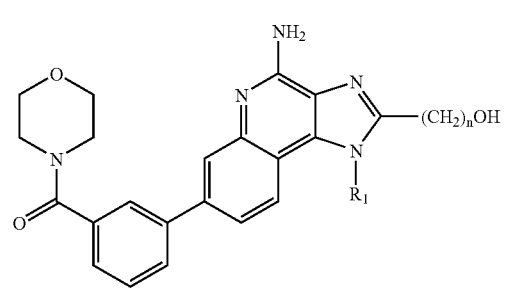
Im Structure In: 4-amino-2-(CH₂)ₙOH-imidazoquinoline with 7-(thiazol-4-ylmethoxy) substituent, N1-R₁

Structure Io: 4-amino-2-(CH₂)ₙOH-imidazoquinoline with 7-(3-(methylsulfonylamino)phenyl) substituent, N1-R₁

Structure Ip: 4-amino-2-(CH₂)ₙOH-imidazoquinoline with 7-(3-(pyrrolidin-1-ylcarbonyl)phenyl) substituent, N1-R₁

| n | R₁ |
|---|---|
| 1 | 2-[(cyclohexylcarbonyl)amino]-2-methylpropyl |
| 1 | 2-[(cyclopropylcarbonyl)amino]ethyl |
| 1 | 4-[(cyclopropylcarbonyl)amino]butyl |
| 1 | 2,3-dihydroxypropyl |
| 1 | 2,2-dimethyl-3-(methylsulfonyl)propyl |
| 1 | 2-fluoro-2-methylpropyl |
| 1 | 2-hydroxy-2-methylpropyl |
| 1 | 2-methylpropyl |
| 1 | 2-methyl-2-({[(1-methylethyl)amino]carbonyl}amino)propyl |
| 1 | 2-{[(1-methylethyl)carbonyl]amino}ethyl |
| 1 | 4-{[(1-methylethyl)carbonyl]amino}butyl |
| 1 | 2-methyl-2-[(methylsulfonyl)amino]propyl |
| 1 | 4-[(methylsulfonyl)amino]butyl |
| 1 | 2-[(methylsulfonyl)amino]ethyl |
| 1 | 4-[(4-morpholinecarbonyl)amino]butyl |
| 1 | 2-[(4-morpholinecarbonyl)amino]ethyl |
| 1 | tetrahydro-2H-pyran-4-ylmethyl |
| 1 | (4-hydroxytetrahydro-2H-pyran-4-yl)methyl |
| 1 | (1-hydroxycyclobutyl)methyl |
| 1 | (1-hydroxycyclopentyl)methyl |
| 1 | (1-hydroxycyclohexyl)methyl |
| 2 | 2-[(cyclohexylcarbonyl)amino]-2-methylpropyl |
| 2 | 2-[(cyclopropylcarbonyl)amino]ethyl |
| 2 | 4-[(cyclopropylcarbonyl)amino]butyl |
| 2 | 2,3-dihydroxypropyl |
| 2 | 2,2-dimethyl-3-(methylsulfonyl)propyl |
| 2 | 2-fluoro-2-methylpropyl |
| 2 | 2-hydroxy-2-methylpropyl |
| 2 | 2-methylpropyl |
| 2 | 2-methyl-2-({[(1-methylethyl)amino]carbonyl}amino)propyl |
| 2 | 2-{[(1-methylethyl)carbonyl]amino}ethyl |
| 2 | 4-{[(1-methylethyl)carbonyl]amino}butyl |
| 2 | 2-methyl-2-[(methylsulfonyl)amino]propyl |
| 2 | 4-[(methylsulfonyl)amino]butyl |
| 2 | 2-[(methylsulfonyl)amino]ethyl |
| 2 | 4-[(4-morpholinecarbonyl)amino]butyl |
| 2 | 2-[(4-morpholinecarbonyl)amino]ethyl |
| 2 | tetrahydro-2H-pyran-4-ylmethyl |
| 2 | (4-hydroxytetrahydro-2H-pyran-4-yl)methyl |
| 2 | (1-hydroxycyclobutyl)methyl |
| 2 | (1-hydroxycyclopentyl)methyl |
| 2 | (1-hydroxycyclohexyl)methyl |

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Oreiner Bio-One, Inc., Longwood, Fla.) centrifuge frit tubes containing density gradient medium. The PBMC layer is collected and washed twice with DPBS or HBSS and re-suspended at 4×10⁶ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is 2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype calorimetric sandwich ELISA (Catalog Number 41105) from PBL Biomedical Laboratories, Piscataway, N.J. Results are expressed in pg/mL.

| Analog | Chemical Name | Reference |
|---|---|---|
| 1 | N-[2-(4-Amino-2-methyl-1H-imidazo[4,5-c]quinolin-1-yl)-1,1-dimethylethyl]methanesulfonamide | U.S. Pat. No. 6,677,349[#] |
| 2 | N-[2-(4-Amino-2-ethyl-1H-imidazo[4,5-c]quinolin-1-yl)-1,1-dimethylethyl]methanesulfonamide | U.S. Pat. No. 6,677,349[#] |
| 3 | N-[2-(4-Amino-2-propyl-1H-imidazo[4,5-c]quinolin-1-yl)-1,1-dimethylethyl]methanesulfonamide | U.S. Pat. No. 6,677,349[#] |
| 4 | N-[2-(4-Amino-2-ethoxymethyl-1H-imidazo[4,5-c]quinolin-1-yl)-1,1-dimethylethyl]methanesulfonamide | U.S. Pat. No. 6,677,349 Example 268 |
| 5 | N-{2-[4-Amino-2-(2-methoxyethyl)-1H-imidazo[4,5-c]quinolin-1-yl]-1,1-dimethylethyl}methanesulfonamide | Example 6 Part D |

[#]This compound is not specifically exemplified but can be readily prepare using the synthetic methods disclosed in the cited reference The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response (pg/mL) is the maximal response attained in the dose response curve.

Compounds used in the methods of the invention and close analogs were tested for their ability to induce cytokine biosynthesis using the test method described above. The analogs used are shown in the table below.

Figure 2:
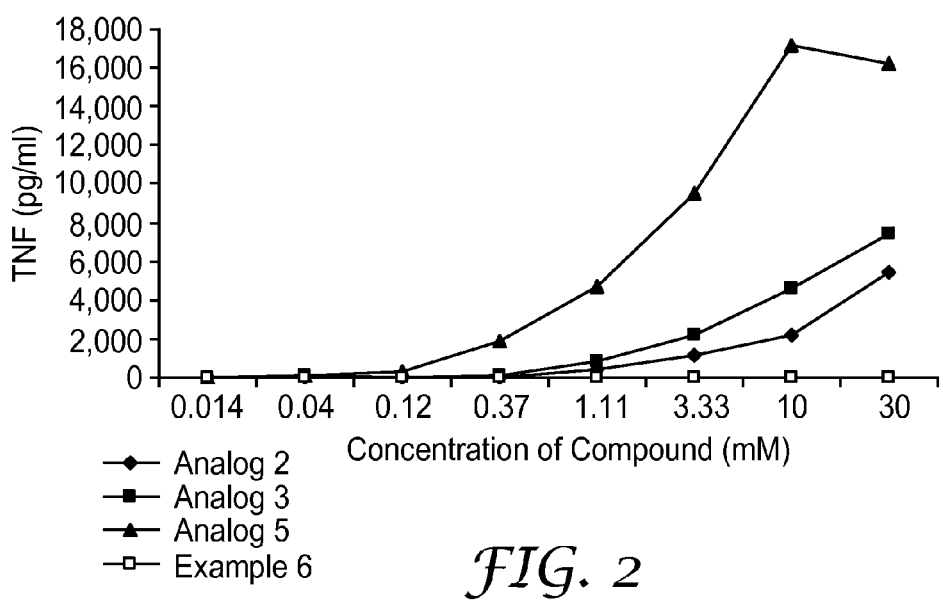
FIG. 2 shows the TNF-α dose response curves (corresponding to values shown in Table 7 below) for Example 6, Analog 2, Analog 3, and Analog 5.
Figure 3:
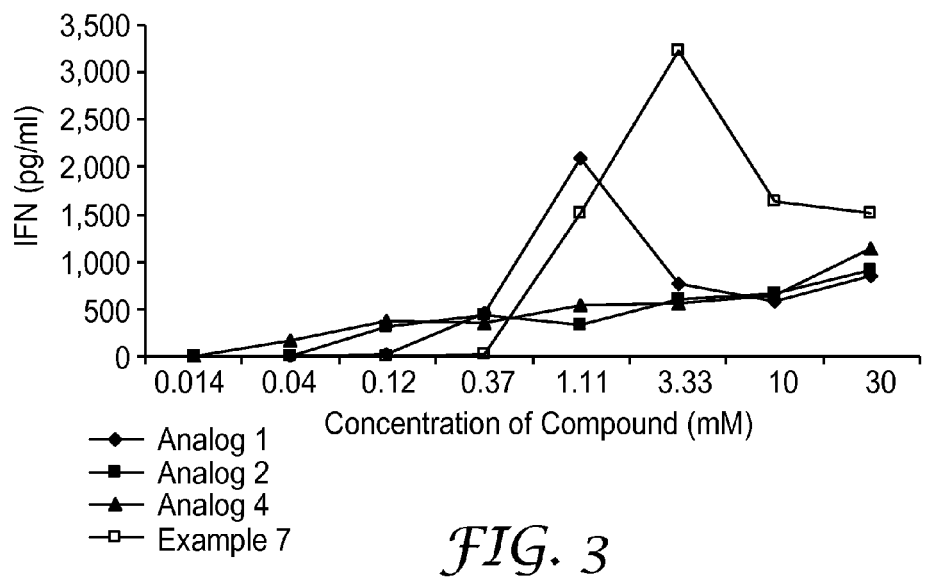
FIG. 3 shows the IFN-α dose response curves (corresponding to values shown in Table 7 below) for Example 7, Analog 1, Analog 2, and Analog 4.
Figure 4:
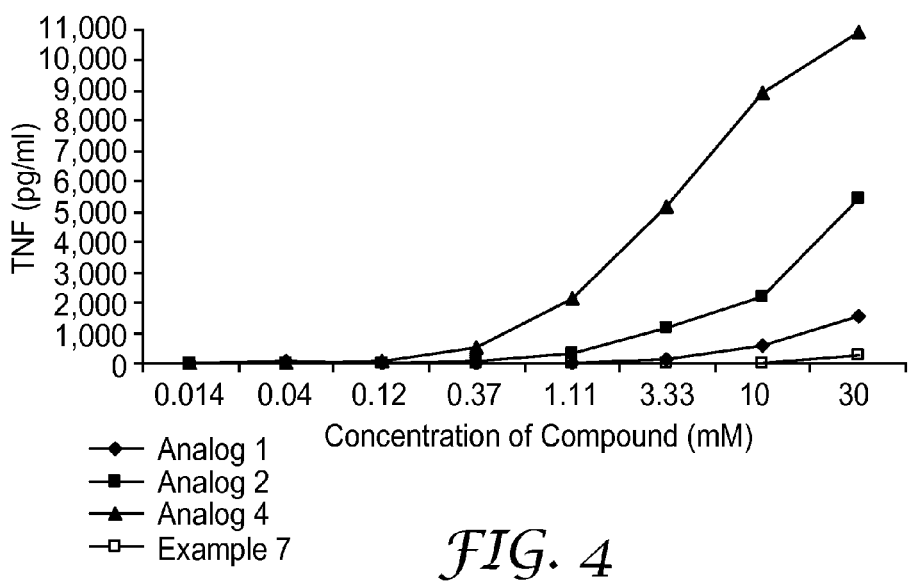
FIG. 4 shows the TNF-α dose response curves (corresponding to values shown in Table 7 below) for Example 7, Analog 1, Analog 2, and Analog 4.

The compounds of Examples 6 and 7 and several closely related analogs were tested using the test method described above. The IFN-α dose response curves for Example 6, Analog 2, Analog 3 and Analog 5 are shown in FIG. 1. The TNF-α dose response curves for Example 6, Analog 2, Analog 3 and Analog 5 are shown in FIG. 2. The IFN-α dose response curves for Example 7, Analog 1, Analog 2 and Analog 4 are shown in FIG. 3. The TNF-α dose response curves for Example 7, Analog 1, Analog 2 and Analog 4 are shown in FIG. 4. The minimum effective concentration for the induction of IFN-α, minimum effective concentration for the induction of TNF-α, the maximal response for IFN-α, and the maximal response for TNF-α are shown in Table 7 below where # is the number of separate experiments in which the compound was tested. When a compound was tested in more than one experiment the values shown are the median values.

TABLE 7

| Compound | $R_2$ | Minimum Effective Concentration (μM) | | Maximal Response (pg/mL) | | # |
|---|---|---|---|---|---|---|
| | | IFN | TNF | IFN | TNF | |
| Example 7 | —$CH_2OH$ | 3.330 | 30.00 | 2250 | 121 | 5 |
| Example 6 | —$(CH_2)_2OH$ | 1.11 | >30 | 7521 | — | 3 |
| Analog 1 | —$CH_3$ | 0.370 | 3.330 | 1846 | 1518 | 7 |
| Analog 2 | —$CH_2CH_3$ | 0.120 | 1.110 | 831 | 3670 | 4 |
| Analog 3 | —$(CH_2)_2CH_3$ | 0.120 | 0.370 | 832 | 7245 | 9 |
| Analog 4 | —$CH_2OCH_2CH_3$ | 0.040 | 0.370 | 889 | 10125 | 22 |
| Analog 5 | —$(CH_2)_2OCH_3$ | 0.014 | 0.12 | 825 | 12518 | 6 |

Further compounds used in the methods of the invention and close analogs were tested for their ability to induce cytokine biosynthesis using the test method described above. The analogs used are shown in the table below.

| Analog | Chemical Name | Reference |
|---|---|---|
| 6 | 1-(4-amino-2-ethoxymethyl-1H-imidazo[4,5-c][1,5]naphthyridin-1-yl)-2-methylpropan-2-ol | Example 148 Part E |
| 7 | 1-[4-amino-2-(2-methoxyethyl)-1H-imidazo[4,5-c][1,5]naphthyridin-1-yl]-2-methylpropan-2-ol | Example 149 Part J |

Figure 5:
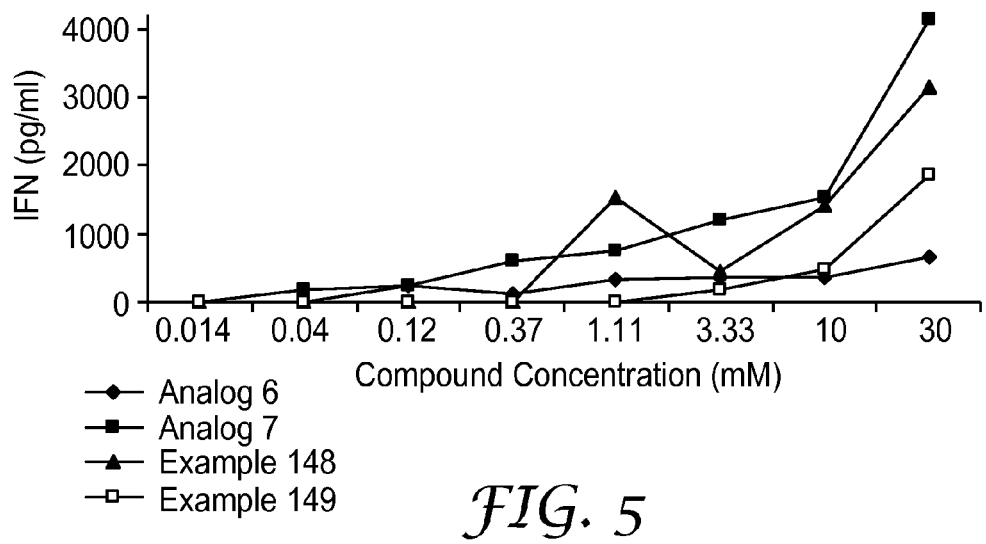
FIG. 5 shows the IFN-α dose response curves (corresponding to values shown in Table 8 below) for Example 148, Example 149, Analog 6, and Analog 7.
Figure 6:
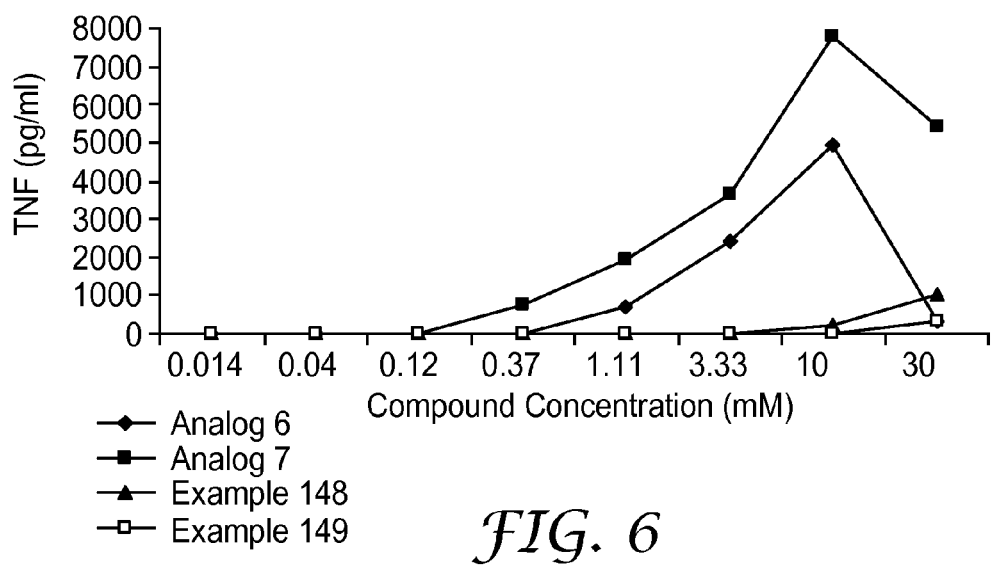
FIG. 6 shows the TNF-α dose response curves (corresponding to values shown in Table 8 below) for Example 148, Example 149, Analog 6, and Analog 7.

The compounds of Examples 148 and 149 and several closely related analogs were tested using the test method described above. The IFN-α dose response curves for Example 148, Example 149, Analog 6, and Analog 7 are shown in FIG. 5. The TNF-α dose response curves for Example 148, Example 149, Analog 6, and Analog 7 are shown in FIG. 6. The minimum effective concentration for the induction of IFN-α, minimum effective concentration for the induction of TNF-α, the maximal response for IFN-α, and the maximal response for TNF-α are shown in Table 8 below where # is the number of separate experiments in which the compound was tested. When a compound was tested in more than one experiment the values shown are the median values.

TABLE 8

| Compound | $R_2$ | Minimum Effective Concentration (μM) | | Maximal Response (pg/mL) | | # |
|---|---|---|---|---|---|---|
| | | IFN | TNF | IFN | TNF | |
| Example 148 | —$CH_2OH$ | 1.11 | 10.0 | 3038 | 684 | 2 |
| Example 149 | —$(CH_2)_2OH$ | 3.33 | 30.0 | 1849 | 342 | 1 |
| Analog 6 | —$CH_2OCH_2CH_3$ | 0.12 | 1.11 | 658 | 4921 | 1 |
| Analog 7 | —$(CH_2)_2OCH_3$ | 0.04 | 0.37 | 4143 | 7762 | 1 |

A further compound used in the methods of the invention and close analogs were tested for their ability to induce cytokine biosynthesis using the test method described above. The analogs used are shown in the table below.

| Analog | Chemical Name | Reference |
|---|---|---|
| 8 | 1-(4-amino-2-ethyl-7-pyridin-3-yl-1H-imidazo[4,5-c]quinolin-1-yl)-2-methylpropan-2-ol | U.S. Patent Publication 2004/0147543 Example 142 |
| 9 | 1-(4-amino-2-propyl-7-pyridin-3-yl-1H-imidazo[4,5-c]quinolin-1-yl)-2-methylpropan-2-ol | U.S. Patent Publication 2004/0147543 Example 418 |
| 10 | 1-(4-amino-2-ethoxymethyl-7-pyridin-3-yl-1H-imidazo[4,5-c]quinolin-1-yl)-2-methylpropan-2-ol | U.S. Patent Publication 2004/0147543 Example 126 |

Figure 7:
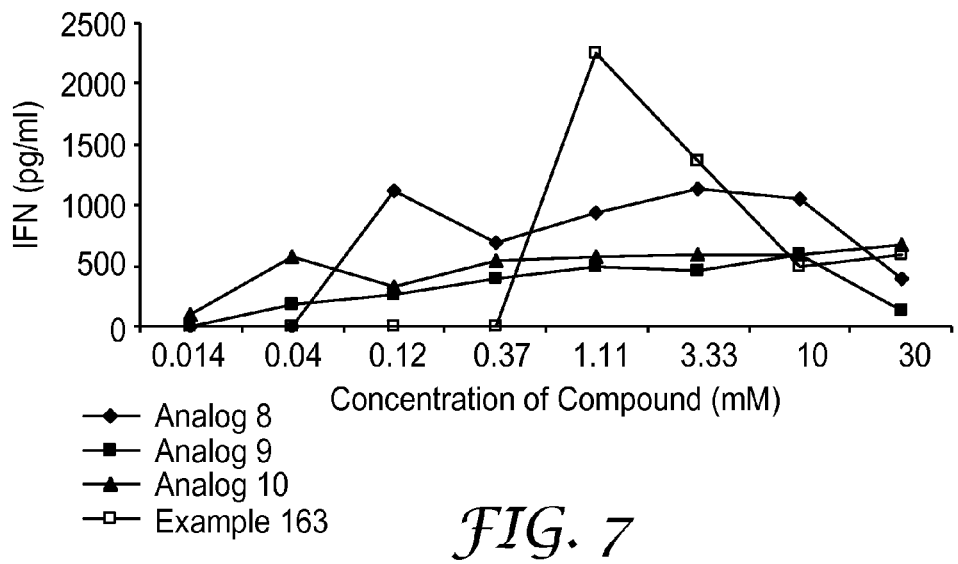
FIG. 7 shows the IFN-α dose response curves (corresponding to values shown in Table 9 below) for Example 163, Analog 8, Analog 9, and Analog 10.
Figure 8:
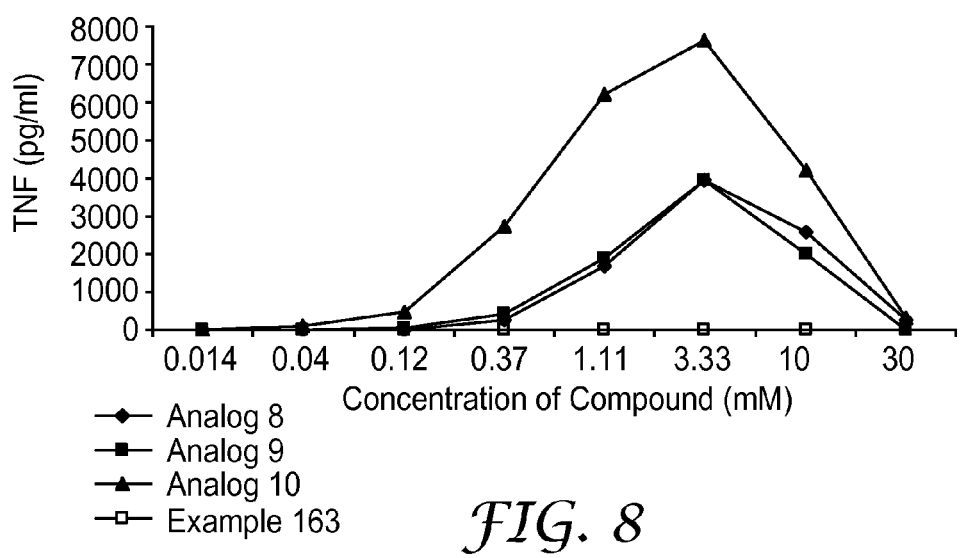
FIG. 8 shows the TNF-α dose response curves (corresponding to values shown in Table 9 below) for Example 163, Analog 8, Analog 9, and Analog 10.

The compound of Example 163 and several closely related analogs were tested using the test method described above. The IFN-α dose response curves are shown in FIG. 7. The TNF-α dose response curves are shown in FIG. 8. The minimum effective concentration for the induction of IFN-α, minimum effective concentration for the induction of TNF-α, the maximal response for IFN-α, and the maximal response for TNF-α are shown in Table 9 below where # is the number of separate experiments in which the compound was tested. When a compound was tested in more than one experiment the values shown are the median values.

TABLE 9

| Compound | $R_2$ | Minimum Effective Concentration (μM) | | Maximal Response (pg/mL) | | # |
|---|---|---|---|---|---|---|
| | | IFN | TNF | IFN | TNF | |
| Example 163 | —$CH_2OH$ | 1.11 | >30 | 2251 | * | 1 |
| Analog 8 | —$CH_2CH_3$ | 0.12 | 0.37 | 1118 | 3234 | 4 |
| Analog 9 | —$(CH_2)_2CH_3$ | 0.04 | 0.37 | 597 | 3951 | 1 |
| Analog 10 | —$CH_2OCH_2CH_3$ | 0.04 | 0.12 | 840 | 0.12 | 5 |

* Below experimental background level of 40 pg/mL.

Compounds of the invention and close analogs were tested for their ability to induce cytokine biosynthesis using the test method described above. The minimum effective concentration for the induction of IFN-α, minimum effective concentration for the induction of TNF-α, the maximal response for IFN-α, and the maximal response for TNF-α are shown in Table 10 below where # is the number of separate experiments in which the compound was tested. When a compound was tested in more than one experiment the values shown are the median values.

TABLE 10

[Structure: 4-amino-imidazoquinoline core with R₂ at 2-position, R₁ on N1, R₃ at 7-position]

| Compound | R₂ | R₁ | R₃ | Minimum Effective Concentration (μM) IFN | TNF | Maximal Response (pg/mL) IFN | TNF | # |
|---|---|---|---|---|---|---|---|---|
| Example 163 | –CH₂CH₂OH | –CH(CH₃)(C(CH₃)₂OH)... 2-methyl-2-hydroxybutyl | 3-pyridyl | 0.37 | 10 | 2886 | 51 | 3 |
| Analog 8 | –CH₂CH₃ | 2-methyl-2-hydroxybutyl | 3-pyridyl | 0.12 | 0.37 | 1652 | 3571 | 6 |
| Analog 9 | –CH₂CH₂CH₃ | 2-methyl-2-hydroxybutyl | 3-pyridyl | 0.04 | 0.37 | 597 | 3951 | 1 |
| Analog 10 | –CH₂OCH₂CH₃ | 2-methyl-2-hydroxybutyl | 3-pyridyl | 0.04 | 0.12 | 840 | 7867 | 7 |
| Analog 11 | –CH₂OCH₃ | 2-methyl-2-hydroxybutyl | 3-pyridyl | 0.37 | 1.11 | 829 | 3445 | 4 |
| Analog 12 | –CH₂CH₂OCH₃ | 2-methyl-2-hydroxybutyl | 3-pyridyl | 0.014 | 0.014 | 1065 | 8386 | 8 |
| Example 189 | –CH₂CH₂OH | 2-methyl-2-hydroxybutyl | 5-(hydroxymethyl)pyridin-3-yl | 0.37 | >30 | 4357 | * | 3 |
| Analog 13 | –CH₂OCH₃ | 2-methyl-2-hydroxybutyl | 5-(hydroxymethyl)pyridin-3-yl | 0.12 | 3.33 | 1771 | 8000 | 4 |
| Analog 14 | –CH₂OCH₂CH₃ | 2-methyl-2-hydroxybutyl | 5-(hydroxymethyl)pyridin-3-yl | 0.014 | 0.12 | 6308 | 18284 | 4 |

TABLE 10-continued

| Compound | R₂ | R₁ | R₃ | Minimum Effective Concentration (μM) | | Maximal Response (pg/mL) | | # |
|---|---|---|---|---|---|---|---|---|
| | | | | IFN | TNF | IFN | TNF | |
| Analog 15 | -CH₂CH₂CH₃ (ethyl) | 2-hydroxy-2-methylbutyl | (5-methylpyridin-3-yl)methanol | 0.014 | 1.11 | 2084 | 10087 | 5 |
| Analog 16 | -CH₂CH₂OCH₃ | 2-hydroxy-2-methylbutyl | (5-methylpyridin-3-yl)methanol | 0.014 | 0.04 | 5868 | 16296 | 2 |
| Analog 17 | -CH₂CH₂CH₂CH₃ | 2-hydroxy-2-methylbutyl | (5-methylpyridin-3-yl)methanol | 0.014 | 0.12 | 1079 | 16482 | 2 |
| Example 191 | -CH₂CH₂OH | 1-(4-ethylpiperidin-1-yl)-2-methylpropan-1-one | 3-methylpyridine | 1.11 | >30 | 969 | * | 1 |
| Analog 18 | -CH₂OCH₂CH₃ | 1-(4-ethylpiperidin-1-yl)-2-methylpropan-1-one | 3-methylpyridine | 0.12 | 0.37 | 2979 | 1449 | 2 |
| Analog 19 | -CH₂CH₃ | 1-(4-ethylpiperidin-1-yl)-2-methylpropan-1-one | 3-methylpyridine | 0.12 | 1.11 | 1686 | 619 | 8 |
| Analog 20 | -CH₂CH₂CH₃ | 1-(4-ethylpiperidin-1-yl)-2-methylpropan-1-one | 3-methylpyridine | 0.12 | 0.37 | 1157 | 1054 | 2 |

TABLE 10-continued

| Compound | R₂ | R₁ | R₃ | Minimum Effective Concentration (μM) IFN | Minimum Effective Concentration (μM) TNF | Maximal Response (pg/mL) IFN | Maximal Response (pg/mL) TNF | # |
|---|---|---|---|---|---|---|---|---|
| Example 156 | propyl-OH | butyl-pyrrolidinone | phenyl | >30 | >30 | * | * | 1 |
| Analog 21 | propyl-OCH₃ | butyl-pyrrolidinone | phenyl | 0.12 | 1.11 | 1880 | 201 | 2 |
| Analog 22 | ethyl-OCH₂CH₃ | butyl-pyrrolidinone | phenyl | 0.37 | 1.11 | 1665 | 62 | 1 |
| Example 157 | propyl-OH | 2-methyl-2-hydroxybutyl | phenyl | 0.37 | 3.33 | 1274 | 67 | 1 |
| Analog 23 | propyl-OCH₃ | 2-methyl-2-hydroxybutyl | 3-pyridyl | 0.014 | 0.014 | 260 | 2296 | 1 |
| Analog 24 | ethyl-OCH₂CH₃ | 2-methyl-2-hydroxybutyl | phenyl | 0.014 | 0.12 | 440 | 2238 | 1 |
| Example 158 | propyl-OH | 2-methylpropyl | 3-pyridyl | 0.37 | 3.33 | 1180 | 42 | 1 |
| Analog 25 | propyl-OCH₃ | 2-methylpropyl | 3-pyridyl | 0.014 | 0.04 | 1199 | 3151 | 3 |

TABLE 10-continued

[Structure: 4-amino-imidazoquinoline core with R1, R2, R3 substituents]

| Compound | R2 | R1 | R3 | Minimum Effective Concentration (μM) IFN | TNF | Maximal Response (pg/mL) IFN | TNF | # |
|---|---|---|---|---|---|---|---|---|
| Analog 26 | –CH2–O–CH2CH3 | –CH(CH3)CH2CH3 | 3-pyridyl | 0.014 | 0.12 | 591 | 647 | 1 |
| Example 159 | –CH2CH2–OH | –CH(CH3)CH2CH3 | (5-methylpyridin-3-yl)methanol | 0.12 | 10 | 1891 | 349 | 1 |
| Analog 27 | –CH2CH2–O–CH3 | –CH(CH3)CH2CH3 | (5-methylpyridin-3-yl)methanol | 0.014 | 0.04 | 1332 | 9563 | 2 |
| Analog 28 | –CH2–O–CH2CH3 | –CH(CH3)CH2CH3 | (5-methylpyridin-3-yl)methanol | 0.04 | 0.37 | 1263 | 3885 | 3 |
| Example 195 | –CH2–OH | pentyl-NH-C(O)-NH-propyl | 3-pyridyl | 0.37 | 30 | 5089 | 81 | 1 |
| Analog 29 | –CH2–O–CH2CH3 | pentyl-NH-C(O)-NH-propyl | 3-pyridyl | 0.04 | 1.11 | 936 | 1059 | 2 |

TABLE 10-continued

[Structure: 4-amino-imidazoquinoline core with NH₂ at top, R₂ at 2-position, R₁ on N1, R₃ at 7-position]

| Compound | R₂ | R₁ | R₃ | Minimum Effective Concentration (µM) IFN | TNF | Maximal Response (pg/mL) IFN | TNF | # |
|---|---|---|---|---|---|---|---|---|
| Analog 30 | —CH₂CH₂CH₃ (propyl) | —(CH₂)₅—NH—C(=O)—NH—CH₂CH₂CH₃ | 3-pyridyl | 0.37 | 0.37 | 531 | 5284 | 1 |
| Example 196 | —OH | —(CH₂)₅—NH—C(=O)—CH₂CH₂CH₃ | 3-pyridyl | 0.12 | >30 | 3516 | * | 1 |
| Analog 31 | —CH₂—O—CH₂CH₃ | —(CH₂)₅—NH—C(=O)—CH₂CH₂CH₃ | 3-pyridyl | 0.12 | 1.11 | 965 | 991 | 2 |
| Analog 32 | —CH₂CH₂CH₃ | —(CH₂)₅—NH—C(=O)—CH₂CH₂CH₃ | 3-pyridyl | 0.12 | 0.37 | 862 | 1647 | 2 |

TABLE 10-continued

[Structure: 4-amino-imidazoquinoline core with R1 on N1, R2 at 2-position, R3 at 7-position]

| Compound | R2 | R1 | R3 | Minimum Effective Concentration (μM) | | Maximal Response (pg/mL) | | # |
|---|---|---|---|---|---|---|---|---|
| | | | | IFN | TNF | IFN | TNF | |
| Example 197 | —CH2OH | pentyl-NH-C(O)-NH-cyclopentyl | 3-methylpyridin-yl | 0.04 | 10 | 4373 | 600 | 1 |
| Analog 33 | —CH2-O-CH2CH3 | pentyl-NH-C(O)-NH-cyclopentyl | 3-methylpyridin-yl | 0.014 | 1.11 | 925 | 1618 | 2 |
| Analog 34 | —CH2CH2CH3 | pentyl-NH-C(O)-NH-cyclopentyl | 3-methylpyridin-yl | 0.014 | 0.37 | 649 | 9019 | 1 |
| Example 198 | —CH2OH | pentyl-NH-C(O)-cyclopentyl | 3-methylpyridin-yl | 0.12 | 3.33 | 2745 | 410 | 1 |

TABLE 10-continued

| Compound | R₂ | R₁ | R₃ | Minimum Effective Concentration (μM) | | Maximal Response (pg/mL) | | # |
|---|---|---|---|---|---|---|---|---|
| | | | | IFN | TNF | IFN | TNF | |
| Analog 35 | ethoxymethyl | 5-(cyclopentanecarboxamido)pentyl | 3-pyridyl | 0.04 | 0.37 | 969 | 1366 | 2 |
| Analog 36 | propyl | 5-(cyclopentanecarboxamido)pentyl | 3-pyridyl | 0.12 | 0.37 | 521 | 2222 | 1 |
| Example 199 | hydroxymethyl | 5-(isobutyramido)pentyl | 3-pyridyl | 0.37 | 10 | 5880 | 217 | 1 |
| Analog 37 | ethoxymethyl | 5-(isobutyramido)pentyl | 3-pyridyl | 0.12 | 1.11 | 1194 | 728 | 2 |

TABLE 10-continued

[Core structure: 4-amino-1H-imidazo[4,5-c]quinoline with R2 at 2-position, R1 on N1, R3 at 7-position]

| Compound | R₂ | R₁ | R₃ | Minimum Effective Concentration (μM) IFN | TNF | Maximal Response (pg/mL) IFN | TNF | # |
|---|---|---|---|---|---|---|---|---|
| Analog 38 | -CH₂CH₂CH₃ | -(CH₂)₄-NH-C(=O)-CH(CH₃)₂ | pyridin-3-yl | 0.12 | 0.37 | 1610 | 960 | 2 |
| Example 160 | -CH₂CH₂-OH | -(CH₂)₄-(2-oxopyrrolidin-1-yl) | pyridin-3-yl | 30 | >30 | 109 | * | 1 |
| Analog 39 | -CH₂CH₂-OCH₃ | -(CH₂)₄-(2-oxopyrrolidin-1-yl) | pyridin-3-yl | 0.12 | 1.11 | 753 | 380 | 3 |
| Example 161 | -CH₂CH₂-OH | -(CH₂)₄-(2-oxopyrrolidin-1-yl) | pyridin-4-yl | >30 | >30 | * | * | 1 |
| Analog 40 | -CH₂CH₂-OCH₃ | -(CH₂)₄-(2-oxopyrrolidin-1-yl) | pyridin-4-yl | 0.37 | 3.33 | 1179 | 943 | 3 |
| Example 164 | -CH₂-OH | -C(CH₃)₂-CH₂-OH (2-hydroxy-2-methylpropyl) | 3-methylphenyl | 30 | >30 | 87 | * | 1 |

TABLE 10-continued

Core structure: 4-amino-imidazo[4,5-c]quinoline with R₂ at 2-position, R₁ at N1, R₃ at 7-position.

| Compound | R₂ | R₁ | R₃ | MEC IFN (μM) | MEC TNF (μM) | Max IFN (pg/mL) | Max TNF (pg/mL) | # |
|---|---|---|---|---|---|---|---|---|
| Analog 41 | —CH₂—O—CH₂CH₃ | —C(CH₃)₂(OH)CH₂— (2-hydroxy-2-methylbutyl) | 3,5-dimethylphenyl | 0.014 | 0.12 | 541 | 10184 | 1 |
| Example 165 | —CH₂OH | 2-hydroxy-2-methylbutyl | 4-methylphenyl | 0.37 | 0.37 | 1681 | 7423 | 1 |
| Analog 42 | —CH₂—O—CH₂CH₃ | 2-hydroxy-2-methylbutyl | 4-methylphenyl | 0.12 | 0.12 | 650 | 4456 | 1 |
| Example 168 | —CH₂OH | 2-hydroxy-2-methylbutyl | 3-hydroxyphenyl | 0.37 | 10 | 12641 | 352 | 1 |
| Analog 43 | —CH₂—O—CH₂CH₃ | 2-hydroxy-2-methylbutyl | 3-hydroxyphenyl | 0.04 | 0.04 | 740 | 3955 | 1 |
| Example 201 | —CH₂OH | 2-(4-ethylpiperidin-1-yl)-3-methyl-2-oxo (isobutyryl-4-ethylpiperidinyl) | (5-methylpyridin-3-yl)methyl-OH | >30 | >30 | * | * | 1 |
| Analog 44 | —CH₂—O—CH₂CH₃ | 2-(4-ethylpiperidin-1-yl)-3-methyl-2-oxo | (5-methylpyridin-3-yl)methyl-OH | 0.04 | 1.11 | 1382 | 3128 | 1 |
| Example 205 | —CH₂OH | cyclohexylmethyl | (5-methylpyridin-3-yl)methyl-OH | 3.33 | >30 | 1087 | * | 1 |

TABLE 10-continued

[Structure: 4-amino imidazoquinoline core with R1 on N1, R2 at 2-position, R3 at 7-position]

| Compound | R2 | R1 | R3 | Minimum Effective Concentration (μM) IFN | TNF | Maximal Response (pg/mL) IFN | TNF | # |
|---|---|---|---|---|---|---|---|---|
| Analog 45 | —CH(CH3)OCH2CH3 | —CH2-cyclohexyl | 5-methyl-3-pyridinyl-CH(OH)— | 0.014 | 1.11 | 1062 | 2865 | 2 |
| Example 206 | —CH2OH | —CH2-cyclohexyl | 3-(morpholine-4-carbonyl)phenyl | 1.11 | >30 | 1266 | * | 1 |
| Analog 46 | —CH(CH3)OCH2CH3 | —CH2-cyclohexyl | 3-(morpholine-4-carbonyl)phenyl | 0.014 | 0.37 | 815 | 1054 | 1 |

* Below experimental background level
All analogs are either specifically exemplified in or are readily prepared using the synthetic methods disclosed in U.S. Patent Application Publication 2004/0147543

Compounds of the invention and close analogs were tested for their ability to induce cytokine biosynthesis using the test method described above. The minimum effective concentration for the induction of IFN-α, minimum effective concentration for the induction of TNF-α, the maximal response for IFN-α, and the maximal response for TNF-α are shown in Table 11 below where # is the number of separate experiments in which the compound was tested. When a compound was tested in more than one experiment the values shown are the median values.

TABLE 11

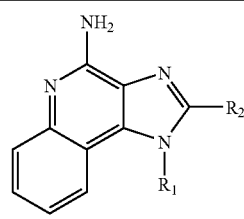

| Compound | R1 | R2 | Minimum Effective Concentration (μM) IFN | TNF | Maximal Response (pg/mL) IFN | TNF | # |
|---|---|---|---|---|---|---|---|
| Example 7 | —CH2C(CH3)2NHS(O)2CH3 | —CH2OH | 3.33 | 30 | 1670 | 154 | 6 |
| Example 6 | —CH2C(CH3)2NHS(O)2CH3 | —(CH2)2OH | 1.11 | 30 | 6527 | * | 4 |
| Analog 1 | —CH2C(CH3)2NHS(O)2CH3 | —CH3 | 0.37 | 3.33 | 1846 | 1518 | 9 |
| Analog 2 | —CH2C(CH3)2NHS(O)2CH3 | —CH2CH3 | 0.12 | 1.11 | 1096 | 9675 | 6 |

TABLE 11-continued

[Structure: 4-amino-1H-imidazo[4,5-c]quinoline with R₂ at 2-position and R₁ on N1]

| Compound | R₁ | R₂ | Minimum Effective Concentration (μM) IFN | TNF | Maximal Response (pg/mL) IFN | TNF | # |
|---|---|---|---|---|---|---|---|
| Analog 3 | —CH₂C(CH₃)₂NHS(O)₂CH₃ | —CH₂CH₂CH₃ | 0.12 | 0.37 | 832 | 9780 | 11 |
| Analog 4 | —CH₂C(CH₃)₂NHS(O)₂CH₃ | —CH₂OCH₂CH₃ | 0.04 | 0.37 | 1138 | 10665 | 33 |
| Analog 5 | —CH₂C(CH₃)₂NHS(O)₂CH₃ | —(CH₂)₂OCH₃ | 0.014 | 0.12 | 1308 | 13908 | 8 |
| Analog 47 | —CH₂C(CH₃)₂NHS(O)₂CH₃ | —CH₂OCH₃ | 0.37 | 3.33 | 1638 | 7151 | 1 |
| Example 368 | —(CH₂)₄NHS(O)₂CH₃ | —CH₂OH | 0.37 | >30 | 7220 | * | 3 |
| Example 3 | —(CH₂)₄NHS(O)₂CH₃ | —(CH₂)₂OH | 0.37 | >30 | 2340 | * | 4 |
| Analog 48 | —(CH₂)₄NHS(O)₂CH₃ | —CH₃ | 0.12 | 10 | 7293 | 526 | 13 |
| Analog 49 | —(CH₂)₄NHS(O)₂CH₃ | —CH₂CH₃ | 0.04 | 3.33 | 2712 | 679 | 79 |
| Analog 50 | —(CH₂)₄NHS(O)₂CH₃ | —CH₂CH₂CH₃ | 0.12 | 1.11 | 2184 | 850 | 22 |
| Analog 51 | —(CH₂)₄NHS(O)₂CH₃ | —CH₂OCH₂CH₃ | 0.04 | 1.11 | 2581 | 1439 | 10 |
| Analog 52 | —(CH₂)₄NHS(O)₂CH₃ | —(CH₂)₂OCH₃ | 0.014 | 0.37 | 7594 | 1931 | 13 |
| Example 115 | —(CH₂)₄NHC(O)—N(morpholine) | —(CH₂)₂OH | 1.11 | >30 | 8361 | * | 1 |
| Analog 53 | —(CH₂)₄NHC(O)—N(morpholine) | —CH₃ | 0.12 | 10 | 1538 | 1400 | 1 |
| Analog 54 | —(CH₂)₄NHC(O)—N(morpholine) | —CH₂CH₃ | 0.37 | 3.33 | 4975 | 2570 | 1 |
| Analog 55 | —(CH₂)₄NHC(O)—N(morpholine) | —CH₂CH₂CH₃ | 0.12 | 1.11 | 11255 | 1298 | 3 |
| Analog 56 | —(CH₂)₄NHC(O)—N(morpholine) | —CH₂OCH₂CH₃ | 0.12 | 1.11 | 3433 | 1580 | 2 |
| Analog 57 | —(CH₂)₄NHC(O)—N(morpholine) | —(CH₂)₂OCH₃ | 0.014 | 0.04 | 8889 | 3494 | 8 |
| Example 122 | —(CH₂)₃NHS(O)₂CH₃ | —(CH₂)₂OH | 3.33 | >30 | 9651 | * | 3 |
| Aanalog 58 | —(CH₂)₃NHS(O)₂CH₃ | —CH₃ | 1.11 | 30 | 2778 | * | 11 |
| Analog 59 | —(CH₂)₃NHS(O)₂CH₃ | —CH₂CH₃ | 1.11 | 30 | 1912 | 238 | 2 |
| Analog 60 | —(CH₂)₃NHS(O)₂CH₃ | —CH₂CH₂CH₃ | 1.11 | 10 | 2148 | 109 | 3 |
| Analog 61 | —(CH₂)₃NHS(O)₂CH₃ | —CH₂OCH₂CH₃ | 0.37 | 10 | 1338 | 463 | 9 |
| Analog 62 | —(CH₂)₃NHS(O)₂CH₃ | —(CH₂)₂OCH₃ | 0.014 | 1.11 | 3995 | 954 | 9 |
| Example 131 | —CH₂C(CH₃)₂CH₂NHS(O)₂CH₃ | —(CH₂)₂OH | 0.37 | >30 | 8361 | * | 1 |
| Analog 63 | —CH₂C(CH₃)₂CH₂NHS(O)₂CH₃ | —CH₃ | 0.37 | 10 | 1019 | 805 | 2 |
| Analog 64 | —CH₂C(CH₃)₂CH₂NHS(O)₂CH₃ | —CH₂CH₃ | 0.12 | 3.33 | 1431 | 1453 | 3 |
| Analog 65 | —CH₂C(CH₃)₂CH₂NHS(O)₂CH₃ | —CH₂CH₂CH₃ | 0.12 | 10 | 1711 | 1929 | 2 |
| Analog 66 | —CH₂C(CH₃)₂CH₂NHS(O)₂CH₃ | —CH₂OCH₂CH₃ | 0.12 | 0.37 | 561 | 3768 | 5 |
| Analog 67 | —CH₂C(CH₃)₂CH₂NHS(O)₂CH₃ | —(CH₂)₂OCH₃ | 0.014 | 0.04 | 1805 | 5467 | 10 |
| Example 36 | —(CH₂)₂NHS(O)₂CH₃ | —(CH₂)₂OH | 10 | >30 | 3316 | * | 1 |
| Analog 68 | —(CH₂)₂NHS(O)₂CH₃ | —CH₃ | 0.12 | 10 | 1610 | 820 | 3 |
| Analog 69 | —(CH₂)₂NHS(O)₂CH₃ | —CH₂CH₃ | 0.12 | 10 | 1610 | 820 | 3 |
| Analog 70 | —(CH₂)₂NHS(O)₂CH₃ | —CH₂CH₂CH₃ | 30 | 10 | 2003 | 11432 | 2 |
| Analog 71 | —(CH₂)₂NHS(O)₂CH₃ | —CH₂OCH₂CH₃ | 0.12 | 3.33 | 1465 | 4918 | 9 |
| Analog 72 | —(CH₂)₂NHS(O)₂CH₃ | —(CH₂)₂OCH₃ | 0.014 | 0.04 | 5858 | 8547 | 6 |
| Example 125 | —(CH₂)₅S(O)₂CH₃ | —(CH₂)₂OH | 0.37 | >30 | 8361 | * | 1 |
| Analog 73 | —(CH₂)₅S(O)₂CH₃ | —CH₃ | 0.37 | 3.33 | 1294 | 771 | 21 |
| Analog 74 | —(CH₂)₅S(O)₂CH₃ | —CH₂CH₃ | 0.12 | 1.11 | 1062 | 1545 | 7 |
| Analog 75 | —(CH₂)₅S(O)₂CH₃ | —CH₂CH₂CH₃ | 0.12 | 1.11 | 828 | 848 | 3 |
| Analog 76 | —(CH₂)₅S(O)₂CH₃ | —(CH₂)₂OCH₃ | 0.014 | 1.11 | 2695 | 6169 | 2 |

TABLE 11-continued

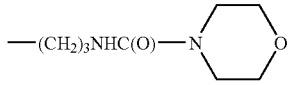

| Compound | R₁ | R₂ | Minimum Effective Concentration (μM) IFN | Minimum Effective Concentration (μM) TNF | Maximal Response (pg/mL) IFN | Maximal Response (pg/mL) TNF | # |
|---|---|---|---|---|---|---|---|
| Example 133 | —(CH₂)₂O(CH₂)₂N(CH₃)S(O)₂CH₃ | —(CH₂)₂OH | 0.37 | >30 | 8361 | * | 1 |
| Analog 77 | —(CH₂)₂O(CH₂)₂N(CH₃)S(O)₂CH₃ | —CH₃ | 0.12 | 1.11 | 1001 | 3571 | 1 |
| Analog 78 | —(CH₂)₂O(CH₂)₂N(CH₃)S(O)₂CH₃ | —CH₂CH₃ | 0.12 | 1.11 | 1803 | 2525 | 1 |
| Analog 79 | —(CH₂)₂O(CH₂)₂N(CH₃)S(O)₂CH₃ | —CH₂CH₂CH₃ | 0.37 | 3.33 | 1055 | 1312 | 2 |
| Analog 80 | —(CH₂)₂O(CH₂)₂N(CH₃)S(O)₂CH₃ | —(CH₂)₂OCH₃ | 0.014 | 0.37 | 1630 | 2191 | 4 |
| Example 99 | —(CH₂)₃NHC(O)NHCH(CH₃)₂ | —(CH₂)₂OH | 0.37 | >30 | 21829 | * | 1 |
| Analog 81 | —(CH₂)₃NHC(O)NHCH(CH₃)₂ | —CH₃ | 3.33 | 10 | 1134 | 490 | 1 |
| Analog 82 | —(CH₂)₃NHC(O)NHCH(CH₃)₂ | —CH₂CH₂CH₃ | 0.12 | 1.11 | 6571 | 3740 | 2 |
| Analog 83 | —(CH₂)₃NHC(O)NHCH(CH₃)₂ | —(CH₂)₂OCH₃ | 0.12 | 1.11 | 1289 | 1259 | 1 |
| Example 120 | —(CH₂)₃NH₂ | —(CH₂)₂OH | 3.33 | >30 | 5636 | * | 1 |
| Analog 84 | —(CH₂)₃NH₂ | —CH₃ | 3.33 | >30 | 421 | * | 1 |
| Analog 85 | —(CH₂)₃NH₂ | —CH₂OCH₂CH₃ | 0.12 | 30 | 1325 | 411 | 1 |
| Analog 86 | —(CH₂)₃NH₂ | —(CH₂)₂OCH₃ | 0.04 | 1.11 | 3433 | 1674 | 1 |
| Example 128 | —(CH₂)₃NHC(O)—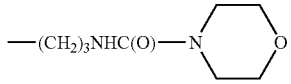 | —(CH₂)₂OH | 30 | >30 | 75 | * | 3 |
| Analog 87 | —(CH₂)₃NHC(O)—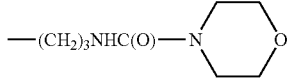 | —CH₃ | 0.37 | 30 | 4843 | 463 | 2 |
| Analog 88 | —(CH₂)₃NHC(O)—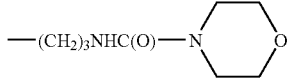 | —CH₂OCH₂CH₃ | 0.12 | 1.11 | 6670 | 1379 | 2 |
| Analog 89 | —(CH₂)₃NHC(O)—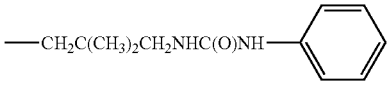 | —(CH₂)₂OCH₃ | 0.014 | 0.014 | 5915 | 6169 | 2 |
| Example 130 | —CH₂C(CH₃)₂CH₂NHC(O)NH—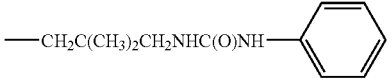 | —(CH₂)₂OH | 0.014 | 3.33 | 8361 | 2001 | 1 |
| Analog 90 | —CH₂C(CH₃)₂CH₂NHC(O)NH—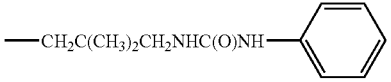 | —CH₂CH₃ | 0.014 | 0.12 | 922 | 2098 | 2 |
| Analog 91 | —CH₂C(CH₃)₂CH₂NHC(O)NH—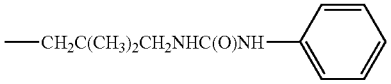 | —CH₂OCH₂CH₃ | 0.014 | 0.04 | 1133 | 3618 | 2 |
| Analog 92 | —CH₂C(CH₃)₂CH₂NHC(O)NH—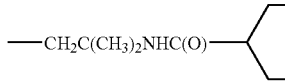 | —(CH₂)₂OCH₃ | 0.014 | 0.04 | 570 | 6449 | 2 |
| Example 5 | —CH₂C(CH₃)₂NHC(O)—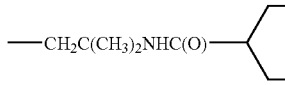 | —CH₂OH | 0.37 | 10 | 17274 | 1130 | 1 |
| Analog 93 | —CH₂C(CH₃)₂NHC(O)—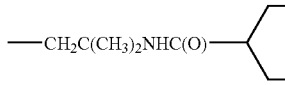 | —CH₂OCH₂CH₃ | 0.37 | 0.37 | 1052 | 12173 | 13 |

TABLE 11-continued

[Structure: 4-amino-imidazoquinoline core with R2 at 2-position and R1 on N1]

| Compound | R₁ | R₂ | MEC IFN (μM) | MEC TNF (μM) | Max IFN (pg/mL) | Max TNF (pg/mL) | # |
|---|---|---|---|---|---|---|---|
| Analog 94 | —CH₂C(CH₃)₂CH₂NHC(O)-phenyl | —CH₂OCH₃ | 1.11 | 3.33 | 2518 | 9721 | 1 |
| Example 124 | —CH₂C(CH₃)₂CH₂NHC(O)-phenyl | —(CH₂)₂OH | 0.12 | 3.33 | 3980 | 1446 | 1 |
| Analog 95 | —CH₂C(CH₃)₂CH₂NHC(O)-phenyl | —CH₂OCH₂OCH₃ | 0.04 | 0.37 | 832 | 1820 | 5 |
| Analog 96 | —CH₂C(CH₃)₂CH₂NHC(O)-phenyl | —(CH₂)₂OCH₃ | 0.014 | 0.014 | 2133 | 1812 | 1 |
| Example 126 | —(CH₂)₃NHC(O)NH(CH₂)₃CH₃ | —(CH₂)₂OH | 1.11 | >30 | 8361 | * | 1 |
| Analog 97 | —(CH₂)₃NHC(O)NH(CH₂)₃CH₃ | —CH₂OCH₂CH₃ | 0.37 | 3.33 | 827 | 963 | 5 |
| Analog 98 | —(CH₂)₃NHC(O)NH(CH₂)₃CH₃ | —(CH₂)₂OCH₃ | 0.014 | 0.04 | 5915 | 6169 | 2 |
| Example 129 | —CH₂C(CH₃)₂CH₂NH₂ | —(CH₂)₂OH | 0.37 | 30 | 2702 | 85 | 1 |
| Analog 99 | —CH₂C(CH₃)₂CH₂NH₂ | —CH₂CH₃ | 0.04 | 0.37 | 405 | 13846 | 1 |
| Analog 100 | —CH₂C(CH₃)₂CH₂NH₂ | —(CH₂)₂OCH₃ | 0.014 | 0.04 | 571 | 17626 | 1 |
| Example 132 | —(CH₂)₃NHC(O)-phenyl | —(CH₂)₂OH | 0.37 | >30 | 8361 | * | 1 |
| Analog 101 | —(CH₂)₃NHC(O)-phenyl | —CH₃ | 1.11 | 3.33 | 571 | 156 | 3 |
| Analog 102 | —(CH₂)₃NHC(O)-phenyl | —(CH₂)₂OCH₃ | 0.014 | 1.11 | 1504 | 3080 | 2 |
| Example 137 | —(CH₂)₂NHC(O)NHCH₂CH₃ | —(CH₂)₂OH | 30 | 30 | 801 | 73 | 1 |
| Analog 103 | —(CH₂)₂NHC(O)NHCH₂CH₃ | —CH₂CH₃ | 3.33 | 10 | 1031 | 3250 | 2 |
| Analog 104 | —(CH₂)₂NHC(O)NHCH₂CH₃ | —(CH₂)₂OCH₃ | 0.014 | 0.12 | 2587 | 7719 | 4 |
| Example 138 | —(CH₂)₂NHC(O)CH₂CH(CH₃)₂ | —(CH₂)₂OH | 3.33 | >30 | 36 | * | 1 |
| Analog 105 | —(CH₂)₂NHC(O)CH₂CH(CH₃)₂ | —CH₂CH₃ | 3.33 | 30 | 851 | 587 | 2 |
| Analog 106 | —(CH₂)₂NHC(O)CH₂CH(CH₃)₂ | —(CH₂)₂OCH₃ | 0.12 | 3.33 | 1204 | 5694 | 5 |
| Example 142 | —CH₂C(CH₃)₂NHC(O)NHCH(CH₃)₂ | —CH₂OH | 1.11 | >30 | 1554 | * | 1 |
| Analog 107 | —CH₂C(CH₃)₂NHC(O)NHCH(CH₃)₂ | —CH₂CH₂CH₃ | 1.11 | 3.33 | 1428 | 6363 | 3 |
| Analog 108 | —CH₂C(CH₃)₂NHC(O)NHCH(CH₃)₂ | —CH₂OCH₂CH₃ | 0.37 | 1.11 | 966 | 10587 | 4 |
| Example 1 | —(CH₂)₃NHS(O)₂-(4-methylphenyl) | —(CH₂)₂OH | 0.37 | 10 | 1072 | 143 | 1 |
| Analog 109 | —(CH₂)₃NHS(O)₂-(4-methylphenyl) | —(CH₂)₂OCH₃ | 0.04 | 0.37 | 638 | 6169 | 2 |

TABLE 11-continued

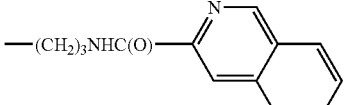

| Compound | R₁ | R₂ | Minimum Effective Concentration (μM) | | Maximal Response (pg/mL) | | # |
|---|---|---|---|---|---|---|---|
| | | | IFN | TNF | IFN | TNF | |
| Example 2 | —(CH₂)₃NHC(O)—  | —(CH₂)₂OH | 3.33 | 3.33 | 507 | 45 | 1 |
| Analog 110 | —(CH₂)₃NHC(O)— 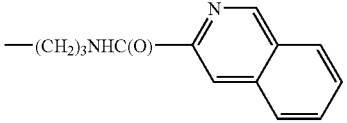 | —(CH₂)₂OCH₃ | 0.12 | 1.11 | 647 | 6169 | 2 |
| Example 4 | —CH₂C(CH₃)₂NH₂ | —CH₂OH | 0.37 | 3.33 | 1893 | 41 | 2 |
| Analog 111 | —CH₂C(CH₃)₂NH₂ | —CH₂OCH₂CH₃ | 0.12 | 0.37 | 656 | 11475 | 7 |
| Example 111 | —(CH₂)₄NHC(O)—  | —(CH₂)₂OH | 0.12 | 1.11 | 7753 | 983 | 1 |
| Analog 112 | —(CH₂)₄NHC(O)— 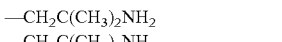 | —(CH₂)₂OCH₃ | 0.014 | 0.04 | 2127 | 1462 | 7 |
| Example 112 | —(CH₂)₄NHS(O)₂—  | —(CH₂)₂OH | 1.11 | 30 | 8361 | 76 | 1 |
| Analog 113 | —(CH₂)₄NHS(O)₂— 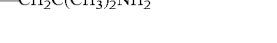 | —(CH₂)₂OCH₃ | 0.014 | 0.04 | 6032 | 3786 | 4 |
| Example 114 | —(CH₂)₄NH₂ | —(CH₂)₂OH | 30 | >30 | 23 | * | 1 |
| Analog 114 | —(CH₂)₄NH₂ | —(CH₂)₂OCH₃ | 0.04 | 0.37 | 127231 | 724 | 1 |
| Example 116 | —(CH₂)₄NHC(O)—  | —(CH₂)₂OH | 0.37 | 30 | 8361 | 1112 | 1 |
| Analog 115 | —(CH₂)₄NHC(O)— 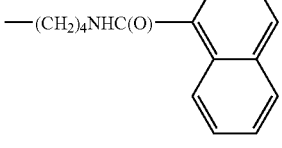 | —(CH₂)₂OCH₃ | 0.014 | 0.04 | 7545 | 9340 | 2 |

TABLE 11-continued

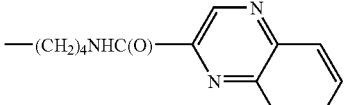

| Compound | R₁ | R₂ | Minimum Effective Concentration (μM) IFN | Minimum Effective Concentration (μM) TNF | Maximal Response (pg/mL) IFN | Maximal Response (pg/mL) TNF | # |
|---|---|---|---|---|---|---|---|
| Example 117 | —(CH₂)₄NHC(O)-quinoxalin-2-yl | —(CH₂)₂OH | 0.37 | 3.33 | 5520 | 1938 | 1 |
| Analog 116 | —(CH₂)₄NHC(O)-quinoxalin-2-yl | —(CH₂)₂OCH₃ | 0.014 | 0.04 | 1129 | 7261 | 3 |
| Example 118 | —(CH₂)₈NHC(O)NH-phenyl | —(CH₂)₂OH | 0.37 | >30 | 5177 | * | 1 |
| Analog 117 | —(CH₂)₈NHC(O)NH-phenyl | —(CH₂)₂OCH₃ | 0.014 | 0.12 | 1257 | 1372 | 1 |
| Example 119 | —(CH₂)₈NHS(O)₂CH₃ | —(CH₂)₂OH | 0.04 | 3.33 | 8361 | 693 | 1 |
| Analog 118 | —(CH₂)₈NHS(O)₂CH₃ | —(CH₂)₂OCH₃ | 0.014 | 0.014 | 1914 | 1853 | 2 |
| Example 121 | —(CH₂)₈NHC(O)-phenyl | —(CH₂)₂OH | 0.37 | 3.33 | 2441 | 180 | 1 |
| Analog 119 | —(CH₂)₈NHC(O)-phenyl | —(CH₂)₂OCH₃ | 0.014 | 0.014 | 1584 | 1995 | 1 |
| Example 134 | —(CH₂)₂O(CH₂)₂N(CH₃)C(O)-phenyl | —(CH₂)₂OH | 3.33 | 30 | 8361 | 315 | 1 |
| Analog 120 | —(CH₂)₂O(CH₂)₂N(CH₃)C(O)-phenyl | —(CH₂)₂OCH₃ | 0.04 | 0.37 | 1394 | 3317 | 1 |
| Example 135 | —(CH₂)₂O(CH₂)₂N(CH₃)C(O)-cyclohexyl | —(CH₂)₂OH | 3.33 | 30 | 2464 | 146 | 1 |
| Analog 121 | —(CH₂)₂O(CH₂)₂N(CH₃)C(O)-cyclohexyl | —(CH₂)₂OCH₃ | 0.37 | 1.11 | 1234 | 4849 | 2 |
| Example 140 | —(CH₂)₂O(CH₂)₂NHC(O)(CH₂)₁₄CH₃ | —(CH₂)₂OH | 1.11 | >30 | 673 | * | 1 |
| Analog 121 | —(CH₂)₂O(CH₂)₂NHC(O)(CH₂)₁₄CH₃ | —(CH₂)₂OCH₃ | 0.014 | 0.014 | 2556 | 11033 | 9 |
| Example 141 | —(CH₂)₃NHC(O)CH(CH₃)₂ | —(CH₂)₂OH | 0.04 | 30 | 14046 | 243 | 1 |
| Analog 123 | —(CH₂)₃NHC(O)CH(CH₃)₂ | —CH₃ | 1.11 | 10 | 3011 | 405 | 2 |
| Example 364 | —CH₂C(CH₃)₂CH₂S(O)₂CH₃ | —CH₂OH | 1.11 | 30 | 5343 | 164 | 1 |
| Analog 124 | —CH₂C(CH₃)₂CH₂S(O)₂CH₃ | —CH₂OCH₂CH₃ | 0.12 | 0.37 | 1924 | 9513 | 4 |

TABLE 11-continued

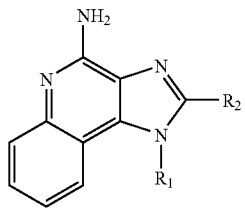

| Compound | $R_1$ | $R_2$ | Minimum Effective Concentration (μM) | | Maximal Response (pg/mL) | | # |
|---|---|---|---|---|---|---|---|
| | | | IFN | TNF | IFN | TNF | |
| Example 365 | —$(CH_2)_2NHC(O)NHCH(CH_3)_2$ | —$CH_2OH$ | 0.37 | 3.33 | 1488 | 74 | 1 |
| Analog 125 | —$(CH_2)_2NHC(O)NHCH(CH_3)_2$ | —$CH_2OCH_2CH_3$ | 0.37 | 10 | 2045 | 7512 | 7 |

*TNF below experimental background of 40 pg/mL

Analogs 1-5, 47-52, 58-74, 109, 113, and 118 are either specifically exemplified in or are readily prepared using the synthetic methods disclosed in U.S. Pat. Nos. 6,331,539 and 6,677,349.
Analogs 53-57, 81-83, 87-91, 97, 98, 103, 104, 107, and 108 are either specifically exemplified in or are readily prepared using the synthetic methods disclosed in U.S. Pat. Nos. 6,541,485 and 6,573,273.
Analogs 73-76 and 124 are either specifically exemplified in or are readily prepared using the synthetic methods disclosed in U.S. Pat. No. 6,664,264.
Analogs 77-80 are either specifically exemplified in or are readily prepared using the synthetic methods disclosed in U.S. Pat. No. 6,683,088.
Analogs 84-86, 99, 100, 111, and 114 are either specifically exemplified in or are readily prepared using the synthetic methods disclosed in U.S. Pat. Nos. 6,069,149 and 6,677,349.
Analogs 93-96, 101, 102, 105, 106, 110, 112, 115, 116, 119, and 123 are either specifically exemplified in or are readily prepared using the synthetic methods disclosed in U.S. Pat. Nos. 6,451,810 and 6,756,382.
Analogs 120-122 are either specifically exemplified in or are readily prepared using the synthetic methods disclosed in U.S. Pat. No. 6,664,265.

Compounds of the invention and in some instances, close analogs (Table 13 below), were tested for their ability to induce cytokine biosynthesis using the test method described above. The minimum effective concentration for the induction of IFN-α, minimum effective concentration for the induction of TNF-α, the maximal response for IFN-α, and the maximal response for TNF-α are shown in Table 12 below where # is the number of separate experiments in which the compound was tested. When a compound was tested in more than one experiment the values shown are the median values.

TABLE 12

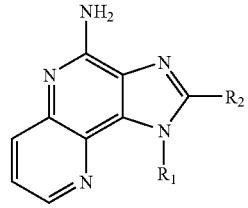

| Compound | $R_1$ | $R_2$ | Minimum Effective Concentration (μM) | | Maximal Response (pg/mL) | | # |
|---|---|---|---|---|---|---|---|
| | | | IFN | TNF | IFN | TNF | |
| Example 148 | —$CH_2C(CH_3)_2OH$ | —$CH_2OH$ | 1.11 | 10 | 2290 | 1316 | 3 |
| Example 149 | —$CH_2C(CH_3)_2OH$ | —$(CH_2)_2OH$ | 3.33 | 30 | 2063 | 331 | 2 |
| Analog 6 | —$CH_2C(CH_3)_2OH$ | —$CH_2OCH_2CH_3$ | 0.12 | 1.11 | 1674 | 7275 | 2 |
| Analog 7 | —$CH_2C(CH_3)_2OH$ | —$(CH_2)_2OCH_3$ | 0.04 | 0.37 | 3142 | 7503 | 2 |
| Analog 126 | —$CH_2C(CH_3)_2OH$ | —$CH_3$ | 0.37 | 3.33 | 1952 | 6519 | 1 |
| Analog 127 | —$CH_2C(CH_3)_2OH$ | —$CH_2CH_3$ | 0.37 | 3.33 | 2150 | 3863 | 1 |
| Analog 128 | —$CH_2C(CH_3)_2OH$ | —$CH_2CH_2CH_3$ | 0.12 | 1.11 | 2484 | 5526 | 1 |
| Example 143 | —$CH_2C(CH)_3NH(CO)$—⟨cyclohexyl⟩ | —$CH_2OH$ | 1.11 | 10 | 1467 | 798 | 1 |
| Analog 129 | —$CH_2C(CH)_3NH(CO)$—⟨cyclohexyl⟩ | —$CH_2OCH_2CH_3$ | 0.014 | 0.014 | 1647 | 8691 | 1 |
| Example 144 | —$CH_2C(CH_3)_2NHS(O)_2CH_3$ | —$CH_2OH$ | 10 | 30 | 1914 | 170 | 1 |
| Analog 130 | —$CH_2C(CH_3)_2NHS(O)_2CH_3$ | —$CH_2OCH_2CH_3$ | 0.04 | 0.37 | 2465 | 9234 | 1 |
| Example 551 | —$CH_2CF(CH_3)_2$ | —$CH_2OH$ | 1.11 | 3.33 | 1833 | 1922 | 1 |
| Example 552 | —$CH_2CF(CH_3)_2$ | —$(CH_2)_2OH$ | 1.11 | 10 | 1646 | 84 | 1 |
| Analog 131 | —$CH_2CF(CH_3)_2$ | —$CH_3$ | 0.37 | 10 | 2120 | 1679 | 2 |
| Example 633 | —$CH_2CH(CH_3)_2$ | —$CH_2OH$ | 1.11 | 30 | 1592 | 363 | 1 |

TABLE 12-continued

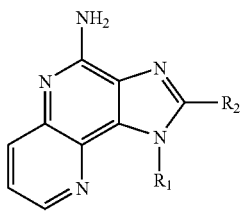

| Compound | R₁ | R₂ | Minimum Effective Concentration (μM) | | Maximal Response (pg/mL) | | # |
|---|---|---|---|---|---|---|---|
| | | | IFN | TNF | IFN | TNF | |
| Analog 132 | —CH₂CH(CH₃)₂ | —CH₂OCH₂CH₃ | 0.12 | 1.11 | 1524 | 3160 | 2 |
| Analog 133 | —CH₂CH(CH₃)₂ | —CH₃ | 0.37 | 1.11 | 1117 | 699 | 12 |
| Example 145 | —(CH₂)₄NHS(O)₂CH₃ | —(CH₂)₂OH | 1.11 | 30 | 3008 | 7 | 2 |
| Example 146 | —(CH₂)₄NHS(O)₂CH₃ | —CH₂OH | 10 | >30 | 1520 | * | 1 |
| Example 147 | —(CH₂)₄NHS(O)₂CH₃ | —(CH₂)₂OH | 30 | >30 | 49 | * | 1 |

* Below the experimental background of 40 pg/mL

TABLE 13

| Analog | Chemical Name | Reference |
|---|---|---|
| 6 | 1-(4-amino-2-ethoxymethyl-1H-imidazo[4,5-c][1,5]naphthyridin-1-yl)-2-methylpropan-2-ol | Example 148 Part E |
| 7 | 1-[4-amino-2-(2-methoxyethyl)-1H-imidazo[4,5-c][1,5]naphthyridin-1-yl]-2-methylpropan-2-ol | Example 149 Part J |
| 126 | 1-(4-amino-2-methyl-1H-imidazo[4,5-c][1,5]naphthyridin-1-yl)-2-methylpropan-2-ol | U.S. Pat. No. 6,194,425** |
| 127 | 1-(4-amino-2-ethyl-1H-imidazo[4,5-c][1,5]naphthyridin-1-yl)-2-methylpropan-2-ol | U.S. Pat. No. 6,194,425** |
| 128 | 1-(4-amino-2-propyl-1H-imidazo[4,5-c][1,5]naphthyridin-1-yl)-2-methylpropan-2-ol | U.S. Pat. No. 6,194,425** |
| 129 | N-[2-(4-amino-2-ethoxymethyl-1H-imidazo[4,5-c][1,5]naphthyridin-1-yl)-1,1-dimethylethyl]cyclohexanecarboxamide | Example 143 Part H |
| 130 | N-[2-(4-amino-2-ethoxoxymethyl-1H-imidazo[4,5-c][1,5]naphthyridin-1-yl)-1,1-dimethylethyl]methanesulfonamide | Example 144 Part A |
| 131 | 1-(2-fluoro-2-methylpropyl)-2-methyl-1H-imidazo[4,5-c][1,5]naphthyridin-4-amine | U.S. Pat. No. 6,194,425** |
| 132 | 2-ethoxymethyl-1-(2-methylpropyl)-1H-imidazo[4,5-c][1,5]naphthyridin-4-amine | U.S. Pat. No. 6,194,425** |
| 133 | 2-methyl-1-(2-methylpropyl)-1H-imidazo[4,5-c][1,5]naphthyridin-4-amine | U.S. Pat. No. 6,194,425 Example 36 |

**Although not a working example, the compound is readily prepared using the disclosed synthetic methods.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of preferentially inducing the biosynthesis of IFN-α over TNF-α in an animal comprising administering an effective amount of a compound of Formula I:

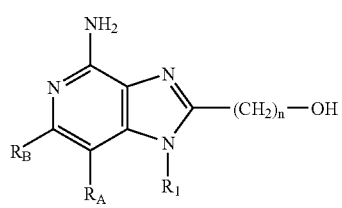

wherein:
n is 1 or 2;
$R_A$ and $R_B$ are each independently selected from the group consisting of:
hydrogen,
halogen,
alkyl,
alkenyl, alkoxy,
alkylthio and
—N(R$_9$)$_2$;

or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups, or substituted by one R$_3$ group, or substituted by one R$_3$ group and one R group;

or when taken together, R$_A$ and R$_B$ form a fused 5 to 7 membered saturated ring, optionally containing one heteroatom selected from the group consisting of N and S, and unsubstituted or substituted at a carbon atom by one or more R groups;

R is selected from the group consisting of:
halogen,
hydroxy,
alkyl,
alkenyl,
haloalkyl,
alkoxy,
alkylthio, and
—N(R$_9$)$_2$;

R$_1$ is selected from the group consisting of:
—R$_4$,
—X—R$_4$,
—X—Y—R$_4$,
—X—Y—X—Y—R$_4$, and
—X—R$_5$;

R$_3$ is selected from the group consisting of:
—Z—R$_4$,
—Z—X—R$_4$,
—Z—X—Y—R$_4$,
—Z—X—Y—X—Y—R$_4$, and
—Z—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

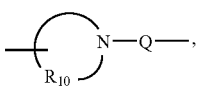

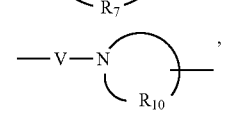

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

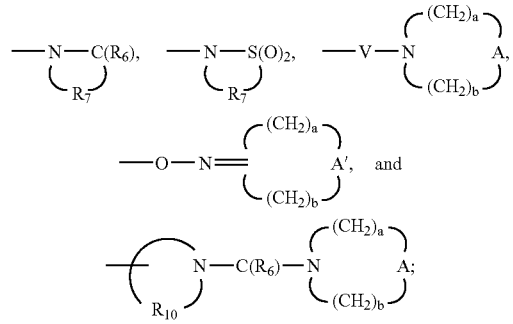

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —C(O)—, —CH$_2$—, —S(O)$_{0-2}$—, and —N(Q-R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;

or a pharmaceutically acceptable salt thereof to the animal.

2. The method of claim 1 wherein n is 1.

3. The method of claim 1 wherein n is 2.

4. The method of claim 1 wherein $R_A$ and $R_B$ form a fused benzene ring which is unsubstituted or substituted by one or more R groups, or substituted by one $R_3$ group, or substituted by one $R_3$ group and one R group.

5. The method of claim 1 wherein $R_A$ and $R_B$ form a fused pyridine ring which is unsubstituted or substituted by one or more R groups, or substituted by one $R_3$ group, or substituted by one $R_3$ group and one R group.

6. The method of claim 1 wherein $R_A$ and $R_B$ form a fused 5 to 7 membered saturated ring, optionally containing one heteroatom selected from the group consisting of N and S, wherein the ring is unsubstituted or substituted by one or more R groups.

7. The method of claim 1 wherein $R_1$ is selected from the group consisting of:
—$R_4$,
—X—$R_4$,
—X—Y—$R_4$,
—X—Y—$X^1$—$Y^1$—$R_4$, and
—X—$R_5$; wherein X is alkylene that is optionally interrupted or terminated by heterocyclylene and optionally interrupted by one —O— group;

Y is selected from the group consisting of:

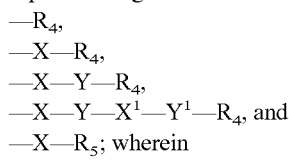

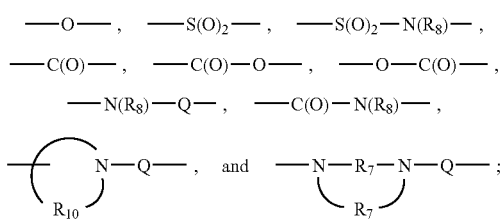

$X^1$ is selected from the group consisting of alkylene and arylene;

$Y^1$ is selected from the group consisting of:
—S—,
—C(O)—,
—C(O)—O—,
—C(O)—N($R_8$)—,
—S(O)$_2$—N($R_8$)—, and
—N($R_8$)—C(O)—;

$R_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo;

$R_5$ is selected from the group consisting of:

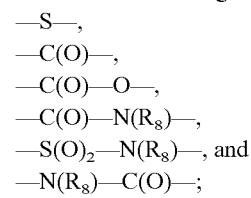

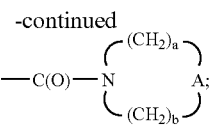

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_{10}$ is $C_{3-8}$ alkylene;
A is selected from the group consisting of —O—, —C(O)—, and —N($R_4$)—;
Q is selected from the group consisting of a bond, —C($R_6$)—, —S(O)$_2$—, —C($R_6$)—N($R_8$)—W—, —S(O)$_2$—N($R_8$)—, —C(O)—O—, and —C(O)—S—;
W is selected from the group consisting of a bond and —C(O)—; and
a and b are independently integers from 1 to 6 with the proviso that a+b is ≤7.

8. The method of claim 1 wherein $R_1$ is selected from the group consisting of $C_{1-5}$ alkyl, $C_{2-5}$ alkynyl, aryl$C_{1-4}$ alkylenyl, cycloalkyl$C_{1-4}$ alkylenyl, $C_{1-4}$ alkyl-S(O)$_2$—$C_{1-4}$ alkylenyl, aryl-S(O)$_2$—$C_{1-4}$ alkylenyl, $C_{1-4}$ alkyl-S(O)$_2$—$C_{1-4}$ alkylenyl-O—$C_{1-4}$ alkylenyl, $C_{1-4}$ alkyl-S(O)$_2$—NH—$C_{1-4}$ alkylenyl, hydroxy$C_{1-4}$ alkylenyl, dihydroxy$C_{1-4}$-alkylenyl, halo$C_{1-4}$ alkylenyl, amino$C_{1-4}$ alkylenyl, $C_{1-4}$ alkyl-C(O)—O—$C_{1-4}$ alkylenyl, $C_{1-6}$ alkyl-C(O)—NH—$C_{1-4}$ alkylenyl, aryl-C(O)—NH—$C_{1-4}$ alkylenyl wherein aryl is unsubstituted or substituted with one or two halogen groups, heteroaryl-C(O)—NH—$C_{1-4}$ alkylenyl, di($C_{1-4}$ alkyl)amino-S(O)$_2$—NH—$C_{1-4}$ alkylenyl, aryl-S(O)$_2$—NH—$C_{1-4}$ alkylenyl, aryl-NH—C(O)—NH—$C_{1-4}$ alkylenyl, heteroaryl-NH—C(S)—NH—$C_{1-4}$ alkylenyl, di($C_{1-4}$ alkyl)amino-C(O)—NH—$C_{1-4}$ alkylenyl, $C_{1-4}$ alkylamino-C(O)—NH—$C_{1-4}$ alkylenyl, di($C_{1-4}$ alkyl)amino-S(O)$_2$—$C_{1-4}$ alkylenyl, $C_{1-4}$ alkylamino-S(O)$_2$—$C_{1-4}$ alkylenyl, amino-S(O)$_2$—$C_{1-4}$ alkylenyl, heteroaryl$C_{1-4}$ alkylenyl wherein heteroaryl is unsubstituted or substituted by a substituent selected from the group consisting of aryl, heteroaryl, and alkyl, and heterocyclyl$C_{1-4}$ alkylenyl wherein heterocyclyl is unsubstituted or substituted by one, two, or three substituents selected from the group consisting of alkyl, aryl, heteroaryl, and oxo.

9. The method of claim 1 wherein $R_1$ is selected from the group consisting of alkyl, aminoalkyl, dihydroxyalkyl, haloalkyl, and hydroxyalkyl.

10. The method of claim 1 wherein $R_1$ is heterocyclylalkylenyl wherein heterocyclyl is unsubstituted or substituted by one or more substituents independently selected from the group consisting of alkyl, aryl, heteroaryl, hydroxy, and oxo.

11. The method of claim 1 wherein $R_1$ is —X—Y—$R_4$ wherein X is $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —S(O)$_2$ wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

12. The method of claim 1 wherein $R_1$ is —X—Y—$R_4$ wherein X is $C_{1-6}$ alkylene which may be interrupted by an —O— group; Y is selected from the group consisting of —N(R_8)—C(O)—, —N(R_8)—S(O)_2—, —N(R_8)—C(O)—N(R_8)—, —N(R_8)—S(O)_2—N(R_8)—, —S(O)_2—, and

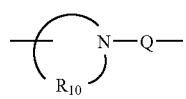

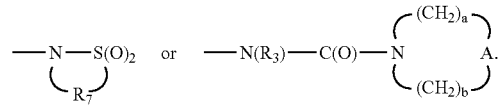

wherein Q is —C(O)—, —C(O)—NH—, or —S(O)_2—, R_{10} is pentylene, R_8 is hydrogen or methyl; and R_4 is selected from the group consisting of $C_{1-6}$ alkyl, hydroxy$C_{1-6}$ alkyl, isoquinolinyl, N-methylimidazolyl, pyridinyl, quinolinyl, benzyl, 1-phenylethyl, phenyl, and phenyl substituted by a substituent selected from the group consisting of chloro, cyano, fluoro, hydroxy, and methyl.

13. The method of claim 1 wherein R_1 is —X—R_5 wherein X is $C_{1-6}$alkylene, and R_5 is

14. The method of claim 1 wherein R_3 is selected from the group consisting of aryl, arylalkyleneoxy, heteroaryl, and heteroarylalkyleneoxy, wherein aryl, arylalkyleneoxy, heteroaryl, and heteroarylalkyleneoxy, are unsubstituted or substituted with one or more substituents selected from the group consisting of alkyl, alkoxy, halogen, hydroxy, and hydroxyalkyl.

15. The method of claim 1 wherein R_3 nor R is present.

16. The method of claim 1 wherein the compound or salt is administered systemically.

* * * * *

UNITED STATES PATENT AND TRADEMARK OFFICE
CERTIFICATE OF CORRECTION

PATENT NO. : 8,846,710 B2
APPLICATION NO. : 11/884982
DATED : September 30, 2014
INVENTOR(S) : Tushar Kshirsagar It is certified that error appears in the above-identified patent and that said Letters Patent is hereby corrected as shown below:

In the Specification

Column 18
Line 57, delete "$N(R_9)$" and insert -- $N(R_8)$ --, therefor.

Line 62, delete "allyl," and insert -- alkyl, --, therefor.

Column 23
Line 34, delete "$N(R_9)$" and insert -- $N(R_8)$ --, therefor.

Line 35, delete "$N(R_9)$" and insert -- $N(R_8)$ --, therefor.

Column 27
Line 12, delete "allyl." and insert -- alkyl. --, therefor.

Column 28
Line 64, delete "R'" and insert -- R" --, therefor.

Column 30
Line 24, delete "$N(R_9)$" and insert -- $N(R_8)$ --, therefor.

Line 47, delete "ethylene," and insert -- ethylene. --, therefor.

Column 33
Line 13, delete "allyl" and insert -- alkyl --, therefor.

Column 103
Line 44, delete "11H" and insert -- 1H --, therefor.

Signed and Sealed this
Second Day of June, 2015

Michelle K. Lee
*Director of the United States Patent and Trademark Office*

Column 124
Line 50, delete "to of" and insert -- of --, therefor.

Column 128
Line 4 (Analytical Data), delete "l5.73;" and insert -- 15.73; --, therefor.

Column 136
Line 5 (Analytical Data), delete "4l8" and insert -- 418 --, therefor.

Column 270
Line 33, delete "(Oreiner" and insert -- (Greiner --, therefor.